US012655432B2

(12) United States Patent
Khvorova et al.

(10) Patent No.: US 12,655,432 B2
(45) Date of Patent: Jun. 16, 2026

(54) OLIGONUCLEOTIDES FOR SOD1 MODULATION

(71) Applicant: UNIVERSITY OF MASSACHUSETTS, Boston, MA (US)

(72) Inventors: Anastasia Khvorova, Westborough, MA (US); James W. Gilbert, Worcester, MA (US); Chantal Ferguson, Worcester, MA (US); Robert Brown, Needham, MA (US); Alexandra Weiss, Bolton, MA (US)

(73) Assignee: UNIVERSITY OF MASSACHUSETTS, Westborough, MA (US)

( * ) Notice: Subject to any disclaimer, the term of this patent is extended or adjusted under 35 U.S.C. 154(b) by 0 days.

(21) Appl. No.: 17/982,993

(22) Filed: Nov. 8, 2022

(65) Prior Publication Data

US 2023/0193281 A1 Jun. 22, 2023

Related U.S. Application Data

(60) Provisional application No. 63/276,854, filed on Nov. 8, 2021.

(51) Int. Cl.
*C12N 15/113* (2010.01)
*A61P 25/28* (2006.01)

(52) U.S. Cl.
CPC .......... *C12N 15/1137* (2013.01); *A61P 25/28* (2018.01); *C12N 2310/14* (2013.01); *C12N 2310/315* (2013.01); *C12N 2310/321* (2013.01); *C12N 2310/322* (2013.01); *C12N 2320/32* (2013.01)

(58) Field of Classification Search
CPC ........... C12N 15/1137; C12N 2310/14; C12N 2310/315; C12N 2310/321; C12N 2310/322; C12N 2320/32; A61P 25/28
See application file for complete search history.

(56) References Cited

U.S. PATENT DOCUMENTS 5,328,470 A 7/1994 Nabel et al.
5,684,143 A 11/1997 Gryaznov et al.
5,814,014 A 9/1998 Elsberry et al.
5,858,988 A 1/1999 Wang
6,093,180 A 7/2000 Elsberry
6,177,403 B1 1/2001 Stedman
6,291,438 B1 9/2001 Wang
7,459,547 B2 12/2008 Zamore et al.
7,732,593 B2 6/2010 Zamore et al.
7,750,144 B2 7/2010 Zamore et al.
7,772,203 B2 8/2010 Zamore et al.
8,304,530 B2 11/2012 Zamore et al.
8,309,704 B2 11/2012 Zamore et al.
8,309,705 B2 11/2012 Zamore et al.
8,329,892 B2 12/2012 Zamore et al.
8,431,544 B1 4/2013 Agrawal et al.
10,478,503 B2 * 11/2019 Khvorova ............ A61K 47/551
11,279,930 B2 3/2022 Khvorova et al.
2005/0220766 A1 10/2005 Amalfitano et al.
2006/0078542 A1 4/2006 Mah et al.
2007/0259827 A1 11/2007 Aronin et al.
2008/0269149 A1 10/2008 Bowles et al.
2010/0186103 A1 7/2010 Gao et al.
2011/0039914 A1 * 2/2011 Pavco ................ C12N 15/1136 435/375
2014/0296486 A1 10/2014 Gao et al.
2017/0037410 A1 * 2/2017 Swayze ................... A61P 43/00
2017/0314028 A1 * 11/2017 Hou .................. C12N 15/1137
2020/0087663 A1 3/2020 Khvorova et al.
2020/0157547 A1 5/2020 Sah et al.
2020/0385737 A1 12/2020 Khvorova et al.
2020/0385740 A1 12/2020 Khvorova et al.
2022/0010309 A1 1/2022 Khvorova et al.

FOREIGN PATENT DOCUMENTS

WO WO 2003/029459 A2 4/2003
WO WO 2006/066203 A2 6/2006
WO WO 2017/030973 A1 2/2017
WO WO 2017/132669 A1 8/2017
WO WO 2018/031933 A2 2/2018
WO WO 2022/174000 A2 8/2022
WO WO 2023/081908 A2 5/2023

OTHER PUBLICATIONS

Chi et al., "Safety of antisense oligonucleotide and siRNA-based therapeutics", Drug Discovery Today, vol. 22, No. May 5, 2017, pp. 823-831. (Year: 2017).*
Alisky, et al., Gene Therapy for Amyotrophic Lateral Sclerosis and Other Motor Neuron Diseases, Human Gene Therapy, vol. 11, No. 17, pp. 2315-2329, Nov. 20, 2000.
Atwell, et al., Stable Heterodimers From Remodeling The Domain Interface Of A Homodimer Using A Phage Display Library, Journal Of Molecular Biology, vol. 270, No. 1, pp. 26-35, Jul. 4, 1997.
Billy, et al., Specific Interference With Gene Expression Induced By Long, Double-Stranded RNA In Mouse Embryonal Teratocarcinoma Cell Lines, Proceedings of the National Academy of Sciences, vol. 98, No. 25, pp. 14428-14433, Dec. 4, 2001.
Braasch, et al., RNA Interference in Mammalian Cells by Chemically-Modified RNA, Biochemistry, vol. 42, No. 26, pp. 7967-7975, Jun. 11, 2003.
Brummelkamp, et al., A System for Stable Expression of Short Interfering RNAs in Mammalian Cells, Science, vol. 296, No. 5567, pp. 550-553, Apr. 19, 2002.
Chen, et al., Gene Therapy For Brain Tumors: Regression Of Experimental Gliomas By Adenovirus-Mediated Gene Transfer In Vivo, Proceedings of the National Academy of Sciences, vol. 91, No. 8, pp. 3054-3057, Apr. 1994.

(Continued)

*Primary Examiner* — Abigail Vanhorn
*Assistant Examiner* — Stephanie L Sullivan
(74) *Attorney, Agent, or Firm* — LATHROP GPM LLP; James H. Velema, Esq.

(57) ABSTRACT

This disclosure relates to novel SOD1 targeting sequences. Novel SOD1 targeting oligonucleotides for the treatment of SOD1-related familial amyotrophic lateral sclerosis (ALS).

18 Claims, 26 Drawing Sheets

Specification includes a Sequence Listing.

(56) References Cited

OTHER PUBLICATIONS

Davidson, et al., A Model System For In Vivo Gene Transfer Into The Central Nervous System Using An Adenoviral Vector, Nature Genetics, vol. 3, No. 3, pp. 219-223, Mar. 1993.
Davidson, et al., Recombinant Adeno-Associated Virus Type 2, 4, and 5 Vectors: Transduction of Variant Cell Types And Regions In The Mammalian Central Nervous System, Proceedings of the National Academy of Sciences, vol. 97, No. 7, pp. 3428-3432, Mar. 28, 2000.
Eckstein, Fritz, Phosphorothioate Oligodeoxynucleotides: What Is Their Origin and What Is Unique About Them?, Antisense and Nucleic Acid Drug Development, vol. 10, No. 2, pp. 117-121, Apr. 2000.
Elmen, et al., Locked Nucleic Acid (LNA) Mediated Improvements in siRNA Stability And Functionality, Nucleic Acids Research, vol. 33, No. 1, pp. 439-447, Jan. 14, 2005.
Fattal, et al., Biodegradable Polyalkylcyanoacrylate Nanoparticles For The Delivery Of Oligonucleotides, Journal of Controlled Release, vol. 53, No. 1-3, pp. 137-143, Apr. 30, 1998.
Fisher, et al., Transduction With Recombinant Adeno-Associated Virus For Gene Therapy Is Limited By Leading-Strand Synthesis, Journal of Virology, vol. 70, No. 1, pp. 520-532, Jan. 1996.
Godard, et al., Antisense Effects of Cholesterol-Oligodeoxynucleotide Conjugates Associated with Poly(alkylcyanoacrylate) Nanoparticles, European Journal of Biochemistry banner, vol. 232, No. 2, pp. 404-410, Sep. 1, 1995.
Herdewijn, Piet, Heterocyclic Modifications of Oligonucleotides and Antisense Technology, Antisense and Nucleic Acid Drug Development, vol. 10, Issue 4, pp. 297-310, Aug. 2000.
International Search Report and Written Opinion received for PCT Patent Application No. PCT/US2022/079444, mailed on Jul. 25, 2023.
Karlin, et al., Applications And Statistics For Multiple High-Scoring Segments In Molecular Sequences, Proceedings of the National Academy of Sciences of the USA, vol. 90, pp. 5873-5877, Jun. 1, 1993.
Karlin, et al., Methods For Assessing The Statistical Significance Of Molecular Sequence Features By Using General Scoring Schemes, Proceedings of the National Academy of science of the USA, vol. 87, No. 6, pp. 2264-2268, Mar. 1, 1990.
Lagos-Quintana, et al., Identification of Novel Genes Coding for Small Expressed RNAs, Science, vol. 294, No. 5543, pp. 853-858, Oct. 26, 2001.
Lagos-Quintana, et al., Identification of Tissue-Specific MicroRNAs from Mouse, Current Biology, vol. 12, No. 9, pp. 735-739, Apr. 30, 2002.
Lam, et al., A New Type of Synthetic Peptide Library For Identifying Ligand-Binding Activity, Nature, vol. 354, pp. 82-84, Nov. 7, 1991.
Lambert, et al., Nanoparticulate Systems For The Delivery Of Antisense Oligonucleotides, Advanced Drug Delivery Reviews, vol. 47, No. 1, pp. 99-112, Mar. 23, 2001.
Lim, et al., Vertebrate MicroRNA Genes, Science, vol. 299, No. 5612, 1540 Page., Mar. 7, 2003.
McCampbell, et al., Antisense Oligonucleotides Extend Survival and Reverse Decrement in Muscle Response in ALS Models, Journal of Clinical Investigation, vol. 128, No. 8, pp. 3558-3567, Aug. 2018.
Miyagishi, et al., U6 promoter-driven siRNAs With Four Uridine 3' Overhangs Efficiently Suppress Targeted Gene Expression In Mammalian Cells, Nature Biotechnology, vol. 20, No. 5, pp. 497-500, May 1, 2002.
Nielsen, et al., Sequence-Selective Recognition of DNA by Strand Displacement With A Thymine-Substituted Polyamide, Science, vol. 254, No. 5037, pp. 1497-1500, Dec. 6, 1991.
Petersen, et al., LNA: A Versatile Tool for Therapeutics and Genomics, Trends in Biotechnology, vol. 21, No. 2, pp. 74-81, Feb. 2003.
Rusckowski, et al., Biodistribution and Metabolism of a Mixed Backbone Oligonucleotide (GEM 231) Following Single and Multiple Dose Administration in Mice, Antisense and Nucleic Acid Drug Development, vol. 10, No. 5, pp. 333-345, Oct. 2000.
Schwab, et al., An Approach For New Anticancer Drugs:Oncogene-Targeted Antisense DNA, Annals of Oncology, vol. 5, Supplement 4, pp. S55-S58, Jan. 1, 1994.
Stein, et al., Inhibition of Vesivirus Infections in Mammalian Tissue Culture with Antisense Morpholino Oligomers, Antisense and Nucleic Acid Drug Development, vol. 11, No. 5, pp. 317-325, Oct. 2001.
Stein, et al., Systemic and Central Nervous System Correction of Lysosomal Storage in Mucopolysaccharidosis Type VII Mice, Journal of Virology, vol. 73, No. 4, pp. 3424-3429, Apr. 1999.
Vorobjev, et al., Nuclease Resistance and RNase H Sensitivity of Oligonucleotides Bridged by Oligomethylenediol and Oligoethylene Glycol Linkers, Antisense and Nucleic Acid Drug Development, vol. 11, No. 2, pp. 77-85, Apr. 2011.
Wright, et al., Identification Of Factors That Contribute To Recombinant AAV2 Particle Aggregation And Methods To Prevent Its Occurrence During Vector Purification And Formulation, Molecular Therapy, vol. 12, No. 1, pp. 171-178, Jul. 2005.
Zhang, et al., Several rAAV Vectors Efficiently Cross the Blood-brain Barrier and Transduce Neurons and Astrocytes in the Neonatal Mouse Central Nervous System, Molecular Therapy, vol. 19, Issue 8, pp. 1440-1448, Aug. 1, 2011.
Abati et al., "Silence superoxide dismutase 1 (SOD1): a promising therapeutic target for amyotrophic lateral sclerosis (ALS)", Expert Opinion on Therapeutic Targets, Mar. 3, 2020, 24(4): 295-310.
Partial Supplementary European Search Report for European Patent Application No. 22891152.5, dated Jan. 21, 2026.
Van Zundert et al., "Silencing strategies for therapy of SOD1-mediated ALS", Neurosci Letters, Jan. 1, 2017, 636: 32-39, Epublished Aug. 6, 2016.

* cited by examiner

| ASO | Sequence/Chemistry |
|---|---|
| ASO 1 | CAoGGoATACATTTCTACoAGoCT |
| ASO 2 | TToAoATGTTTATCAoGoGAT |
| 333611 | CCGTCGCCCTTCAGCACGCA |

Days old

Days old

Days old

OLIGONUCLEOTIDES FOR SOD1 MODULATION

RELATED APPLICATIONS

This application claims the benefit of U.S. Provisional Application No. 63/276,854, filed Nov. 8, 2021, the content of which is incorporated by reference in its entirety for all purposes.

STATEMENT REGARDING FEDERALLY SPONSORED RESEARCH OR DEVELOPMENT

This invention was made with government support under Grant No. NS010433 awarded by the National Institutes of Health. The Government has certain rights in the invention.

SEQUENCE LISTING

The content of the electronically submitted sequence listing in XML format (Name: 735426_UM9-271_ST26.xml; Size: 1,271,508 bytes; and Date of Creation: Feb. 21, 2023) is incorporated herein by reference in its entirety.

FIELD OF THE DISCLOSURE

This disclosure relates to novel SOD1 targeting sequences, novel branched oligonucleotides, and novel methods for treating and preventing SOD1-related familial amyotrophic lateral sclerosis.

BACKGROUND

Amyotrophic lateral sclerosis (ALS) is the most common neuromuscular disorder which selectively affects motor neurons in the spinal cord and brain. This fatal neurodegenerative disorder leads to progressive muscle weakness, paralysis and death within 3-5 years after onset of symptoms, with no cure yet available. ALS affects ~10 persons per 100,000 people and the two FDA-approved drug, Riluzole and Edaravone, only slightly prolong survival of patients. Thus, the development of therapeutics that fulfil this clear unmet medical need are essential to transform not only survival but the quality of life of patients with ALS Superoxide Dismutase 1 (SOD1), a major cytoplasmic antioxidant enzyme, is a well-established historical target of ALS. More than 170 mutations have been detected throughout the SOD1 gene, accounting for 20-25% of familial ALS cases. Many of these mutations, spread across the coding sequence, have little to no effect on dismutase activity, and has led to a hypothesis that SOD1 driven ALS is a result of a toxic gain of function, rather than loss of native dismutase activity. A proportion of each ALS-causing SOD1 mutant may fail to fold properly, thus implicating accumulation of misfolded SOD1 as a possible toxic contributor in ALS. Accordingly, there exists a need for effective SOD1-targeting therapeutics for the treatment of ALS.

SUMMARY

In one aspect, the disclosure provides an RNA molecule having a length of from about 8 nucleotides to about 80 nucleotides; and a nucleic acid sequence that is substantially complementary to a SOD1 nucleic acid sequence of any one of SEQ ID NOs: 1-11. In certain embodiments, the RNA molecule is from 8 nucleotides to 80 nucleotides in length (e.g., 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, 30 nucleotides, 31 nucleotides, 32 nucleotides, 33 nucleotides, 34 nucleotides, 35 nucleotides, 36 nucleotides, 37 nucleotides, 38 nucleotides, 39 nucleotides, 40 nucleotides, 41 nucleotides, 42 nucleotides, 43 nucleotides, 44 nucleotides, 45 nucleotides, 46 nucleotides, 47 nucleotides, 48 nucleotides, 49 nucleotides, 50 nucleotides, 51 nucleotides, 52 nucleotides, 53 nucleotides, 54 nucleotides, 55 nucleotides, 56 nucleotides, 57 nucleotides, 58 nucleotides, 59 nucleotides, 60 nucleotides, 61 nucleotides, 62 nucleotides, 63 nucleotides, 64 nucleotides, 65 nucleotides, 66 nucleotides, 67 nucleotides, 68 nucleotides, 69 nucleotides, 70 nucleotides, 71 nucleotides, 72 nucleotides, 73 nucleotides, 74 nucleotides, 75 nucleotides, 76 nucleotides, 77 nucleotides, 78 nucleotides, 79 nucleotides, or 80 nucleotides in length).

In certain embodiments, the RNA molecule is from 10 to 50 nucleotides in length (e.g., 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, 30 nucleotides, 31 nucleotides, 32 nucleotides, 33 nucleotides, 34 nucleotides, 35 nucleotides, 36 nucleotides, 37 nucleotides, 38 nucleotides, 39 nucleotides, 40 nucleotides, 41 nucleotides, 42 nucleotides, 43 nucleotides, 44 nucleotides, 45 nucleotides, 46 nucleotides, 47 nucleotides, 48 nucleotides, 49 nucleotides, or 50 nucleotides in length).

In certain embodiments, the RNA molecule comprises about 15 nucleotides to about 25 nucleotides in length. In certain embodiments, the RNA molecule is from 15 to 25 nucleotides in length (e.g., 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, or 25 nucleotides in length).

In certain embodiments, the RNA molecule has a nucleic acid sequence that is substantially complementary to a SOD1 nucleic acid sequence of any one of SEQ ID NOs: 12-22.

In certain embodiments, the RNA molecule comprises single stranded (ss) RNA or double stranded (ds) RNA.

In certain embodiments, the RNA molecule is a dsRNA comprising a sense strand and an antisense strand. The antisense strand may comprise a nucleic acid sequence that is substantially complementary to a SOD1 nucleic acid sequence of any one of SEQ ID NOs: 1-11. For example, in certain embodiments, the antisense sequence is substantially complementary to the nucleic acid sequence of SEQ ID NO: 1. In certain embodiments, the antisense sequence is substantially complementary to the nucleic acid sequence of SEQ ID NO: 2. In certain embodiments, the antisense sequence is substantially complementary to the nucleic acid sequence of SEQ ID NO: 3. In certain embodiments, the antisense sequence is substantially complementary to the nucleic acid sequence of SEQ ID NO: 4. In certain embodiments, the antisense sequence is substantially complementary to the nucleic acid sequence of SEQ ID NO: 5. In certain embodiments, the antisense sequence is substantially complementary to the nucleic acid sequence of SEQ ID NO: 6. In certain embodiments, the antisense sequence is substantially complementary to the nucleic acid sequence of SEQ ID NO: 7. In certain embodiments, the antisense sequence is substantially complementary to the nucleic acid sequence of SEQ ID NO: 8. In certain embodiments, the antisense sequence is substantially complementary to the nucleic acid sequence of SEQ ID NO: 9. In certain embodiments, the antisense sequence is substantially complementary to the nucleic acid sequence of SEQ ID NO: 10. In certain embodiments, the antisense sequence is substantially complementary to the nucleic acid sequence of SEQ ID NO: 11.

In certain embodiments, the dsRNA comprises an antisense strand having complementarity to at least 10, 11, 12 or 13 contiguous nucleotides of a SOD1 nucleic acid sequence of any one of SEQ ID NOs: 1-11. For example, in certain embodiments, the dsRNA comprises an antisense strand having complementarity to a segment of from 10 to 25 contiguous nucleotides of the nucleic acid sequence of any one of SEQ ID NOs: 1-11 (e.g., a segment of from 10 to 25 contiguous nucleotides of the nucleic acid sequence of SEQ ID NO: 1, a segment of from 10 to 25 contiguous nucleotides of the nucleic acid sequence of SEQ ID NO: 2, a segment of from 10 to 25 contiguous nucleotides of the nucleic acid sequence of SEQ ID NO: 3, a segment of from 10 to 25 contiguous nucleotides of the nucleic acid sequence of SEQ ID NO: 4, a segment of from 10 to 25 contiguous nucleotides of the nucleic acid sequence of SEQ ID NO: 5, a segment of from 10 to 25 contiguous nucleotides of the nucleic acid sequence of SEQ ID NO: 6, a segment of from 10 to 25 contiguous nucleotides of the nucleic acid sequence of SEQ ID NO: 7, a segment of from 10 to 25 contiguous nucleotides of the nucleic acid sequence of SEQ ID NO: 8, a segment of from 10 to 25 contiguous nucleotides of the nucleic acid sequence of SEQ ID NO: 9, a segment of from 10 to 25 contiguous nucleotides of the nucleic acid sequence of SEQ ID NO: 10, a segment of from 10 to 25 contiguous nucleotides of the nucleic acid sequence of SEQ ID NO: 11).

In certain embodiments, the dsRNA comprises an antisense strand having complementarity to a segment of from 15 to 25 contiguous nucleotides of the nucleic acid sequence of any one of SEQ ID NOs: 1-11. For example, the antisense strand may have complementarity to a segment of 15 contiguous nucleotides, 16 contiguous nucleotides, 17 contiguous nucleotides, 18 contiguous nucleotides, 19 contiguous nucleotides, 20 contiguous nucleotides, 21 contiguous nucleotides, 22 contiguous nucleotides, 23 contiguous nucleotides, 24 contiguous nucleotides, or 25 contiguous nucleotides of the nucleic acid sequence of SEQ ID NO: 1. In certain embodiments, the antisense strand has complementarity to a segment of 15 contiguous nucleotides, 16 contiguous nucleotides, 17 contiguous nucleotides, 18 contiguous nucleotides, 19 contiguous nucleotides, 20 contiguous nucleotides, 21 contiguous nucleotides, 22 contiguous nucleotides, 23 contiguous nucleotides, 24 contiguous nucleotides, or 25 contiguous nucleotides of the nucleic acid sequence of SEQ ID NO: 2. In certain embodiments, the antisense strand has complementarity to a segment of 15 contiguous nucleotides, 16 contiguous nucleotides, 17 contiguous nucleotides, 18 contiguous nucleotides, 19 contiguous nucleotides, 20 contiguous nucleotides, 21 contiguous nucleotides, 22 contiguous nucleotides, 23 contiguous nucleotides, 24 contiguous nucleotides, or 25 contiguous nucleotides of the nucleic acid sequence of SEQ ID NO: 3. In certain embodiments, the antisense strand has complementarity to a segment of 15 contiguous nucleotides, 16 contiguous nucleotides, 17 contiguous nucleotides, 18 contiguous nucleotides, 19 contiguous nucleotides, 20 contiguous nucleotides, 21 contiguous nucleotides, 22 contiguous nucleotides, 23 contiguous nucleotides, 24 contiguous nucleotides, or 25 contiguous nucleotides of the nucleic acid sequence of SEQ ID NO: 4. In certain embodiments, the antisense strand has complementarity to a segment of 15 contiguous nucleotides, 16 contiguous nucleotides, 17 contiguous nucleotides, 18 contiguous nucleotides, 19 contiguous nucleotides, 20 contiguous nucleotides, 21 contiguous nucleotides, 22 contiguous nucleotides, 23 contiguous nucleotides, 24 contiguous nucleotides, or 25 contiguous nucleotides of the nucleic acid sequence of SEQ ID NO: 5. In certain embodiments, the antisense strand has complementarity to a segment of 15 contiguous nucleotides, 16 contiguous nucleotides, 17 contiguous nucleotides, 18 contiguous nucleotides, 19 contiguous nucleotides, 20 contiguous nucleotides, 21 contiguous nucleotides, 22 contiguous nucleotides, 23 contiguous nucleotides, 24 contiguous nucleotides, or 25 contiguous nucleotides of the nucleic acid sequence of SEQ ID NO: 6. In certain embodiments, the antisense strand has complementarity to a segment of 15 contiguous nucleotides, 16 contiguous nucleotides, 17 contiguous nucleotides, 18 contiguous nucleotides, 19 contiguous nucleotides, 20 contiguous nucleotides, 21 contiguous nucleotides, 22 contiguous nucleotides, 23 contiguous nucleotides, 24 contiguous nucleotides, or 25 contiguous nucleotides of the nucleic acid sequence of SEQ ID NO: 7. In certain embodiments, the antisense strand has complementarity to a segment of 15 contiguous nucleotides, 16 contiguous nucleotides, 17 contiguous nucleotides, 18 contiguous nucleotides, 19 contiguous nucleotides, 20 contiguous nucleotides, 21 contiguous nucleotides, 22 contiguous nucleotides, 23 contiguous nucleotides, 24 contiguous nucleotides, or 25 contiguous nucleotides of the nucleic acid sequence of SEQ ID NO: 8.

In certain embodiments, the dsRNA comprises an antisense strand having no more than 3 mismatches with a SOD1 nucleic acid sequence of any one of SEQ ID NOs: 1-11. For example, the antisense strand may have from 0-3 mismatches (e.g., 0 mismatches, 1 mismatch, 2 mismatches, or 3 mismatches) relative to the nucleic acid sequence of SEQ ID NO: 1. In certain embodiments, the antisense strand has from 0-3 mismatches (e.g., 0 mismatches, 1 mismatch, 2 mismatches, or 3 mismatches) relative to the nucleic acid sequence of SEQ ID NO: 2. In certain embodiments, the antisense strand has from 0-3 mismatches (e.g., 0 mismatches, 1 mismatch, 2 mismatches, or 3 mismatches) relative to the nucleic acid sequence of SEQ ID NO: 3. In certain embodiments, the antisense strand has from 0-3 mismatches (e.g., 0 mismatches, 1 mismatch, 2 mismatches, or 3 mismatches) relative to the nucleic acid sequence of SEQ ID NO: 4. In certain embodiments, the antisense strand has from 0-3 mismatches (e.g., 0 mismatches, 1 mismatch, 2 mismatches, or 3 mismatches) relative to the nucleic acid sequence of SEQ ID NO: 5. In certain embodiments, the antisense strand has from 0-3 mismatches (e.g., 0 mismatches, 1 mismatch, 2 mismatches, or 3 mismatches) relative to the nucleic acid sequence of SEQ ID NO: 6. In certain embodiments, the antisense strand has from 0-3 mismatches (e.g., 0 mismatches, 1 mismatch, 2 mismatches, or 3 mismatches) relative to the nucleic acid sequence of SEQ ID NO: 7. In certain embodiments, the antisense strand has from 0-3 mismatches (e.g., 0 mismatches, 1 mismatch, 2 mismatches, or 3 mismatches) relative to the nucleic acid sequence of SEQ ID NO: 8.

In certain embodiments, the dsRNA comprises an antisense strand that is fully complementary to a SOD1 nucleic acid sequence of any one of SEQ ID NOs: 1-11.

In certain embodiments, the antisense strand of the dsRNA comprises a nucleic acid sequence that is substantially complementary to a SOD1 nucleic acid sequence of any one of SEQ ID NOs: 12-22. For example, in certain embodiments, the antisense sequence is substantially complementary to the nucleic acid sequence of SEQ ID NO: 9. In certain embodiments, the antisense sequence is substantially complementary to the nucleic acid sequence of SEQ ID NO: 10. In certain embodiments, the antisense sequence is substantially complementary to the nucleic acid sequence of SEQ ID NO: 11. In certain embodiments, the antisense sequence is substantially complementary to the nucleic acid sequence of SEQ ID NO: 12. In certain embodiments, the antisense sequence is substantially complementary to the nucleic acid sequence of SEQ ID NO: 13. In certain embodiments, the antisense sequence is substantially complementary to the nucleic acid sequence of SEQ ID NO: 14. In certain embodiments, the antisense sequence is substantially complementary to the nucleic acid sequence of SEQ ID NO: 15. In certain embodiments, the antisense sequence is substantially complementary to the nucleic acid sequence of SEQ ID NO: 16.

In certain embodiments, the dsRNA comprises an antisense strand having complementarity to at least 10, 11, 12 or 13 contiguous nucleotides of a SOD1 nucleic acid sequence of any one of SEQ ID NOs: 12-22. For example, in certain embodiments, the dsRNA comprises an antisense strand having complementarity to a segment of at least 10, at least 11, at least 12, or at least 13 contiguous nucleotides of the nucleic acid sequence of SEQ ID NO: 9. In certain embodiments, the dsRNA comprises an antisense strand having complementarity to a segment of at least 10, at least 11, at least 12, or at least 13 contiguous nucleotides of the nucleic acid sequence of SEQ ID NO: 10. In certain embodiments, the dsRNA comprises an antisense strand having complementarity to a segment of at least 10, at least 11, at least 12, or at least 13 contiguous nucleotides of the nucleic acid sequence of SEQ ID NO: 11. In certain embodiments, the dsRNA comprises an antisense strand having complementarity to a segment of at least 10, at least 11, at least 12, or at least 13 contiguous nucleotides of the nucleic acid sequence of SEQ ID NO: 12. In certain embodiments, the dsRNA comprises an antisense strand having complementarity to a segment of at least 10, at least 11, at least 12, or at least 13 contiguous nucleotides of the nucleic acid sequence of SEQ ID NO: 13. In certain embodiments, the dsRNA comprises an antisense strand having complementarity to a segment of at least 10, at least 11, at least 12, or at least 13 contiguous nucleotides of the nucleic acid sequence of SEQ ID NO: 14. In certain embodiments, the dsRNA comprises an antisense strand having complementarity to a segment of at least 10, at least 11, at least 12, or at least 13 contiguous nucleotides of the nucleic acid sequence of SEQ ID NO: 15. In certain embodiments, the dsRNA comprises an antisense strand having complementarity to a segment of at least 10, at least 11, at least 12, or at least 13 contiguous nucleotides of the nucleic acid sequence of SEQ ID NO: 16.

In certain embodiments, the dsRNA comprises an antisense strand having no more than 3 mismatches with a SOD1 nucleic acid sequence of any one of SEQ ID NOs: 12-22. For example, the antisense strand may have from 0-3 mismatches (e.g., 0 mismatches, 1 mismatch, 2 mismatches, or 3 mismatches) relative to the nucleic acid sequence of SEQ ID NO: 9. In certain embodiments, the antisense strand has from 0-3 mismatches (e.g., 0 mismatches, 1 mismatch, 2 mismatches, or 3 mismatches) relative to the nucleic acid sequence of SEQ ID NO: 10. In certain embodiments, the antisense strand has from 0-3 mismatches (e.g., 0 mismatches, 1 mismatch, 2 mismatches, or 3 mismatches) relative to the nucleic acid sequence of SEQ ID NO: 11. In certain embodiments, the antisense strand has from 0-3 mismatches (e.g., 0 mismatches, 1 mismatch, 2 mismatches, or 3 mismatches) relative to the nucleic acid sequence of SEQ ID NO: 16. In certain embodiments, the antisense strand has from 0-3 mismatches (e.g., 0 mismatches, 1 mismatch, 2 mismatches, or 3 mismatches) relative to the nucleic acid sequence of SEQ ID NO: 12. In certain embodiments, the antisense strand has from 0-3 mismatches (e.g., 0 mismatches, 1 mismatch, 2 mismatches, or 3 mismatches) relative to the nucleic acid sequence of SEQ ID NO: 13. In certain embodiments, the antisense strand has from 0-3 mismatches (e.g., 0 mismatches, 1 mismatch, 2 mismatches, or 3 mismatches) relative to the nucleic acid sequence of SEQ ID NO: 14. In certain embodiments, the antisense strand has from 0-3 mismatches (e.g., 0 mismatches, 1 mismatch, 2 mismatches, or 3 mismatches) relative to the nucleic acid sequence of SEQ ID NO: 15. In certain embodiments, the antisense strand has from 0-3 mismatches (e.g., 0 mismatches, 1 mismatch, 2 mismatches, or 3 mismatches) relative to the nucleic acid sequence of SEQ ID NO: 16.

In certain embodiments, the dsRNA comprises an antisense strand that is fully complementary to a SOD1 nucleic acid sequence of any one of SEQ ID NOs: 12-22.

In certain embodiments, the antisense strand and/or sense strand is from about 15 nucleotides to about 30 nucleotides in length (e.g., the antisense stand and/or sense strand may be 15, 16, 17, 18, 19, 20, 21, 22, 23, 24, 25, 26, 27, 28, 29, or 30 nucleotides in length). In certain embodiments, the antisense strand and/or sense strand comprises about 15 nucleotides to 25 nucleotides in length. For example, in certain embodiments, the antisense strand and/or sense strand is 15, 16, 17, 18, 19, 20, 21, 22, 23, 24, or 25 nucleotides in length.

In certain embodiments, the antisense strand is 20 nucleotides in length. In certain embodiments, the antisense strand is 21 nucleotides in length. In certain embodiments, the antisense strand is 22 nucleotides in length. In certain embodiments, the sense strand is 15 nucleotides in length. In certain embodiments, the sense strand is 16 nucleotides in length. In certain embodiments, the sense strand is 18 nucleotides in length. In certain embodiments, the sense strand is 20 nucleotides in length.

In certain embodiments, the antisense strand is 20 nucleotides in length and the sense strand is 15 nucleotides in length or 16 nucleotides in length.

In certain embodiments, the antisense strand is 21 nucleotides in length and the sense strand is 15 nucleotides in length or 16 nucleotides in length.

In certain embodiments, the antisense strand is 20 nucleotides in length or 21 nucleotides in length and the sense strand is 15 nucleotides in length.

In certain embodiments, the antisense strand is 20 nucleotides in length or 21 nucleotides in length and the sense strand is 16 nucleotides in length.

In certain embodiments, the antisense strand is 20 nucleotides in length and the sense strand is 15 nucleotides in length.

In certain embodiments, the antisense strand is 21 nucleotides in length and the sense strand is 16 nucleotides in length.

In certain embodiments, the dsRNA comprises a double-stranded region of 15 base pairs to 30 base pairs (e.g., 15 base pairs, 16 base pairs, 17 base pairs, 18 base pairs, 19 base pairs, 20 base pairs, 21 base pairs, 22 base pairs, 23 base pairs, 24 base pairs, 25 base pairs, 26 base pairs, 27 base pairs, 28 base pairs, 29 base pairs, or 30 base pairs). In certain embodiments, the dsRNA comprises a double-stranded region of 15 base pairs to 20 base pairs (e.g., 15 base pairs, 16 base pairs, 17 base pairs, 18 base pairs, 19 base pairs, or 20 base pairs). In certain embodiments, the dsRNA comprises a double-stranded region of 15 base pairs. In certain embodiments, the dsRNA comprises a double-stranded region of 16 base pairs. In certain embodiments, the dsRNA comprises a double-stranded region of 18 base pairs. In certain embodiments, the dsRNA comprises a double-stranded region of 20 base pairs.

In certain embodiments, the dsRNA comprises a blunt-end. In certain embodiments, the dsRNA comprises at least one single stranded nucleotide overhang. In certain embodiments, the dsRNA comprises about a 2-nucleotide to 5-nucleotide single stranded nucleotide overhang.

In certain embodiments, the dsRNA comprises naturally occurring nucleotides.

In certain embodiments, the dsRNA comprises at least one modified nucleotide.

In certain embodiments, the modified nucleotide comprises a 2'-O-methyl modified nucleotide, a 2'-deoxy-2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, a non-natural base comprising nucleotide, or a mixture thereof.

In certain embodiments, the dsRNA comprises at least one modified internucleotide linkage.

In certain embodiments, the modified internucleotide linkage comprises a phosphorothioate internucleotide linkage. In certain embodiments, the dsRNA comprises 4-16 phosphorothioate internucleotide linkages (e.g., 4, 5, 6, 7, 8, 9, 10, 11, 12, 13, 14, 15, or 16 phosphorothioate linkages). In certain embodiments, the dsRNA comprises 8-13 phosphorothioate internucleotide linkages (e.g., 9, 10, 11, 12, or 13 phosphorothioate linkages).

In certain embodiments, the dsRNA comprises at least one modified internucleotide linkage of Formula I:

(I)

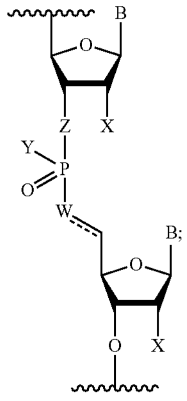

wherein:

B is a base pairing moiety;

W is selected from the group consisting of O, $OCH_2$, OCH, $CH_2$, and CH;

X is selected from the group consisting of halo, hydroxy, and $C_{1-6}$ alkoxy;

Y is selected from the group consisting of $O^-$, OH, OR, $NH^-$, $NH_2$, $S^-$, and SH;

Z is selected from the group consisting of O and $CH_2$;

R is a protecting group; and

⎓ is an optional double bond.

In certain embodiments, when W is CH, ⎓ is a double bond.

In certain embodiments, when W is selected from the group consisting of 0, $OCH_2$, OCH, $CH_2$, ⎓ is a single bond.

In certain embodiments, the dsRNA comprises at least 80% chemically modified nucleotides (e.g., 80%, 81%, 82%, 83%, 84%, 85%, 86%, 87%, 88%, 89%, 90%, 91%, 92%, 93%, 94%, 95%, 96%, 97%, 98%, 99%, or 100% chemically modified nucleotides). In certain embodiments, the dsRNA is fully chemically modified. In certain embodiments, the dsRNA comprises at least 70% 2'-O-methyl nucleotide modifications (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% 2'-O-methyl modifications).

In certain embodiments, the dsRNA comprises from about 80% to about 90% 2'-O-methyl nucleotide modifications (e.g., about 80%, 81%, 82%, 83%, 84%, 85%, 86%, 87%, 88%, 89%, or 90% 2'-O-methyl nucleotide modifications). In certain embodiments, the dsRNA comprises from about 83% to about 86% 2'-O-methyl modifications (e.g., about 83%, 84%, 85%, or 86% 2'-O-methyl modifications).

In certain embodiments, the dsRNA comprises from about 70% to about 80% 2'-O-methyl nucleotide modifications (e.g., about 70%, 71%, 72%, 73%, 74%, 75%, 76%, 77%, 78%, 79%, or 80% 2'-O-methyl nucleotide modifications). In certain embodiments, the dsRNA comprises from about 75% to about 78% 2'-O-methyl modifications (e.g., about 75%, 76%, 77%, or 78% 2'-O-methyl modifications).

In certain embodiments, the antisense strand comprises at least 80% chemically modified nucleotides (e.g., 80%, 81%, 82%, 83%, 84%, 85%, 86%, 87%, 88%, 89%, 90%, 91%, 92%, 93%, 94%, 95%, 96%, 97%, 98%, 99%, or 100% chemically modified nucleotides). In certain embodiments, the antisense strand is fully chemically modified. In certain embodiments, the antisense strand comprises at least 70% 2'-O-methyl nucleotide modifications (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% 2'-O-methyl modifications). In certain embodiments, the antisense strand is fully chemically modified. In certain embodiments, the antisense strand comprises at least 50% 2'-O-methyl nucleotide modifications (e.g., 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% 2'-O-methyl modifications). In certain embodiments, the antisense strand comprises about 70% to 90% 2'-O-methyl nucleotide modifications (e.g., about 70%, 71%, 72%, 73%, 74%, 75%, 76%, 77%, 78%, 79%, 80%, 81%, 82%, 83%, 84%, 85%, 86%, 87%, 88%, 89%, or 90% 2'-O-methyl modifications). In certain embodiments, the antisense strand comprises from about 85% to about 90% 2'-O-methyl modifications (e.g., about 85%, 86%, 87%, 88%, 89%, or 90% 2'-O-methyl modifications).

In certain embodiments, the antisense strand comprises about 75% to 85% 2'-O-methyl nucleotide modifications (e.g., about 75%, 76%, 77%, 78%, 79%, 80%, 81%, 82%, 83%, 84%, or 85% 2'-O-methyl modifications). In certain embodiments, the antisense strand comprises from about 76% to about 80% 2'-O-methyl modifications (e.g., about 76%, 77%, 78%, 79%, or 80% 2'-O-methyl modifications).

In certain embodiments, the sense strand comprises at least 80% chemically modified nucleotides (e.g., 80%, 81%, 82%, 83%, 84%, 85%, 86%, 87%, 88%, 89%, 90%, 91%, 92%, 93%, 94%, 95%, 96%, 97%, 98%, 99%, or 100% chemically modified nucleotides). In certain embodiments, the sense strand is fully chemically modified. In certain embodiments, the sense strand comprises at least 65% 2'-O-methyl nucleotide modifications (e.g., 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% 2'-O-methyl modifications). In certain embodiments, the sense strand comprises 100% 2'-O-methyl nucleotide modifications.

In certain embodiments, the sense strand comprises from about 70% to about 85% 2'-O-methyl nucleotide modifications (e.g., about 70%, 71%, 72%, 73%, 74%, 75%, 76%, 77%, 78%, 79%, 80%, 81%, 82%, 83%, 84%, or 85% 2'-O-methyl nucleotide modifications). In certain embodiments, the sense strand comprises from about 75% to about 80% 2'-O-methyl nucleotide modifications (e.g., about 75%, 76%, 77%, 78%, 79%, or 80% 2'-O-methyl nucleotide modifications).

In certain embodiments, the sense strand comprises from about 65% to about 75% 2'-O-methyl nucleotide modifications (e.g., about 65%, 66%, 67%, 68%, 69%, 70%, 71%, 72%, 73%, 74%, or 75% 2'-O-methyl nucleotide modifications). In certain embodiments, the sense strand comprises from about 67% to about 73% 2'-O-methyl nucleotide modifications (e.g., about 67%, 68%, 69%, 70%, 71%, 72%, or 73% 2'-O-methyl nucleotide modifications).

In certain embodiments, the sense strand comprises one or more nucleotide mismatches between the antisense strand and the sense strand. In certain embodiments, the one or more nucleotide mismatches are present at positions 2, 6, and 12 from the 5' end of sense strand. In certain embodiments, the nucleotide mismatches are present at positions 2, 6, and 12 from the 5' end of the sense strand.

In certain embodiments, the antisense strand comprises a 5' phosphate, a 5'-alkyl phosphonate, a 5' alkylene phosphonate, or a 5' alkenyl phosphonate.

In certain embodiments, the antisense strand comprises a 5' vinyl phosphonate.

In certain embodiments, the dsRNA comprises an antisense strand and a sense strand, each strand with a 5' end and a 3' end, wherein: (1) the antisense strand has a nucleic acid sequence that is substantially complementary to a SOD1 nucleic acid sequence of any one of SEQ ID NOs: 1-11; (2) the antisense strand comprises alternating 2'-methoxy-ribonucleotides and 2'-fluoro-ribonucleotides; (3) the nucleotides at positions 2 and 14 from the 5' end of the antisense strand are not 2'-methoxy-ribonucleotides; (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises alternating 2'-methoxy-ribonucleotides and 2'-fluoro-ribonucleotides; and (7) the nucleotides at positions 1-2 from the 5' end of the sense strand are connected to each other via phosphorothioate internucleotide linkages.

In certain embodiments, the dsRNA comprises an antisense strand and a sense strand, each strand with a 5' end and a 3' end, wherein: (1) the antisense strand has a nucleic acid sequence that is substantially complementary to a SOD1 nucleic acid sequence of any one of SEQ ID NOs: 1-11; (2) the antisense strand comprises at least 70% 2'-O-methyl modifications (e.g., from about 75% to about 80% or from about 85% to about 90% 2'-O-methyl modifications); (3) the nucleotide at position 14 from the 5' end of the antisense strand are not 2'-methoxy-ribonucleotides; (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises at least 65% 2'-O-methyl modifications (e.g., from about 65% to about 75% or from about 75% to about 80% 2'-O-methyl modifications); and (7) the nucleotides at positions 1-2 from the 5' end of the sense strand are connected to each other via phosphorothioate internucleotide linkages.

In certain embodiments, the dsRNA comprises an antisense strand and a sense strand, each strand with a 5' end and a 3' end, wherein: (1) the antisense strand has a nucleic acid sequence that is substantially complementary to a SOD1 nucleic acid sequence of any one of SEQ ID NOs: 1-11; (2) the antisense strand comprises at least 85% 2'-O-methyl modifications; (3) the nucleotides at positions 2 and 14 from the 5' end of the antisense strand are not 2'-methoxy-ribonucleotides; (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises 100% 2'-O-methyl modifications; and (7) the nucleotides at positions 1-2 from the 5' end of the sense strand are connected to each other via phosphorothioate internucleotide linkages.

In certain embodiments, the dsRNA comprises an antisense strand and a sense strand, each strand with a 5' end and a 3' end, wherein: (1) the antisense strand has a nucleic acid sequence that is substantially complementary to a SOD1 nucleic acid sequence of any one of SEQ ID NOs: 1-11; (2) the antisense strand comprises at least 75% 2'-O-methyl modifications; (3) the nucleotides at positions 4, 5, 6, and 14 from the 5' end of the antisense strand are not 2'-methoxy-ribonucleotides; (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises 100% 2'-O-methyl modifications; and (7) the nucleotides at positions 1-2 from the 5' end of the sense strand are connected to each other via phosphorothioate internucleotide linkages.

In certain embodiments, the dsRNA comprises an antisense strand and a sense strand, each strand with a 5' end and a 3' end, wherein: (1) the antisense strand has a nucleic acid sequence that is substantially complementary to a SOD1 nucleic acid sequence of any one of SEQ ID NOs: 1-11; (2) the antisense strand comprises at least 85% 2'-O-methyl modifications (e.g., from about 85% to about 90% 2'-O-methyl modifications); (3) the nucleotides at positions 2 and 14 from the 5' end of the antisense strand are not 2'-methoxy-ribonucleotides (e.g., the nucleotides at positions 2 and 14 from the 5' end of the antisense strand may be 2'-fluoro nucleotides); (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises at least 75% 2'-O-methyl modifications (e.g., from about 75% to about 80% 2'-O-methyl modifications); (7) the nucleotides at positions 7, 10, and 11 from the 3' end of the sense strand are not 2'-methoxy-ribonucleotides (e.g., the nucleotides at positions 7, 10, and 11 from the 3' end of the sense strand are 2'-fluoro nucleotides); and (8) the nucleotides at positions 1-2 from the 5' end of the sense strand are connected to each other via phosphorothioate internucleotide linkages.

In certain embodiments, the dsRNA comprises an antisense strand and a sense strand, each strand with a 5' end and a 3' end, wherein: (1) the antisense strand has a nucleic acid sequence that is substantially complementary to a SOD1 nucleic acid sequence of any one of SEQ ID NOs: 1-11; (2) the antisense strand comprises at least 75% 2'-O-methyl modifications (e.g., from about 75% to about 80% 2'-O-methyl modifications); (3) the nucleotides at positions 2, 4, 5, 6, and 14 from the 5' end of the antisense strand are not 2'-methoxy-ribonucleotides (e.g., the nucleotides at positions 2, 6, 14, and 16 from the 5' end of the antisense strand may be 2'-fluoro nucleotides); (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises 100% 2'-O-methyl modifications; and (7) the nucleotides at positions 1-2 from the 5' end of the sense strand are connected to each other via phosphorothioate internucleotide linkages.

In certain embodiments, the dsRNA comprises an antisense strand and a sense strand, each strand with a 5' end and a 3' end, wherein: (1) the antisense strand has a nucleic acid sequence that is substantially complementary to a SOD1 nucleic acid sequence of any one of SEQ ID NOs: 1-11; (2) the antisense strand comprises at least 75% 2'-O-methyl modifications (e.g., from about 75% to about 80% 2'-O-methyl modifications); (3) the nucleotides at positions 2, 6, 14, and 16 from the 5' end of the antisense strand are not 2'-methoxy-ribonucleotides (e.g., the nucleotides at positions 2, 6, 14, and 16 from the 5' end of the antisense strand may be 2'-fluoro nucleotides); (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises at least 65% 2'-O-methyl modifications (e.g., from about 65% to about 75% 2'-O-methyl modifications); (7) the nucleotides at positions 7, 9, 10, and 11 from the 3' end of the sense strand are not 2'-methoxy-ribonucleotides (e.g., the nucleotides at positions 7, 9, 10, and 11 from the 3' end of the sense strand are 2'-fluoro nucleotides); and (8) the nucleotides at positions 1-2 from the 5' end of the sense strand are connected to each other via phosphorothioate internucleotide linkages.

In certain embodiments, the dsRNA comprises an antisense strand and a sense strand, each strand with a 5' end and a 3' end, wherein: (1) the antisense strand comprises a sequence substantially complementary to a SOD1 nucleic acid sequence of SEQ ID NOs: 1-11; (2) the antisense strand comprises at least 75% 2'-O-methyl modifications; (3) the nucleotides at positions 2, 6, and 14 from the 5' end of the antisense strand are not 2'-methoxy-ribonucleotides; (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises at least 80% 2'-O-methyl modifications; (7) the nucleotides at positions 7, 10, and 11 from the 3' end of the sense strand are not 2'-methoxy-ribonucleotides; and (8) the nucleotides at positions 1-2 from the 5' end of the sense strand are connected to each other via phosphorothioate internucleotide linkages.

In certain embodiments, the dsRNA comprises an antisense strand and a sense strand, each strand with a 5' end and a 3' end, wherein: (1) the antisense strand comprises a sequence substantially complementary to a SOD1 nucleic acid sequence of any one of SEQ ID NOs: 1-11 (e.g., SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, or SEQ ID NO: 11); (2) the antisense strand comprises at least 50% 2'-O-methyl modifications; (3) the nucleotides at positions 2 and 14 from the 5' end of the antisense strand are not 2'-methoxy-ribonucleotides; (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises at least 65% 2'-O-methyl modifications; (7) the nucleotides at positions 3, 7, 9, 11, and 13 from the 3' end of the sense strand are not 2'-methoxy-ribonucleotides; and (8) the nucleotides at positions 1-2 from the 5' end of the sense strand are connected to each other via phosphorothioate internucleotide linkages.

In one aspect, the disclosure provides a dsRNA comprising an antisense strand and a sense strand, each strand with a 5' end and a 3' end, wherein: (1) the antisense strand comprises a sequence substantially complementary to a SOD1 nucleic acid sequence of any one of SEQ ID NOs: 1-11 (e.g., SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, or SEQ ID NO: 11); (2) the antisense strand comprises the chemical modification pattern of: (mX)#(fX)#(mX)(fX)(fX)(fX)(mX)(fX)(mX)(fX)(mX)(fX)(mX)(fX)#(mX)#(fX)#(mX)#(mX)#(mX)#(fX)#(mX); (3) a portion of the antisense strand is complementary to a portion of the sense strand; and (4) the sense strand comprises the chemical modification pattern of: (mX)#(mX)#(mX)(fX)(mX)(fX)(mX)(fX)(mX)(fX)(mX)(mX)(mX)(fX)#(mX)#(mX), wherein "m" corresponds to a 2'-O-methyl modification; "f" corresponds to a 2'-fluoro modification; "#" corresponds to a phosphorothioate internucleotide linkage; and "X" corresponds to any nucleotide of A, U, G, or C.

In one aspect, the disclosure provides a dsRNA comprising an antisense strand and a sense strand, each strand with a 5' end and a 3' end, wherein: (1) the antisense strand comprises a sequence substantially complementary to a SOD1 nucleic acid sequence of any one of SEQ ID NOs: 1-11; (2) the antisense strand comprises the chemical modification pattern of: (mX)#(fX)#(mX)(mX)(mX)(fX)(mX)(mX)(mX)(mX)(mX)(mX)(mX)(fX)#(mX)#(fX)#(mX)#(mX)#(mX)#(fX)#(mX); (3) a portion of the antisense strand is complementary to a portion of the sense strand; and (4) the sense strand comprises the chemical modification pattern of: (mX)#(mX)#(mX)(mX)(mX)(fX)(fX)(fX)(mX)(fX)(mX)(mX)(mX)(mX)#(mX)#(mX), wherein "m" corresponds to a 2'-O-methyl modification; "f" corresponds to a 2'-fluoro modification; "#" corresponds to a phosphorothioate internucleotide linkage; and "X" corresponds to any nucleotide of A, U, G, or C.

In certain embodiments, a functional moiety is linked to the 5' end and/or 3' end of the antisense strand. In certain embodiments, a functional moiety is linked to the 5' end and/or 3' end of the sense strand. In certain embodiments, a functional moiety is linked to the 3' end of the sense strand.

In certain embodiments, the functional moiety comprises a hydrophobic moiety.

In certain embodiments, the hydrophobic moiety is selected from the group consisting of fatty acids, steroids, secosteroids, lipids, gangliosides, nucleoside analogs, endocannabinoids, vitamins, and a mixture thereof.

In certain embodiments, the steroid selected from the group consisting of cholesterol and Lithocholic acid (LCA).

In certain embodiments, the fatty acid selected from the group consisting of Eicosapentaenoic acid (EPA), Docosahexaenoic acid (DHA) and Docosanoic acid (DCA).

In certain embodiments, the vitamin is selected from the group consisting of choline, vitamin A, vitamin E, and derivatives or metabolites thereof.

In certain embodiments, the vitamin is selected from the group consisting of retinoic acid and alpha-tocopheryl succinate.

In certain embodiments, the functional moiety is linked to the antisense strand and/or sense strand by a linker.

In certain embodiments, the linker comprises a divalent or trivalent linker.

In certain embodiments, the divalent or trivalent linker is selected from the group consisting of:

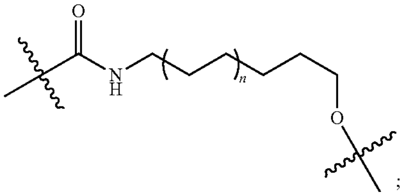
;
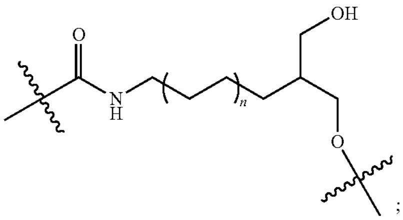
;
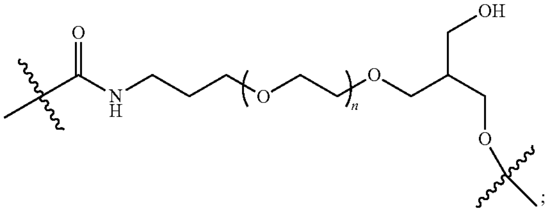
;
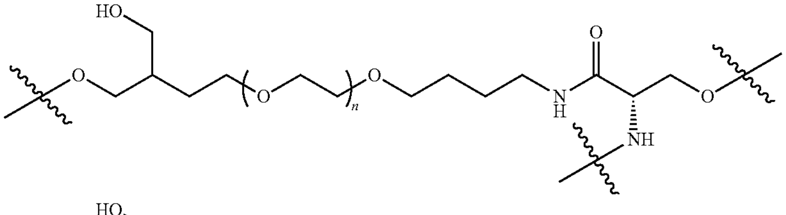
; and
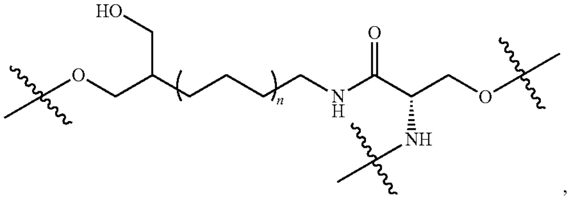
, wherein n is 1, 2, 3, 4, or 5.

In certain embodiments, the linker comprises an ethylene glycol chain, an alkyl chain, a peptide, an RNA, a DNA, a phosphodiester, a phosphorothioate, a phosphoramidate, an amide, a carbamate, or a combination thereof.

In certain embodiments, when the linker is a trivalent linker, the linker further links a phosphodiester or phosphodiester derivative.

In certain embodiments, the phosphodiester or phosphodiester derivative is selected from the group consisting of:

(Zc1)

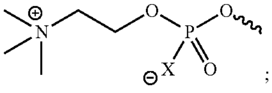
;

-continued (Zc2)

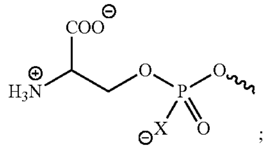

;

(Zc3)

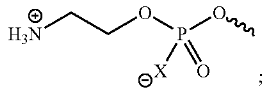

; and (Zc4)

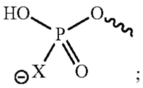

;

wherein X is O, S or $BH_3$.

In certain embodiments, the nucleotides at positions 1 and 2 from the 3' end of sense strand, and the nucleotides at positions 1 and 2 from the 5' end of antisense strand, are connected to adjacent ribonucleotides via phosphorothioate linkages.

In one aspect, the disclosure provides a pharmaceutical composition for inhibiting the expression of SOD1 gene in an organism, comprising the dsRNA recited above and a pharmaceutically acceptable carrier.

In certain embodiments, the dsRNA inhibits the expression of said SOD1 gene by at least 50%. In certain embodiments, the dsRNA inhibits the expression of said SOD1 gene by at least 80%.

In one aspect, the disclosure provides a method for inhibiting expression of SOD1 gene in a cell, the method comprising: (a) introducing into the cell a double-stranded ribonucleic acid (dsRNA) recited above; and (b) maintaining the cell produced in step (a) for a time sufficient to obtain degradation of the mRNA transcript of the SOD1 gene, thereby inhibiting expression of the SOD1 gene in the cell.

In one aspect, the disclosure provides a method of treating or managing a neurodegenerative disease comprising administering to a patient in need of such treatment or management a therapeutically effective amount of said dsRNA recited above.

In certain embodiments, the dsRNA is administered to the brain of the patient.

In certain embodiments, the dsRNA is administered by intracerebroventricular (ICV) injection, intrastriatal (IS) injection, intravenous (IV) injection, subcutaneous (SQ) injection or a combination thereof.

In certain embodiments, administering the dsRNA causes a decrease in SOD1 gene mRNA in one or more of the hippocampus, striatum, cortex, cerebellum, thalamus, hypothalamus, and spinal cord.

In certain embodiments, the dsRNA inhibits the expression of said SOD1 gene by at least 50%. In certain embodiments, the dsRNA inhibits the expression of said SOD1 gene by at least 80%.

In one aspect, the disclosure provides a vector comprising a regulatory sequence operably linked to a nucleotide sequence that encodes an RNA molecule substantially complementary to a SOD1 nucleic acid sequence of SEQ ID NOs: 1-11.

In certain embodiments, the RNA molecule inhibits the expression of said SOD1 gene by at least 50%. In certain embodiments, the RNA molecule inhibits the expression of said SOD1 gene by at least 80%. In certain embodiments, the RNA molecule inhibits the expression of said SOD1 gene by at least 90%.

In certain embodiments, the RNA molecule comprises ssRNA or dsRNA.

In certain embodiments, the dsRNA comprises a sense strand and an antisense strand, wherein the antisense strand comprises a sequence substantially complementary to a SOD1 nucleic acid sequence of SEQ ID NOs: 1-11.

In one aspect, the disclosure provides a cell comprising the vector recited above.

In one aspect, the disclosure provides a recombinant adeno-associated virus (rAAV) comprising the vector above and an AAV capsid.

In one aspect, the disclosure provides a branched RNA compound comprising two or more RNA molecules, such as two or more RNA molecules that each comprise from 15 to 40 nucleotides in length (e.g., 15, 16, 17, 18, 19, 20, 21, 22, 23, 24, 25, 26, 27, 28, 29, 30, 31, 32, 33, 34, 35, 36, 37, 38, 39, or 40 nucleotides in length), wherein each RNA molecule comprises a portion having a nucleic acid sequence that is substantially complementary to a segment of a SOD1 mRNA. The two RNA molecules may be connected to one another by one or more moieties independently selected from a linker, a spacer and a branching point.

In certain embodiments, the branched RNA molecule comprises one or both of ssRNA and dsRNA.

In certain embodiments, the branched RNA molecule comprises an antisense oligonucleotide.

In certain embodiments, each RNA molecule comprises a dsRNA comprising a sense strand and an antisense strand, wherein each antisense strand independently comprises a sequence that is substantially complementary to a SOD1 nucleic acid sequence of any one of SEQ ID NOs: 1-11.

In certain embodiments, the branched RNA compound comprises two or more copies of the RNA molecule of any of the above aspects or embodiments of the disclosure covalently bound to one another (e.g., by way of a linker, spacer, or branching point).

In certain embodiments, the branched RNA compound comprises a portion of a nucleic acid sequence that is substantially complementary to a SOD1 nucleic acid sequence of any one of SEQ ID NOs: 1-11. For example, the branched RNA compound may comprise two or more dsRNA molecules that are covalently bound to one another (e.g., by way of a linker, spacer, or branching point) and that each comprise an antisense strand having complementarity to at least 10, 11, 12 or 13 contiguous nucleotides of a SOD1 nucleic acid sequence of any one of SEQ ID NOs: 1-11. For example, in certain embodiments, the dsRNA comprises an antisense strand having complementarity to a segment of from 10 to 25 contiguous nucleotides of the nucleic acid sequence of any one of SEQ ID NOs: 1-11 (e.g., a segment of from 10 to 25 contiguous nucleotides of the nucleic acid sequence of SEQ ID NO: 1, a segment of from 10 to 25 contiguous nucleotides of the nucleic acid sequence of SEQ ID NO: 2, a segment of from 10 to 25 contiguous nucleotides of the nucleic acid sequence of SEQ ID NO: 3, a segment of from 10 to 25 contiguous nucleotides of the nucleic acid sequence of SEQ ID NO: 4, a segment of from 10 to 25 contiguous nucleotides of the nucleic acid sequence of SEQ ID NO: 5, a segment of from 10 to 25 contiguous nucleotides of the nucleic acid sequence of SEQ ID NO: 6, a segment of from 10 to 25 contiguous nucleotides of the nucleic acid sequence of SEQ ID NO: 7, or a segment of from 10 to 25 contiguous nucleotides of the nucleic acid sequence of SEQ ID NO: 8.

In certain embodiments, each dsRNA in the branched RNA compound comprises an antisense strand having complementarity to a segment of from 15 to 25 contiguous nucleotides of the nucleic acid sequence of any one of SEQ ID NOs: 1-11. For example, the antisense strand may have complementarity to a segment of 15 contiguous nucleotides, 16 contiguous nucleotides, 17 contiguous nucleotides, 18 contiguous nucleotides, 19 contiguous nucleotides, 20 contiguous nucleotides, 21 contiguous nucleotides, 22 contiguous nucleotides, 23 contiguous nucleotides, 24 contiguous nucleotides, or 25 contiguous nucleotides of the nucleic acid sequence of SEQ ID NO: 1. In certain embodiments, the antisense strand has complementarity to a segment of 15 contiguous nucleotides, 16 contiguous nucleotides, 17 contiguous nucleotides, 18 contiguous nucleotides, 19 contiguous nucleotides, 20 contiguous nucleotides, 21 contiguous nucleotides, 22 contiguous nucleotides, 23 contiguous nucleotides, 24 contiguous nucleotides, or 25 contiguous nucleotides of the nucleic acid sequence of SEQ ID NO: 2. In certain embodiments, the antisense strand has complementarity to a segment of 15 contiguous nucleotides, 16 contiguous nucleotides, 17 contiguous nucleotides, 18 contiguous nucleotides, 19 contiguous nucleotides, 20 contiguous nucleotides, 21 contiguous nucleotides, 22 contiguous nucleotides, 23 contiguous nucleotides, 24 contiguous nucleotides, or 25 contiguous nucleotides of the nucleic acid sequence of SEQ ID NO: 3. In certain embodiments, the antisense strand has complementarity to a segment of 15 contiguous nucleotides, 16 contiguous nucleotides, 17 contiguous nucleotides, 18 contiguous nucleotides, 19 contiguous nucleotides, 20 contiguous nucleotides, 21 contiguous nucleotides, 22 contiguous nucleotides, 23 contiguous nucleotides, 24 contiguous nucleotides, or 25 contiguous nucleotides of the nucleic acid sequence of SEQ ID NO: 4. In certain embodiments, the antisense strand has complementarity to a segment of 15 contiguous nucleotides, 16 contiguous nucleotides, 17 contiguous nucleotides, 18 contiguous nucleotides, 19 contiguous nucleotides, 20 contiguous nucleotides, 21 contiguous nucleotides, 22 contiguous nucleotides, 23 contiguous nucleotides, 24 contiguous nucleotides, or 25 contiguous nucleotides of the nucleic acid sequence of SEQ ID NO: 5. In certain embodiments, the antisense strand has complementarity to a segment of 15 contiguous nucleotides, 16 contiguous nucleotides, 17 contiguous nucleotides, 18 contiguous nucleotides, 19 contiguous nucleotides, 20 contiguous nucleotides, 21 contiguous nucleotides, 22 contiguous nucleotides, 23 contiguous nucleotides, 24 contiguous nucleotides, or 25 contiguous nucleotides of the nucleic acid sequence of SEQ ID NO: 6. In certain embodiments, the antisense strand has complementarity to a segment of 15 contiguous nucleotides, 16 contiguous nucleotides, 17 contiguous nucleotides, 18 contiguous nucleotides, 19 contiguous nucleotides, 20 contiguous nucleotides, 21 contiguous nucleotides, 22 contiguous nucleotides, 23 contiguous nucleotides, 24 contiguous nucleotides, or 25 contiguous nucleotides of the nucleic acid sequence of SEQ ID NO: 7. In certain embodiments, the antisense strand has complementarity to a segment of 15 contiguous nucleotides, 16 contiguous nucleotides, 17 contiguous nucleotides, 18 contiguous nucleotides, 19 contiguous nucleotides, 20 contiguous nucleotides, 21 contiguous nucleotides, 22 contiguous nucleotides, 23 contiguous nucleotides, 24 contiguous nucleotides, or 25 contiguous nucleotides of the nucleic acid sequence of SEQ ID NO: 8.

In certain embodiments, each dsRNA in the branched RNA compound comprises an antisense strand having no more than 3 mismatches with a SOD1 nucleic acid sequence of any one of SEQ ID NOs: 1-11. For example, the antisense strand may have from 0-3 mismatches (e.g., 0 mismatches, 1 mismatch, 2 mismatches, or 3 mismatches) relative to the nucleic acid sequence of SEQ ID NO: 1. In certain embodiments, the antisense strand has from 0-3 mismatches (e.g., 0 mismatches, 1 mismatch, 2 mismatches, or 3 mismatches) relative to the nucleic acid sequence of SEQ ID NO: 2. In certain embodiments, the antisense strand has from 0-3 mismatches (e.g., 0 mismatches, 1 mismatch, 2 mismatches, or 3 mismatches) relative to the nucleic acid sequence of SEQ ID NO: 3. In certain embodiments, the antisense strand has from 0-3 mismatches (e.g., 0 mismatches, 1 mismatch, 2 mismatches, or 3 mismatches) relative to the nucleic acid sequence of SEQ ID NO: 4. In certain embodiments, the antisense strand has from 0-3 mismatches (e.g., 0 mismatches, 1 mismatch, 2 mismatches, or 3 mismatches) relative to the nucleic acid sequence of SEQ ID NO: 5. In certain embodiments, the antisense strand has from 0-3 mismatches (e.g., 0 mismatches, 1 mismatch, 2 mismatches, or 3 mismatches) relative to the nucleic acid sequence of SEQ ID NO: 6. In certain embodiments, the antisense strand has from 0-3 mismatches (e.g., 0 mismatches, 1 mismatch, 2 mismatches, or 3 mismatches) relative to the nucleic acid sequence of SEQ ID NO: 7. In certain embodiments, the antisense strand has from 0-3 mismatches (e.g., 0 mismatches, 1 mismatch, 2 mismatches, or 3 mismatches) relative to the nucleic acid sequence of SEQ ID NO: 8.

In certain embodiments, each dsRNA in the branched RNA compound comprises an antisense strand that is fully complementary to a SOD1 nucleic acid sequence of any one of SEQ ID NOs: 1-11.

In certain embodiments, the branched RNA compound comprises a portion having a nucleic acid sequence that is substantially complementary to one or more of a SOD1 nucleic acid sequence of any one of SEQ ID NOs: 12-22.

In certain embodiments, the RNA molecule comprises an antisense oligonucleotide.

In certain embodiments, each RNA molecule comprises 15 to 25 nucleotides in length.

In certain embodiments, the antisense strand and/or sense strand comprises about 15 nucleotides to 25 nucleotides in length. For example, in certain embodiments, the antisense strand and/or sense strand is 15, 16, 17, 18, 19, 20, 21, 22, 23, 24, or 25 nucleotides in length. In certain embodiments, the antisense strand is 20 nucleotides in length. In certain embodiments, the antisense strand is 21 nucleotides in length. In certain embodiments, the antisense strand is 22 nucleotides in length. In certain embodiments, the sense strand is 15 nucleotides in length. In certain embodiments, the sense strand is 16 nucleotides in length. In certain embodiments, the sense strand is 18 nucleotides in length. In certain embodiments, the sense strand is 20 nucleotides in length.

In certain embodiments, the antisense strand is 20 nucleotides in length and the sense strand is 15 nucleotides in length or 16 nucleotides in length.

In certain embodiments, the antisense strand is 21 nucleotides in length and the sense strand is 15 nucleotides in length or 16 nucleotides in length.

In certain embodiments, the antisense strand is 20 nucleotides in length or 21 nucleotides in length and the sense strand is 15 nucleotides in length.

In certain embodiments, the antisense strand is 20 nucleotides in length or 21 nucleotides in length and the sense strand is 16 nucleotides in length.

In certain embodiments, the antisense strand is 20 nucleotides in length and the sense strand is 15 nucleotides in length.

In certain embodiments, the antisense strand is 21 nucleotides in length and the sense strand is 16 nucleotides in length.

In certain embodiments, the dsRNA comprises a double-stranded region of 15 base pairs to 20 base pairs. In certain embodiments, the dsRNA comprises a double-stranded region of 15 base pairs. In certain embodiments, the dsRNA comprises a double-stranded region of 16 base pairs. In certain embodiments, the dsRNA comprises a double-stranded region of 18 base pairs. In certain embodiments, the dsRNA comprises a double-stranded region of 20 base pairs.

In certain embodiments, the dsRNA comprises a blunt-end.

In certain embodiments, the dsRNA comprises at least one single stranded nucleotide overhang. In certain embodiments, the dsRNA comprises between a 2-nucleotide to 5-nucleotide single stranded nucleotide overhang.

In certain embodiments, the dsRNA comprises naturally occurring nucleotides.

In certain embodiments, the dsRNA comprises at least one modified nucleotide.

In certain embodiments, the modified nucleotide comprises a 2'-O-methyl modified nucleotide, a 2'-deoxy-2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, or a non-natural base comprising nucleotide.

In certain embodiments, the dsRNA comprises at least one modified internucleotide linkage.

In certain embodiments, the modified internucleotide linkage comprises a phosphorothioate internucleotide linkage. In certain embodiments, the branched RNA compound comprises 4-16 phosphorothioate internucleotide linkages. In certain embodiments, the branched RNA compound comprises 8-13 phosphorothioate internucleotide linkages.

In certain embodiments, the dsRNA comprises at least one modified internucleotide linkage of Formula I:

(I)

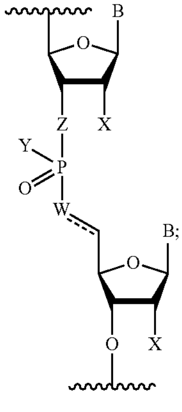

wherein:

B is a base pairing moiety;

W is selected from the group consisting of O, $OCH_2$, OCH, $CH_2$, and CH;

X is selected from the group consisting of halo, hydroxy, and $C_{1-6}$ alkoxy;

Y is selected from the group consisting of $O^-$, OH, OR, $NH^-$, $NH_2$, $S^-$, and SH;

Z is selected from the group consisting of O and $CH_2$;

R is a protecting group; and $\overline{---}$ is an optional double bond.

In certain embodiments, when W is CH, $\overline{---}$ is a double bond.

In certain embodiments, when W is selected from the group consisting of O, $OCH_2$, OCH, $CH_2$, $\overline{---}$ is a single bond.

In certain embodiments, the dsRNA comprises at least 80% chemically modified nucleotides (e.g., 80%, 81%, 82%, 83%, 84%, 85%, 86%, 87%, 88%, 89%, 90%, 91%, 92%, 93%, 94%, 95%, 96%, 97%, 98%, 99%, or 100% chemically modified nucleotides). In certain embodiments, the dsRNA is fully chemically modified. In certain embodiments, the dsRNA comprises at least 70% 2'-O-methyl nucleotide modifications (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% 2'-O-methyl modifications).

In certain embodiments, the antisense strand comprises at least 80% chemically modified nucleotides.

In certain embodiments, the antisense strand is fully chemically modified.

In certain embodiments, the antisense strand comprises at least 70% 2'-O-methyl nucleotide modifications. In certain embodiments, the antisense strand comprises about 70% to 90% 2'-O-methyl nucleotide modifications. In certain embodiments, the antisense strand comprises from about 85% to about 90% 2'-O-methyl modifications (e.g., about 85%, 86%, 87%, 88%, 89%, or 90% 2'-O-methyl modifications).

In certain embodiments, the antisense strand comprises about 75% to 85% 2'-O-methyl nucleotide modifications (e.g., about 75%, 76%, 77%, 78%, 79%, 80%, 81%, 82%, 83%, 84%, or 85% 2'-O-methyl modifications). In certain embodiments, the antisense strand comprises from about 76% to about 80% 2'-O-methyl modifications (e.g., about 76%, 77%, 78%, 79%, or 80% 2'-O-methyl modifications).

In certain embodiments, the sense strand comprises at least 80% chemically modified nucleotides. In certain embodiments, the sense strand is fully chemically modified. In certain embodiments, the sense strand comprises at least 65% 2'-O-methyl nucleotide modifications. In certain embodiments, the sense strand comprises 100% 2'-O-methyl nucleotide modifications.

In certain embodiments, the sense strand comprises one or more nucleotide mismatches between the antisense strand and the sense strand. In certain embodiments, the one or more nucleotide mismatches are present at positions 2, 6, and 12 from the 5' end of sense strand. In certain embodiments, the nucleotide mismatches are present at positions 2, 6, and 12 from the 5' end of the sense strand.

In certain embodiments, the dsRNA comprises an antisense strand and a sense strand, each strand with a 5' end and a 3' end, wherein: (1) the antisense strand has a nucleic acid sequence that is substantially complementary to a SOD1 nucleic acid sequence of any one of SEQ ID NOs: 1-11; (2) the antisense strand comprises alternating 2'-methoxy-ribonucleotides and 2'-fluoro-ribonucleotides; (3) the nucleotides at positions 2 and 14 from the 5' end of the antisense strand are not 2'-methoxy-ribonucleotides; (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises alternating 2'-methoxy-ribonucleotides and 2'-fluoro-ribonucleotides; and (7) the nucleotides at positions 1-2 from the 5' end of the sense strand are connected to each other via phosphorothioate internucleotide linkages.

In certain embodiments, the dsRNA comprises an antisense strand and a sense strand, each strand with a 5' end and a 3' end, wherein: (1) the antisense strand has a nucleic acid sequence that is substantially complementary to a SOD1 nucleic acid sequence of any one of SEQ ID NOs: 1-11; (2) the antisense strand comprises at least 70% 2'-O-methyl modifications (e.g., from about 75% to about 80% or from about 85% to about 90% 2'-O-methyl modifications); (3) the nucleotide at position 14 from the 5' end of the antisense strand are not 2'-methoxy-ribonucleotides; (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises at least 65% 2'-O-methyl modifications (e.g., from about 65% to about 75% or from about 75% to about 80% 2'-O-methyl modifications); and (7) the nucleotides at positions 1-2 from the 5' end of the sense strand are connected to each other via phosphorothioate internucleotide linkages.

In certain embodiments, the dsRNA comprises an antisense strand and a sense strand, each strand with a 5' end and a 3' end, wherein: (1) the antisense strand has a nucleic acid sequence that is substantially complementary to a SOD1 nucleic acid sequence of any one of SEQ ID NOs: 1-11; (2) the antisense strand comprises at least 85% 2'-O-methyl modifications; (3) the nucleotides at positions 2 and 14 from the 5' end of the antisense strand are not 2'-methoxy-ribonucleotides; (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises 100% 2'-O-methyl modifications; and (7) the nucleotides at positions 1-2 from the 5' end of the sense strand are connected to each other via phosphorothioate internucleotide linkages.

In certain embodiments, the dsRNA comprises an antisense strand and a sense strand, each strand with a 5' end and a 3' end, wherein: (1) the antisense strand has a nucleic acid sequence that is substantially complementary to a SOD1 nucleic acid sequence of any one of SEQ ID NOs: 1-11; (2) the antisense strand comprises at least 75% 2'-O-methyl modifications; (3) the nucleotides at positions 4, 5, 6, and 14 from the 5' end of the antisense strand are not 2'-methoxy-ribonucleotides; (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises 100% 2'-O-methyl modifications; and (7) the nucleotides at positions 1-2 from the 5' end of the sense strand are connected to each other via phosphorothioate internucleotide linkages.

In certain embodiments, the dsRNA comprises an antisense strand and a sense strand, each strand with a 5' end and a 3' end, wherein: (1) the antisense strand has a nucleic acid sequence that is substantially complementary to a SOD1 nucleic acid sequence of any one of SEQ ID NOs: 1-11; (2) the antisense strand comprises at least 85% 2'-O-methyl modifications (e.g., from about 85% to about 90% 2'-O-methyl modifications); (3) the nucleotides at positions 2 and 14 from the 5' end of the antisense strand are not 2'-methoxy-ribonucleotides (e.g., the nucleotides at positions 2 and 14 from the 5' end of the antisense strand may be 2'-fluoro nucleotides); (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises at least 75% 2'-O-methyl modifications (e.g., from about 75% to about 80% 2'-O-methyl modifications); (7) the nucleotides at positions 7, 10, and 11 from the 3' end of the sense strand are not 2'-methoxy-ribonucleotides (e.g., the nucleotides at positions 7, 10, and 11 from the 3' end of the sense strand are 2'-fluoro nucleotides); and (8) the nucleotides at positions 1-2 from the 5' end of the sense strand are connected to each other via phosphorothioate internucleotide linkages.

In certain embodiments, the dsRNA comprises an antisense strand and a sense strand, each strand with a 5' end and a 3' end, wherein: (1) the antisense strand has a nucleic acid sequence that is substantially complementary to a SOD1 nucleic acid sequence of any one of SEQ ID NOs: 1-11; (2) the antisense strand comprises at least 75% 2'-O-methyl modifications (e.g., from about 75% to about 80% 2'-O-methyl modifications); (3) the nucleotides at positions 2, 4, 5, 6, and 14 from the 5' end of the antisense strand are not 2'-methoxy-ribonucleotides (e.g., the nucleotides at positions 2, 4, 5, 6, 14, and 16 from the 5' end of the antisense strand may be 2'-fluoro nucleotides); (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises 100% 2'-O-methyl modifications; and (7) the nucleotides at positions 1-2 from the 5' end of the sense strand are connected to each other via phosphorothioate internucleotide linkages.

In certain embodiments, the dsRNA comprises an antisense strand and a sense strand, each strand with a 5' end and a 3' end, wherein: (1) the antisense strand has a nucleic acid sequence that is substantially complementary to a SOD1 nucleic acid sequence of any one of SEQ ID NOs: 1-11; (2) the antisense strand comprises at least 75% 2'-O-methyl modifications (e.g., from about 75% to about 80% 2'-O-methyl modifications); (3) the nucleotides at positions 2, 6, 14, and 16 from the 5' end of the antisense strand are not 2'-methoxy-ribonucleotides (e.g., the nucleotides at positions 2, 6, 14, and 16 from the 5' end of the antisense strand may be 2'-fluoro nucleotides); (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises at least 65% 2'-O-methyl modifications (e.g., from about 65% to about 75% 2'-O-methyl modifications); (7) the nucleotides at positions 7, 9, 10, and 11 from the 3' end of the sense strand are not 2'-methoxy-ribonucleotides; and (8) the nucleotides at positions 1-2 from the 5' end of the sense strand are connected to each other via phosphorothioate internucleotide linkages.

In certain embodiments, the dsRNA comprises an antisense strand and a sense strand, each strand with a 5' end and a 3' end, wherein: (1) the antisense strand has a nucleic acid sequence that is substantially complementary to a SOD1 nucleic acid sequence of any one of SEQ ID NOs: 1-11; (2) the antisense strand comprises at least 75% 2'-O-methyl modifications; (3) the nucleotides at positions 2, 6, and 14 from the 5' end of the antisense strand are not 2'-methoxy-ribonucleotides; (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises at least 80% 2'-O-methyl modifications; (7) the nucleotides at positions 7, 10, and 11 from the 3' end of the sense strand are not 2'-methoxy-ribonucleotides; and (8) the nucleotides at positions 1-2 from the 5' end of the sense strand are connected to each other via phosphorothioate internucleotide linkages.

In certain embodiments of the branched RNA compound, the dsRNA comprises an antisense strand and a sense strand, each strand with a 5' end and a 3' end, wherein: (1) the antisense strand comprises a sequence substantially complementary to a SOD1 nucleic acid sequence of any one of SEQ ID NOs: 1-11 (e.g., SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, or SEQ ID NO: 11); (2) the antisense strand comprises at least 50% 2'-O-methyl modifications; (3) the nucleotides at positions 2 and 14 from the 5' end of the antisense strand are not 2'-methoxy-ribonucleotides; (4) the nucleotides at positions 1-2 to 1-7 from the 3' end of the antisense strand are connected to each other via phosphorothioate internucleotide linkages; (5) a portion of the antisense strand is complementary to a portion of the sense strand; (6) the sense strand comprises at least 65% 2'-O-methyl modifications; (7) the nucleotides at positions 3, 7, 9, 11, and 13 from the 3' end of the sense strand are not 2'-methoxy-ribonucleotides; and (8) the nucleotides at positions 1-2 from the 5' end of the sense strand are connected to each other via phosphorothioate internucleotide linkages.

In one aspect, the disclosure provides a branched RNA compound comprising two or more dsRNA, said dsRNA comprising an antisense strand and a sense strand, each strand with a 5' end and a 3' end, wherein: (1) the antisense strand comprises a sequence substantially complementary to a SOD1 nucleic acid sequence of any one of SEQ ID NOs: 1-11 (e.g., SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, or SEQ ID NO: 11); (2) the antisense strand comprises the chemical modification pattern of: (mX)#(fX)#(mX)(fX)(fX)(fX)(mX)(fX)(mX)(fX)(mX)(fX)(mX)(fX)#(mX)#(a)#(mX)#(m X)#(mX)#(fX)#(mX); (3) a portion of the antisense strand is complementary to a portion of the sense strand; and (4) the sense strand comprises the chemical modification pattern of: (mX)#(mX)#(mX)(fX)(mX)(fX)(mX)(fX)(mX)(fX)(mX)(mX)(mX)(fX)#(mX)#(mX), wherein "m" corresponds to a 2'-O-methyl modification; "f" corresponds to a 2'-fluoro modification; "#" corresponds to a phosphorothioate internucleotide linkage; and "X" corresponds to any nucleotide of A, U, G, or C, wherein the two or more dsRNA are connected to one another by one or more moieties independently selected from a linker, a spacer and a branching point.

In one aspect, the disclosure provides a branched RNA compound comprising two or more dsRNA, said dsRNA comprising an antisense strand and a sense strand, each strand with a 5' end and a 3' end, wherein: (1) the antisense strand comprises a sequence substantially complementary to a SOD1 nucleic acid sequence of any one of SEQ ID NOs: 1-11 (e.g., SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, or SEQ ID NO: 11); (2) the antisense strand comprises the chemical modification pattern of: (mX)#(fX)#(mX)(mX)(mX)(fX)(mX)(mX)(mX)(mX)(mX)(mX)(mX)(fX)#(mX)#(fX)#(mX) #(mX)#(mX)#(fX)#(mX); (3) a portion of the antisense strand is complementary to a portion of the sense strand; and (4) the sense strand comprises the chemical modification pattern of: (mX)#(mX)#(mX)(mX)(mX)(fX)(fX)(fX)(mX)(fX)(mX)(mX)(mX)(mX)#(mX)#(mX), wherein "m" corresponds to a 2'-O-methyl modification; "f" corresponds to a 2'-fluoro modification; "#" corresponds to a phosphorothioate internucleotide linkage; and "X" corresponds to any nucleotide of A, U, G, or C, wherein the two or more dsRNA are connected to one another by one or more moieties independently selected from a linker, a spacer and a branching point.

In certain embodiments of the branched RNA compound, the antisense strand comprises a 5' phosphate, a 5'-alkyl phosphonate, a 5' alkylene phosphonate, a 5' alkenyl phosphonate, or a mixture thereof.

In certain embodiments of the branched RNA compound, the antisense strand comprises a 5' vinyl phosphonate.

In certain embodiments of the branched RNA compound, the linker comprises an ethylene glycol chain, an alkyl chain, a peptide, an RNA, a DNA, a phosphate, a phosphonate, a phosphoramidate, an ester, an amide, a triazole, or combinations thereof.

In certain embodiments of the branched RNA compound, the linker is structure L1:

(L1)

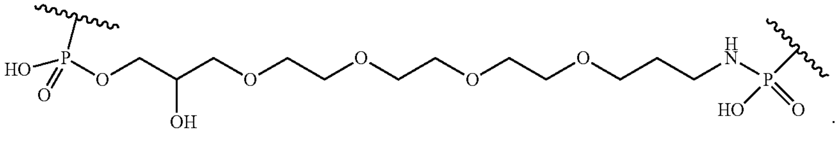

.

In certain embodiments of the branched RNA compound, the linker is structure L2:

(L2)

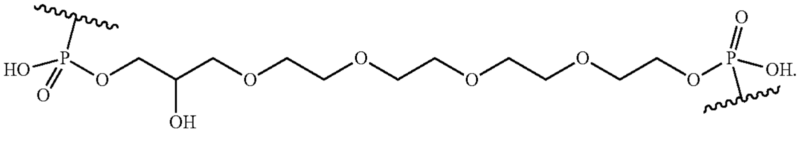

.

In certain embodiments, a functional moiety is linked to the 5' end and/or 3' end of the antisense strand. In certain embodiments, a functional moiety is linked to the 5' end and/or 3' end of the sense strand. In certain embodiments, a functional moiety is linked to the 3' end of the sense strand.

In certain embodiments, the functional moiety comprises a hydrophobic moiety.

In certain embodiments, the hydrophobic moiety is selected from the group consisting of fatty acids, steroids, secosteroids, lipids, gangliosides, nucleoside analogs, endocannabinoids, vitamins, and a mixture thereof.

In certain embodiments, the steroid is selected from the group consisting of cholesterol and Lithocholic acid (LCA).

In certain embodiments, the fatty acid is selected from the group consisting of Eicosapentaenoic acid (EPA), Docosahexaenoic acid (DHA) and Docosanoic acid (DCA).

In certain embodiments, the vitamin is selected from the group consisting of choline, vitamin A, vitamin E, derivatives thereof, and metabolites thereof.

In certain embodiments, the vitamin is selected from the group consisting of retinoic acid and alpha-tocopheryl succinate.

In certain embodiments, the functional moiety is linked to the antisense strand and/or sense strand by a linker.

In certain embodiments, the linker comprises a divalent or trivalent linker.

In certain embodiments, the divalent or trivalent linker is selected from the group consisting of:

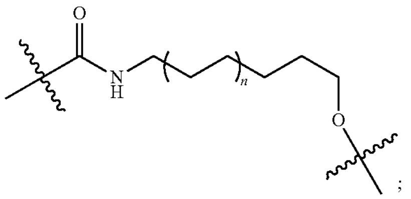
;
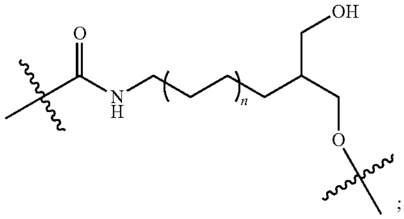
;
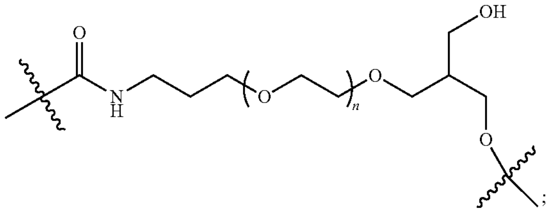
;
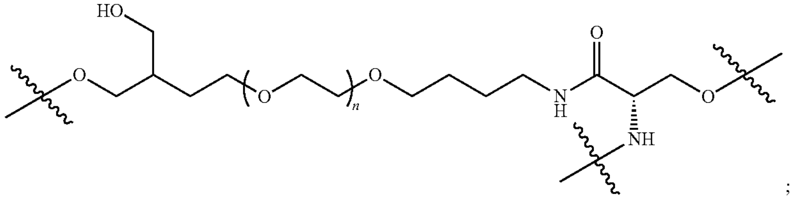
; and
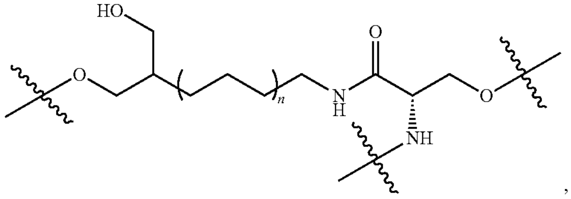
, wherein n is 1, 2, 3, 4, or 5.

In certain embodiments, the linker comprises an ethylene glycol chain, an alkyl chain, a peptide, an RNA, a DNA, a phosphodiester, a phosphorothioate, a phosphoramidate, an amide, a carbamate, or a combination thereof.

In certain embodiments, when the linker is a trivalent linker, the linker further links a phosphodiester or phosphodiester derivative.

In certain embodiments, the phosphodiester or phosphodiester derivative is selected from the group consisting of:

(Zc1)

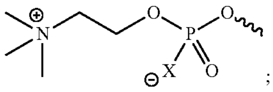

;

(Zc2)

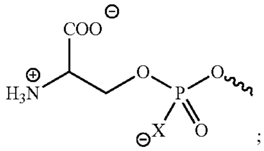

;

(Zc3)

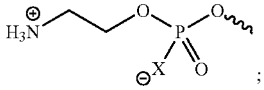

; and (Zc4)

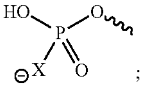

;

wherein X is O, S or $BH_3$.

In certain embodiments, the nucleotides at positions 1 and 2 from the 3' end of sense strand, and the nucleotides at positions 1 and 2 from the 5' end of antisense strand, are connected to adjacent ribonucleotides via phosphorothioate linkages.

In one aspect, the disclosure provides a compound of formula (I):

$$L\text{-}(N)_n \qquad (I)$$

wherein:

L comprises an ethylene glycol chain, an alkyl chain, a peptide, an RNA, a DNA, a phosphate, a phosphonate, a phosphoramidate, an ester, an amide, a triazole, or combinations thereof, wherein formula (I) optionally further comprises one or more branch point B, and one or more spacer S, wherein B is independently for each occurrence a polyvalent organic species or derivative thereof;

S comprises independently for each occurrence an ethylene glycol chain, an alkyl chain, a peptide, an RNA, a DNA, a phosphate, a phosphonate, a phosphoramidate, an ester, an amide, a triazole, or a combination thereof;

n is 2, 3, 4, 5, 6, 7 or 8; and

N is a double stranded nucleic acid, such as a dsRNA molecule of any of the above aspects or embodiments of the disclosure. In certain embodiments, each N is from 15 to 40 bases in length.

In certain embodiments, each N comprises a sense strand and an antisense strand; wherein the antisense strand comprises a sequence substantially complementary to a SOD1 nucleic acid sequence of any one of SEQ ID NOs: 1-11; and wherein the sense strand and antisense strand each independently comprise one or more chemical modifications.

In certain embodiments, the compound comprises a structure selected from formulas (I-1)-(I-9):

N—L—N (I-1)

N—S—L—S—N (I-2)

-continued (I-3)

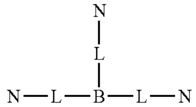

(I-4)

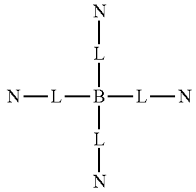

(I-5)

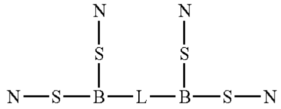

(I-6)

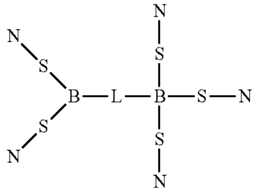

(I-7)

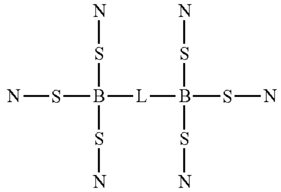

(I-8)

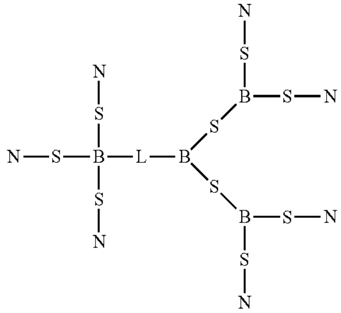

(I-9)

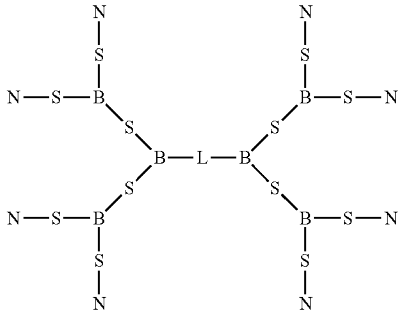

In certain embodiments, the antisense strand comprises a 5' terminal group R selected from the group consisting of:
R[1]
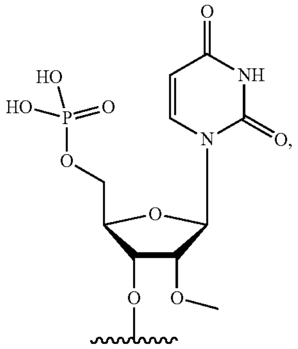
R[2]
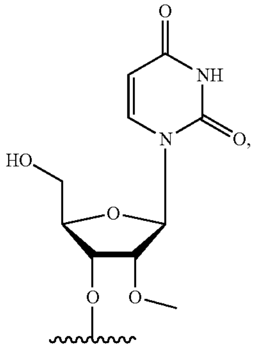
R[3]
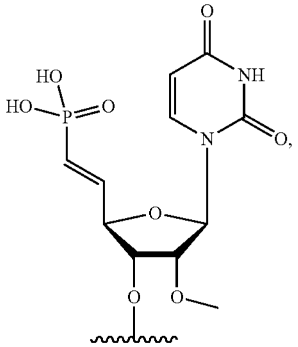
R[4]
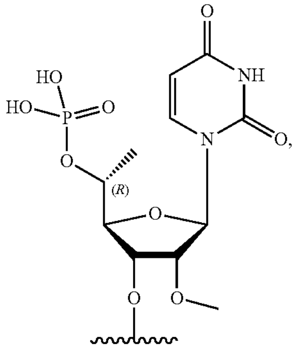
-continued
R[5]
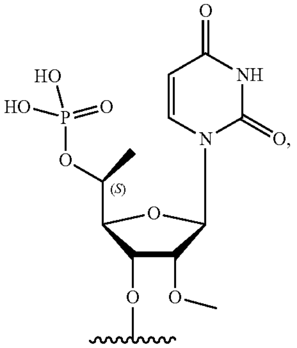
R[6]
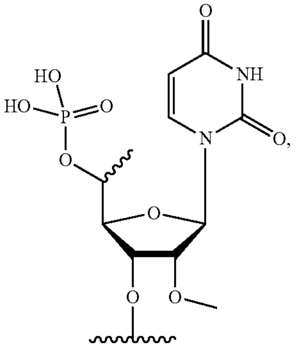
R[7]
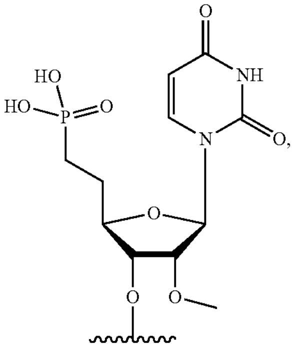
and
R[8]
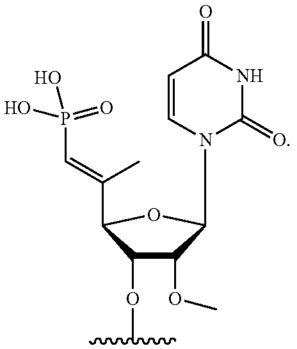

In certain embodiments, the compound comprises the structure of formula (II):

(II)

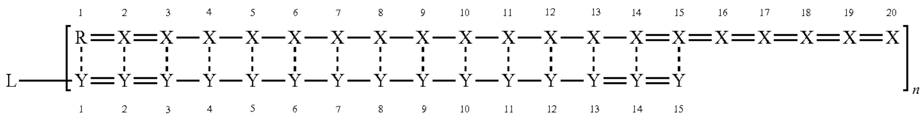

wherein

X, for each occurrence, independently, is selected from adenosine, guanosine, uridine, cytidine, and chemically-modified derivatives thereof;

Y, for each occurrence, independently, is selected from adenosine, guanosine, uridine, cytidine, and chemically-modified derivatives thereof;

- represents a phosphodiester intemucleoside linkage;

=represents a phosphorothioate intemucleoside linkage; and

--- represents, individually for each occurrence, a base-pairing interaction or a mismatch.

In certain embodiments, the compound comprises the structure of formula (IV):

(IV)

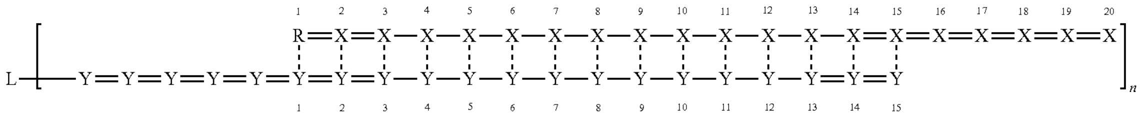

wherein

X, for each occurrence, independently, is selected from adenosine, guanosine, uridine, cytidine, and chemically-modified derivatives thereof;

Y, for each occurrence, independently, is selected from adenosine, guanosine, uridine, cytidine, and chemically-modified derivatives thereof;

- represents a phosphodiester internucleoside linkage;

=represents a phosphorothioate internucleoside linkage; and

--- represents, individually for each occurrence, a base-pairing interaction or a mismatch.

In certain embodiments, L is structure L1:

(L1)

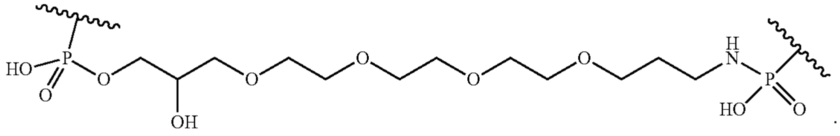

.

In certain embodiments, R is $R^3$ and n is 2.

In certain embodiments, L is structure L2:

(L2)

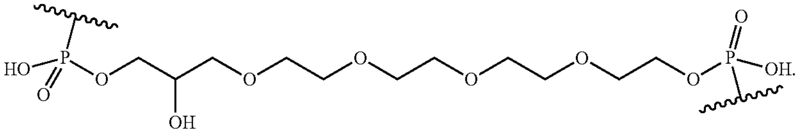

In certain embodiments, R is $R^3$ and n is 2.

In one aspect, the disclosure provides a delivery system for therapeutic nucleic acids having the structure of Formula (VI):

L-(cNA)$_n$ (VI)

wherein:

L comprises an ethylene glycol chain, an alkyl chain, a peptide, an RNA, a DNA, a phosphate, a phosphonate, a phosphoramidate, an ester, an amide, a triazole, or combinations thereof wherein formula (VI) optionally further comprises one or more branch point B, and one or more spacer S, wherein B comprises independently for each occurrence a polyvalent organic species or derivative thereof;

S comprises independently for each occurrence an ethylene glycol chain, an alkyl chain, a peptide, RNA, DNA, a phosphate, a phosphonate, a phosphoramidate, an ester, an amide, a triazole, or combinations thereof;

each cNA, independently, is a carrier nucleic acid comprising one or more chemical modifications;

each cNA, independently, comprises at least 15 contiguous nucleotides of a SOD1 nucleic acid sequence of any one of SEQ ID NOs: 1-11; and n is 2, 3, 4, 5, 6, 7 or 8.

In certain embodiments, the delivery system comprises a structure selected from formulas (VI-1)-(VI-9):

(VI-1)

ANc—L—cNA (VI-2)

ANc—S—L—S—cNA (VI-3)

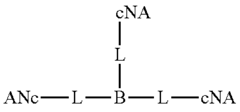

(VI-4)

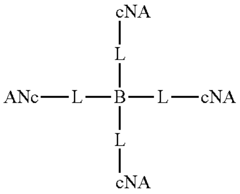

(VI-5)

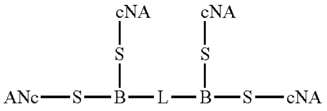

-continued (VI-6)

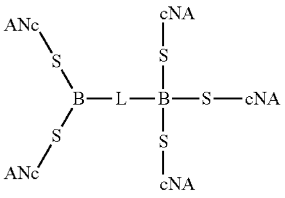

(VI-7)

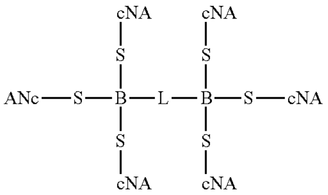

(VI-8)

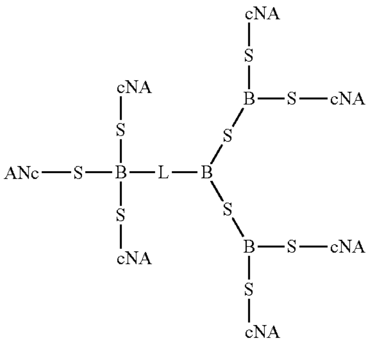

(VI-9)

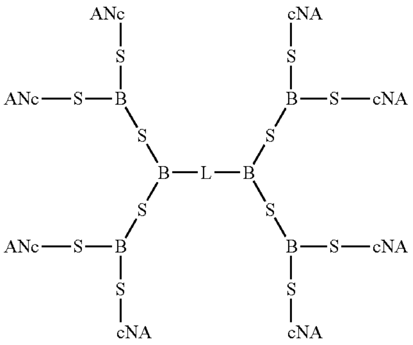

In certain embodiments, each cNA independently comprises chemically-modified nucleotides.

In certain embodiments, delivery system further comprises n therapeutic nucleic acids (NA), wherein each NA is hybridized to at least one cNA.

In certain embodiments, each NA independently comprises at least 16 contiguous nucleotides.

In certain embodiments, each NA independently comprises 16-20 contiguous nucleotides.

In certain embodiments, each NA comprises an unpaired overhang of at least 2 nucleotides.

In certain embodiments, the nucleotides of the overhang are connected via phosphorothioate linkages.

In certain embodiments, each NA, independently, is selected from the group consisting of DNAs, siRNAs, antagomiRs, miRNAs, gapmers, mixmers, and guide RNAs.

In certain embodiments, each NA is substantially complementary to a SOD1 nucleic acid sequence of any one of SEQ ID NOs: 1-11.

In one aspect, the disclosure provides a pharmaceutical composition for inhibiting the expression of SOD1 gene in an organism, comprising a compound recited above or a system recited above, and a pharmaceutically acceptable carrier.

In certain embodiments, the compound or system inhibits the expression of the SOD1 gene by at least 50%. In certain embodiments, the compound or system inhibits the expression of the SOD1 gene by at least 80%. In certain embodiments, the compound or system inhibits the expression of the SOD1 gene by at least 90%.

In one aspect, the disclosure provides a method for inhibiting expression of SOD1 gene in a cell, the method comprising: (a) introducing into the cell a compound recited above or a system recited above; and (b) maintaining the cell produced in step (a) for a time sufficient to obtain degradation of the mRNA transcript of the SOD1 gene, thereby inhibiting expression of the SOD1 gene in the cell.

In one aspect, the disclosure provides a method of treating or managing a neurodegenerative disease comprising administering to a patient in need of such treatment or management a therapeutically effective amount of a compound recited above or a system recited above.

In certain embodiments, the dsRNA is administered to the brain of the patient.

In certain embodiments, the dsRNA is administered by intracerebroventricular (ICV) injection, intrastriatal (IS) injection, intravenous (IV) injection, subcutaneous (SQ) injection, or a combination thereof.

In certain embodiments, administering the dsRNA causes a decrease in SOD1 gene mRNA in one or more of the hippocampus, striatum, cortex, cerebellum, thalamus, hypothalamus, and spinal cord.

In certain embodiments, the dsRNA inhibits the expression of said SOD1 gene by at least 50%. In certain embodiments, the dsRNA inhibits the expression of said SOD1 gene by at least 80%. In certain embodiments, the dsRNA inhibits the expression of said SOD1 gene by at least 90%.

In another aspect, the disclosure provides a method of treating or managing amyotrophic lateral sclerosis (ALS) comprising administering to a patient in need of such treatment or management a therapeutically effective amount of an oligonucleotide comprising a sequence substantially complementary to a SOD1 nucleic acid sequence.

In another aspect, the disclosure provides a method of treating or managing amyotrophic lateral sclerosis (ALS) comprising administering to a patient in need of such treatment or management a therapeutically effective amount of a dsRNA as recited above, a vector as recited above, a compound as recited above, or a system as recited above.

In another aspect, the disclosure provides a double stranded RNA (dsRNA) molecule comprising a sense strand and an antisense strand, wherein the sense strand comprises a nucleic acid sequence set forth in SEQ ID NO: 23 and the antisense strand comprises a nucleic acid sequence set forth in SEQ ID NO: 24.

BRIEF DESCRIPTION OF THE DRAWINGS

(FIG. 18C) depicts survival between P3 and P3B chemical scaffolds. Animals were treated at 8 weeks old with SOD-123 siRNA (compared to untreated controls). Each animal received a single bilateral ICV injection of siRNA (20 nmol).

DETAILED DESCRIPTION

Figure 1:
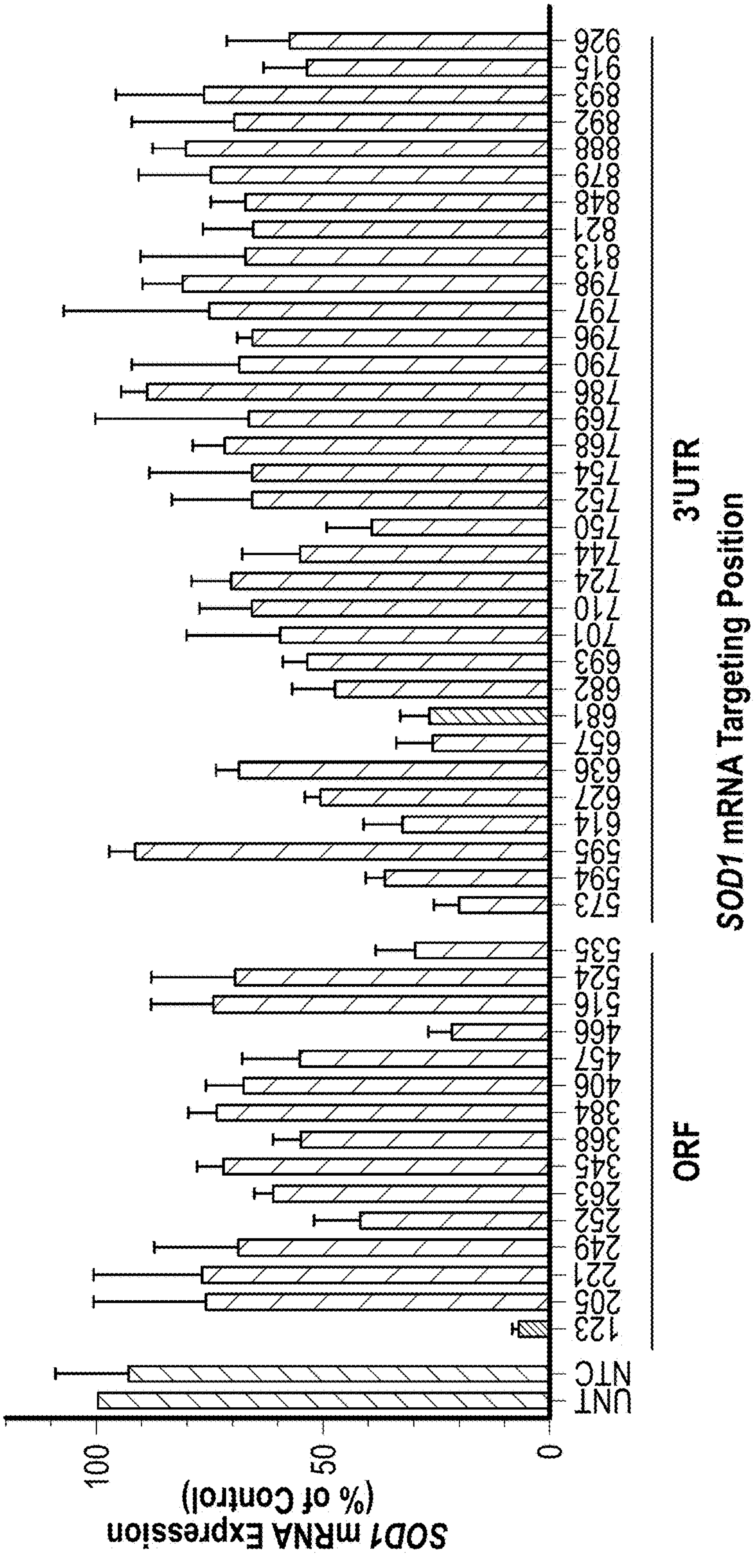
FIG. 1 depicts a screen of siRNAs targeting sequences of human SOD1 mRNA in human Hela cells. The siRNAs were each tested at a concentration of 1.5 μM and the mRNA levels were evaluated at a 72-hour timepoint.

Novel SOD1 target sequences are provided. Also provided are novel RNA molecules, such as siRNAs and branched RNA compounds containing the same, that target the SOD1 mRNA, such as one or more target sequences of the disclosure.

Unless otherwise specified, nomenclature used in connection with cell and tissue culture, molecular biology, immunology, microbiology, genetics and protein and nucleic acid chemistry and hybridization described herein are those well-known and commonly used in the art. Unless otherwise specified, the methods and techniques provided herein are performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, delivery, and treatment of patients.

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

So that the disclosure may be more readily understood, certain terms are first defined.

The term "nucleoside" refers to a molecule having a purine or pyrimidine base covalently linked to a ribose or deoxyribose sugar. Exemplary nucleosides include adenosine, guanosine, cytidine, uridine and thymidine. Additional exemplary nucleosides include inosine, 1-methyl inosine, pseudouridine, 5,6-dihydrouridine, ribothymidine, 2N-methylguanosine and N2,N2-dimethylguanosine (also referred to as "rare" nucleosides). The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester or phosphorothioate linkage between 5' and 3' carbon atoms.

The term "RNA" or "RNA molecule" or "ribonucleic acid molecule" refers to a polymer of ribonucleotides (e.g., 2, 3, 4, 5, 10, 15, 20, 25, 30, or more ribonucleotides). The term "DNA" or "DNA molecule" or "deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

As used herein, the term "small interfering RNA" ("siRNA")(also referred to in the art as "short interfering RNAs") refers to an RNA (or RNA analog) comprising between about 10-50 nucleotides (or nucleotide analogs), which is capable of directing or mediating RNA interference. In certain embodiments, a siRNA comprises between about 15-30 nucleotides or nucleotide analogs, or between about 16-25 nucleotides (or nucleotide analogs), or between about 18-23 nucleotides (or nucleotide analogs), or between about 19-22 nucleotides (or nucleotide analogs)(e.g., 19, 20, 21 or 22 nucleotides or nucleotide analogs). The term "short" siRNA refers to a siRNA comprising about 21 nucleotides (or nucleotide analogs), for example, 19, 20, 21 or 22 nucleotides. The term "long" siRNA refers to a siRNA comprising about 24-25 nucleotides, for example, 23, 24, 25 or 26 nucleotides. Short siRNAs may, in some instances, include fewer than 19 nucleotides, e.g., 16, 17 or 18 nucleotides, provided that the shorter siRNA retains the ability to mediate RNAi. Likewise, long siRNAs may, in some instances, include more than 26 nucleotides, provided that the longer siRNA retains the ability to mediate RNAi absent further processing, e.g., enzymatic processing, to a short siRNA.

The term "nucleotide analog" or "altered nucleotide" or "modified nucleotide" refers to a non-standard nucleotide, including non-naturally occurring ribonucleotides or deoxyribonucleotides. Exemplary nucleotide analogs are modified at any position so as to alter certain chemical properties of the nucleotide yet retain the ability of the nucleotide analog to perform its intended function. Examples of positions of the nucleotide, which may be derivatized include: the 5 position, e.g., 5-(2-amino)propyl uridine, 5-bromo uridine, 5-propyne uridine, 5-propenyl uridine, etc.; the 6 position, e.g., 6-(2-amino)propyl uridine; and the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs, such as those described in Herdewijn, Antisense Nucleic Acid Drug Dev., 2000 Aug. 10(4):297-310.

Nucleotide analogs may also comprise modifications to the sugar portion of the nucleotides. For example, the 2' OH-group may be replaced by a group selected from H, OR, R, F, Cl, Br, I, SH, SR, $NH_2$, NHR, $NR_2$, or COOR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions, which allow the nucleotide to perform its intended function, such as described in, for example, Eckstein, Antisense Nucleic Acid Drug Dev. 2000 Apr. 10(2):117-21, Rusckowski et al. Antisense Nucleic Acid Drug Dev. 2000 Oct. 10(5):333-45, Stein, Antisense Nucleic Acid Drug Dev. 2001 Oct. 11(5): 317-25, Vorobjev et al. Antisense Nucleic Acid Drug Dev. 2001 Apr. 11(2): 77-85, and U.S. Pat. No. 5,684,143. Certain of the above-referenced modifications (e.g., phosphate group modifications) decrease the rate of hydrolysis of, for example, polynucleotides comprising said analogs in vivo or in vitro.

The term "oligonucleotide" refers to a short polymer of nucleotides and/or nucleotide analogs.

The term "RNA analog" refers to a polynucleotide (e.g., a chemically synthesized polynucleotide) having at least one altered or modified nucleotide as compared to a corresponding unaltered or unmodified RNA, but retaining the same or similar nature or function as the corresponding unaltered or unmodified RNA. As discussed above, the oligonucleotides may be linked with linkages, which result in a lower rate of hydrolysis of the RNA analog as compared to an RNA molecule with phosphodiester linkages. For example, the nucleotides of the analog may comprise methylenediol, ethylene diol, oxymethylthio, oxyethylthio, oxycarbonyloxy, phosphorodiamidate, phosphoroamidate, and/or phosphorothioate linkages. Some RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate RNA interference.

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA, which direct the degradative mechanism to other similar RNA sequences. Alternatively, RNAi can be initiated by the hand of man, for example, to silence the expression of target genes.

An RNAi agent, e.g., an RNA silencing agent, having a strand, which is "sequence sufficiently complementary to a target mRNA sequence to direct target-specific RNA interference (RNAi)" means that the strand has a sequence sufficient to trigger the destruction of the target mRNA by the RNAi machinery or process.

As used herein, the term "isolated RNA" (e.g., "isolated siRNA" or "isolated siRNA precursor") refers to RNA molecules, which are substantially free of other cellular material, or culture medium when produced by recombinant techniques, or substantially free of chemical precursors or other chemicals when chemically synthesized.

As used herein, the term "RNA silencing" refers to a group of sequence-specific regulatory mechanisms (e.g. RNA interference (RNAi), transcriptional gene silencing (TGS), post-transcriptional gene silencing (PTGS), quelling, co-suppression, and translational repression) mediated by RNA molecules, which result in the inhibition or "silencing" of the expression of a corresponding protein-coding gene. RNA silencing has been observed in many types of organisms, including plants, animals, and fungi.

The term "discriminatory RNA silencing" refers to the ability of an RNA molecule to substantially inhibit the expression of a "first" or "target" polynucleotide sequence while not substantially inhibiting the expression of a "second" or "non-target" polynucleotide sequence," e.g., when both polynucleotide sequences are present in the same cell. In certain embodiments, the target polynucleotide sequence corresponds to a target gene, while the non-target polynucleotide sequence corresponds to a non-target gene. In other embodiments, the target polynucleotide sequence corresponds to a target allele, while the non-target polynucleotide sequence corresponds to a non-target allele. In certain embodiments, the target polynucleotide sequence is the DNA sequence encoding the regulatory region (e.g. promoter or enhancer elements) of a target gene. In other embodiments, the target polynucleotide sequence is a target mRNA encoded by a target gene.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

As used herein, the term "transgene" refers to any nucleic acid molecule, which is inserted by artifice into a cell, and becomes part of the genome of the organism that develops from the cell. Such a transgene may include a gene that is partly or entirely heterologous (i.e., foreign) to the transgenic organism, or may represent a gene homologous to an endogenous gene of the organism. The term "transgene" also means a nucleic acid molecule that includes one or more selected nucleic acid sequences, e.g., DNAs, that encode one or more engineered RNA precursors, to be expressed in a transgenic organism, e.g., animal, which is partly or entirely heterologous, i.e., foreign, to the transgenic animal, or homologous to an endogenous gene of the transgenic animal, but which is designed to be inserted into the animal's genome at a location which differs from that of the natural gene. A transgene includes one or more promoters and any other DNA, such as introns, necessary for expression of the selected nucleic acid sequence, all operably linked to the selected sequence, and may include an enhancer sequence.

A gene "involved" in a disease or disorder includes a gene, the normal or aberrant expression or function of which effects or causes the disease or disorder or at least one symptom of said disease or disorder.

The term "gain-of-function mutation" as used herein, refers to any mutation in a gene in which the protein encoded by said gene (i.e., the mutant protein) acquires a function not normally associated with the protein (i.e., the wild type protein) and causes or contributes to a disease or disorder. The gain-of-function mutation can be a deletion, addition, or substitution of a nucleotide or nucleotides in the gene, which gives rise to the change in the function of the encoded protein. In one embodiment, the gain-of-function mutation changes the function of the mutant protein or causes interactions with other proteins. In another embodiment, the gain-of-function mutation causes a decrease in or removal of normal wild-type protein, for example, by interaction of the altered, mutant protein with said normal, wild-type protein.

As used herein, the term "target gene" is a gene whose expression is to be substantially inhibited or "silenced." This silencing can be achieved by RNA silencing, e.g., by cleaving the mRNA of the target gene or translational repression of the target gene. The term "non-target gene" is a gene whose expression is not to be substantially silenced. In one embodiment, the polynucleotide sequences of the target and non-target gene (e.g. mRNA encoded by the target and non-target genes) can differ by one or more nucleotides. In another embodiment, the target and non-target genes can differ by one or more polymorphisms (e.g., Single Nucleotide Polymorphisms or SNPs). In another embodiment, the target and non-target genes can share less than 100% sequence identity. In another embodiment, the non-target gene may be a homologue (e.g. an orthologue or paralogue) of the target gene.

A "target allele" is an allele (e.g., a SNP allele) whose expression is to be selectively inhibited or "silenced." This silencing can be achieved by RNA silencing, e.g., by cleaving the mRNA of the target gene or target allele by a siRNA. The term "non-target allele" is an allele whose expression is not to be substantially silenced. In certain embodiments, the target and non-target alleles can correspond to the same target gene. In other embodiments, the target allele corresponds to, or is associated with, a target gene, and the non-target allele corresponds to, or is associated with, a non-target gene. In one embodiment, the polynucleotide sequences of the target and non-target alleles can differ by one or more nucleotides. In another embodiment, the target and non-target alleles can differ by one or more allelic polymorphisms (e.g., one or more SNPs). In another embodiment, the target and non-target alleles can share less than 100% sequence identity.

The term "polymorphism" as used herein, refers to a variation (e.g., one or more deletions, insertions, or substitutions) in a gene sequence that is identified or detected when the same gene sequence from different sources or subjects (but from the same organism) are compared. For example, a polymorphism can be identified when the same gene sequence from different subjects are compared. Identification of such polymorphisms is routine in the art, the methodologies being similar to those used to detect, for example, breast cancer point mutations. Identification can be made, for example, from DNA extracted from a subject's lymphocytes, followed by amplification of polymorphic regions using specific primers to said polymorphic region. Alternatively, the polymorphism can be identified when two alleles of the same gene are compared. In certain embodiments, the polymorphism is a single nucleotide polymorphism (SNP).

A variation in sequence between two alleles of the same gene within an organism is referred to herein as an "allelic polymorphism." In certain embodiments, the allelic polymorphism corresponds to a SNP allele. For example, the allelic polymorphism may comprise a single nucleotide variation between the two alleles of a SNP. The polymorphism can be at a nucleotide within a coding region but, due to the degeneracy of the genetic code, no change in amino acid sequence is encoded. Alternatively, polymorphic sequences can encode a different amino acid at a particular position, but the change in the amino acid does not affect protein function. Polymorphic regions can also be found in non-encoding regions of the gene. In exemplary embodiments, the polymorphism is found in a coding region of the gene or in an untranslated region (e.g., a 5' UTR or 3' UTR) of the gene.

As used herein, the term "allelic frequency" is a measure (e.g., proportion or percentage) of the relative frequency of an allele (e.g., a SNP allele) at a single locus in a population of individuals. For example, where a population of individuals carry n loci of a particular chromosomal locus (and the gene occupying the locus) in each of their somatic cells, then the allelic frequency of an allele is the fraction or percentage of loci that the allele occupies within the population. In certain embodiments, the allelic frequency of an allele (e.g., an SNP allele) is at least 10% (e.g., at least 15%, 20%, 25%, 30%, 35%, 40% or more) in a sample population.

As used herein, the term "sample population" refers to a population of individuals comprising a statistically significant number of individuals. For example, the sample population may comprise 50, 75, 100, 200, 500, 1000 or more individuals. In certain embodiments, the sample population may comprise individuals, which share at least on common disease phenotype (e.g., a gain-of-function disorder) or mutation (e.g., a gain-of-function mutation).

As used herein, the term "heterozygosity" refers to the fraction of individuals within a population that are heterozygous (e.g., contain two or more different alleles) at a particular locus (e.g., at a SNP). Heterozygosity may be calculated for a sample population using methods that are well known to those skilled in the art.

The term "polyglutamine domain," as used herein, refers to a segment or domain of a protein that consist of consecutive glutamine residues linked to peptide bonds. In one embodiment the consecutive region includes at least 5 glutamine residues.

As described herein, the term "SOD1" refers to the gene encoding for the protein Superoxide Dismutase 1 (SOD1). SOD1 is one of three human superoxide dismutase proteins which destroy free superoxide radicals. Several mutations in SOD1 have been associated with familial amyotrophic lateral sclerosis, including A4V, H46R, and G93A.

The term "expanded polyglutamine domain" or "expanded polyglutamine segment," as used herein, refers to a segment or domain of a protein that includes at least 35 consecutive glutamine residues linked by peptide bonds. Such expanded segments are found in subjects afflicted with a polyglutamine disorder, as described herein, whether or not the subject manifests symptoms.

The term "mutant SOD1 gene" as used herein, refers to SOD1 genes containing mutations leading to coding changes in the resultant protein sequence. Exemplary mutant SOD1 genes, but are not limited to, A4V, H46R, and/or G93A.

The term "mutant SOD1 gene associated diseases" as used herein, refers to any disease or disorder characterized by mutation located within the SOD1 gene, the mutation being causative of the disease or disorder. An example of mutant SOD1 gene associated diseases includes, but is not limited to amyotrophic lateral sclerosis (ALS).

The phrase "examining the function of a gene in a cell or organism" refers to examining or studying the expression, activity, function or phenotype arising therefrom.

As used herein, the term "RNA silencing agent" refers to an RNA, which is capable of inhibiting or "silencing" the expression of a target gene. In certain embodiments, the RNA silencing agent is capable of preventing complete processing (e.g., the full translation and/or expression) of a mRNA molecule through a post-transcriptional silencing mechanism. RNA silencing agents include small (<50 b.p.), noncoding RNA molecules, for example RNA duplexes comprising paired strands, as well as precursor RNAs from which such small non-coding RNAs can be generated. Exemplary RNA silencing agents include siRNAs, miRNAs, siRNA-like duplexes, antisense oligonucleotides, GAPMER molecules, and dual-function oligonucleotides, as well as precursors thereof. In one embodiment, the RNA silencing agent is capable of inducing RNA interference. In another embodiment, the RNA silencing agent is capable of mediating translational repression.

As used herein, the term "rare nucleotide" refers to a naturally occurring nucleotide that occurs infrequently, including naturally occurring deoxyribonucleotides or ribonucleotides that occur infrequently, e.g., a naturally occurring ribonucleotide that is not guanosine, adenosine, cytosine, or uridine. Examples of rare nucleotides include, but are not limited to, inosine, 1-methyl inosine, pseudouridine, 5,6-dihydrouridine, ribothymidine, 2N-methylguanosine and 2,2N,N-dimethylguanosine.

The term "engineered," as in an engineered RNA precursor, or an engineered nucleic acid molecule, indicates that the precursor or molecule is not found in nature, in that all or a portion of the nucleic acid sequence of the precursor or molecule is created or selected by a human. Once created or selected, the sequence can be replicated, translated, transcribed, or otherwise processed by mechanisms within a cell. Thus, an RNA precursor produced within a cell from a transgene that includes an engineered nucleic acid molecule is an engineered RNA precursor.

As used herein, the term "microRNA" ("miRNA"), also known in the art as "small temporal RNAs" ("stRNAs"), refers to a small (10-50 nucleotide) RNA, which are genetically encoded (e.g., by viral, mammalian, or plant genomes) and are capable of directing or mediating RNA silencing. An "miRNA disorder" shall refer to a disease or disorder characterized by an aberrant expression or activity of a miRNA.

As used herein, the term "dual functional oligonucleotide" refers to a RNA silencing agent having the formula T-L-μ, wherein T is an mRNA targeting moiety, L is a linking moiety, and μ is a miRNA recruiting moiety. As used herein, the terms "mRNA targeting moiety," "targeting moiety," "mRNA targeting portion" or "targeting portion" refer to a domain, portion or region of the dual functional oligonucleotide having sufficient size and sufficient complementarity to a portion or region of an mRNA chosen or targeted for silencing (i.e., the moiety has a sequence sufficient to capture the target mRNA).

As used herein, the term "linking moiety" or "linking portion" refers to a domain, portion or region of the RNA-silencing agent which covalently joins or links the mRNA.

As used herein, the term "antisense strand" of an RNA silencing agent, e.g., an siRNA or RNA silencing agent, refers to a strand that is substantially complementary to a section of about 10-50 nucleotides, e.g., about 15-30, 16-25, 18-23 or 19-22 nucleotides of the mRNA of the gene targeted for silencing. The antisense strand or first strand has sequence sufficiently complementary to the desired target mRNA sequence to direct target-specific silencing, e.g., complementarity sufficient to trigger the destruction of the desired target mRNA by the RNAi machinery or process (RNAi interference) or complementarity sufficient to trigger translational repression of the desired target mRNA.

The term "sense strand" or "second strand" of an RNA silencing agent, e.g., an siRNA or RNA silencing agent, refers to a strand that is complementary to the antisense strand or first strand. Antisense and sense strands can also be referred to as first or second strands, the first or second strand having complementarity to the target sequence and the respective second or first strand having complementarity to said first or second strand. miRNA duplex intermediates or siRNA-like duplexes include a miRNA strand having sufficient complementarity to a section of about 10-50 nucleotides of the mRNA of the gene targeted for silencing and a miRNA* strand having sufficient complementarity to form a duplex with the miRNA strand.

As used herein, the term "guide strand" refers to a strand of an RNA silencing agent, e.g., an antisense strand of an siRNA duplex or siRNA sequence, that enters into the RISC complex and directs cleavage of the target mRNA.

As used herein, the term "asymmetry," as in the asymmetry of the duplex region of an RNA silencing agent (e.g., the stem of an shRNA), refers to an inequality of bond strength or base pairing strength between the termini of the RNA silencing agent (e.g., between terminal nucleotides on a first strand or stem portion and terminal nucleotides on an opposing second strand or stem portion), such that the 5' end of one strand of the duplex is more frequently in a transient unpaired, e.g., single-stranded, state than the 5' end of the complementary strand. This structural difference determines that one strand of the duplex is preferentially incorporated into a RISC complex. The strand whose 5' end is less tightly paired to the complementary strand will preferentially be incorporated into RISC and mediate RNAi.

As used herein, the term "bond strength" or "base pair strength" refers to the strength of the interaction between pairs of nucleotides (or nucleotide analogs) on opposing strands of an oligonucleotide duplex (e.g., an siRNA duplex), due primarily to H-bonding, van der Waals interactions, and the like, between said nucleotides (or nucleotide analogs).

As used herein, the "5' end," as in the 5' end of an antisense strand, refers to the 5' terminal nucleotides, e.g., between one and about 5 nucleotides at the 5' terminus of the antisense strand. As used herein, the "3' end," as in the 3' end of a sense strand, refers to the region, e.g., a region of between one and about 5 nucleotides, that is complementary to the nucleotides of the 5' end of the complementary antisense strand.

As used herein the term "destabilizing nucleotide" refers to a first nucleotide or nucleotide analog capable of forming a base pair with second nucleotide or nucleotide analog such that the base pair is of lower bond strength than a conventional base pair (i.e., Watson-Crick base pair). In certain embodiments, the destabilizing nucleotide is capable of forming a mismatch base pair with the second nucleotide. In other embodiments, the destabilizing nucleotide is capable of forming a wobble base pair with the second nucleotide. In yet other embodiments, the destabilizing nucleotide is capable of forming an ambiguous base pair with the second nucleotide.

As used herein, the term "base pair" refers to the interaction between pairs of nucleotides (or nucleotide analogs) on opposing strands of an oligonucleotide duplex (e.g., a duplex formed by a strand of a RNA silencing agent and a target mRNA sequence), due primarily to H-bonding, van der Waals interactions, and the like between said nucleotides (or nucleotide analogs). As used herein, the term "bond strength" or "base pair strength" refers to the strength of the base pair.

As used herein, the term "mismatched base pair" refers to a base pair consisting of non-complementary or non-Watson-Crick base pairs, for example, not normal complementary G:C, A:T or A:U base pairs. As used herein the term "ambiguous base pair" (also known as a non-discriminatory base pair) refers to a base pair formed by a universal nucleotide.

As used herein, term "universal nucleotide" (also known as a "neutral nucleotide") include those nucleotides (e.g. certain destabilizing nucleotides) having a base (a "universal base" or "neutral base") that does not significantly discriminate between bases on a complementary polynucleotide when forming a base pair. Universal nucleotides are predominantly hydrophobic molecules that can pack efficiently into antiparallel duplex nucleic acids (e.g., double-stranded DNA or RNA) due to stacking interactions. The base portion of universal nucleotides typically comprise a nitrogen-containing aromatic heterocyclic moiety.

As used herein, the terms "sufficient complementarity" or "sufficient degree of complementarity" mean that the RNA silencing agent has a sequence (e.g. in the antisense strand, mRNA targeting moiety or miRNA recruiting moiety), which is sufficient to bind the desired target RNA, respectively, and to trigger the RNA silencing of the target mRNA.

As used herein, the term "translational repression" refers to a selective inhibition of mRNA translation. Natural translational repression proceeds via miRNAs cleaved from shRNA precursors. Both RNAi and translational repression are mediated by RISC. Both RNAi and translational repression occur naturally or can be initiated by the hand of man, for example, to silence the expression of target genes.

Various methodologies of the instant disclosure include a step that involves comparing a value, level, feature, characteristic, property, etc. to a "suitable control," referred to interchangeably herein as an "appropriate control." A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing an RNA silencing agent of the disclosure into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and example are illustrative only and not intended to be limiting.

Various aspects of the disclosure are described in further detail in the following subsections.

I. Novel Target Sequences

In certain exemplary embodiments, RNA silencing agents of the disclosure are capable of targeting a SOD1 nucleic acid sequence of any one of SEQ ID NOs: 1-11, as recited in Table 4. In certain exemplary embodiments, RNA silencing agents of the disclosure are capable of targeting one or more of a SOD1 nucleic acid sequence selected from the group consisting of SEQ ID NOs: 12-22, as recited in Table 4.

Genomic sequence for each target sequence can be found in, for example, the publicly available database maintained by the NCBI.

II. siRNA Design

In some embodiments, siRNAs are designed as follows. First, a portion of the target gene (e.g., the SOD1 gene), e.g., one or more of the target sequences set forth in Table 4 is selected. Cleavage of mRNA at these sites should eliminate translation of corresponding protein. Antisense strands were designed based on the target sequence and sense strands were designed to be complementary to the antisense strand. Hybridization of the antisense and sense strands forms the siRNA duplex. The antisense strand includes about 19 to 25 nucleotides, e.g., 19, 20, 21, 22, 23, 24 or 25 nucleotides. In other embodiments, the antisense strand includes 20, 21, 22 or 23 nucleotides. The sense strand includes about 14 to 25 nucleotides, e.g., 14, 15, 16, 17, 18, 19, 20, 21, 22, 23, 24 or 25 nucleotides. In other embodiments, the sense strand is 15 nucleotides. In other embodiments, the sense strand is 18 nucleotides. In other embodiments, the sense strand is 20 nucleotides. The skilled artisan will appreciate, however, that siRNAs having a length of less than 19 nucleotides or greater than 25 nucleotides can also function to mediate RNAi. Accordingly, siRNAs of such length are also within the scope of the instant disclosure, provided that they retain the ability to mediate RNAi. Longer RNAi agents have been demonstrated to elicit an interferon or PKR response in certain mammalian cells, which may be undesirable. In certain embodiments, the RNAi agents of the disclosure do not elicit a PKR response (i.e., are of a sufficiently short length). However, longer RNAi agents may be useful, for example, in cell types incapable of generating a PKR response or in situations where the PKR response has been down-regulated or dampened by alternative means.

The sense strand sequence can be designed such that the target sequence is essentially in the middle of the strand. Moving the target sequence to an off-center position can, in some instances, reduce efficiency of cleavage by the siRNA. Such compositions, i.e., less efficient compositions, may be desirable for use if off-silencing of the wild-type mRNA is detected.

The antisense strand can be the same length as the sense strand and includes complementary nucleotides. In one embodiment, the strands are fully complementary, i.e., the strands are blunt-ended when aligned or annealed. In another embodiment, the strands align or anneal such that 1-, 2-, 3-, 4-, 5-, 6-, 7-, or 8-nucleotide overhangs are generated, i.e., the 3' end of the sense strand extends 1, 2, 3, 4, 5, 6, 7, or 8 nucleotides further than the 5' end of the antisense strand and/or the 3' end of the antisense strand extends 1, 2, 3, 4, 5, 6, 7, or 8 nucleotides further than the 5' end of the sense strand. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material.

To facilitate entry of the antisense strand into RISC (and thus increase or improve the efficiency of target cleavage and silencing), the base pair strength between the 5' end of the sense strand and 3' end of the antisense strand can be altered, e.g., lessened or reduced, as described in detail in U.S. Pat. Nos. 7,459,547, 7,772,203 and 7,732,593, entitled "Methods and Compositions for Controlling Efficacy of RNA Silencing" (filed Jun. 2, 2003) and U.S. Pat. Nos. 8,309,704, 7,750,144, 8,304,530, 8,329,892 and 8,309,705, entitled "Methods and Compositions for Enhancing the Efficacy and Specificity of RNAi" (filed Jun. 2, 2003), the contents of which are incorporated in their entirety by this reference. In one embodiment of these aspects of the disclosure, the base-pair strength is less due to fewer G:C base pairs between the 5' end of the first or antisense strand and the 3' end of the second or sense strand than between the 3' end of the first or antisense strand and the 5' end of the second or sense strand. In another embodiment, the base pair strength is less due to at least one mismatched base pair between the 5' end of the first or antisense strand and the 3' end of the second or sense strand. In certain exemplary embodiments, the mismatched base pair is selected from the group consisting of G:A, C:A, C:U, G:G, A:A, C:C and U:U. In another embodiment, the base pair strength is less due to at least one wobble base pair, e.g., G:U, between the 5' end of the first or antisense strand and the 3' end of the second or sense strand. In another embodiment, the base pair strength is less due to at least one base pair comprising a rare nucleotide, e.g., inosine (I). In certain exemplary embodiments, the base pair is selected from the group consisting of an I:A, I:U and I:C. In yet another embodiment, the base pair strength is less due to at least one base pair comprising a modified nucleotide. In certain exemplary embodiments, the modified nucleotide is selected from the group consisting of 2-amino-G, 2-amino-A, 2,6-diamino-G, and 2,6-diamino-A.

The design of siRNAs suitable for targeting the SOD1 target sequences set forth in Table 4 is described in detail below. siRNAs can be designed according to the above exemplary teachings for any other target sequences found in the SOD1 gene. Moreover, the technology is applicable to targeting any other target sequences, e.g., non-disease-causing target sequences.

To validate the effectiveness by which siRNAs destroy mRNAs (e.g., SOD1 mRNA), the siRNA can be incubated with cDNA (e.g., SOD1 cDNA) in a *Drosophila*-based in vitro mRNA expression system. Radiolabeled with $^{32}P$, newly synthesized mRNAs (e.g., SOD1 mRNA) are detected autoradiographically on an agarose gel. The presence of cleaved mRNA indicates mRNA nuclease activity. Suitable controls include omission of siRNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence. Sites of siRNA-mRNA complementation are selected which result in optimal mRNA specificity and maximal mRNA cleavage.

III. RNAi Agents

The present disclosure includes RNAi molecules, such as siRNA molecules designed, for example, as described above. The siRNA molecules of the disclosure can be chemically synthesized, or can be transcribed in vitro from a DNA template, or in vivo from e.g., shRNA, or by using recombinant human DICER enzyme, to cleave in vitro transcribed dsRNA templates into pools of 20-, 21- or 23-bp duplex RNA mediating RNAi. The siRNA molecules can be designed using any method known in the art.

In one aspect, instead of the RNAi agent being an interfering ribonucleic acid, e.g., an siRNA or shRNA as described above, the RNAi agent can encode an interfering ribonucleic acid, e.g., an shRNA, as described above. In other words, the RNAi agent can be a transcriptional template of the interfering ribonucleic acid. Thus, RNAi agents of the present disclosure can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21-23 nucleotides (Brummelkamp et al., 2002; Lee et al., 2002, Supra; Miyagishi et al., 2002; Paddison et al., 2002, supra; Paul et al., 2002, supra; Sui et al., 2002 supra; Yu et al., 2002, supra. More information about shRNA design and use can be found on the internet at the following addresses: katandin.cshl.org:9331/RNAi/docs/BseRI-BamHI Strategy. pdf and katandin.cshl.org:9331/RNAi/docs/Web version of PCR strategy 1. pdf).

Expression constructs of the present disclosure include any construct suitable for use in the appropriate expression system and include, but are not limited to, retroviral vectors, linear expression cassettes, plasmids and viral or virally-derived vectors, as known in the art. Such expression constructs can include one or more inducible promoters, RNA Pol III promoter systems, such as U6 snRNA promoters or H1 RNA polymerase III promoters, or other promoters known in the art. The constructs can include one or both strands of the siRNA. Expression constructs expressing both strands can also include loop structures linking both strands, or each strand can be separately transcribed from separate promoters within the same construct. Each strand can also be transcribed from a separate expression construct. (Tuschl, T., 2002, Supra).

Synthetic siRNAs can be delivered into cells by methods known in the art, including cationic liposome transfection and electroporation. To obtain longer term suppression of the target genes (e.g., SOD1 genes) and to facilitate delivery under certain circumstances, one or more siRNA can be expressed within cells from recombinant DNA constructs. Such methods for expressing siRNA duplexes within cells from recombinant DNA constructs to allow longer-term target gene suppression in cells are known in the art, including mammalian Pol III promoter systems (e.g., H1 or U6/snRNA promoter systems (Tuschl, T., 2002, supra) capable of expressing functional double-stranded siRNAs; (Bagella et al., 1998; Lee et al., 2002, supra; Miyagishi et al., 2002, supra; Paul et al., 2002, supra; Yu et al., 2002, supra; Sui et al., 2002, supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al., 1998; Lee et al., 2002, supra; Miyagishi et al., 2002, supra; Paul et al., 2002, supra; Yu et al., 2002), supra; Sui et al., 2002, supra). Constructs containing siRNA sequence under the control of T7 promoter also make functional siRNAs when co-transfected into the cells with a vector expressing T7 RNA polymerase (Jacque et al., 2002, supra). A single construct may contain multiple sequences coding for siRNAs, such as multiple regions of the gene encoding SOD1, targeting the same gene or multiple genes, and can be driven, for example, by separate PolIII promoter sites.

Animal cells express a range of noncoding RNAs of approximately 22 nucleotides termed micro RNA (miRNAs), which can regulate gene expression at the post transcriptional or translational level during animal development. One common feature of miRNAs is that they are all excised from an approximately 70 nucleotide precursor RNA stem-loop, probably by Dicer, an RNase III-type enzyme, or a homolog thereof. By substituting the stem sequences of the miRNA precursor with sequence complementary to the target mRNA, a vector construct that expresses the engineered precursor can be used to produce siRNAs to initiate RNAi against specific mRNA targets in mammalian cells (Zeng et al., 2002, supra). When expressed by DNA vectors containing polymerase III promoters, micro-RNA designed hairpins can silence gene expression (McManus et al., 2002, supra). MicroRNAs targeting polymorphisms may also be useful for blocking translation of mutant proteins, in the absence of siRNA-mediated gene-silencing. Such applications may be useful in situations, for example, where a designed siRNA caused off-target silencing of wild type protein.

Viral-mediated delivery mechanisms can also be used to induce specific silencing of targeted genes through expression of siRNA, for example, by generating recombinant adenoviruses harboring siRNA under RNA Pol II promoter transcription control (Xia et al., 2002, supra). Infection of HeLa cells by these recombinant adenoviruses allows for diminished endogenous target gene expression. Injection of the recombinant adenovirus vectors into transgenic mice expressing the target genes of the siRNA results in in vivo reduction of target gene expression. Id. In an animal model, whole-embryo electroporation can efficiently deliver synthetic siRNA into post-implantation mouse embryos (Calegari et al., 2002). In adult mice, efficient delivery of siRNA can be accomplished by "high-pressure" delivery technique, a rapid injection (within 5 seconds) of a large volume of siRNA containing solution into animal via the tail vein (Liu et al., 1999, supra; McCaffrey et al., 2002, supra; Lewis et al., 2002. Nanoparticles and liposomes can also be used to deliver siRNA into animals. In certain exemplary embodiments, recombinant adeno-associated viruses (rAAVs) and their associated vectors can be used to deliver one or more siRNAs into cells, e.g., neural cells (e.g., brain cells)(US Patent Applications 2014/0296486, 2010/0186103, 2008/0269149, 2006/0078542 and 2005/0220766).

The nucleic acid compositions of the disclosure include both unmodified siRNAs and modified siRNAs, such as crosslinked siRNA derivatives or derivatives having non-nucleotide moieties linked, for example to their 3' or 5' ends. Modifying siRNA derivatives in this way may improve cellular uptake or enhance cellular targeting activities of the resulting siRNA derivative, as compared to the corresponding siRNA, and are useful for tracing the siRNA derivative in the cell, or improving the stability of the siRNA derivative compared to the corresponding siRNA.

Engineered RNA precursors, introduced into cells or whole organisms as described herein, will lead to the production of a desired siRNA molecule. Such an siRNA molecule will then associate with endogenous protein components of the RNAi pathway to bind to and target a specific mRNA sequence for cleavage and destruction. In this fashion, the mRNA, which will be targeted by the siRNA generated from the engineered RNA precursor, and will be depleted from the cell or organism, leading to a decrease in the concentration of the protein encoded by that mRNA in the cell or organism. The RNA precursors are typically nucleic acid molecules that individually encode either one strand of a dsRNA or encode the entire nucleotide sequence of an RNA hairpin loop structure.

The nucleic acid compositions of the disclosure can be unconjugated or can be conjugated to another moiety, such as a nanoparticle, to enhance a property of the compositions, e.g., a pharmacokinetic parameter such as absorption, efficacy, bioavailability and/or half-life. The conjugation can be accomplished by methods known in the art, e.g., using the methods of Lambert et al., Drug Deliv. Rev.: 47(1), 99-112 (2001)(describes nucleic acids loaded to polyalkylcyanoacrylate (PACA) nanoparticles); Fattal et al., J. Control Release 53(1-3):137-43 (1998)(describes nucleic acids bound to nanoparticles); Schwab et al., Ann. Oncol. 5 Suppl. 4:55-8 (1994)(describes nucleic acids linked to intercalating agents, hydrophobic groups, polycations or PACA nanoparticles); and Godard et al., Eur. J. Biochem. 232(2):404-10 (1995)(describes nucleic acids linked to nanoparticles).

The nucleic acid molecules of the present disclosure can also be labeled using any method known in the art. For instance, the nucleic acid compositions can be labeled with a fluorophore, e.g., Cy3, fluorescein, or rhodamine. The labeling can be carried out using a kit, e.g., the SILENCER™ siRNA labeling kit (Ambion). Additionally, the siRNA can be radiolabeled, e.g., using $^3H$, $^{32}P$ or another appropriate isotope.

Moreover, because RNAi is believed to progress via at least one single-stranded RNA intermediate, the skilled artisan will appreciate that ss-siRNAs (e.g., the antisense strand of a ds-siRNA) can also be designed (e.g., for chemical synthesis), generated (e.g., enzymatically generated), or expressed (e.g., from a vector or plasmid) as described herein and utilized according to the claimed methodologies. Moreover, in invertebrates, RNAi can be triggered effectively by long dsRNAs (e.g., dsRNAs about 100-1000 nucleotides in length, such as about 200-500, for example, about 250, 300, 350, 400 or 450 nucleotides in length) acting as effectors of RNAi. (Brondani et al., Proc Natl Acad Sci USA. 2001 Dec. 4; 98(25):14428-33. Epub 2001 Nov. 27.)

IV. Anti-SOD1 RNA Silencing Agents

In certain embodiment, the present disclosure provides novel anti-SOD1 RNA silencing agents (e.g., siRNA, shRNA, and antisense oligonucleotides), methods of making said RNA silencing agents, and methods (e.g., research and/or therapeutic methods) for using said improved RNA silencing agents (or portions thereof) for RNA silencing of SOD1 protein. The RNA silencing agents comprise an antisense strand (or portions thereof), wherein the antisense strand has sufficient complementary to a target SOD1 mRNA to mediate an RNA-mediated silencing mechanism (e.g. RNAi).

In certain embodiments, siRNA compounds are provided having one or any combination of the following properties: (1) fully chemically-stabilized (i.e., no unmodified 2'-OH residues); (2) asymmetry; (3) 11-20 base pair duplexes; (4) greater than 50% 2'-methoxy modifications, such as 70%-100% 2'-methoxy modifications, although an alternating pattern of chemically-modified nucleotides (e.g., 2'-fluoro and 2'-methoxy modifications), are also contemplated; and (5) single-stranded, fully phosphorothioated tails of 5-8 bases. In certain embodiments, the number of phosphorothioate modifications is varied from 4 to 16 total. In certain embodiments, the number of phosphorothioate modifications is varied from 8 to 13 total.

In certain embodiments, the siRNA compounds described herein can be conjugated to a variety of targeting agents, including, but not limited to, cholesterol, docosahexaenoic acid (DHA), phenyltropanes, cortisol, vitamin A, vitamin D, N-acetylgalactosamine (GalNac), and gangliosides. The cholesterol-modified version showed 5-10 fold improvement in efficacy in vitro versus previously used chemical stabilization patterns (e.g., wherein all purine but not pyrimidines are modified) in wide range of cell types (e.g., HeLa, neurons, hepatocytes, trophoblasts).

Certain compounds of the disclosure having the structural properties described above and herein may be referred to as "hsiRNA-ASP" (hydrophobically-modified, small interfering RNA, featuring an advanced stabilization pattern). In addition, this hsiRNA-ASP pattern showed a dramatically improved distribution through the brain, spinal cord, delivery to liver, placenta, kidney, spleen and several other tissues, making them accessible for therapeutic intervention.

The compounds of the disclosure can be described in the following aspects and embodiments.

In a first aspect, provided herein is a double stranded RNA (dsRNA) comprising an antisense strand and a sense strand, each strand comprising at least 14 contiguous nucleotides, with a 5' end and a 3' end, wherein:

(1) the antisense strand comprises a sequence substantially complementary to a SOD1 nucleic acid sequence of any one of SEQ ID NOs: 1-11;
(2) the antisense strand comprises alternating 2'-methoxy-ribonucleotides and 2'-fluoro-ribonucleotides;
(3) the nucleotides at positions 2 and 14 from the 5' end of the antisense strand are not 2'-methoxy-ribonucleotides;
(4) the nucleotides at positions 1-2 to 1-7 from the 3' end of the antisense strand are connected to each other via phosphorothioate internucleotide linkages;
(5) a portion of the antisense strand is complementary to a portion of the sense strand;
(6) the sense strand comprises alternating 2'-methoxy-ribonucleotides and 2'-fluoro-ribonucleotides; and
(7) the nucleotides at positions 1-2 from the 5' end of the sense strand are connected to each other via phosphorothioate internucleotide linkages.

In a second aspect, provided herein is a dsRNA comprising an antisense strand and a sense strand, each strand comprising at least 14 contiguous nucleotides, with a 5' end and a 3' end, wherein:

(1) the antisense strand comprises a sequence substantially complementary to a SOD1 nucleic acid sequence of any one of SEQ ID NOs: 1-11;
(2) the antisense strand comprises at least 70% 2'-O-methyl modifications;
(3) the nucleotide at position 14 from the 5' end of the antisense strand are not 2'-methoxy-ribonucleotides;
(4) the nucleotides at positions 1-2 to 1-7 from the 3' end of the antisense strand are connected to each other via phosphorothioate internucleotide linkages;
(5) a portion of the antisense strand is complementary to a portion of the sense strand;
(6) the sense strand comprises at least 70% 2'-O-methyl modifications; and
(7) the nucleotides at positions 1-2 from the 5' end of the sense strand are connected to each other via phosphorothioate internucleotide linkages.

In a third aspect, provided herein is a dsRNA comprising an antisense strand and a sense strand, each strand comprising at least 14 contiguous nucleotides, with a 5' end and a 3' end, wherein:

(1) the antisense strand comprises a sequence substantially complementary to a SOD1 nucleic acid sequence of any one of SEQ ID NOs: 1-11;
(2) the antisense strand comprises at least 85% 2'-O-methyl modifications;
(3) the nucleotides at positions 2 and 14 from the 5' end of the antisense strand are not 2'-methoxy-ribonucleotides;
(4) the nucleotides at positions 1-2 to 1-7 from the 3' end of the antisense strand are connected to each other via phosphorothioate internucleotide linkages;
(5) a portion of the antisense strand is complementary to a portion of the sense strand;
(6) the sense strand comprises 100% 2'-O-methyl modifications; and
(7) the nucleotides at positions 1-2 from the 5' end of the sense strand are connected to each other via phosphorothioate internucleotide linkages.

In a fourth aspect, provided herein is a dsRNA comprising an antisense strand and a sense strand, each strand comprising at least 14 contiguous nucleotides, with a 5' end and a 3' end, wherein:

(1) the antisense strand comprises a sequence substantially complementary to a SOD1 nucleic acid sequence of any one of SEQ ID NOs: 1-11;
(2) the antisense strand comprises at least 75% 2'-O-methyl modifications;
(3) the nucleotides at positions 4, 5, 6, and 14 from the 5' end of the antisense strand are not 2'-methoxy-ribonucleotides;
(4) the nucleotides at positions 1-2 to 1-7 from the 3' end of the antisense strand are connected to each other via phosphorothioate internucleotide linkages;
(5) a portion of the antisense strand is complementary to a portion of the sense strand;
(6) the sense strand comprises 100% 2'-O-methyl modifications; and
(7) the nucleotides at positions 1-2 from the 5' end of the sense strand are connected to each other via phosphorothioate internucleotide linkages.

In a fifth aspect, provided herein is a dsRNA comprising an antisense strand and a sense strand, each strand comprising at least 14 contiguous nucleotides, with a 5' end and a 3' end, wherein:

(1) the antisense strand comprises a sequence substantially complementary to a SOD1 nucleic acid sequence of any one of SEQ ID NOs: 1-11;
(2) the antisense strand comprises at least 75% 2'-O-methyl modifications;

(3) the nucleotides at positions 2, 4, 5, 6, and 14 from the 5' end of the antisense strand are not 2'-methoxy-ribonucleotides;
(4) the nucleotides at positions 1-2 to 1-7 from the 3' end of the antisense strand are connected to each other via phosphorothioate internucleotide linkages;
(5) a portion of the antisense strand is complementary to a portion of the sense strand;
(6) the sense strand comprises 100% 2'-O-methyl modifications; and
(7) the nucleotides at positions 1-2 from the 5' end of the sense strand are connected to each other via phosphorothioate internucleotide linkages.

In a sixth aspect, provided herein is a dsRNA comprising an antisense strand and a sense strand, each strand comprising at least 14 contiguous nucleotides, with a 5' end and a 3' end, wherein:
(1) the antisense strand comprises a sequence substantially complementary to a SOD1 nucleic acid sequence of any one of SEQ ID NOs: 1-11;
(2) the antisense strand comprises at least 75% 2'-O-methyl modifications;
(3) the nucleotides at positions 2, 6, 14, and 16 from the 5' end of the antisense strand are not 2'-methoxy-ribonucleotides;
(4) the nucleotides at positions 1-2 to 1-7 from the 3' end of the antisense strand are connected to each other via phosphorothioate internucleotide linkages;
(5) a portion of the antisense strand is complementary to a portion of the sense strand;
(6) the sense strand comprises at least 70% 2'-O-methyl modifications;
(7) the nucleotides at positions 7, 9, 10, and 11 from the 3' end of the sense strand are not 2'-methoxy-ribonucleotides; and
(8) the nucleotides at positions 1-2 from the 5' end of the sense strand are connected to each other via phosphorothioate internucleotide linkages.

In a seventh aspect, provided herein is a dsRNA comprising an antisense strand and a sense strand, each strand comprising at least 14 contiguous nucleotides, with a 5' end and a 3' end, wherein:
(1) the antisense strand comprises a sequence substantially complementary to a SOD1 nucleic acid sequence of any one of SEQ ID NOs: 1-11;
(2) the antisense strand comprises at least 75% 2'-O-methyl modifications;
(3) the nucleotides at positions 2, 6, and 14 from the 5' end of the antisense strand are not 2'-methoxy-ribonucleotides;
(4) the nucleotides at positions 1-2 to 1-7 from the 3' end of the antisense strand are connected to each other via phosphorothioate internucleotide linkages;
(5) a portion of the antisense strand is complementary to a portion of the sense strand;
(6) the sense strand comprises at least 80% 2'-O-methyl modifications;
(7) the nucleotides at positions 7, 10, and 11 from the 3' end of the sense strand are not 2'-methoxy-ribonucleotides; and
(8) the nucleotides at positions 1-2 from the 5' end of the sense strand are connected to each other via phosphorothioate internucleotide linkages.

a) Design of Anti-SOD1 siRNA Molecules

An siRNA molecule of the application is a duplex made of a sense strand and complementary antisense strand, the antisense strand having sufficient complementary to a SOD1 mRNA to mediate RNAi. In certain embodiments, the siRNA molecule has a length from about 10-50 or more nucleotides, i.e., each strand comprises 10-50 nucleotides (or nucleotide analogs). In other embodiments, the siRNA molecule has a length from about 15-30, e.g., 15, 16, 17, 18, 19, 20, 21, 22, 23, 24, 25, 26, 27, 28, 29, or 30 nucleotides in each strand, wherein one of the strands is sufficiently complementary to a target region. In certain embodiments, the strands are aligned such that there are at least 1, 2, 3, 4, 5, 6, 7, 8, 9, or 10 bases at the end of the strands, which do not align (i.e., for which no complementary bases occur in the opposing strand), such that an overhang of 1, 2, 3, 4, 5, 6, 7, 8, 9, or 10 residues occurs at one or both ends of the duplex when strands are annealed.

Usually, siRNAs can be designed by using any method known in the art, for instance, by using the following protocol:

1. The siRNA should be specific for a target sequence, e.g., a target sequence set forth in the Examples. The first strand should be complementary to the target sequence, and the other strand is substantially complementary to the first strand. (See Examples for exemplary sense and antisense strands.) Exemplary target sequences are selected from any region of the target gene that leads to potent gene silencing. Regions of the target gene include, but are not limited to, the 5' untranslated region (5'-UTR) of a target gene, the 3' untranslated region (3'-UTR) of a target gene, an exon of a target gene, or an intron of a target gene. Cleavage of mRNA at these sites should eliminate translation of corresponding SOD1 protein. Target sequences from other regions of the SOD1 gene are also suitable for targeting. A sense strand is designed based on the target sequence.

2. The sense strand of the siRNA is designed based on the sequence of the selected target site. In certain embodiments, the sense strand includes about 15 to 25 nucleotides, e.g., 15, 16, 17, 18, 19, 20, 21, 22, 23, 24 or 25 nucleotides. In certain embodiments, the sense strand includes 15, 16, 17, 18, 19, or 20 nucleotides. In certain embodiments, the sense strand is 15 nucleotides in length. In certain embodiments, the sense strand is 18 nucleotides in length. In certain embodiments, the sense strand is 20 nucleotides in length. The skilled artisan will appreciate, however, that siRNAs having a length of less than 15 nucleotides or greater than 25 nucleotides can also function to mediate RNAi. Accordingly, siRNAs of such length are also within the scope of the instant disclosure, provided that they retain the ability to mediate RNAi. Longer RNA silencing agents have been demonstrated to elicit an interferon or Protein Kinase R (PKR) response in certain mammalian cells which may be undesirable. In certain embodiments, the RNA silencing agents of the disclosure do not elicit a PKR response (i.e., are of a sufficiently short length). However, longer RNA silencing agents may be useful, for example, in cell types incapable of generating a PKR response or in situations where the PKR response has been down-regulated or dampened by alternative means.

The siRNA molecules of the disclosure have sufficient complementarity with the target sequence such that the siRNA can mediate RNAi. In general, siRNA containing nucleotide sequences sufficiently complementary to a target sequence portion of the target gene to effect RISC-mediated cleavage of the target gene are contemplated. Accordingly, in a certain embodiment, the antisense strand of the siRNA is designed to have a sequence sufficiently complementary to a portion of the target. For example, the antisense strand may have 100% complementarity to the target site. However, 100% complementarity is not required. Greater than 80% identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% complementarity, between the antisense strand and the target RNA sequence is contemplated. The present application has the advantage of being able to tolerate certain sequence variations to enhance efficiency and specificity of RNAi. In one embodiment, the antisense strand has 4, 3, 2, 1, or 0 mismatched nucleotide(s) with a target region, such as a target region that differs by at least one base pair between a wild-type and mutant allele, e.g., a target region comprising the gain-of-function mutation, and the other strand is identical or substantially identical to the first strand. Moreover, siRNA sequences with small insertions or deletions of 1 or 2 nucleotides may also be effective for mediating RNAi. Alternatively, siRNA sequences with nucleotide analog substitutions or insertions can be effective for inhibition.

Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=number of identical positions/total number of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10.

In another embodiment, the alignment is optimized by introducing appropriate gaps and the percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389-3402. In another embodiment, the alignment is optimized by introducing appropriate gaps and percent identity is determined over the entire length of the sequences aligned (i.e., a global alignment). A non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

3. The antisense or guide strand of the siRNA is routinely the same length as the sense strand and includes complementary nucleotides. In one embodiment, the guide and sense strands are fully complementary, i.e., the strands are blunt-ended when aligned or annealed. In another embodiment, the strands of the siRNA can be paired in such a way as to have a 3' overhang of 1 to 7 (e.g., 2, 3, 4, 5, 6 or 7), or 1 to 4, e.g., 2, 3 or 4 nucleotides. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material. Thus, in another embodiment, the nucleic acid molecules may have a 3' overhang of 2 nucleotides, such as TT. The overhanging nucleotides may be either RNA or DNA. As noted above, it is desirable to choose a target region wherein the mutant:wild type mismatch is a purine:purine mismatch.

4. Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at National Center for Biotechnology Information website.

5. Select one or more sequences that meet your criteria for evaluation.

Further general information about the design and use of siRNA may be found in "The siRNA User Guide," available at The Max-Plank-Institut fur Biophysikalische Chemie website.

Alternatively, the siRNA may be defined functionally as a nucleotide sequence (or oligonucleotide sequence) that is capable of hybridizing with the target sequence (e.g., 400 mM NaCl, 40 mM PIPES pH 6.4, 1 mM EDTA, 50° C. or 70° C. hybridization for 12-16 hours; followed by washing). Additional hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$(° C.)=2(# of A+T bases)+4(# of G+C bases). For hybrids between 18 and 49 base pairs in length, $T_m$(° C.)=81.5+16.6 (log 10[Na+])+0.41 (% G+C)-(600/N), where N is the number of bases in the hybrid, and [Na+] is the concentration of sodium ions in the hybridization buffer ([$Na^+$] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference.

Negative control siRNAs should have the same nucleotide composition as the selected siRNA, but without significant sequence complementarity to the appropriate genome. Such negative controls may be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

6. To validate the effectiveness by which siRNAs destroy target mRNAs (e.g., wild-type or mutant SOD1 mRNA), the siRNA may be incubated with target cDNA (e.g., SOD1 cDNA) in a *Drosophila*-based in vitro mRNA expression system. Radiolabeled with $^{32}P$, newly synthesized target mRNAs (e.g., SOD1 mRNA) are detected autoradiographically on an agarose gel. The presence of cleaved target mRNA indicates mRNA nuclease activity. Suitable controls include omission of siRNA and use of non-target cDNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

Anti-SOD1 siRNAs may be designed to target any of the target sequences described supra. Said siRNAs comprise an antisense strand, which is sufficiently complementary with the target sequence to mediate silencing of the target sequence. In certain embodiments, the RNA silencing agent is a siRNA.

In certain embodiments, the siRNA comprises a sense strand comprising a sequence set forth in Table 6 and Table 6, and an antisense strand comprising a sequence set forth in Table 5 and Table 6.

Sites of siRNA-mRNA complementation are selected, which result in optimal mRNA specificity and maximal mRNA cleavage.

b) siRNA-Like Molecules siRNA-like molecules of the disclosure have a sequence (i.e., have a strand having a sequence) that is "sufficiently complementary" to a target sequence of an SOD1 mRNA to direct gene silencing either by RNAi or translational repression. siRNA-like molecules are designed in the same way as siRNA molecules, but the degree of sequence identity between the sense strand and target RNA approximates that observed between a miRNA and its target. In general, as the degree of sequence identity between a miRNA sequence and the corresponding target gene sequence is decreased, the tendency to mediate post-transcriptional gene silencing by translational repression rather than RNAi is increased. Therefore, in an alternative embodiment, where post-transcriptional gene silencing by translational repression of the target gene is desired, the miRNA sequence has partial complementarity with the target gene sequence. In certain embodiments, the miRNA sequence has partial complementarity with one or more short sequences (complementarity sites) dispersed within the target mRNA (e.g. within the 3'-UTR of the target mRNA)(Hutvagner and Zamore, Science, 2002; Zeng et al., Mol. Cell, 2002; Zeng et al., RNA, 2003; Doench et al., Genes & Dev., 2003). Since the mechanism of translational repression is cooperative, multiple complementarity sites (e.g., 2, 3, 4, 5, or 6) may be targeted in certain embodiments.

The capacity of a siRNA-like duplex to mediate RNAi or translational repression may be predicted by the distribution of non-identical nucleotides between the target gene sequence and the nucleotide sequence of the silencing agent at the site of complementarity. In one embodiment, where gene silencing by translational repression is desired, at least one non-identical nucleotide is present in the central portion of the complementarity site so that duplex formed by the miRNA guide strand and the target mRNA contains a central "bulge" (Doench J G et al., Genes & Dev., 2003). In another embodiment 2, 3, 4, 5, or 6 contiguous or non-contiguous non-identical nucleotides are introduced. The non-identical nucleotide may be selected such that it forms a wobble base pair (e.g., G:U) or a mismatched base pair (G:A, C:A, C:U, G:G, A:A, C:C, U:U). In a further embodiment, the "bulge" is centered at nucleotide positions 12 and 13 from the 5' end of the miRNA molecule.

c) Short Hairpin RNA (shRNA) Molecules

In certain featured embodiments, the instant disclosure provides shRNAs capable of mediating RNA silencing of an SOD1 target sequence with enhanced selectivity. In contrast to siRNAs, shRNAs mimic the natural precursors of micro RNAs (miRNAs) and enter at the top of the gene silencing pathway. For this reason, shRNAs are believed to mediate gene silencing more efficiently by being fed through the entire natural gene silencing pathway.

miRNAs are noncoding RNAs of approximately 22 nucleotides, which can regulate gene expression at the post transcriptional or translational level during plant and animal development. One common feature of miRNAs is that they are all excised from an approximately 70 nucleotide precursor RNA stem-loop termed pre-miRNA, probably by Dicer, an RNase III-type enzyme, or a homolog thereof. Naturally-occurring miRNA precursors (pre-miRNA) have a single strand that forms a duplex stem including two portions that are generally complementary, and a loop, that connects the two portions of the stem. In typical pre-miRNAs, the stem includes one or more bulges, e.g., extra nucleotides that create a single nucleotide "loop" in one portion of the stem, and/or one or more unpaired nucleotides that create a gap in the hybridization of the two portions of the stem to each other. Short hairpin RNAs, or engineered RNA precursors, of the present application are artificial constructs based on these naturally occurring pre-miRNAs, but which are engineered to deliver desired RNA silencing agents (e.g., siRNAs of the disclosure). By substituting the stem sequences of the pre-miRNA with sequence complementary to the target mRNA, a shRNA is formed. The shRNA is processed by the entire gene silencing pathway of the cell, thereby efficiently mediating RNAi.

The requisite elements of a shRNA molecule include a first portion and a second portion, having sufficient complementarity to anneal or hybridize to form a duplex or double-stranded stem portion. The two portions need not be fully or perfectly complementary. The first and second "stem" portions are connected by a portion having a sequence that has insufficient sequence complementarity to anneal or hybridize to other portions of the shRNA. This latter portion is referred to as a "loop" portion in the shRNA molecule. The shRNA molecules are processed to generate siRNAs. shRNAs can also include one or more bulges, i.e., extra nucleotides that create a small nucleotide "loop" in a portion of the stem, for example a one-, two- or three-nucleotide loop. The stem portions can be the same length, or one portion can include an overhang of, for example, 1-5 nucleotides. The overhanging nucleotides can include, for example, uracils (Us), e.g., all Us. Such Us are notably encoded by thymidines (Ts) in the shRNA-encoding DNA which signal the termination of transcription.

In shRNAs (or engineered precursor RNAs) of the instant disclosure, one portion of the duplex stem is a nucleic acid sequence that is complementary (or anti-sense) to the SOD1 target sequence. In certain embodiments, one strand of the stem portion of the shRNA is sufficiently complementary (e.g., antisense) to a target RNA (e.g., mRNA) sequence to mediate degradation or cleavage of said target RNA via RNA interference (RNAi). Thus, engineered RNA precursors include a duplex stem with two portions and a loop connecting the two stem portions. The antisense portion can be on the 5' or 3' end of the stem. The stem portions of a shRNA are about 15 to about 50 nucleotides in length. In certain embodiments, the two stem portions are about 18 or 19 to about 21, 22, 23, 24, 25, 30, 35, 37, 38, 39, or 40 or more nucleotides in length. In certain embodiments, the length of the stem portions should be 21 nucleotides or greater. When used in mammalian cells, the length of the stem portions should be less than about 30 nucleotides to avoid provoking non-specific responses like the interferon pathway. In non-mammalian cells, the stem can be longer than 30 nucleotides. In fact, the stem can include much larger sections complementary to the target mRNA (up to, and including the entire mRNA). In fact, a stem portion can include much larger sections complementary to the target mRNA (up to, and including the entire mRNA).

The two portions of the duplex stem must be sufficiently complementary to hybridize to form the duplex stem. Thus, the two portions can be, but need not be, fully or perfectly complementary. In addition, the two stem portions can be the same length, or one portion can include an overhang of 1, 2, 3, or 4 nucleotides. The overhanging nucleotides can include, for example, uracils (Us), e.g., all Us. The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop in the shRNAs or engineered RNA precursors can be 2, 3, 4, 5, 6, 7, 8, 9, or more, e.g., 15 or 20, or more nucleotides in length.

The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop portion in the shRNA can be about 2 to about 20 nucleotides in length, i.e., about 2, 3, 4, 5, 6, 7, 8, 9, or more, e.g., 15 or 20, or more nucleotides in length. In certain embodiments, a loop consists of or comprises a "tetraloop" sequence. Exemplary tetraloop sequences include, but are not limited to, the sequences GNRA, where N is any nucleotide and R is a purine nucleotide, GGGG, and UUUU.

In certain embodiments, shRNAs of the present application include the sequences of a desired siRNA molecule described supra. In other embodiments, the sequence of the antisense portion of a shRNA can be designed essentially as described above or generally by selecting an 18, 19, 20, 21 nucleotide, or longer, sequence from within the target RNA (e.g., SOD1 mRNA), for example, from a region 100 to 200 or 300 nucleotides upstream or downstream of the start of translation. In general, the sequence can be selected from any portion of the target RNA (e.g., mRNA) including the 5' UTR (untranslated region), coding sequence, or 3' UTR. This sequence can optionally follow immediately after a region of the target gene containing two adjacent AA nucleotides. The last two nucleotides of the nucleotide sequence can be selected to be UU. This 21 or so nucleotide sequence is used to create one portion of a duplex stem in the shRNA. This sequence can replace a stem portion of a wild-type pre-miRNA sequence, e.g., enzymatically, or is included in a complete sequence that is synthesized. For example, one can synthesize DNA oligonucleotides that encode the entire stem-loop engineered RNA precursor, or that encode just the portion to be inserted into the duplex stem of the precursor, and using restriction enzymes to build the engineered RNA precursor construct, e.g., from a wild-type pre-miRNA.

Engineered RNA precursors include, in the duplex stem, the 21-22 or so nucleotide sequences of the siRNA or siRNA-like duplex desired to be produced in vivo. Thus, the stem portion of the engineered RNA precursor includes at least 18 or 19 nucleotide pairs corresponding to the sequence of an exonic portion of the gene whose expression is to be reduced or inhibited. The two 3' nucleotides flanking this region of the stem are chosen so as to maximize the production of the siRNA from the engineered RNA precursor and to maximize the efficacy of the resulting siRNA in targeting the corresponding mRNA for translational repression or destruction by RNAi in vivo and in vitro.

In certain embodiments, shRNAs of the disclosure include miRNA sequences, optionally end-modified miRNA sequences, to enhance entry into RISC. The miRNA sequence can be similar or identical to that of any naturally occurring miRNA (see e.g. The miRNA Registry; Griffiths-Jones S, Nuc. Acids Res., 2004). Over one thousand natural miRNAs have been identified to date and together they are thought to comprise about 1% of all predicted genes in the genome. Many natural miRNAs are clustered together in the introns of pre-mRNAs and can be identified in silico using homology-based searches (Pasquinelli et al., 2000; Lagos-Quintana et al., 2001; Lau et al., 2001; Lee and Ambros, 2001) or computer algorithms (e.g. MiRScan, MiRSeeker) that predict the capability of a candidate miRNA gene to form the stem loop structure of a pri-mRNA (Grad et al., Mol. Cell., 2003; Lim et al., Genes Dev., 2003; Lim et al., Science, 2003; Lai E C et al., Genome Bio., 2003). An online registry provides a searchable database of all published miRNA sequences (The miRNA Registry at the Sanger Institute website; Griffiths-Jones S, Nuc. Acids Res., 2004). Exemplary, natural miRNAs include lin-4, let-7, miR-10, mirR-15, miR-16, miR-168, miR-175, miR-196 and their homologs, as well as other natural miRNAs from humans and certain model organisms including *Drosophila melanogaster, Caenorhabditis elegans*, zebrafish, *Arabidopsis thalania, Mus musculus*, and *Rattus norvegicus* as described in International PCT Publication No. WO 03/029459.

Naturally-occurring miRNAs are expressed by endogenous genes in vivo and are processed from a hairpin or stem-loop precursor (pre-miRNA or pri-miRNAs) by Dicer or other RNAses (Lagos-Quintana et al., Science, 2001; Lau et al., Science, 2001; Lee and Ambros, Science, 2001; Lagos-Quintana et al., Curr. Biol., 2002; Mourelatos et al., Genes Dev., 2002; Reinhart et al., Science, 2002; Ambros et al., Curr. Biol., 2003; Brennecke et al., 2003; Lagos-Quintana et al., RNA, 2003; Lim et al., Genes Dev., 2003; Lim et al., Science, 2003). miRNAs can exist transiently in vivo as a double-stranded duplex, but only one strand is taken up by the RISC complex to direct gene silencing. Certain miRNAs, e.g., plant miRNAs, have perfect or near-perfect complementarity to their target mRNAs and, hence, direct cleavage of the target mRNAs. Other miRNAs have less than perfect complementarity to their target mRNAs and, hence, direct translational repression of the target mRNAs. The degree of complementarity between a miRNA and its target mRNA is believed to determine its mechanism of action. For example, perfect or near-perfect complementarity between a miRNA and its target mRNA is predictive of a cleavage mechanism (Yekta et al., Science, 2004), whereas less than perfect complementarity is predictive of a translational repression mechanism. In certain embodiments, the miRNA sequence is that of a naturally-occurring miRNA sequence, the aberrant expression or activity of which is correlated with a miRNA disorder.

d) Dual Functional Oligonucleotide Tethers

In other embodiments, the RNA silencing agents of the present disclosure include dual functional oligonucleotide tethers useful for the intercellular recruitment of a miRNA. Animal cells express a range of miRNAs, noncoding RNAs of approximately 22 nucleotides which can regulate gene expression at the post transcriptional or translational level. By binding a miRNA bound to RISC and recruiting it to a target mRNA, a dual functional oligonucleotide tether can repress the expression of genes involved e.g., in the arteriosclerotic process. The use of oligonucleotide tethers offers several advantages over existing techniques to repress the expression of a particular gene. First, the methods described herein allow an endogenous molecule (often present in abundance), a miRNA, to mediate RNA silencing. Accordingly, the methods described herein obviate the need to introduce foreign molecules (e.g., siRNAs) to mediate RNA silencing. Second, the RNA-silencing agents and the linking moiety (e.g., oligonucleotides such as the 2'-O-methyl oligonucleotide), can be made stable and resistant to nuclease activity. As a result, the tethers of the present disclosure can be designed for direct delivery, obviating the need for indirect delivery (e.g. viral) of a precursor molecule or plasmid designed to make the desired agent within the cell. Third, tethers and their respective moieties, can be designed to conform to specific mRNA sites and specific miRNAs. The designs can be cell and gene product specific. Fourth, the methods disclosed herein leave the mRNA intact, allowing one skilled in the art to block protein synthesis in short pulses using the cell's own machinery. As a result, these methods of RNA silencing are highly regulatable.

The dual functional oligonucleotide tethers ("tethers") of the disclosure are designed such that they recruit miRNAs (e.g., endogenous cellular miRNAs) to a target mRNA so as to induce the modulation of a gene of interest. In certain embodiments, the tethers have the formula T-L-μ, wherein T is an mRNA targeting moiety, L is a linking moiety, and μ is a miRNA recruiting moiety. Any one or more moiety may be double stranded. In certain embodiments, each moiety is single stranded.

Moieties within the tethers can be arranged or linked (in the 5' to 3' direction) as depicted in the formula T-L-μ (i.e., the 3' end of the targeting moiety linked to the 5' end of the linking moiety and the 3' end of the linking moiety linked to the 5' end of the miRNA recruiting moiety). Alternatively, the moieties can be arranged or linked in the tether as follows: μ-T-L (i.e., the 3' end of the miRNA recruiting moiety linked to the 5' end of the linking moiety and the 3' end of the linking moiety linked to the 5' end of the targeting moiety).

The mRNA targeting moiety, as described above, is capable of capturing a specific target mRNA. According to the disclosure, expression of the target mRNA is undesirable, and, thus, translational repression of the mRNA is desired. The mRNA targeting moiety should be of sufficient size to effectively bind the target mRNA. The length of the targeting moiety will vary greatly, depending, in part, on the length of the target mRNA and the degree of complementarity between the target mRNA and the targeting moiety. In various embodiments, the targeting moiety is less than about 200, 100, 50, 30, 25, 20, 19, 18, 17, 16, 15, 14, 13, 12, 11, 10, 9, 8, 7, 6, or 5 nucleotides in length. In a certain embodiment, the targeting moiety is about 15 to about 25 nucleotides in length.

The miRNA recruiting moiety, as described above, is capable of associating with a miRNA. According to the present application, the miRNA may be any miRNA capable of repressing the target mRNA. Mammals are reported to have over 250 endogenous miRNAs (Lagos-Quintana et al. (2002) Current Biol. 12:735-739; Lagos-Quintana et al. (2001) Science 294:858-862; and Lim et al. (2003) Science 299:1540). In various embodiments, the miRNA may be any art-recognized miRNA.

The linking moiety is any agent capable of linking the targeting moieties such that the activity of the targeting moieties is maintained. Linking moieties can be oligonucleotide moieties comprising a sufficient number of nucleotides, such that the targeting agents can sufficiently interact with their respective targets. Linking moieties have little or no sequence homology with cellular mRNA or miRNA sequences. Exemplary linking moieties include one or more 2'-O-methylnucleotides, e.g., 2'-β-methyladenosine, 2' methylthymidine, 2'-O-methylguanosine or 2'-O-methyluridine.

e) Gene Silencing Oligonucleotides

In certain exemplary embodiments, gene expression (i.e., SOD1 gene expression) can be modulated using oligonucleotide-based compounds comprising two or more single stranded antisense oligonucleotides that are linked through their 5'-ends that allow the presence of two or more accessible 3'-ends to effectively inhibit or decrease SOD1 gene expression. Such linked oligonucleotides are also known as Gene Silencing Oligonucleotides (GSOs). (See, e.g., U.S. Pat. No. 8,431,544 assigned to Idera Pharmaceuticals, Inc., incorporated herein by reference in its entirety for all purposes.)

The linkage at the 5' ends of the GSOs is independent of the other oligonucleotide linkages and may be directly via 5', 3' or 2' hydroxyl groups, or indirectly, via a non-nucleotide linker or a nucleoside, utilizing either the 2' or 3' hydroxyl positions of the nucleoside. Linkages may also utilize a functionalized sugar or nucleobase of a 5' terminal nucleotide.

GSOs can comprise two identical or different sequences conjugated at their 5'-5' ends via a phosphodiester, phosphorothioate or non-nucleoside linker. Such compounds may comprise 15 to 27 nucleotides that are complementary to specific portions of mRNA targets of interest for antisense down regulation of a gene product. GSOs that comprise identical sequences can bind to a specific mRNA via Watson-Crick hydrogen bonding interactions and inhibit protein expression. GSOs that comprise different sequences are able to bind to two or more different regions of one or more mRNA target and inhibit protein expression. Such compounds are comprised of heteronucleotide sequences complementary to target mRNA and form stable duplex structures through Watson-Crick hydrogen bonding. Under certain conditions, GSOs containing two free 3'-ends (5'-5'-attached antisense) can be more potent inhibitors of gene expression than those containing a single free 3'-end or no free 3'-end.

In some embodiments, the non-nucleotide linker is glycerol or a glycerol homolog of the formula $HO—(CH_2)_o—CH(OH)—(CH_2)_p—OH$, wherein o and p independently are integers from 1 to about 6, from 1 to about 4 or from 1 to about 3. In some other embodiments, the non-nucleotide linker is a derivative of 1,3-diamino-2-hydroxypropane. Some such derivatives have the formula $HO—(CH_2)_m—C(O)NH—CH_2—CH(OH)—CH_2—NHC(O)—(CH_2)_m—OH$, wherein m is an integer from 0 to about 10, from 0 to about 6, from 2 to about 6 or from 2 to about 4.

Some non-nucleotide linkers permit attachment of more than two GSO components. For example, the non-nucleotide linker glycerol has three hydroxyl groups to which GSO components may be covalently attached. Some oligonucleotide-based compounds of the disclosure, therefore, comprise two or more oligonucleotides linked to a nucleotide or a non-nucleotide linker. Such oligonucleotides according to the disclosure are referred to as being "branched."

In certain embodiments, GSOs are at least 14 nucleotides in length. In certain exemplary embodiments, GSOs are 15 to 40 nucleotides long or 20 to 30 nucleotides in length. Thus, the component oligonucleotides of GSOs can independently be 14, 15, 16, 17, 18, 19, 20, 21, 22, 23, 24, 25, 26, 27, 28, 29, 30, 31, 32, 33, 34, 35, 36, 37, 38, 39 or 40 nucleotides in length.

These oligonucleotides can be prepared by the art recognized methods, such as phosphoramidate or H-phosphonate chemistry, which can be carried out manually or by an automated synthesizer. These oligonucleotides may also be modified in a number of ways without compromising their ability to hybridize to mRNA. Such modifications may include at least one internucleotide linkage of the oligonucleotide being an alkylphosphonate, phosphorothioate, phosphorodithioate, methylphosphonate, phosphate ester, alkylphosphonothioate, phosphoramidate, carbamate, carbonate, phosphate hydroxyl, acetamidate, carboxymethyl ester, or a combination of these and other internucleotide linkages between the 5' end of one nucleotide and the 3' end of another nucleotide, in which the 5' nucleotide phosphodiester linkage has been replaced with any number of chemical groups.

V. Modified Anti-SOD1 RNA Silencing Agents

In certain aspects of the disclosure, an RNA silencing agent (or any portion thereof) of the present application, as described supra, may be modified, such that the activity of the agent is further improved. For example, the RNA silencing agents described in Section II supra, may be modified with any of the modifications described infra. The modifications can, in part, serve to further enhance target discrimination, to enhance stability of the agent (e.g., to prevent degradation), to promote cellular uptake, to enhance the target efficiency, to improve efficacy in binding (e.g., to the targets), to improve patient tolerance to the agent, and/or to reduce toxicity.

1) Modifications to Enhance Target Discrimination

In certain embodiments, the RNA silencing agents of the present application may be substituted with a destabilizing nucleotide to enhance single nucleotide target discrimination (see U.S. application Ser. No. 11/698,689, filed Jan. 25, 2007 and U.S. Provisional Application No. 60/762,225 filed Jan. 25, 2006, both of which are incorporated herein by reference). Such a modification may be sufficient to abolish the specificity of the RNA silencing agent for a non-target mRNA (e.g. wild-type mRNA), without appreciably affecting the specificity of the RNA silencing agent for a target mRNA (e.g. gain-of-function mutant mRNA).

In certain embodiments, the RNA silencing agents of the present application are modified by the introduction of at least one universal nucleotide in the antisense strand thereof. Universal nucleotides comprise base portions that are capable of base pairing indiscriminately with any of the four conventional nucleotide bases (e.g. A, G, C, U). A universal nucleotide is contemplated because it has relatively minor effect on the stability of the RNA duplex or the duplex formed by the guide strand of the RNA silencing agent and the target mRNA. Exemplary universal nucleotides include those having an inosine base portion or an inosine analog base portion selected from the group consisting of deoxyinosine (e.g. 2'-deoxyinosine), 7-deaza-2'-deoxyinosine, 2'-aza-2'-deoxyinosine, PNA-inosine, morpholino-inosine, LNA-inosine, phosphoramidate-inosine, 2'-O-methoxyethyl-inosine, and 2'-OMe-inosine. In certain embodiments, the universal nucleotide is an inosine residue or a naturally occurring analog thereof.

In certain embodiments, the RNA silencing agents of the disclosure are modified by the introduction of at least one destabilizing nucleotide within 5 nucleotides from a specificity-determining nucleotide (i.e., the nucleotide which recognizes the disease-related polymorphism). For example, the destabilizing nucleotide may be introduced at a position that is within 5, 4, 3, 2, or 1 nucleotide(s) from a specificity-determining nucleotide. In exemplary embodiments, the destabilizing nucleotide is introduced at a position which is 3 nucleotides from the specificity-determining nucleotide (i.e., such that there are 2 stabilizing nucleotides between the destablilizing nucleotide and the specificity-determining nucleotide). In RNA silencing agents having two strands or strand portions (e.g. siRNAs and shRNAs), the destabilizing nucleotide may be introduced in the strand or strand portion that does not contain the specificity-determining nucleotide. In certain embodiments, the destabilizing nucleotide is introduced in the same strand or strand portion that contains the specificity-determining nucleotide.

2) Modifications to Enhance Efficacy and Specificity

In certain embodiments, the RNA silencing agents of the disclosure may be altered to facilitate enhanced efficacy and specificity in mediating RNAi according to asymmetry design rules (see U.S. Pat. Nos. 8,309,704, 7,750,144, 8,304,530, 8,329,892 and 8,309,705). Such alterations facilitate entry of the antisense strand of the siRNA (e.g., a siRNA designed using the methods of the present application or an siRNA produced from a shRNA) into RISC in favor of the sense strand, such that the antisense strand preferentially guides cleavage or translational repression of a target mRNA, and thus increasing or improving the efficiency of target cleavage and silencing. In certain embodiments, the asymmetry of an RNA silencing agent is enhanced by lessening the base pair strength between the antisense strand 5' end (AS 5') and the sense strand 3' end (S 3') of the RNA silencing agent relative to the bond strength or base pair strength between the antisense strand 3' end (AS 3') and the sense strand 5' end (S'5) of said RNA silencing agent.

In one embodiment, the asymmetry of an RNA silencing agent of the present application may be enhanced such that there are fewer G:C base pairs between the 5' end of the first or antisense strand and the 3' end of the sense strand portion than between the 3' end of the first or antisense strand and the 5' end of the sense strand portion. In another embodiment, the asymmetry of an RNA silencing agent of the disclosure may be enhanced such that there is at least one mismatched base pair between the 5' end of the first or antisense strand and the 3' end of the sense strand portion. In certain embodiments, the mismatched base pair is selected from the group consisting of G:A, C:A, C:U, G:G, A:A, C:C and U:U. In another embodiment, the asymmetry of an RNA silencing agent of the disclosure may be enhanced such that there is at least one wobble base pair, e.g., G:U, between the 5' end of the first or antisense strand and the 3' end of the sense strand portion. In another embodiment, the asymmetry of an RNA silencing agent of the disclosure may be enhanced such that there is at least one base pair comprising a rare nucleotide, e.g., inosine (I). In certain embodiments, the base pair is selected from the group consisting of an I:A, I:U and I:C. In yet another embodiment, the asymmetry of an RNA silencing agent of the disclosure may be enhanced such that there is at least one base pair comprising a modified nucleotide. In certain embodiments, the modified nucleotide is selected from the group consisting of 2-amino-G, 2-amino-A, 2,6-diamino-G, and 2,6-diamino-A.

3) RNA Silencing Agents with Enhanced Stability

The RNA silencing agents of the present application can be modified to improve stability in serum or in growth medium for cell cultures. In order to enhance the stability, the 3'-residues may be stabilized against degradation, e.g., they may be selected such that they consist of purine nucleotides, such as adenosine or guanosine nucleotides. Alternatively, substitution of pyrimidine nucleotides by modified analogues, e.g., substitution of uridine by 2'-deoxythymidine is tolerated and does not affect the efficiency of RNA interference.

In a one aspect, the present application features RNA silencing agents that include first and second strands wherein the second strand and/or first strand is modified by the substitution of internal nucleotides with modified nucleotides, such that in vivo stability is enhanced as compared to a corresponding unmodified RNA silencing agent. As defined herein, an "internal" nucleotide is one occurring at any position other than the 5' end or 3' end of nucleic acid molecule, polynucleotide or oligonucleotide. An internal nucleotide can be within a single-stranded molecule or within a strand of a duplex or double-stranded molecule. In one embodiment, the sense strand and/or antisense strand is modified by the substitution of at least one internal nucleotide. In another embodiment, the sense strand and/or antisense strand is modified by the substitution of at least 2, 3, 4, 5, 6, 7, 8, 9, 10, 11, 12, 13, 14, 15, 16, 17, 18, 19, 20, 21, 22, 23, 24, 25 or more internal nucleotides. In another embodiment, the sense strand and/or antisense strand is modified by the substitution of at least 5%, 10%, 15%, 20%, 25%, 30%, 35%, 40%, 45%, 50%, 55%, 60%, 65%, 70%, 75%, 80%, 85%, 90%, 95% or more of the internal nucleotides. In yet another embodiment, the sense strand and/or antisense strand is modified by the substitution of all of the internal nucleotides.

In one aspect, the present application features RNA silencing agents that are at least 80% chemically modified. In certain embodiments, the RNA silencing agents may be fully chemically modified, i.e., 100% of the nucleotides are chemically modified. In another aspect, the present application features RNA silencing agents comprising 2'-OH ribose groups that are at least 80% chemically modified. In certain embodiments, the RNA silencing agents comprise 2'-OH ribose groups that are about 80%, 85%, 90%, 95%, or 100% chemically modified.

In certain embodiments, the RNA silencing agents may contain at least one modified nucleotide analogue. The nucleotide analogues may be located at positions where the target-specific silencing activity, e.g., the RNAi mediating activity or translational repression activity is not substantially affected, e.g., in a region at the 5'-end and/or the 3'-end of the siRNA molecule. Moreover, the ends may be stabilized by incorporating modified nucleotide analogues.

Exemplary nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In exemplary backbone-modified ribonucleotides, the phosphoester group connecting to adjacent ribonucleotides is replaced by a modified group, e.g., of phosphothioate group. In exemplary sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

In certain embodiments, the modifications are 2'-fluoro, 2'-amino and/or 2'-thio modifications. Modifications include 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine, 2,6-diaminopurine, 4-thio-uridine, and/or 5-amino-allyl-uridine. In a certain embodiment, the 2'-fluoro ribonucleotides are every uridine and cytidine. Additional exemplary modifications include 5-bromo-uridine, 5-iodo-uridine, 5-methyl-cytidine, ribo-thymidine, 2-aminopurine, 2'-amino-butyryl-pyrene-uridine, 5-fluoro-cytidine, and 5-fluoro-uridine. 2'-deoxy-nucleotides and 2'-Ome nucleotides can also be used within modified RNA-silencing agents moities of the instant disclosure. Additional modified residues include, deoxy-abasic, inosine, N3-methyl-uridine, N6,N6-dimethyl-adenosine, pseudouridine, purine ribonucleoside and ribavirin. In a certain embodiment, the 2' moiety is a methyl group such that the linking moiety is a 2'-O-methyl oligonucleotide.

In a certain embodiment, the RNA silencing agent of the present application comprises Locked Nucleic Acids (LNAs). LNAs comprise sugar-modified nucleotides that resist nuclease activities (are highly stable) and possess single nucleotide discrimination for mRNA (Elmen et al., Nucleic Acids Res., (2005), 33(1): 439-447; Braasch et al. (2003) Biochemistry 42:7967-7975, Petersen et al. (2003) Trends Biotechnol 21:74-81). These molecules have 2'-O, 4'-C-ethylene-bridged nucleic acids, with possible modifications such as 2'-deoxy-2"-fluorouridine. Moreover, LNAs increase the specificity of oligonucleotides by constraining the sugar moiety into the 3'-endo conformation, thereby pre-organizing the nucleotide for base pairing and increasing the melting temperature of the oligonucleotide by as much as 10° C. per base.

In another exemplary embodiment, the RNA silencing agent of the present application comprises Peptide Nucleic Acids (PNAs). PNAs comprise modified nucleotides in which the sugar-phosphate portion of the nucleotide is replaced with a neutral 2-amino ethylglycine moiety capable of forming a polyamide backbone, which is highly resistant to nuclease digestion and imparts improved binding specificity to the molecule (Nielsen, et al., Science, (2001), 254: 1497-1500).

Also contemplated are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

In other embodiments, cross-linking can be employed to alter the pharmacokinetics of the RNA silencing agent, for example, to increase half-life in the body. Thus, the present application includes RNA silencing agents having two complementary strands of nucleic acid, wherein the two strands are crosslinked. The present application also includes RNA silencing agents which are conjugated or unconjugated (e.g., at its 3' terminus) to another moiety (e.g.

a non-nucleic acid moiety such as a peptide), an organic compound (e.g., a dye), or the like). Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Other exemplary modifications include: (a) 2' modification, e.g., provision of a 2' OMe moiety on a U in a sense or antisense strand, but especially on a sense strand, or provision of a 2' OMe moiety in a 3' overhang, e.g., at the 3' terminus (3' terminus means at the 3' atom of the molecule or at the most 3' moiety, e.g., the most 3' P or 2' position, as indicated by the context); (b) modification of the backbone, e.g., with the replacement of an 0 with an S, in the phosphate backbone, e.g., the provision of a phosphorothioate modification, on the U or the A or both, especially on an antisense strand; e.g., with the replacement of a 0 with an S; (c) replacement of the U with a C5 amino linker; (d) replacement of an A with a G (sequence changes can be located on the sense strand and not the antisense strand in certain embodiments); and (d) modification at the 2', 6', 7', or 8' position. Exemplary embodiments are those in which one or more of these modifications are present on the sense but not the antisense strand, or embodiments where the antisense strand has fewer of such modifications. Yet other exemplary modifications include the use of a methylated P in a 3' overhang, e.g., at the 3' terminus; combination of a 2' modification, e.g., provision of a 2' O Me moiety and modification of the backbone, e.g., with the replacement of a 0 with an S, e.g., the provision of a phosphorothioate modification, or the use of a methylated P, in a 3' overhang, e.g., at the 3' terminus; modification with a 3' alkyl; modification with an abasic pyrrolidone in a 3' overhang, e.g., at the 3' terminus; modification with naproxen, ibuprofen, or other moieties which inhibit degradation at the 3' terminus.

Heavily Modified RNA Silencing Agents

In certain embodiments, the RNA silencing agent comprises at least 80% chemically modified nucleotides. In certain embodiments, the RNA silencing agent is fully chemically modified, i.e., 100% of the nucleotides are chemically modified.

In certain embodiments, the RNA silencing agent is 2'-O-methyl rich, i.e., comprises greater than 50% 2'-O-methyl content. In certain embodiments, the RNA silencing agent comprises at least about 55%, 60%, 65%, 70%, 75%, 80%, 85%, 90%, 95%, or 100% 2'-O-methyl nucleotide content. In certain embodiments, the RNA silencing agent comprises at least about 70% 2'-O-methyl nucleotide modifications. In certain embodiments, the RNA silencing agent comprises between about 70% and about 90% 2'-O-methyl nucleotide modifications. In certain embodiments, the RNA silencing agent is a dsRNA comprising an antisense strand and sense strand. In certain embodiments, the antisense strand comprises at least about 70% 2'-O-methyl nucleotide modifications. In certain embodiments, the antisense strand comprises between about 70% and about 90% 2'-O-methyl nucleotide modifications. In certain embodiments, the sense strand comprises at least about 70% 2'-O-methyl nucleotide modifications. In certain embodiments, the sense strand comprises between about 70% and about 90% 2'-O-methyl nucleotide modifications. In certain embodiments, the sense strand comprises between 100% 2'-O-methyl nucleotide modifications.

2'-O-methyl rich RNA silencing agents and specific chemical modification patterns are further described in U.S. Ser. No. 16/550,076 (filed Aug. 23, 2019) and U.S. Ser. No. 62/891,185 (filed Aug. 23, 2019), each of which is incorporated herein by reference.

Internucleotide Linkage Modifications

In certain embodiments, at least one internucleotide linkage, intersubunit linkage, or nucleotide backbone is modified in the RNA silencing agent. In certain embodiments, all of the internucleotide linkages in the RNA silencing agent are modified. In certain embodiments, the modified internucleotide linkage comprises a phosphorothioate internucleotide linkage. In certain embodiments, the RNA silencing agent comprise 1, 2, 3, 4, 5, 6, 7, 8, 9, 10, 11, 12, 13, 14, 15, 16, 17, 18, 19, 20, 21, 22, 23, 24, or 25 phosphorothioate internucleotide linkages. In certain embodiments, the RNA silencing agent comprises 4-16 phosphorothioate internucleotide linkages. In certain embodiments, the RNA silencing agent comprises 8-13 phosphorothioate internucleotide linkages. In certain embodiments, the RNA silencing agent is a dsRNA comprising an antisense strand and a sense strand, each comprising a 5' end and a 3' end. In certain embodiments, the nucleotides at positions 1 and 2 from the 5' end of sense strand are connected to adjacent ribonucleotides via phosphorothioate internucleotide linkages. In certain embodiments, the nucleotides at positions 1 and 2 from the 3' end of sense strand are connected to adjacent ribonucleotides via phosphorothioate internucleotide linkages. In certain embodiments, the nucleotides at positions 1 and 2 from the 5' end of antisense strand are connected to adjacent ribonucleotides via phosphorothioate internucleotide linkages. In certain embodiments, the nucleotides at positions 1-2 to 1-8 from the 3' end of antisense strand are connected to adjacent ribonucleotides via phosphorothioate internucleotide linkages. In certain embodiments, the nucleotides at positions 1-2, 1-3, 1-4, 1-5, 1-6, 1-7, or 1-8 from the 3' end of antisense strand are connected to adjacent ribonucleotides via phosphorothioate internucleotide linkages. In certain embodiments, the nucleotides at positions 1-2 to 1-7 from the 3' end of antisense strand are connected to adjacent ribonucleotides via phosphorothioate internucleotide linkages.

In one aspect, the disclosure provides a modified oligonucleotide, said oligonucleotide having a 5' end, a 3' end, that is complementary to a target, wherein the oligonucleotide comprises a sense and antisense strand, and at least one modified intersubunit linkage of Formula (I):

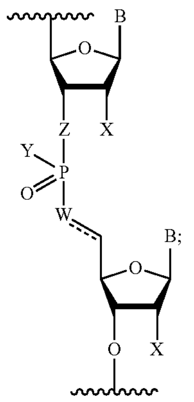

(I)

wherein:

B is a base pairing moiety;

W is selected from the group consisting of O, $OCH_2$, OCH, $CH_2$, and CH;

X is selected from the group consisting of halo, hydroxy, and $C_{1-6}$ alkoxy;

Y is selected from the group consisting of $O^-$, OH, OR, $NH^-$, $NH_2$, $S^-$, and SH;

Z is selected from the group consisting of O and $CH_2$;

R is a protecting group; and $\overline{---}$ is an optional double bond.

In an embodiment of Formula (I), when W is CH, $\overline{---}$ is a double bond.

In an embodiment of Formula (I), when W selected from the group consisting of O, $OCH_2$, OCH, $CH_2$, $\overline{---}$ is a single bond.

In an embodiment of Formula (I), when Y is $O^-$, either Z or W is not O.

In an embodiment of Formula (I), Z is $CH_2$ and W is $CH_2$. In another embodiment, the modified intersubunit linkage of Formula (I) is a modified intersubunit linkage of Formula (II):

(II)

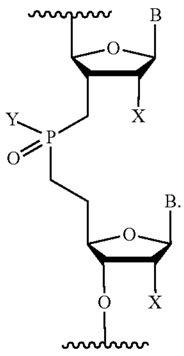

In an embodiment of Formula (I), Z is $CH_2$ and W is O. In another embodiment, wherein the modified intersubunit linkage of Formula (I) is a modified intersubunit linkage of Formula (III):

(III)

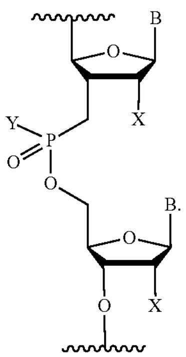

In an embodiment of Formula (I), Z is O and W is $CH_2$. In another embodiment, the modified intersubunit linkage of Formula (I) is a modified intersubunit linkage of Formula (IV):

(IV)

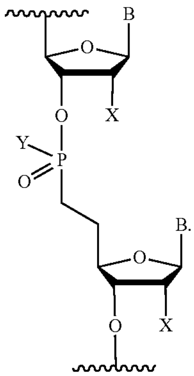

In an embodiment of Formula (I), Z is O and W is CH. In another embodiment, the modified intersubunit linkage of Formula (I) is a modified intersubunit linkage of Formula V:

(V)

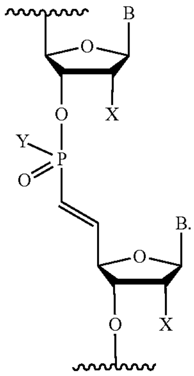

In an embodiment of Formula (I), Z is O and W is $OCH_2$. In another embodiment, the modified intersubunit linkage of Formula (I) is a modified intersubunit linkage of Formula VI:

(VI)

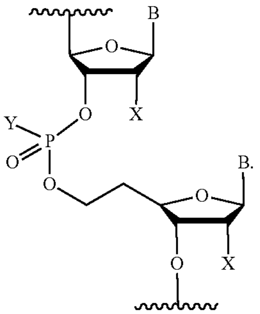

In an embodiment of Formula (I), Z is $CH_2$ and W is CH. In another embodiment, the modified intersubunit linkage of Formula (I) is a modified intersubunit linkage of Formula VII:

(VII)

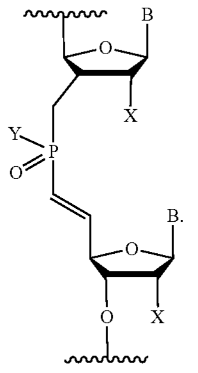

In an embodiment of Formula (I), the base pairing moiety B is selected from the group consisting of adenine, guanine, cytosine, and uracil.

In an embodiment, the modified oligonucleotide is incorporated into siRNA, said modified siRNA having a 5' end, a 3' end, that is complementary to a target, wherein the siRNA comprises a sense and antisense strand, and at least one modified intersubunit linkage of any one or more of Formula (I), Formula (II), Formula (III), Formula (IV), Formula (V), Formula (VI), or Formula (VII).

In an embodiment, the modified oligonucleotide is incorporated into siRNA, said modified siRNA having a 5' end, a 3' end, that is complementary to a target and comprises a sense and antisense strand, wherein the siRNA comprises at least one modified intersubunit linkage is of Formula VIII:

(VIII)

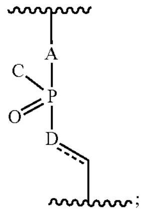

wherein:

D is selected from the group consisting of O, $OCH_2$, OCH, $CH_2$, and CH;

C is selected from the group consisting of $O^-$, OH, OR', $NH^-$, $NH_2$, $S^-$, and SH;

A is selected from the group consisting of O and $CH_2$;

$R^1$ is a protecting group;

is an optional double bond; and the intersubunit is bridging two optionally modified nucleosides.

In an embodiment, when C is $O^-$, either A or D is not O.

In an embodiment, D is $CH_2$. In another embodiment, the modified intersubunit linkage of Formula VIII is a modified intersubunit linkage of Formula (IX):

(IX)

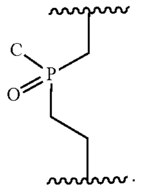

In an embodiment, D is O. In another embodiment, the modified intersubunit linkage of Formula VIII is a modified intersubunit linkage of Formula (X):

(X)

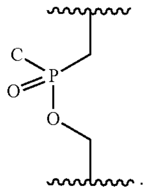

In an embodiment, D is $CH_2$. In another embodiment, the modified intersubunit linkage of Formula (VIII) is a modified intersubunit linkage of Formula (XI):

(XI)

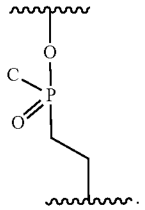

In an embodiment, D is CH. In another embodiment, the modified intersubunit linkage of Formula VIII is a modified intersubunit linkage of Formula (XII):

(XII)

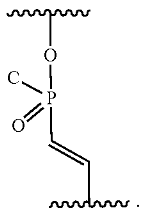

In another embodiment, the modified intersubunit linkage of Formula (VII) is a modified intersubunit linkage of Formula (XIV):

(XIV)

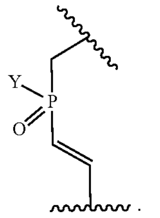

In an embodiment, D is $OCH_2$. In another embodiment, the modified intersubunit linkage of Formula (VII) is a modified intersubunit linkage of Formula (XIII):

(XIII)

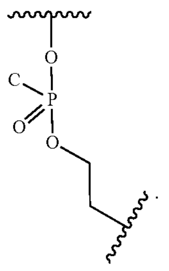

In another embodiment, the modified intersubunit linkage of Formula (VII) is a modified intersubunit linkage of Formula (XXa):

(XXa)

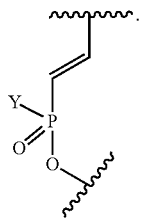

In an embodiment of the modified siRNA linkage, each optionally modified nucleoside is independently, at each occurrence, selected from the group consisting of adenosine, guanosine, cytidine, and uridine.

In certain exemplary embodiments of Formula (I), W is O. In another embodiment, W is $CH_2$. In yet another embodiment, W is CH.

In certain exemplary embodiments of Formula (I), X is OH. In another embodiment, X is $OCH_3$. In yet another embodiment, X is halo.

In a certain embodiment of Formula (I), the modified siRNA does not comprise a 2'-fluoro substituent.

In an embodiment of Formula (I), Y is $O^-$. In another embodiment, Y is OH. In yet another embodiment, Y is OR. In still another embodiment, Y is $NH^-$. In an embodiment, Y is $NH_2$. In another embodiment, Y is S. In yet another embodiment, Y is SH.

In an embodiment of Formula (I), Z is O. In another embodiment, Z is $CH_2$.

In an embodiment, the modified intersubunit linkage is inserted on position 1-2 of the antisense strand. In another embodiment, the modified intersubunit linkage is inserted on position 6-7 of the antisense strand. In yet another embodiment, the modified intersubunit linkage is inserted on position 10-11 of the antisense strand. In still another embodiment, the modified intersubunit linkage is inserted on position 19-20 of the antisense strand. In an embodiment, the modified intersubunit linkage is inserted on positions 5-6 and 18-19 of the antisense strand.

In an exemplary embodiment of the modified siRNA linkage of Formula (VIII), C is $O^-$. In another embodiment, C is OH. In yet another embodiment, C is OR'. In still another embodiment, C is $NH^-$. In an embodiment, C is $NH_2$. In another embodiment, C is S. In yet another embodiment, C is SH.

In an exemplary embodiment of the modified siRNA linkage of Formula (VIII), A is O. In another embodiment, A is $CH_2$. In yet another embodiment, C is OR'. In still another embodiment, C is $NH^-$. In an embodiment, C is $NH_2$. In another embodiment, C is S. In yet another embodiment, C is SH.

In a certain embodiment of the modified siRNA linkage of Formula (VIII), the optionally modified nucleoside is adenosine. In another embodiment of the modified siRNA linkage of Formula (VIII), the optionally modified nucleoside is guanosine. In another embodiment of the modified siRNA linkage of Formula (VIII), the optionally modified nucleoside is cytidine. In another embodiment of the modified siRNA linkage of Formula (VIII), the optionally modified nucleoside is uridine.

In an embodiment of the modified siRNA linkage, wherein the linkage is inserted on position 1-2 of the antisense strand. In another embodiment, the linkage is inserted on position 6-7 of the antisense strand. In yet another embodiment, the linkage is inserted on position 10-11 of the antisense strand. In still another embodiment, the linkage is inserted on position 19-20 of the antisense strand. In an embodiment, the linkage is inserted on positions 5-6 and 18-19 of the antisense strand.

In certain embodiments of Formula (I), the base pairing moiety B is adenine. In certain embodiments of Formula (I), the base pairing moiety B is guanine. In certain embodiments of Formula (I), the base pairing moiety B is cytosine. In certain embodiments of Formula (I), the base pairing moiety B is uracil.

In an embodiment of Formula (I), W is O. In an embodiment of Formula (I), W is $CH_2$. In an embodiment of Formula (I), W is CH.

In an embodiment of Formula (I), X is OH. In an embodiment of Formula (I), X is $OCH_3$. In an embodiment of Formula (I), X is halo.

In an exemplary embodiment of Formula (I), the modified oligonucleotide does not comprise a 2'-fluoro substituent.

In an embodiment of Formula (I), Y is $O^-$. In an embodiment of Formula (I), Y is OH. In an embodiment of Formula (I), Y is OR. In an embodiment of Formula (I), Y is NW. In an embodiment of Formula (I), Y is $NH_2$. In an embodiment of Formula (I), Y is S. In an embodiment of Formula (I), Y is SH.

In an embodiment of Formula (I), Z is O. In an embodiment of Formula (I), Z is $CH_2$.

In an embodiment of the Formula (I), the linkage is inserted on position 1-2 of the antisense strand. In another embodiment of Formula (I), the linkage is inserted on position 6-7 of the antisense strand. In yet another embodiment of Formula (I), the linkage is inserted on position 10-11 of the antisense strand. In still another embodiment of Formula (I), the linkage is inserted on position 19-20 of the antisense strand. In an embodiment of Formula (I), the linkage is inserted on positions 5-6 and 18-19 of the antisense strand.

Modified intersubunit linkages are further described in U.S. Patent Publication No. 2020/0385740A1, and U.S. Ser. No. 17/213,852, each of which is incorporated herein by reference.

4) Conjugated Functional Moieties

In other embodiments, RNA silencing agents may be modified with one or more functional moieties. A functional moiety is a molecule that confers one or more additional activities to the RNA silencing agent. In certain embodiments, the functional moieties enhance cellular uptake by target cells (e.g., neuronal cells). Thus, the disclosure includes RNA silencing agents which are conjugated or unconjugated (e.g., at its 5' and/or 3' terminus) to another moiety (e.g. a non-nucleic acid moiety such as a peptide), an organic compound (e.g., a dye), or the like. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53(1-3):137-43 (1998)(describes nucleic acids bound to nanoparticles); Schwab et al., Ann. Oncol. 5 Suppl. 4:55-8 (1994)(describes nucleic acids linked to intercalating agents, hydrophobic groups, polycations or PACA nanoparticles); and Godard et al., Eur. J. Biochem. 232(2):404-10 (1995)(describes nucleic acids linked to nanoparticles).

In a certain embodiment, the functional moiety is a hydrophobic moiety. In a certain embodiment, the hydrophobic moiety is selected from the group consisting of fatty acids, steroids, secosteroids, lipids, gangliosides and nucleoside analogs, endocannabinoids, and vitamins. In a certain embodiment, the steroid selected from the group consisting of cholesterol and Lithocholic acid (LCA). In a certain embodiment, the fatty acid selected from the group consisting of Eicosapentaenoic acid (EPA), Docosahexaenoic acid (DHA) and Docosanoic acid (DCA). In a certain embodiment, the vitamin selected from the group consisting of choline, vitamin A, vitamin E, and derivatives or metabolites thereof. In a certain embodiment, the vitamin is selected from the group consisting of retinoic acid and alpha-tocopheryl succinate.

In a certain embodiment, an RNA silencing agent of disclosure is conjugated to a lipophilic moiety. In one embodiment, the lipophilic moiety is a ligand that includes a cationic group. In another embodiment, the lipophilic moiety is attached to one or both strands of an siRNA. In an exemplary embodiment, the lipophilic moiety is attached to one end of the sense strand of the siRNA. In another exemplary embodiment, the lipophilic moiety is attached to the 3' end of the sense strand. In certain embodiments, the lipophilic moiety is selected from the group consisting of cholesterol, vitamin E, vitamin K, vitamin A, folic acid, a cationic dye (e.g., Cy3). In an exemplary embodiment, the lipophilic moiety is cholesterol. Other lipophilic moieties include cholic acid, adamantane acetic acid, 1-pyrene butyric acid, dihydrotestosterone, 1,3-Bis-0(hexadecyl) glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl) cholenic acid, dimethoxytrityl, or phenoxazine.

In certain embodiments, the functional moieties may comprise one or more ligands tethered to an RNA silencing agent to improve stability, hybridization thermodynamics with a target nucleic acid, targeting to a particular tissue or cell-type, or cell permeability, e.g., by an endocytosis-dependent or -independent mechanism. Ligands and associated modifications can also increase sequence specificity and consequently decrease off-site targeting. A tethered ligand can include one or more modified bases or sugars that can function as intercalators. These can be located in an internal region, such as in a bulge of RNA silencing agent/target duplex. The intercalator can be an aromatic, e.g., a polycyclic aromatic or heterocyclic aromatic compound. A polycyclic intercalator can have stacking capabilities, and can include systems with 2, 3, or 4 fused rings. The universal bases described herein can be included on a ligand. In one embodiment, the ligand can include a cleaving group that contributes to target gene inhibition by cleavage of the target nucleic acid. The cleaving group can be, for example, a bleomycin (e.g., bleomycin-A5, bleomycin-A2, or bleomycin-B2), pyrene, phenanthroline (e.g., O-phenanthroline), a polyamine, a tripeptide (e.g., lys-tyr-lys tripeptide), or a metal ion chelating group. The metal ion chelating group can include, e.g., an Lu(III) or EU(III) macrocyclic complex, a Zn(II) 2,9-dimethylphenanthroline derivative, a Cu(II) terpyridine, or acridine, which can promote the selective cleavage of target RNA at the site of the bulge by free metal ions, such as Lu(III). In some embodiments, a peptide ligand can be tethered to a RNA silencing agent to promote cleavage of the target RNA, e.g., at the bulge region. For example, 1,8-dimethyl-1,3,6,8,10,13-hexaazacyclotetradecane (cyclam) can be conjugated to a peptide (e.g., by an amino acid derivative) to promote target RNA cleavage. A tethered ligand can be an aminoglycoside ligand, which can cause an RNA silencing agent to have improved hybridization properties or improved sequence specificity. Exemplary aminoglycosides include glycosylated polylysine, galactosylated polylysine, neomycin B, tobramycin, kanamycin A, and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity. An acridine analog, neo-5-acridine, has an increased affinity for the HIV Rev-response element (RRE). In some embodiments, the guanidine analog (the guanidinoglycoside) of an aminoglycoside ligand is tethered to an RNA silencing agent. In a guanidinoglycoside, the amine group on the amino acid is exchanged for a guanidine group. Attachment of a guanidine analog can enhance cell permeability of an RNA silencing agent. A tethered ligand can be a poly-arginine peptide, peptoid or peptidomimetic, which can enhance the cellular uptake of an oligonucleotide agent.

Exemplary ligands are coupled, either directly or indirectly, via an intervening tether, to a ligand-conjugated carrier. In certain embodiments, the coupling is through a covalent bond. In certain embodiments, the ligand is attached to the carrier via an intervening tether. In certain embodiments, a ligand alters the distribution, targeting or lifetime of an RNA silencing agent into which it is incorporated. In certain embodiments, a ligand provides an enhanced affinity for a selected target, e.g., molecule, cell or cell type, compartment, e.g., a cellular or organ compartment, tissue, organ or region of the body, as, e.g., compared to a species absent such a ligand.

Exemplary ligands can improve transport, hybridization, and specificity properties and may also improve nuclease resistance of the resultant natural or modified RNA silencing agent, or a polymeric molecule comprising any combination of monomers described herein and/or natural or modified ribonucleotides. Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophiles, lipids, steroids (e.g., uvaol, hecigenin, diosgenin), terpenes (e.g., triterpenes, e.g., sarsasapogenin, Friedelin, epifriedelanol derivatized lithocholic acid), vitamins (e.g., folic acid, vitamin A, biotin, pyridoxal), carbohydrates, proteins, protein binding agents, integrin targeting molecules, polycationics, peptides, polyamines, and peptide mimics. Ligands can include a naturally occurring substance, (e.g., human serum albumin (HSA), low-density lipoprotein (LDL), or globulin); carbohydrate (e.g., a dextran, pullulan, chitin, chitosan, inulin, cyclodextrin or hyaluronic acid); amino acid, or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, mucin carbohydrate, multivalent lactose, multivalent galactose, N-acetyl-galactosamine (GalNAc) or derivatives thereof, N-acetyl-glucosamine, multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic. Other examples of ligands include dyes, intercalating agents (e.g. acridines and substituted acridines), cross-linkers (e.g. psoralene, mitomycin C), porphyrins (TPPC4, texaphyrin, Sapphyrin), polycyclic aromatic hydrocarbons (e.g., phenazine, dihydrophenazine, phenanthroline, pyrenes), lys-tyr-lys tripeptide, aminoglycosides, guanidium aminoglycodies, artificial endonucleases (e.g. EDTA), lipophilic molecules, e.g, cholesterol (and thio analogs thereof), cholic acid, cholanic acid, lithocholic acid, adamantane acetic acid, 1-pyrene butyric acid, dihydrotestosterone, glycerol (e.g., esters (e.g., mono, bis, or tris fatty acid esters, e.g., $C_{10}$, $C_{11}$, $C_{12}$, $C_{13}$, $C_{14}$, $C_{15}$, $C_{16}$, $C_{17}$, $C_{18}$, $C_{19}$, or $C_2$o fatty acids) and ethers thereof, e.g., $C_{10}$, $C_{11}$, $C_{12}$, $C_{13}$, $C_{14}$, $C_{15}$, $C_{16}$, $C_{17}$, $C_{18}$, $C_{19}$, or $C_2$o alkyl; e.g., 1,3-bis-O(hexadecyl) glycerol, 1,3-bis-O(octaadecyl)glycerol), geranyloxyhexyl group, hexadecylglycerol, borneol, menthol, 1,3-propanediol, heptadecyl group, palmitic acid, stearic acid (e.g., glyceryl distearate), oleic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g. biotin), transport/absorption facilitators (e.g., aspirin, naproxen, vitamin E, folic acid), synthetic ribonucleases (e.g., imidazole, bisimidazole, histamine, imidazole clusters, acridine-imidazole conjugates, $Eu^{3+}$ complexes of tetraazamacrocycles), dinitrophenyl, HRP or AP. In certain embodiments, the ligand is GalNAc or a derivative thereof.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-kB.

The ligand can be a substance, e.g., a drug, which can increase the uptake of the RNA silencing agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin. The ligand can increase the uptake of the RNA silencing agent into the cell by activating an inflammatory response, for example. Exemplary ligands that would have such an effect include tumor necrosis factor alpha (TNF□), interleukin-1 beta, or gamma interferon. In one aspect, the ligand is a lipid or lipid-based molecule. Such a lipid or lipid-based molecule can bind a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA. A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney. In a certain embodiment, the lipid based ligand binds HSA. A lipid-based ligand can bind HSA with a sufficient affinity such that the conjugate will be distributed to a non-kidney tissue. However, it is contemplated that the affinity not be so strong that the HSA-ligand binding cannot be reversed. In another embodiment, the lipid based ligand binds HSA weakly or not at all, such that the conjugate will be distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These can be useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

In another aspect, the ligand is a cell-permeation agent, such as a helical cell-permeation agent. In certain embodiments, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent can be an alpha-helical agent, which may have a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to oligonucleotide agents can affect pharmacokinetic distribution of the RNA silencing agent, such as by enhancing cellular recognition and absorption. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. The peptide moiety can be an L-peptide or D-peptide. In another alternative, the peptide moiety can include a hydrophobic membrane translocation sequence (MTS). A peptide or peptidomimetic can be encoded by a random sequence of DNA, such as a peptide identified from a phage-display library, or one-bead-one-compound (OBOC) combinatorial library (Lam et al., Nature 354:82-84, 1991). In exemplary embodiments, the peptide or peptidomimetic tethered to an RNA silencing agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

In certain embodiments, the functional moiety is linked to the 5' end and/or 3' end of the RNA silencing agent of the disclosure. In certain embodiments, the functional moiety is linked to the 5' end and/or 3' end of an antisense strand of the RNA silencing agent of the disclosure. In certain embodiments, the functional moiety is linked to the 5' end and/or 3' end of a sense strand of the RNA silencing agent of the disclosure. In certain embodiments, the functional moiety is linked to the 3' end of a sense strand of the RNA silencing agent of the disclosure.

In certain embodiments, the functional moiety is linked to the RNA silencing agent by a linker. In certain embodiments, the functional moiety is linked to the antisense strand and/or sense strand by a linker. In certain embodiments, the functional moiety is linked to the 3' end of a sense strand by a linker. In certain embodiments, the linker comprises a divalent or trivalent linker. In certain embodiments, the linker comprises an ethylene glycol chain, an alkyl chain, a peptide, RNA, DNA, a phosphodiester, a phosphorothioate, a phosphoramidate, an amide, a carbamate, or a combination thereof. In certain embodiments, the divalent or trivalent linker is selected from:

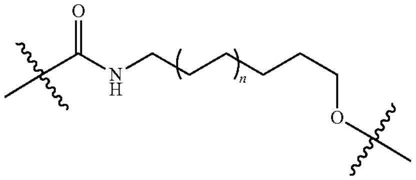
;
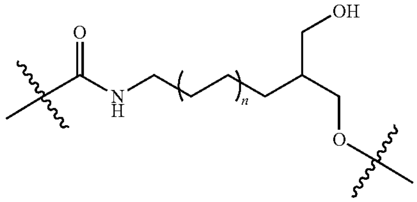
;
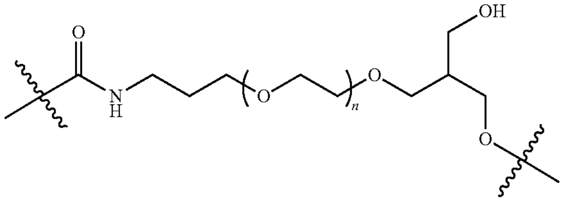
;
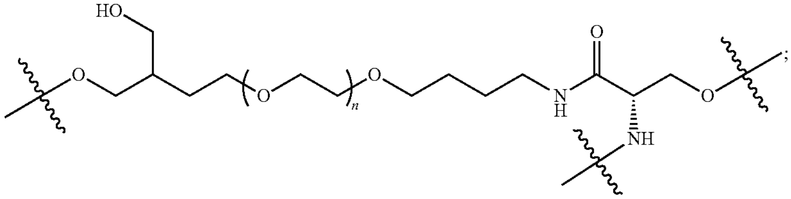
; or
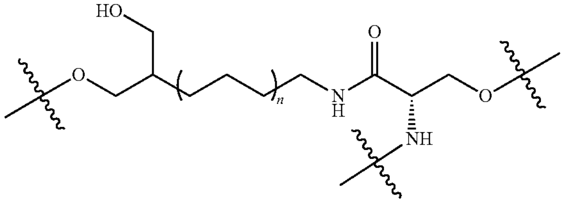

wherein n is 1, 2, 3, 4, or 5.

In certain embodiments, the linker further comprises a phosphodiester or phosphodiester derivative. In certain embodiments, the phosphodiester or phosphodiester derivative is selected from the group consisting of:

(Zc1)

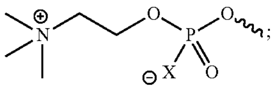

(Zc2)

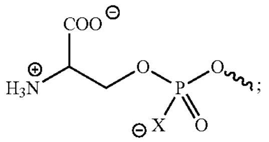

(Zc3)

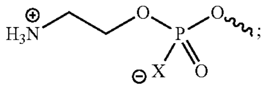 and (Zc4)

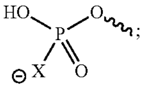

wherein X is O, S or $BH_3$.

The various functional moieties of the disclosure and means to conjugate them to RNA silencing agents are described in further detail in WO2017/030973A1 and WO2018/031933A2, incorporated herein by reference.

VI. Branched Oligonucleotides

Two or more RNA silencing agents as disclosed supra, for example oligonucleotide constructs such as anti-SOD1 siRNAs, may be connected to one another by one or more moieties independently selected from a linker, a spacer and a branching point, to form a branched oligonucleotide RNA silencing agent. In certain embodiments, the branched oligonucleotide RNA silencing agent consists of two siRNAs to form a di-branched siRNA ("di-siRNA") scaffolding for delivering two siRNAs. In representative embodiments, the nucleic acids of the branched oligonucleotide each comprise an antisense strand (or portions thereof), wherein the antisense strand has sufficient complementarity to a target mRNA (e.g., SOD1 mRNA) to mediate an RNA-mediated silencing mechanism (e.g. RNAi).

In exemplary embodiments, the branched oligonucleotides may have two to eight RNA silencing agents attached through a linker. The linker may be hydrophobic. In an embodiment, branched oligonucleotides of the present application have two to three oligonucleotides. In an embodiment, the oligonucleotides independently have substantial chemical stabilization (e.g., at least 40% of the constituent bases are chemically-modified). In an exemplary embodiment, the oligonucleotides have full chemical stabilization (i.e., all the constituent bases are chemically-modified). In some embodiments, branched oligonucleotides comprise one or more single-stranded phosphorothioated tails, each independently having two to twenty nucleotides. In a non-limiting embodiment, each single-stranded tail has two to ten nucleotides.

In certain embodiments, branched oligonucleotides are characterized by three properties: (1) a branched structure, (2) full metabolic stabilization, and (3) the presence of a single-stranded tail comprising phosphorothioate linkers. In certain embodiments, branched oligonucleotides have 2 or 3 branches. It is believed that the increased overall size of the branched structures promotes increased uptake. Also, without being bound by a particular theory of activity, multiple adjacent branches (e.g., 2 or 3) are believed to allow each branch to act cooperatively and thus dramatically enhance rates of internalization, trafficking and release.

Branched oligonucleotides are provided in various structurally diverse embodiments. In some embodiments nucleic acids attached at the branching points are single stranded or double stranded and consist of miRNA inhibitors, gapmers, mixmers, SSOs, PMOs, or PNAs. These single strands can be attached at their 3' or 5' end. Combinations of siRNA and single stranded oligonucleotides could also be used for dual function. In another embodiment, short nucleic acids complementary to the gapmers, mixmers, miRNA inhibitors, SSOs, PMOs, and PNAs are used to carry these active single-stranded nucleic acids and enhance distribution and cellular internalization. The short duplex region has a low melting temperature ($T_m$~37° C.) for fast dissociation upon internalization of the branched structure into the cell.

The Di-siRNA branched oligonucleotides may comprise chemically diverse conjugates, such as the functional moieties described above. Conjugated bioactive ligands may be used to enhance cellular specificity and to promote membrane association, internalization, and serum protein binding. Examples of bioactive moieties to be used for conjugation include DHA, GalNAc, and cholesterol. These moieties can be attached to Di-siRNA either through the connecting linker or spacer, or added via an additional linker or spacer attached to another free siRNA end.

The presence of a branched structure improves the level of tissue retention in the brain more than 100-fold compared to non-branched compounds of identical chemical composition, suggesting a new mechanism of cellular retention and distribution. Branched oligonucleotides have unexpectedly uniform distribution throughout the spinal cord and brain. Moreover, branched oligonucleotides exhibit unexpectedly efficient systemic delivery to a variety of tissues, and very high levels of tissue accumulation.

Branched oligonucleotides comprise a variety of therapeutic nucleic acids, including siRNAs, ASOs, miRNAs, miRNA inhibitors, splice switching, PMOs, PNAs. In some embodiments, branched oligonucleotides further comprise conjugated hydrophobic moieties and exhibit unprecedented silencing and efficacy in vitro and in vivo.

Linkers

In an embodiment of the branched oligonucleotide, each linker is independently selected from an ethylene glycol chain, an alkyl chain, a peptide, RNA, DNA, a phosphate, a phosphonate, a phosphoramidate, an ester, an amide, a triazole, and combinations thereof; wherein any carbon or oxygen atom of the linker is optionally replaced with a nitrogen atom, bears a hydroxyl substituent, or bears an oxo substituent. In one embodiment, each linker is an ethylene glycol chain. In another embodiment, each linker is an alkyl chain. In another embodiment, each linker is a peptide. In another embodiment, each linker is RNA. In another embodiment, each linker is DNA. In another embodiment, each linker is a phosphate. In another embodiment, each linker is a phosphonate. In another embodiment, each linker is a phosphoramidate. In another embodiment, each linker is an ester. In another embodiment, each linker is an amide. In another embodiment, each linker is a triazole.

VII. Compound of Formula (I)

In another aspect, provided herein is a branched oligonucleotide compound of formula (I):

$$L\text{-}(N)_n \qquad (I)$$

wherein L is selected from an ethylene glycol chain, an alkyl chain, a peptide, RNA, DNA, a phosphate, a phosphonate, a phosphoramidate, an ester, an amide, a triazole, and combinations thereof, wherein formula (I) optionally further comprises one or more branch point B, and one or more spacer S; wherein B is independently for each occurrence a polyvalent organic species or derivative thereof; S is independently for each occurrence selected from an ethylene glycol chain, an alkyl chain, a peptide, RNA, DNA, a phosphate, a phosphonate, a phosphoramidate, an ester, an amide, a triazole, and combinations thereof.

Moiety N is an RNA duplex comprising a sense strand and an antisense strand; and n is 2, 3, 4, 5, 6, 7 or 8. In an embodiment, the antisense strand of N comprises a sequence substantially complementary to a SOD1 nucleic acid sequence of any one of SEQ ID NOs: 1-11, as recited in Table 4. In further embodiments, N includes strands that are capable of targeting one or more of a SOD1 nucleic acid sequence selected from the group consisting of SEQ ID NOs: 12-22, as recited in Table 4. The sense strand and antisense strand may each independently comprise one or more chemical modifications.

In an embodiment, the compound of formula (I) has a structure selected from formulas (I-1)-(I-9) of Table 1.

TABLE 1

N—L—N (I-1)

N—S—L—S—N (I-2)

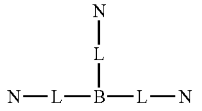
(I-3)

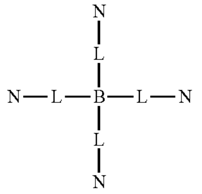
(I-4)

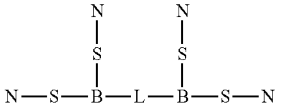
(I-5)

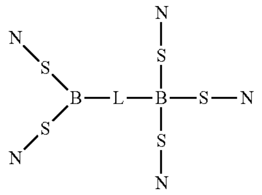
(I-6)

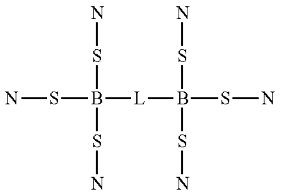
(I-7)

TABLE 1-continued

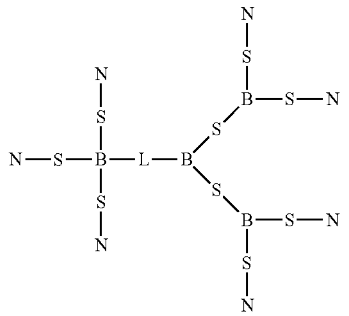
(I-8)

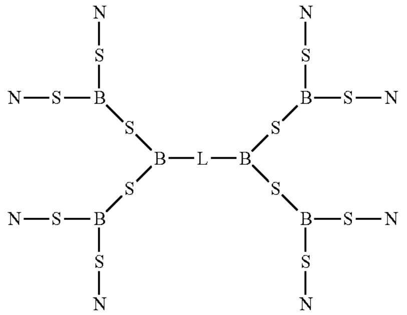
(I-9)

In one embodiment, the compound of formula (I) is formula (I-1). In another embodiment, the compound of formula (I) is formula (I-2). In another embodiment, the compound of formula (I) is formula (I-3). In another embodiment, the compound of formula (I) is formula (I-4). In another embodiment, the compound of formula (I) is formula (I-5). In another embodiment, the compound of formula (I) is formula (I-6). In another embodiment, the compound of formula (I) is formula (I-7). In another embodiment, the compound of formula (I) is formula (I-8). In another embodiment, the compound of formula (I) is formula (I-9).

In an embodiment of the compound of formula (I), each linker is independently selected from an ethylene glycol chain, an alkyl chain, a peptide, RNA, DNA, a phosphate, a phosphonate, a phosphoramidate, an ester, an amide, a triazole, and combinations thereof; wherein any carbon or oxygen atom of the linker is optionally replaced with a nitrogen atom, bears a hydroxyl substituent, or bears an oxo substituent. In one embodiment of the compound of formula (I), each linker is an ethylene glycol chain. In another embodiment, each linker is an alkyl chain. In another embodiment of the compound of formula (I), each linker is a peptide. In another embodiment of the compound of formula (I), each linker is RNA. In another embodiment of the compound of formula (I), each linker is DNA. In another embodiment of the compound of formula (I), each linker is a phosphate. In another embodiment, each linker is a phosphonate. In another embodiment of the compound of formula (I), each linker is a phosphoramidate. In another embodiment of the compound of formula (I), each linker is an ester. In another embodiment of the compound of formula (I), each linker is an amide. In another embodiment of the compound of formula (I), each linker is a triazole.

In one embodiment of the compound of formula (I), B is a polyvalent organic species. In another embodiment of the compound of formula (I), B is a derivative of a polyvalent organic species. In one embodiment of the compound of formula (I), B is a triol or tetrol derivative. In another embodiment, B is a tri- or tetra-carboxylic acid derivative. In another embodiment, B is an amine derivative. In another embodiment, B is a tri- or tetra-amine derivative. In another embodiment, B is an amino acid derivative. In another embodiment of the compound of formula (I), B is selected from the formulas of:

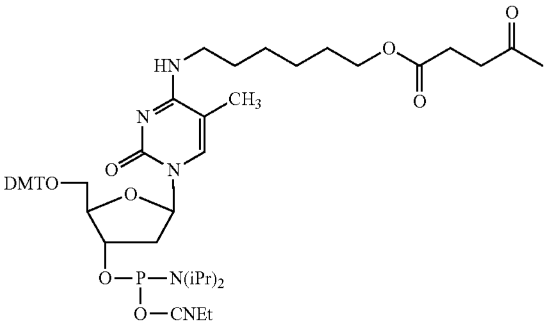

;

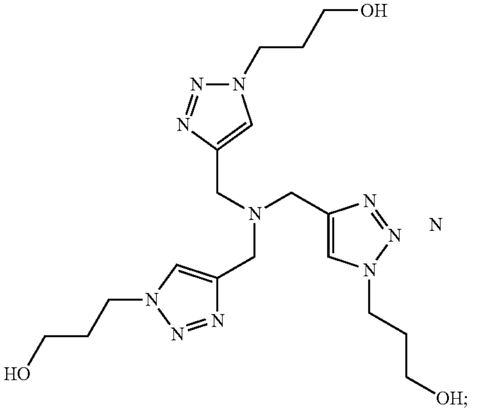

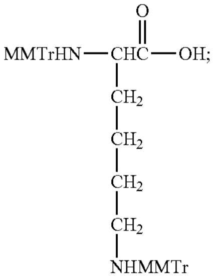

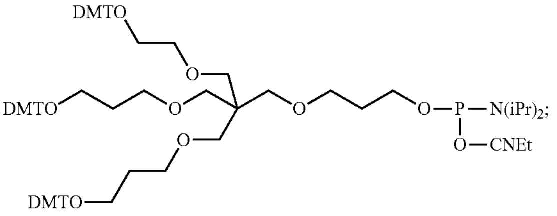

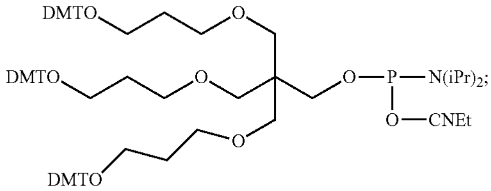

or

-continued

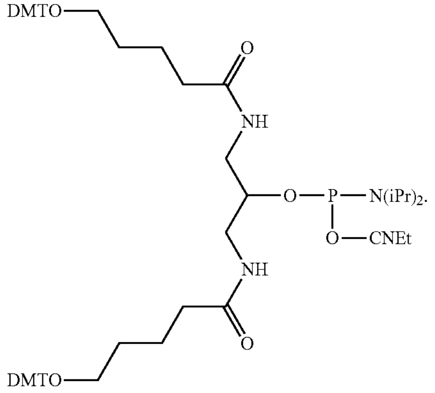

Polyvalent organic species are moieties comprising carbon and three or more valencies (i.e., points of attachment with moieties such as S, L or N, as defined above). Non-limiting examples of polyvalent organic species include triols (e.g., glycerol, phloroglucinol, and the like), tetrols (e.g., ribose, pentaerythritol, 1,2,3,5-tetrahydroxybenzene, and the like), tri-carboxylic acids (e.g., citric acid, 1,3,5-cyclohexanetricarboxylic acid, trimesic acid, and the like), tetra-carboxylic acids (e.g., ethylenediaminetetraacetic acid, pyromellitic acid, and the like), tertiary amines (e.g., tripropargylamine, triethanolamine, and the like), triamines (e.g., diethylenetriamine and the like), tetramines, and species comprising a combination of hydroxyl, thiol, amino, and/or carboxyl moieties (e.g., amino acids such as lysine, serine, cysteine, and the like).

In an embodiment of the compound of formula (I), each nucleic acid comprises one or more chemically-modified nucleotides. In an embodiment of the compound of formula (I), each nucleic acid consists of chemically-modified nucleotides. In certain embodiments of the compound of formula (I), >95%, >90%, >85%, >80%, >75%, >70%, >65%, >60%, >55% or >50% of each nucleic acid comprises chemically-modified nucleotides.

In an embodiment, each antisense strand independently comprises a 5' terminal group R selected from the groups of Table 2.

TABLE 2

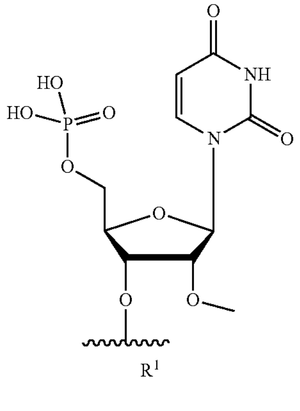

TABLE 2-continued
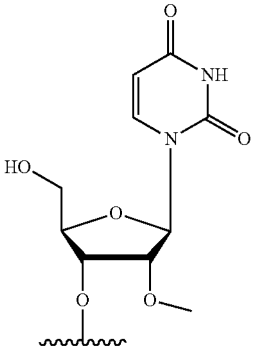
$R^2$
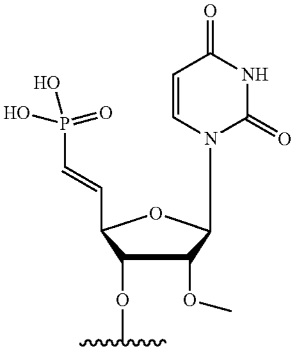
$R^3$
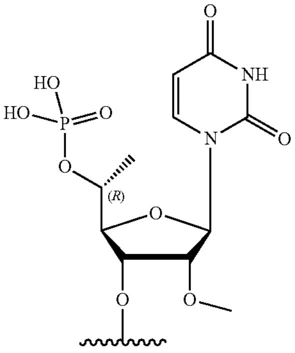
$R^4$
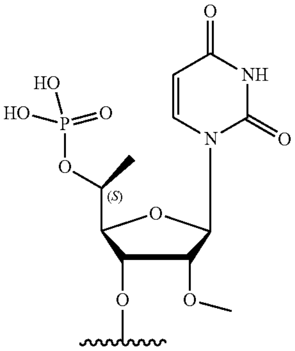
$R^5$
TABLE 2-continued
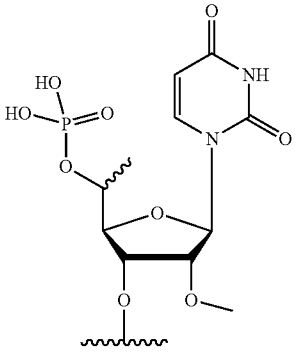
$R^6$
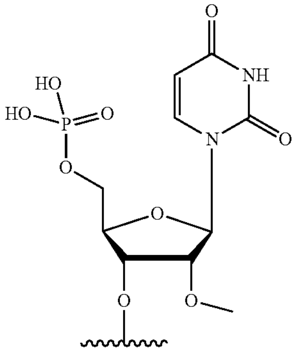
$R^7$
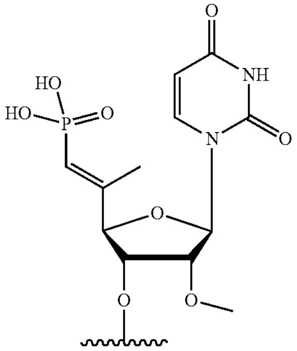
$R^8$
In one embodiment, R is $R_1$. In another embodiment, R is $R_2$. In another embodiment, R is $R_3$. In another embodiment, R is $R_4$. In another embodiment, R is $R_5$. In another embodiment, R is $R_6$. In another embodiment, R is $R_7$. In another embodiment, R is $R_8$.

Structure of Formula (II)

In an embodiment, the compound of formula (I) has the structure of formula (II):

(II)

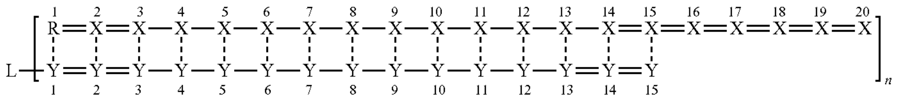

wherein X, for each occurrence, independently, is selected from adenosine, guanosine, uridine, cytidine, and chemically-modified derivatives thereof; Y, for each occurrence, independently, is selected from adenosine, guanosine, uridine, cytidine, and chemically-modified derivatives thereof; - represents a phosphodiester internucleoside linkage; =represents a phosphorothioate internucleoside linkage; and --- represents, individually for each occurrence, a base-pairing interaction or a mismatch.

In certain embodiments, the structure of formula (II) does not contain mismatches. In one embodiment, the structure of formula (II) contains 1 mismatch. In another embodiment, the compound of formula (II) contains 2 mismatches. In another embodiment, the compound of formula (II) contains 3 mismatches. In another embodiment, the compound of formula (II) contains 4 mismatches. In an embodiment, each nucleic acid consists of chemically-modified nucleotides.

In certain embodiments, >95%, >90%, >85%, >80%, >75%, >70%, >65%, >60%, >55% or >50% of X's of the structure of formula (II) are chemically-modified nucleotides. In other embodiments, >95%, >90%, >85%, >80%, >75%, >70%, >65%, >60%, >55% or >50% of X's of the structure of formula (II) are chemically-modified nucleotides.

Structure of Formula (III)

In an embodiment, the compound of formula (I) has the structure of formula (III)

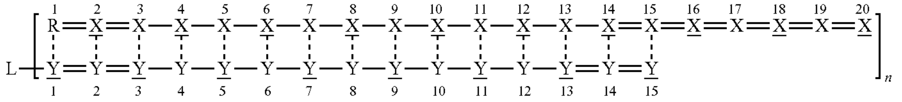

wherein X, for each occurrence, independently, is a nucleotide comprising a 2'-deoxy-2'-fluoro modification; X, for each occurrence, independently, is a nucleotide comprising a 2'-O-methyl modification; Y, for each occurrence, independently, is a nucleotide comprising a 2'-deoxy-2'-fluoro modification; and Y, for each occurrence, independently, is a nucleotide comprising a 2'-O-methyl modification.

In an embodiment, X is chosen from the group consisting of 2'-deoxy-2'-fluoro modified adenosine, guanosine, uridine or cytidine. In an embodiment, X is chosen from the group consisting of 2'-O-methyl modified adenosine, guanosine, uridine or cytidine. In an embodiment, Y is chosen from the group consisting of 2'-deoxy-2'-fluoro modified adenosine, guanosine, uridine or cytidine. In an embodiment, Y is chosen from the group consisting of 2'-O-methyl modified adenosine, guanosine, uridine or cytidine.

In certain embodiments, the structure of formula (III) does not contain mismatches. In one embodiment, the structure of formula (III) contains 1 mismatch. In another embodiment, the compound of formula (III) contains 2 mismatches. In another embodiment, the compound of formula (III) contains 3 mismatches. In another embodiment, the compound of formula (III) contains 4 mismatches.

Structure of Formula (IV)

In an embodiment, the compound of formula (I) has the structure of formula (IV):

(IV)

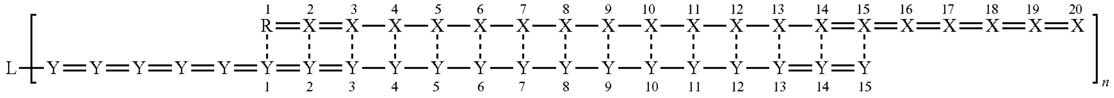

wherein X, for each occurrence, independently, is selected from adenosine, guanosine, uridine, cytidine, and chemically-modified derivatives thereof; Y, for each occurrence, independently, is selected from adenosine, guanosine, uridine, cytidine, and chemically-modified derivatives thereof; - represents a phosphodiester internucleoside linkage; =represents a phosphorothioate internucleoside linkage; and --- represents, individually for each occurrence, a base-pairing interaction or a mismatch.

In certain embodiments, the structure of formula (IV) does not contain mismatches. In one embodiment, the structure of formula (IV) contains 1 mismatch. In another embodiment, the compound of formula (IV) contains 2 mismatches. In another embodiment, the compound of formula (IV) contains 3 mismatches. In another embodiment, the compound of formula (IV) contains 4 mismatches. In an embodiment, each nucleic acid consists of chemically-modified nucleotides.

In certain embodiments, >95%, >90%, >85%, >80%, >75%, >70%, >65%, >60%, >55% or >50% of X's of the structure of formula (IV) are chemically-modified nucleotides. In other embodiments, >95%, >90%, >85%, >80%, >75%, >70%, >65%, >60%, >55% or >50% of X's of the structure of formula (IV) are chemically-modified nucleotides.

Structure of Formula (V)

In an embodiment, the compound of formula (I) has the structure of formula (V):

(V)

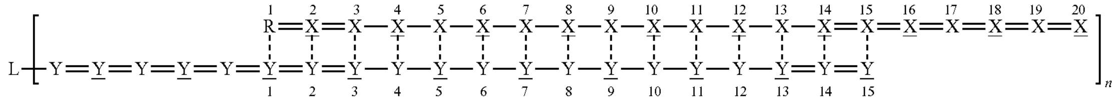

wherein X, for each occurrence, independently, is a nucleotide comprising a 2'-deoxy-2'-fluoro modification; X, for each occurrence, independently, is a nucleotide comprising a 2'-O-methyl modification; Y, for each occurrence, independently, is a nucleotide comprising a 2'-deoxy-2'-fluoro modification; and Y, for each occurrence, independently, is a nucleotide comprising a 2'-O-methyl modification.

In certain embodiments, X is chosen from the group consisting of 2'-deoxy-2'-fluoro modified adenosine, guanosine, uridine or cytidine. In an embodiment, X is chosen from the group consisting of 2'-O-methyl modified adenosine, guanosine, uridine or cytidine. In an embodiment, Y is chosen from the group consisting of 2'-deoxy-2'-fluoro modified adenosine, guanosine, uridine or cytidine. In an embodiment, Y is chosen from the group consisting of 2'-O-methyl modified adenosine, guanosine, uridine or cytidine.

In certain embodiments, the structure of formula (V) does not contain mismatches. In one embodiment, the structure of formula (V) contains 1 mismatch. In another embodiment, the compound of formula (V) contains 2 mismatches. In another embodiment, the compound of formula (V) contains 3 mismatches. In another embodiment, the compound of formula (V) contains 4 mismatches.

Variable Linkers

In an embodiment of the compound of formula (I), L has the structure of L1:

(L1)

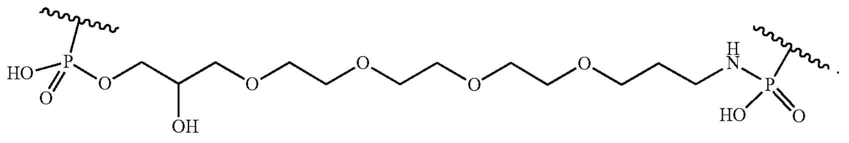

In an embodiment of L1, R is $R^3$ and n is 2.

In an embodiment of the structure of formula (II), L has the structure of L1. In an embodiment of the structure of formula (III), L has the structure of L1. In an embodiment of the structure of formula (IV), L has the structure of L1. In an embodiment of the structure of formula (V), L has the structure of L1. In an embodiment of the structure of formula (VI), L has the structure of L1. In an embodiment of the structure of formula (VI), L has the structure of L1.

In an embodiment of the compound of formula (I), L has the structure of L2:

(L2)

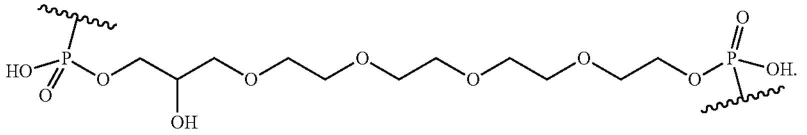

In an embodiment of L2, R is R3 and n is 2. In an embodiment of the structure of formula (II), L has the structure of L2. In an embodiment of the structure of formula (III), L has the structure of L2. In an embodiment of the structure of formula (IV), L has the structure of L2. In an embodiment of the structure of formula (V), L has the structure of L2. In an embodiment of the structure of formula (VI), L has the structure of L2. In an embodiment of the structure of formula (VI), L has the structure of L2.

Delivery System

In a third aspect, provided herein is a delivery system for therapeutic nucleic acids having the structure of formula (VI):

$$L\text{-}(cNA)_n \quad \text{(VI)}$$

wherein L is selected from an ethylene glycol chain, an alkyl chain, a peptide, RNA, DNA, a phosphate, a phosphonate, a phosphoramidate, an ester, an amide, a triazole, and combinations thereof, wherein formula (VI) optionally further comprises one or more branch point B, and one or more spacer S; wherein B is independently for each occurrence a polyvalent organic species or derivative thereof; S is independently for each occurrence selected from an ethylene glycol chain, an alkyl chain, a peptide, RNA, DNA, a phosphate, a phosphonate, a phosphoramidate, an ester, an amide, a triazole, and combinations thereof; each cNA, independently, is a carrier nucleic acid comprising one or more chemical modifications; and n is 2, 3, 4, 5, 6, 7 or 8.

In one embodiment of the delivery system, L is an ethylene glycol chain. In another embodiment of the delivery system, L is an alkyl chain. In another embodiment of the delivery system, L is a peptide. In another embodiment of the delivery system, L is RNA. In another embodiment of the delivery system, L is DNA. In another embodiment of the delivery system, L is a phosphate. In another embodiment of the delivery system, L is a phosphonate. In another embodiment of the delivery system, L is a phosphoramidate. In another embodiment of the delivery system, L is an ester. In another embodiment of the delivery system, L is an amide. In another embodiment of the delivery system, L is a triazole.

In one embodiment of the delivery system, S is an ethylene glycol chain. In another embodiment, S is an alkyl chain. In another embodiment of the delivery system, S is a peptide. In another embodiment, S is RNA. In another embodiment of the delivery system, S is DNA. In another embodiment of the delivery system, S is a phosphate. In another embodiment of the delivery system, S is a phosphonate. In another embodiment of the delivery system, S is a phosphoramidate. In another embodiment of the delivery system, S is an ester. In another embodiment, S is an amide. In another embodiment, S is a triazole.

In one embodiment of the delivery system, n is 2. In another embodiment of the delivery system, n is 3. In another embodiment of the delivery system, n is 4. In another embodiment of the delivery system, n is 5. In another embodiment of the delivery system, n is 6. In another embodiment of the delivery system, n is 7. In another embodiment of the delivery system, n is 8.

In certain embodiments, each cNA comprises >95%, >90%, >85%, >80%, >75%, >70%, >65%, >60%, >55% or >50% chemically-modified nucleotides.

In an embodiment, the compound of formula (VI) has a structure selected from formulas (VI-1)-(VI-9) of Table 3:

TABLE 3

| | |
|---|---|
| ANc—L—cNA | (VI-1) |
| ANc—S—L—S—cNA | (VI-2) |
| 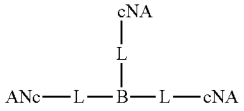 | (VI-3) |
| 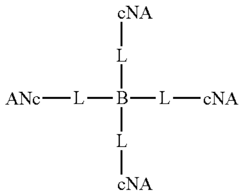 | (VI-4) |
| 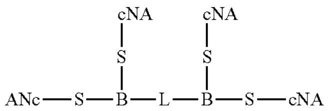 | (VI-5) |
| 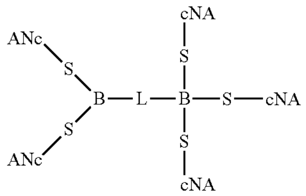 | (VI-6) |

TABLE 3-continued

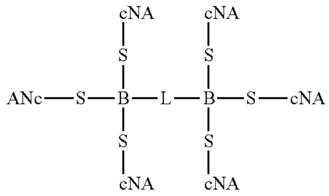

(VI-7)

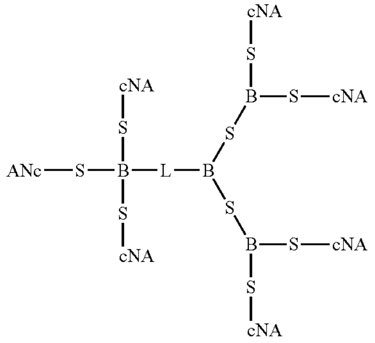

(VI-8)

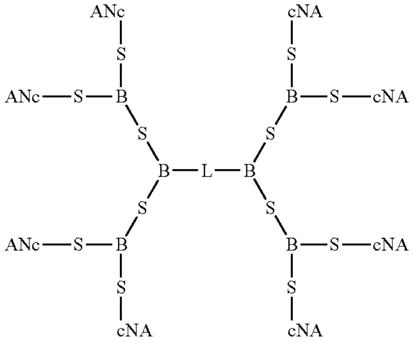

(VI-9)

In an embodiment, the compound of formula (VI) is the structure of formula (VI-1). In an embodiment, the compound of formula (VI) is the structure of formula (VI-2). In an embodiment, the compound of formula (VI) is the structure of formula (VI-3). In an embodiment, the compound of formula (VI) is the structure of formula (VI-4). In an embodiment, the compound of formula (VI) is the structure of formula (VI-5). In an embodiment, the compound of formula (VI) is the structure of formula (VI-6). In an embodiment, the compound of formula (VI) is the structure of formula (VI-7). In an embodiment, the compound of formula (VI) is the structure of formula (VI-8). In an embodiment, the compound of formula (VI) is the structure of formula (VI-9).

In an embodiment, the compound of formulas (VI)(including, e.g., formulas (VI-1)-(VI-9), each cNA independently comprises at least 15 contiguous nucleotides. In an embodiment, each cNA independently consists of chemically-modified nucleotides.

In an embodiment, the delivery system further comprises n therapeutic nucleic acids (NA), wherein each NA comprises a sequence substantially complementary to a SOD1 nucleic acid sequence of any one of SEQ ID NOs: 1-11, as recited in Table 4. In further embodiments, NA includes strands that are capable of targeting one or more of a SOD1 nucleic acid sequence selected from the group consisting of SEQ ID NOs: 12-22, as recited in Table 4.

Also, each NA is hybridized to at least one cNA. In one embodiment, the delivery system is comprised of 2 NAs. In another embodiment, the delivery system is comprised of 3 NAs. In another embodiment, the delivery system is comprised of 4 NAs. In another embodiment, the delivery system is comprised of 5 NAs. In another embodiment, the delivery system is comprised of 6 NAs. In another embodiment, the delivery system is comprised of 7 NAs. In another embodiment, the delivery system is comprised of 8 NAs.

In an embodiment, each NA independently comprises at least 15 contiguous nucleotides. In an embodiment, each NA independently comprises 15-25 contiguous nucleotides. In an embodiment, each NA independently comprises 15 contiguous nucleotides. In an embodiment, each NA independently comprises 16 contiguous nucleotides. In another embodiment, each NA independently comprises 17 contiguous nucleotides. In another embodiment, each NA independently comprises 18 contiguous nucleotides. In another embodiment, each NA independently comprises 19 contiguous nucleotides. In another embodiment, each NA independently comprises 20 contiguous nucleotides. In an embodiment, each NA independently comprises 21 contiguous nucleotides. In an embodiment, each NA independently comprises 22 contiguous nucleotides. In an embodiment, each NA independently comprises 23 contiguous nucleotides. In an embodiment, each NA independently comprises 24 contiguous nucleotides. In an embodiment, each NA independently comprises 25 contiguous nucleotides.

In an embodiment, each NA comprises an unpaired overhang of at least 2 nucleotides. In another embodiment, each NA comprises an unpaired overhang of at least 3 nucleotides. In another embodiment, each NA comprises an unpaired overhang of at least 4 nucleotides. In another embodiment, each NA comprises an unpaired overhang of at least 5 nucleotides. In another embodiment, each NA comprises an unpaired overhang of at least 6 nucleotides. In an embodiment, the nucleotides of the overhang are connected via phosphorothioate linkages.

In an embodiment, each NA, independently, is selected from the group consisting of: DNA, siRNAs, antagomiRs, miRNAs, gapmers, mixmers, or guide RNAs. In one embodiment, each NA, independently, is a DNA. In another embodiment, each NA, independently, is a siRNA. In another embodiment, each NA, independently, is an antagomiR. In another embodiment, each NA, independently, is a miRNA. In another embodiment, each NA, independently, is a gapmer. In another embodiment, each NA, independently, is a mixmer. In another embodiment, each NA, independently, is a guide RNA. In an embodiment, each NA is the same. In an embodiment, each NA is not the same.

In an embodiment, the delivery system further comprising n therapeutic nucleic acids (NA) has a structure selected from formulas (I), (II), (III), (IV), (V), (VI), and embodiments thereof described herein. In one embodiment, the delivery system has a structure selected from formulas (I), (II), (III), (IV), (V), (VI), and embodiments thereof described herein further comprising 2 therapeutic nucleic acids (NA). In another embodiment, the delivery system has a structure selected from formulas (I), (II), (III), (IV), (V), (VI), and embodiments thereof described herein further comprising 3 therapeutic nucleic acids (NA). In one embodiment, the delivery system has a structure selected from formulas (I), (II), (III), (IV), (V), (VI), and embodiments thereof described herein further comprising 4 therapeutic nucleic acids (NA). In one embodiment, the delivery system has a structure selected from formulas (I), (II), (III), (IV), (V), (VI), and embodiments thereof described herein further comprising 5 therapeutic nucleic acids (NA). In one embodiment, the delivery system has a structure selected from formulas (I), (II), (III), (IV), (V), (VI), and embodiments thereof described herein further comprising 6 therapeutic nucleic acids (NA). In one embodiment, the delivery system has a structure selected from formulas (I), (II), (III), (IV), (V), (VI), and embodiments thereof described herein further comprising 7 therapeutic nucleic acids (NA). In one embodiment, the delivery system has a structure selected from formulas (I), (II), (III), (IV), (V), (VI), and embodiments thereof described herein further comprising 8 therapeutic nucleic acids (NA).

In one embodiment, the delivery system has a structure selected from formulas (I), (II), (III), (IV), (V), (VI), further comprising a linker of structure L1 or L2 wherein R is $R^3$ and n is 2. In another embodiment, the delivery system has a structure selected from formulas (I), (II), (III), (IV), (V), (VI), further comprising a linker of structure L1 wherein R is $R^3$ and n is 2. In another embodiment, the delivery system has a structure selected from formulas (I), (II), (III), (IV), (V), (VI), further comprising a linker of structure L2 wherein R is $R^3$ and n is 2.

In an embodiment of the delivery system, the target of delivery is selected from the group consisting of: brain, liver, skin, kidney, spleen, pancreas, colon, fat, lung, muscle, and thymus. In one embodiment, the target of delivery is the brain. In another embodiment, the target of delivery is the striatum of the brain. In another embodiment, the target of delivery is the cortex of the brain. In another embodiment, the target of delivery is the striatum of the brain. In one embodiment, the target of delivery is the liver. In one embodiment, the target of delivery is the skin. In one embodiment, the target of delivery is the kidney. In one embodiment, the target of delivery is the spleen. In one embodiment, the target of delivery is the pancreas. In one embodiment, the target of delivery is the colon. In one embodiment, the target of delivery is the fat. In one embodiment, the target of delivery is the lung. In one embodiment, the target of delivery is the muscle. In one embodiment, the target of delivery is the thymus. In one embodiment, the target of delivery is the spinal cord.

In certain embodiments, compounds of the disclosure are characterized by the following properties: (1) two or more branched oligonucleotides, e.g., wherein there is a non-equal number of 3' and 5' ends; (2) substantially chemically stabilized, e.g., wherein more than 40%, optimally 100%, of oligonucleotides are chemically modified (e.g., no RNA and optionally no DNA); and (3) phoshorothioated single oligonucleotides containing at least 3, phosphorothioated bonds. In certain embodiments, the phoshorothioated single oligonucleotides contain 4-20 phosphorothioated bonds.

It is to be understood that the methods described in this disclosure are not limited to particular methods and experimental conditions disclosed herein; as such methods and conditions may vary. It is also to be understood that the terminology used herein is for the purpose of describing particular embodiments only, and is not intended to be limiting.

Furthermore, the experiments described herein, unless otherwise indicated, use conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY (1987-2008), including all supplements, Molecular Cloning: A Laboratory Manual (Fourth Edition) by M R Green and J. Sambrook and Harlow et al., Antibodies: A Laboratory Manual, Chapter 14, Cold Spring Harbor Laboratory, Cold Spring Harbor (2013, 2nd edition).

Branched oligonucleotides, including synthesis and methods of use, are described in greater detail in WO2017/132669, incorporated herein by reference.

Methods of Introducing Nucleic Acids, Vectors and Host Cells

RNA silencing agents of the disclosure may be directly introduced into the cell (e.g., a neural cell)(i.e., intracellularly); or introduced extracellularly into a cavity, interstitial space, into the circulation of an organism, introduced orally, or may be introduced by bathing a cell or organism in a solution containing the nucleic acid. Vascular or extravascular circulation, the blood or lymph system, and the cerebrospinal fluid are sites where the nucleic acid may be introduced.

The RNA silencing agents of the disclosure can be introduced using nucleic acid delivery methods known in art including injection of a solution containing the nucleic acid, bombardment by particles covered by the nucleic acid, soaking the cell or organism in a solution of the nucleic acid, or electroporation of cell membranes in the presence of the nucleic acid. Other methods known in the art for introducing nucleic acids to cells may be used, such as lipid-mediated carrier transport, chemical-mediated transport, and cationic liposome transfection such as calcium phosphate, and the like. The nucleic acid may be introduced along with other components that perform one or more of the following activities: enhance nucleic acid uptake by the cell or otherwise increase inhibition of the target gene.

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus, the RNA may be introduced along with components that perform one or more of the following activities: enhance RNA uptake by the cell, inhibit annealing of single strands, stabilize the single strands, or other-wise increase inhibition of the target gene.

RNA may be directly introduced into the cell (i.e., intracellularly); or introduced extracellularly into a cavity, interstitial space, into the circulation of an organism, introduced orally, or may be introduced by bathing a cell or organism in a solution containing the RNA. Vascular or extravascular circulation, the blood or lymph system, and the cerebrospinal fluid are sites where the RNA may be introduced.

The cell having the target gene may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

Depending on the particular target gene and the dose of double stranded RNA material delivered, this process may provide partial or complete loss of function for the target gene. A reduction or loss of gene expression in at least 50%, 60%, 70%, 80%, 90%, 95% or 99% or more of targeted cells is exemplary. Inhibition of gene expression refers to the absence (or observable decrease) in the level of protein and/or mRNA product from a target gene. Specificity refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, Enzyme Linked ImmunoSorbent Assay (ELISA), Western blotting, RadioImmunoAssay (RIA), other immunoassays, and Fluorescence Activated Cell Sorting (FACS).

For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin. Depending on the assay, quantitation of the amount of gene expression allows one to determine a degree of inhibition which is greater than 10%, 33%, 50%, 90%, 95% or 99% as compared to a cell not treated according to the present disclosure. Lower doses of injected material and longer times after administration of RNAi agent may result in inhibition in a smaller fraction of cells (e.g., at least 10%, 20%, 50%, 75%, 90%, or 95% of targeted cells). Quantization of gene expression in a cell may show similar amounts of inhibition at the level of accumulation of target mRNA or translation of target protein. As an example, the efficiency of inhibition may be determined by assessing the amount of gene product in the cell; mRNA may be detected with a hybridization probe having a nucleotide sequence outside the region used for the inhibitory double-stranded RNA, or translated polypeptide may be detected with an antibody raised against the polypeptide sequence of that region.

The RNA may be introduced in an amount which allows delivery of at least one copy per cell. Higher doses (e.g., at least 5, 10, 100, 500 or 1000 copies per cell) of material may yield more effective inhibition; lower doses may also be useful for specific applications.

In an exemplary aspect, the efficacy of an RNAi agent of the disclosure (e.g., an siRNA targeting an SOD1 target sequence) is tested for its ability to specifically degrade mutant mRNA (e.g., SOD1 mRNA and/or the production of SOD1 protein) in cells, such as cells in the central nervous system. In certain embodiments, cells in the central nervous system include, but are not limited to, neurons (e.g., striatal or cortical neuronal clonal lines and/or primary neurons), glial cells, and astrocytes. Also suitable for cell-based validation assays are other readily transfectable cells, for example, HeLa cells or COS cells. Cells are transfected with human wild type or mutant cDNAs (e.g., human wild type or mutant SOD1 cDNA). Standard siRNA, modified siRNA or vectors able to produce siRNA from U-looped mRNA are co-transfected. Selective reduction in target mRNA (e.g., SOD1 mRNA) and/or target protein (e.g., SOD1 protein) is measured. Reduction of target mRNA or protein can be compared to levels of target mRNA or protein in the absence of an RNAi agent or in the presence of an RNAi agent that does not target SOD1 mRNA. Exogenously-introduced mRNA or protein (or endogenous mRNA or protein) can be assayed for comparison purposes. When utilizing neuronal cells, which are known to be somewhat resistant to standard transfection techniques, it may be desirable to introduce RNAi agents (e.g., siRNAs) by passive uptake.

Recombinant Adeno-Associated Viruses and Vectors

In certain exemplary embodiments, recombinant adeno-associated viruses (rAAVs) and their associated vectors can be used to deliver one or more siRNAs into cells, e.g., neural cells (e.g., brain cells). AAV is able to infect many different cell types, although the infection efficiency varies based upon serotype, which is determined by the sequence of the capsid protein. Several native AAV serotypes have been identified, with serotypes 1-9 being the most commonly used for recombinant AAV. AAV-2 is the most well-studied and published serotype. The AAV-DJ system includes serotypes AAV-DJ and AAV-DJ/8. These serotypes were created through DNA shuffling of multiple AAV serotypes to produce AAV with hybrid capsids that have improved transduction efficiencies in vitro (AAV-DJ) and in vivo (AAV-DJ/8) in a variety of cells and tissues.

In certain embodiments, widespread central nervous system (CNS) delivery can be achieved by intravascular delivery of recombinant adeno-associated virus 7 (rAAV7), RAAV9 and rAAV10, or other suitable rAAVs (Zhang et al. (2011) Mol. Ther. 19(8):1440-8. doi: 10.1038/mt.2011.98. Epub 2011 May 24). rAAVs and their associated vectors are well-known in the art and are described in US Patent Applications 2014/0296486, 2010/0186103, 2008/0269149, 2006/0078542 and 2005/0220766, each of which is incorporated herein by reference in its entirety for all purposes.

rAAVs may be delivered to a subject in compositions according to any appropriate methods known in the art. An rAAV can be suspended in a physiologically compatible carrier (i.e., in a composition), and may be administered to a subject, i.e., a host animal, such as a human, mouse, rat, cat, dog, sheep, rabbit, horse, cow, goat, pig, guinea pig, hamster, chicken, turkey, a non-human primate (e.g., Macaque) or the like. In certain embodiments, a host animal is a non-human host animal.

Delivery of one or more rAAVs to a mammalian subject may be performed, for example, by intramuscular injection or by administration into the bloodstream of the mammalian subject. Administration into the bloodstream may be by injection into a vein, an artery, or any other vascular conduit. In certain embodiments, one or more rAAVs are administered into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177,403, can also be employed by the skilled artisan to administer virions into the vasculature of an isolated limb to potentially enhance transduction into muscle cells or tissue. Moreover, in certain instances, it may be desirable to deliver virions to the central nervous system (CNS) of a subject. By "CNS" is meant all cells and tissue of the brain and spinal cord of a vertebrate. Thus, the term includes, but is not limited to, neuronal cells, glial cells, astrocytes, cerebrospinal fluid (CSF), interstitial spaces, bone, cartilage and the like. Recombinant AAVs may be delivered directly to the CNS or brain by injection into, e.g., the ventricular region, as well as to the striatum (e.g., the caudate nucleus or putamen of the striatum), spinal cord and neuromuscular junction, or cerebellar lobule, with a needle, catheter or related device, using neurosurgical techniques known in the art, such as by stereotactic injection (see, e.g., Stein et al., J Virol 73:3424-3429, 1999; Davidson et al., PNAS 97:3428-3432, 2000; Davidson et al., Nat. Genet. 3:219-223, 1993; and Alisky and Davidson, Hum. Gene Ther. 11:2315-2329, 2000).

The compositions of the disclosure may comprise an rAAV alone, or in combination with one or more other viruses (e.g., a second rAAV encoding having one or more different transgenes). In certain embodiments, a composition comprises 1, 2, 3, 4, 5, 6, 7, 8, 9, 10 or more different rAAVs each having one or more different transgenes.

An effective amount of an rAAV is an amount sufficient to target infect an animal, target a desired tissue. In some embodiments, an effective amount of an rAAV is an amount sufficient to produce a stable somatic transgenic animal model. The effective amount will depend primarily on factors such as the species, age, weight, health of the subject, and the tissue to be targeted, and may thus vary among animal and tissue. For example, an effective amount of one or more rAAVs is generally in the range of from about 1 ml to about 100 ml of solution containing from about $10^9$ to $10^{16}$ genome copies. In some cases, a dosage between about $10^{11}$ to $10^{12}$ rAAV genome copies is appropriate. In certain embodiments, $10^{12}$ rAAV genome copies is effective to target heart, liver, and pancreas tissues. In some cases, stable transgenic animals are produced by multiple doses of an rAAV.

In some embodiments, rAAV compositions are formulated to reduce aggregation of AAV particles in the composition, particularly where high rAAV concentrations are present (e.g., about $10^{13}$ genome copies/mL or more). Methods for reducing aggregation of rAAVs are well known in the art and, include, for example, addition of surfactants, pH adjustment, salt concentration adjustment, etc. (See, e.g., Wright et al. (2005) Molecular Therapy 12:171-178, the contents of which are incorporated herein by reference.)

"Recombinant AAV (rAAV) vectors" comprise, at a minimum, a transgene and its regulatory sequences, and 5' and 3' AAV inverted terminal repeats (ITRs). It is this recombinant AAV vector which is packaged into a capsid protein and delivered to a selected target cell. In some embodiments, the transgene is a nucleic acid sequence, heterologous to the vector sequences, which encodes a polypeptide, protein, functional RNA molecule (e.g., siRNA) or other gene product, of interest. The nucleic acid coding sequence is operatively linked to regulatory components in a manner which permits transgene transcription, translation, and/or expression in a cell of a target tissue.

The AAV sequences of the vector typically comprise the cis-acting 5' and 3' inverted terminal repeat (ITR) sequences (See, e.g., B. J. Carter, in "Handbook of Parvoviruses", ed., P. Tijsser, CRC Press, pp. 155 168 (1990)). The ITR sequences are usually about 145 basepairs in length. In certain embodiments, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). An example of such a molecule employed in the present disclosure is a "cis-acting" plasmid containing the transgene, in which the selected transgene sequence and associated regulatory elements are flanked by the 5' and 3' AAV ITR sequences. The AAV ITR sequences may be obtained from any known AAV, including mammalian AAV types described further herein.

VIII. Methods of Treatment

In one aspect, the present disclosure provides for both prophylactic and therapeutic methods of treating a subject at risk of (or susceptible to) developing a neurodegenerative disease, such as amyotrophic lateral sclerosis (ALS). In one embodiment, the disease or disorder is related to a mutation in SOD1, such as familial amyotrophic lateral sclerosis (ALS). In a certain embodiment, the disease or disorder is one in which reduction of SOD1 in the CNS reduces clinical manifestations seen in neurodegenerative diseases such as amyotrophic lateral sclerosis (ALS).

"Treatment," or "treating," as used herein, is defined as the application or administration of a therapeutic agent (e.g., a RNA agent or vector or transgene encoding same) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In one aspect, the disclosure provides a method for preventing in a subject, a disease or disorder as described above, by administering to the subject a therapeutic agent (e.g., an RNAi agent or vector or transgene encoding same). Subjects at risk for the disease can be identified by, for example, any or a combination of diagnostic or prognostic assays as described herein. Administration of a prophylactic agent can occur prior to the manifestation of symptoms characteristic of the disease or disorder, such that the disease or disorder is prevented or, alternatively, delayed in its progression.

Another aspect of the disclosure pertains to methods treating subjects therapeutically, i.e., alter onset of symptoms of the disease or disorder. In an exemplary embodiment, the modulatory method of the disclosure involves contacting a CNS cell expressing SOD1 with a therapeutic agent (e.g., a RNAi agent or vector or transgene encoding same) that is specific for a target sequence within the gene (e.g., SOD1 target sequences of Table 4), such that sequence specific interference with the gene is achieved. These methods can be performed in vitro (e.g., by culturing the cell with the agent) or, alternatively, in vivo (e.g., by administering the agent to a subject).

IX. Pharmaceutical Compositions and Methods of Administration

The disclosure pertains to uses of the above-described agents for prophylactic and/or therapeutic treatments as described infra. Accordingly, the modulators (e.g., RNAi agents) of the present disclosure can be incorporated into pharmaceutical compositions suitable for administration. Such compositions typically comprise the nucleic acid molecule, protein, antibody, or modulatory compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the disclosure is formulated to be compatible with its intended route of administration. Examples of routes of administration include parenteral, e.g., intravenous, intradermal, subcutaneous, intraperitoneal, intramuscular, oral (e.g., inhalation), transdermal (topical), and transmucosal administration. In certain exemplary embodiments, the pharmaceutical composition of the disclosure is administered intravenously and is capable of crossing the blood brain barrier to enter the central nervous system In certain exemplary embodiments, a pharmaceutical composition of the disclosure is delivered to the cerebrospinal fluid (CSF) by a route of administration that includes, but is not limited to, intrastriatal (IS) administration, intracerebroventricular (ICV) administration and intrathecal (IT) administration (e.g., via a pump, an infusion or the like).

The nucleic acid molecules of the disclosure can be inserted into expression constructs, e.g., viral vectors, retroviral vectors, expression cassettes, or plasmid viral vectors, e.g., using methods known in the art, including but not limited to those described in Xia et al., (2002), Supra. Expression constructs can be delivered to a subject by, for example, inhalation, orally, intravenous injection, local administration (see U.S. Pat. No. 5,328,470) or by stereotactic injection (see e.g., Chen et al. (1994), Proc. Natl. Acad. Sci. USA, 91, 3054-3057). The pharmaceutical preparation of the delivery vector can include the vector in an acceptable diluent, or can comprise a slow release matrix in which the delivery vehicle is imbedded. Alternatively, where the complete delivery vector can be produced intact from recombinant cells, e.g., retroviral vectors, the pharmaceutical preparation can include one or more cells which produce the gene delivery system.

The nucleic acid molecules of the disclosure can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21 nucleotides. Brummelkamp et al. (2002), Science, 296, 550-553; Lee et al, (2002). supra; Miyagishi and Taira (2002), Nature Biotechnol., 20, 497-500; Paddison et al. (2002), supra; Paul (2002), supra; Sui (2002) supra; Yu et al. (2002), supra.

The expression constructs may be any construct suitable for use in the appropriate expression system and include, but are not limited to retroviral vectors, linear expression cassettes, plasmids and viral or virally-derived vectors, as known in the art. Such expression constructs may include one or more inducible promoters, RNA Pol III promoter systems such as U6 snRNA promoters or H1 RNA polymerase III promoters, or other promoters known in the art. The constructs can include one or both strands of the siRNA. Expression constructs expressing both strands can also include loop structures linking both strands, or each strand can be separately transcribed from separate promoters within the same construct. Each strand can also be transcribed from a separate expression construct, Tuschl (2002), Supra.

In certain embodiments, a composition that includes a compound of the disclosure can be delivered to the nervous system of a subject by a variety of routes. Exemplary routes include intrathecal, parenchymal (e.g., in the brain), nasal, and ocular delivery. The composition can also be delivered systemically, e.g., by intravenous, subcutaneous or intramuscular injection. One route of delivery is directly to the brain, e.g., into the ventricles or the hypothalamus of the brain, or into the lateral or dorsal areas of the brain. The compounds for neural cell delivery can be incorporated into pharmaceutical compositions suitable for administration.

For example, compositions can include one or more species of a compound of the disclosure and a pharmaceutically acceptable carrier. The pharmaceutical compositions of the present disclosure may be administered in a number of ways depending upon whether local or systemic treatment is desired and upon the area to be treated. Administration may be topical (including ophthalmic, intranasal, transdermal), oral or parenteral. Parenteral administration includes intravenous drip, subcutaneous, intraperitoneal or intramuscular injection, intrathecal, or intraventricular (e.g., intracerebroventricular) administration. In certain exemplary embodiments, an RNA silencing agent of the disclosure is delivered across the Blood-Brain-Barrier (BBB) suing a variety of suitable compositions and methods described herein.

The route of delivery can be dependent on the disorder of the patient. For example, a subject diagnosed with a neurodegenerative disease can be administered an anti-SOD1 compounds of the disclosure directly into the brain (e.g., into the globus pallidus or the corpus striatum of the basal ganglia, and near the medium spiny neurons of the corpus striatum). In addition to a compound of the disclosure, a patient can be administered a second therapy, e.g., a palliative therapy and/or disease-specific therapy. The secondary therapy can be, for example, symptomatic (e.g., for alleviating symptoms), neuroprotective (e.g., for slowing or halting disease progression), or restorative (e.g., for reversing the disease process). Other therapies can include psychotherapy, physiotherapy, speech therapy, communicative and memory aids, social support services, and dietary advice.

A compound of the disclosure can be delivered to neural cells of the brain. In certain embodiments, the compounds of the disclosure may be delivered to the brain without direct administration to the central nervous system, i.e., the compounds may be delivered intravenously and cross the blood brain barrier to enter the brain. Delivery methods that do not require passage of the composition across the blood-brain barrier can be utilized. For example, a pharmaceutical composition containing a compound of the disclosure can be delivered to the patient by injection directly into the area containing the disease-affected cells. For example, the pharmaceutical composition can be delivered by injection directly into the brain. The injection can be by stereotactic injection into a particular region of the brain (e.g., the substantia nigra, cortex, hippocampus, striatum, or globus pallidus). The compound can be delivered into multiple regions of the central nervous system (e.g., into multiple regions of the brain, and/or into the spinal cord). The compound can be delivered into diffuse regions of the brain (e.g., diffuse delivery to the cortex of the brain).

In one embodiment, the compound can be delivered by way of a cannula or other delivery device having one end implanted in a tissue, e.g., the brain, e.g., the substantia nigra, cortex, hippocampus, striatum or globus pallidus of the brain. The cannula can be connected to a reservoir containing the compound. The flow or delivery can be mediated by a pump, e.g., an osmotic pump or minipump, such as an Alzet pump (Durect, Cupertino, CA). In one embodiment, a pump and reservoir are implanted in an area distant from the tissue, e.g., in the abdomen, and delivery is effected by a conduit leading from the pump or reservoir to the site of release. Devices for delivery to the brain are described, for example, in U.S. Pat. Nos. 6,093,180, and 5,814,014.

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following example, which is included for purposes of illustration only and is not intended to be limiting.

EXAMPLES

Example 1. In Vitro Identification of SOD1 Targeting Sequences

Figure 2:
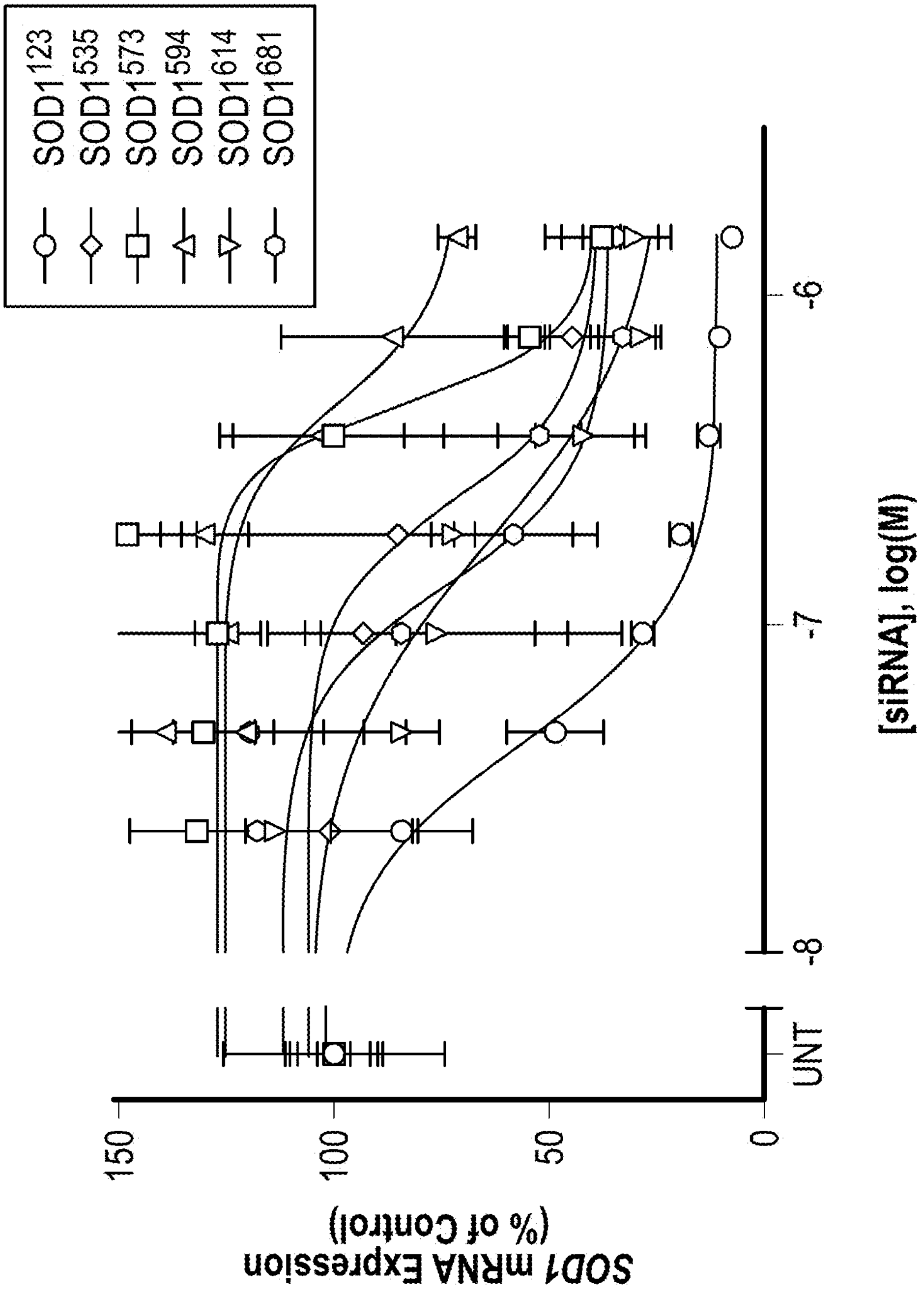
FIG. 2 depicts 8-point dose response curves obtained with SOD1 123, SOD1 535, SOD1 573, SOD1 594, SOD1 614, and SOD1 681 siRNA in human Hela cells. The siRNAs were each tested at a concentration range and the mRNA levels were evaluated at a 72-hour timepoint.
Figure 3:
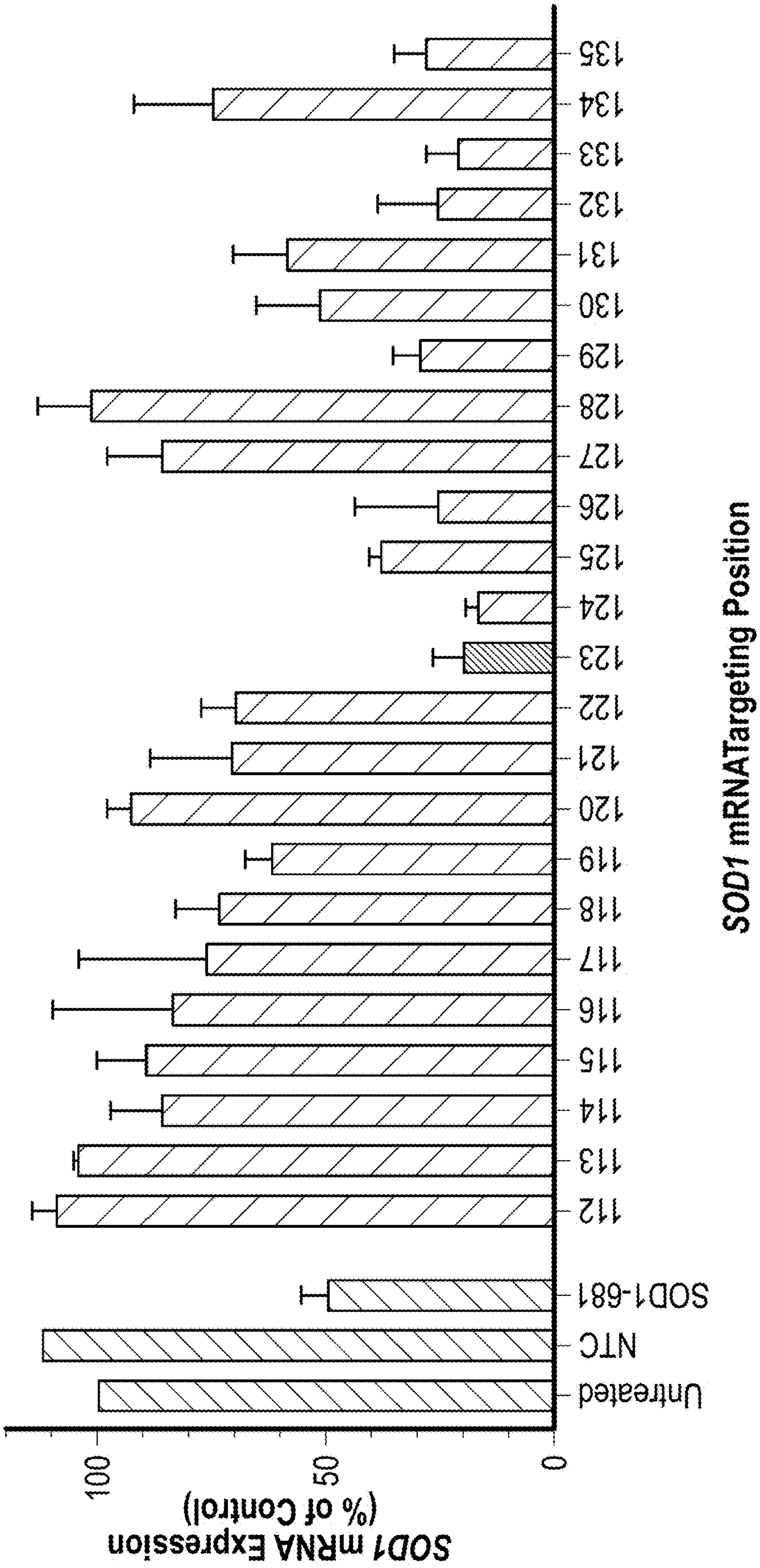
FIG. 3 depicts a focused screen of siRNAs targeting sequences around the hyper-functional site 123 of SOD1 mRNA in human Hela cells. The siRNAs were each tested at a concentration of 1.5 μM and the mRNA levels were evaluated at a 72-hour timepoint.
Figure 4:
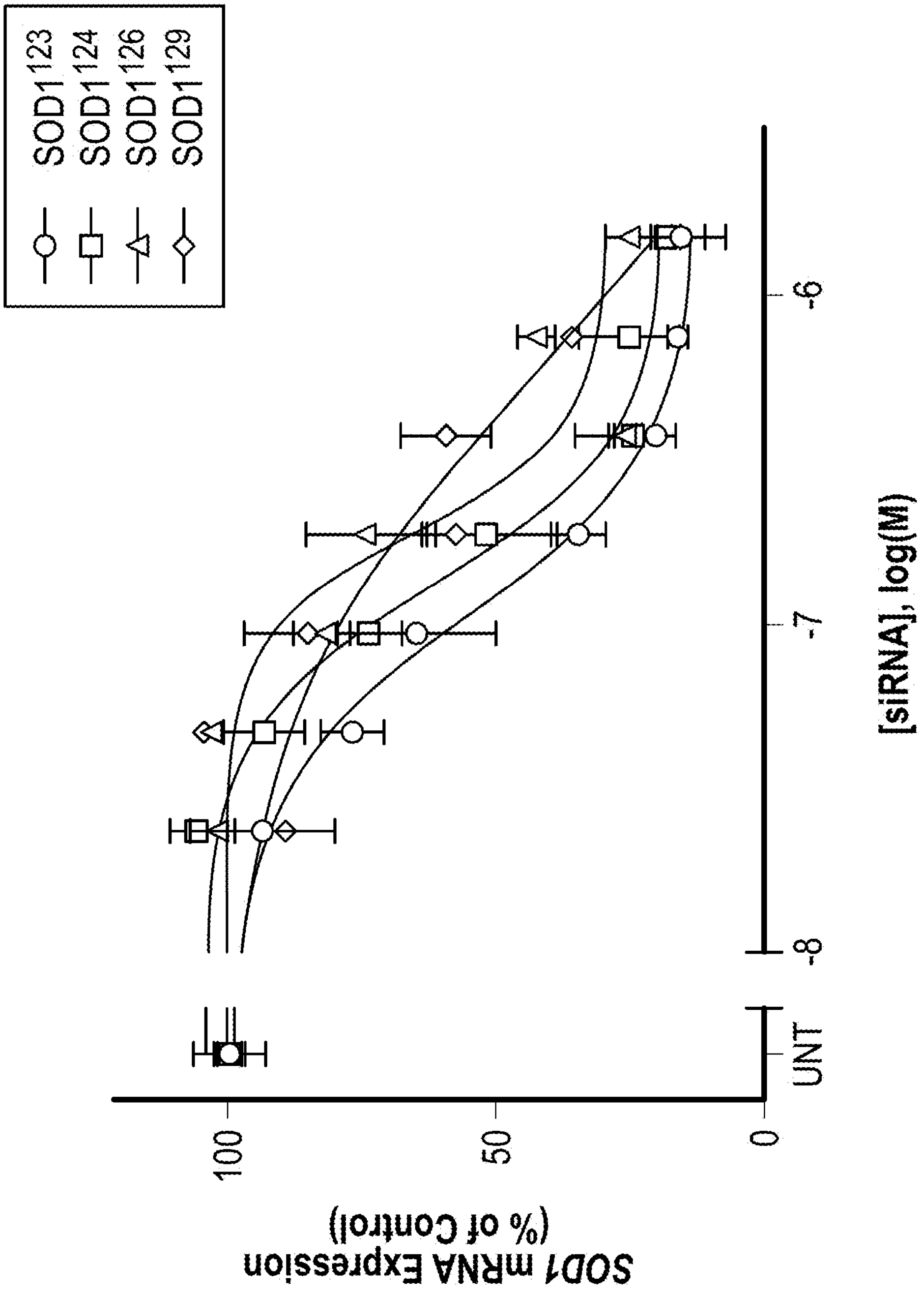
FIG. 4 depicts 8-point dose response curves obtained with SOD1 123, SOD1 124, SOD1 126, and SOD1 129 siRNA in human Hela cells. The siRNAs were each tested at a concentration range and the mRNA levels were evaluated at a 72-hour timepoint.

The SOD1 gene was used as a target for mRNA knockdown and a screen of siRNAs against the SOD1 gene was performed. A panel of siRNAs targeting several different sequences of SOD1 mRNA was developed and screened in Hela cells in vitro and compared to untreated control cells. The siRNAs were each tested at a concentration of 1.5 μM and the mRNA was evaluated at the 72 hours timepoint. FIG. 1 reports the results of the screen against SOD1 mRNA. FIG. 2 reports the 8-point dose response curves in Hela cells for 5 SOD1 targets identified in the screen (SOD1 123, SOD1 573, SOD1 594, SOD1 614, and SOD1 681). Among the tested target sites, the siRNA targeting SOD1 123 was the most efficacious. FIG. 3 reports the results of a focused screen of siRNAs targeting SOD1 mRNA sequences in Hela cells around the hyper-functional site 123 of SOD1 mRNA. The siRNAs for the focused screen were each tested at a concentration of 1.5 μM and the mRNA was evaluated at the 72 hours timepoint. FIG. 4 reports the 8-point dose response curves in Hela cells for 4 SOD1 targets identified in the focused screen, including the highly effected SOD1 123 target.

The 45-nucleotide gene region and 20-nucleotide SOD1 mRNA target sequences are recited below in Table 4. The following siRNA chemical modification pattern was employed for in vitro screens:

siRNA chemical modification pattern of FIG. 1 and FIG. 2:

```
Antisense strand, from 5' to 3' (20-nucleotides
in length):
P(mX)#(fX)#(mX)(mX)(mX)(fX)(mX)(mX)(mX)(mX)(mX)

(mX)(mX)#(fX)#(mX)#(fX)#(mX)#(mX)#(mX)#(fX)

Sense strand, from 5' to 3' (15-nucleotides in
length):
(mX)#(mX)#(mX)(mX)(fX)(fX)(fX)(mX)(fX)(mX)(mX)

(mX)(mX)#(mX)#(mX)-TegChol
```

siRNA chemical modification pattern of FIG. 3 and FIG. 4:

```
Antisense strand, from 5' to 3' (21-nucleotides
in length):
P(mX)#(fX)#(mX)(fX)(fX)(fX)(mX)(fX)(mX)(fX)(mX)

(fX)(mX)(fX)#(mX)#(fX)#(mX)#(mX)#(mX)#(fX)#(mX)

Sense strand, from 5' to 3' (16-nucleotides in
length):
(mX)#(mX)#(mX)(fX)(mX)(fX)(mX)(fX)(mX)(fX)(mX)

(mX)(mX)(fX)#(mX)#(mX)
```

For the above recited chemical modification patterns, "m" corresponds to a 2'-O-methyl modification; "f" corresponds to a 2'-fluoro modification; "X" corresponds to any nucleotide of A, U, G, or C; "#" corresponds to a phosphorothioate internucleotide linkage; "P" corresponds to a 5' phosphate; and "TegChol" corresponds to a 3' cholesterol-triethylene glycol.

TABLE 4

SOD1_target sequences

| ID | Gene Region | SEQ ID NO: | Target Sequence | SEQ ID NO: |
|---|---|---|---|---|
| 112 | GCGTGCTGAAGGGCGACGGCCCAGTGCAGGGCATCATCAATTTCG | 25 | ACGGCCCAGUGCAGGGCAUC | 77 |
| 113 | CGTGCTGAAGGGCGACGGCCCAGTGCAGGGCATCATCAATTTCGA | 26 | CGGCCCAGUGCAGGGCAUCA | 78 |
| 114 | GTGCTGAAGGGCGACGGCCCAGTGCAGGGCATCATCAATTTCGAG | 27 | GGCCCAGUGCAGGGCAUCAU | 79 |
| 115 | TGCTGAAGGGCGACGGCCCAGTGCAGGGCATCATCAATTTCGAGC | 28 | GCCCAGUGCAGGGCAUCAUC | 80 |
| 116 | GCTGAAGGGCGACGGCCCAGTGCAGGGCATCATCAATTTCGAGCA | 29 | CCCAGUGCAGGGCAUCAUCA | 81 |
| 117 | CTGAAGGGCGACGGCCCAGTGCAGGGCATCATCAATTTCGAGCAG | 30 | CCAGUGCAGGGCAUCAUCAA | 82 |
| 118 | TGAAGGGCGACGGCCCAGTGCAGGGCATCATCAATTTCGAGCAGA | 31 | CAGUGCAGGGCAUCAUCAAU | 83 |
| 119 | GAAGGGCGACGGCCCAGTGCAGGGCATCATCAATTTCGAGCAGAA | 32 | AGUGCAGGGCAUCAUCAAUU | 84 |
| 120 | AAGGGCGACGGCCCAGTGCAGGGCATCATCAATTTCGAGCAGAAG | 33 | GUGCAGGGCAUCAUCAAUUU | 85 |
| 121 | AGGGCGACGGCCCAGTGCAGGGCATCATCAATTTCGAGCAGAAGG | 34 | UGCAGGGCAUCAUCAAUUUC | 86 |
| 122 | GGGCGACGGCCCAGTGCAGGGCATCATCAATTTCGAGCAGAAGGA | 35 | GCAGGGCAUCAUCAAUUUCG | 87 |
| 123 | GGCGACGGCCCAGTGCAGGGCATCATCAATTTCGAGCAGAAGGAA | 1 | CAGGGCAUCAUCAAUUUCGA | 12 |

TABLE 4-continued

SOD1_target sequences

| ID | Gene Region | SEQ ID NO: | Target Sequence | SEQ ID NO: |
|---|---|---|---|---|
| 124 | GCGACGGCCCAGTGCAGGGCATCATCAATTTCGAGCAGAAGGAAA | 2 | AGGGCAUCAUCAAUUUCGAG | 13 |
| 125 | CGACGGCCCAGTGCAGGGCATCATCAATTTCGAGCAGAAGGAAAG | 36 | GGGCAUCAUCAAUUUCGAGC | 88 |
| 126 | GACGGCCCAGTGCAGGGCATCATCAATTTCGAGCAGAAGGAAAGT | 3 | GGCAUCAUCAAUUUCGAGCA | 14 |
| 127 | ACGGCCCAGTGCAGGGCATCATCAATTTCGAGCAGAAGGAAAGTA | 37 | GCAUCAUCAAUUUCGAGCAG | 89 |
| 128 | CGGCCCAGTGCAGGGCATCATCAATTTCGAGCAGAAGGAAAGTAA | 38 | CAUCAUCAAUUUCGAGCAGA | 90 |
| 129 | GGCCCAGTGCAGGGCATCATCAATTTCGAGCAGAAGGAAAGTAAT | 4 | AUCAUCAAUUUCGAGCAGAA | 15 |
| 130 | GCCCAGTGCAGGGCATCATCAATTTCGAGCAGAAGGAAAGTAATG | 39 | UCAUCAAUUUCGAGCAGAAG | 91 |
| 131 | CCCAGTGCAGGGCATCATCAATTTCGAGCAGAAGGAAAGTAATGG | 40 | CAUCAAUUUCGAGCAGAAGG | 92 |
| 132 | CCAGTGCAGGGCATCATCAATTTCGAGCAGAAGGAAAGTAATGGA | 5 | AUCAAUUUCGAGCAGAAGGA | 16 |
| 133 | CAGTGCAGGGCATCATCAATTTCGAGCAGAAGGAAAGTAATGGAC | 6 | UCAAUUUCGAGCAGAAGGAA | 17 |
| 134 | AGTGCAGGGCATCATCAATTTCGAGCAGAAGGAAAGTAATGGACC | 41 | CAAUUUCGAGCAGAAGGAAA | 93 |
| 135 | GTGCAGGGCATCATCAATTTCGAGCAGAAGGAAAGTAATGGACCA | 7 | AAUUUCGAGCAGAAGGAAAG | 18 |
| 205 | GACTGACTGAAGGCCTGCATGGATTCCATGTTCATGAGTTTGGAG | 42 | UGCAUGGAUUCCAUGUUCAU | 94 |
| 221 | GCATGGATTCCATGTTCATGAGTTTGGAGATAATACAGCAGGCTG | 43 | UCAUGAGUUUGGAGAUAAUA | 95 |
| 249 | GATAATACAGCAGGCTGTACCAGTGCAGGTCCTCACTTTAATCCT | 44 | UGUACCAGUGCAGGUCCUCA | 96 |
| 252 | AATACAGCAGGCTGTACCAGTGCAGGTCCTCACTTTAATCCTCTA | 45 | ACCAGUGCAGGUCCUCACUU | 97 |
| 263 | CTGTACCAGTGCAGGTCCTCACTTTAATCCTCTATCCAGAAAACA | 46 | UCCUCACUUUAAUCCUCUAU | 98 |
| 345 | TTGGGCAATGTGACTGCTGACAAAGATGGTGTGGCCGATGTGTCT | 47 | GCUGACAAAGAUGGUGUGGC | 99 |
| 368 | AGATGGTGTGGCCGATGTGTCTATTGAAGATTCTGTGATCTCACT | 48 | UGUGUCUAUUGAAGAUUCUG | 100 |
| 384 | GTGTCTATTGAAGATTCTGTGATCTCACTCTCAGGAGACCATTGC | 49 | UCUGUGAUCUCACUCUCAGG | 101 |
| 406 | TCTCACTCTCAGGAGACCATTGCATCATTGGCCGCACACTGGTGG | 50 | ACCAUUGCAUCAUUGGCCGC | 102 |
| 466 | ATGACTTGGGCAAAGGTGGAAATGAAGAAAGTACAAAGACAGGAA | 51 | GUGGAAAUGAAGAAAGUACA | 103 |
| 516 | GGAAGTCGTTTGGCTTGTGGTGTAATTGGGATCGCCCAATAAACA | 52 | UGUGGUGUAAUUGGGAUCGC | 104 |
| 524 | TTTGGCTTGTGGTGTAATTGGGATCGCCCAATAAACATTCCCTTG | 53 | AAUUGGGAUCGCCCAAUAAA | 105 |
| 573 | TAGTCTGAGGCCCCTTAACTCATCTGTTATCCTGCTAGCTGTAGA | 8 | UAACUCAUCUGUUAUCCUGC | 19 |
| 594 | ATCTGTTATCCTGCTAGCTGTAGAAATGTATCCTGATAAACATTA | 9 | AGCUGUAGAAAUGUAUCCUG | 20 |
| 595 | TCTGTTATCCTGCTAGCTGTAGAAATGTATCCTGATAAACATTAA | 54 | GCUGUAGAAAUGUAUCCUGA | 106 |
| 614 | TAGAAATGTATCCTGATAAACATTAAACACTGTAATCTTAAAAGT | 10 | AUAAACAUUAAACACUGUAA | 21 |
| 627 | TGATAAACATTAAACACTGTAATCTTAAAAGTGTAATTGTGTGAC | 55 | ACUGUAAUCUUAAAAGUGUA | 107 |
| 636 | TTAAACACTGTAATCTTAAAAGTGTAATTGTGTGACTTTTTCAGA | 56 | UUAAAAGUGUAAUUGUGUGA | 108 |
| 657 | GTGTAATTGTGTGACTTTTTCAGAGTTGCTTTAAAGTACCTGTAG | 57 | UUUUUCAGAGUUGCUUUAAA | 109 |
| 681 | GTTGCTTTAAAGTACCTGTAGTGAGAAACTGATTTATGATCACTT | 11 | CUGUAGUGAGAAACUGAUUU | 22 |
| 682 | TTGCTTTAAAGTACCTGTAGTGAGAAACTGATTTATGATCACTTG | 58 | UGUAGUGAGAAACUGAUUUA | 110 |
| 693 | TACCTGTAGTGAGAAACTGATTTATGATCACTTGGAAGATTTGTA | 59 | ACUGAUUUAUGAUCACUUGG | 111 |
| 701 | GTGAGAAACTGATTTATGATCACTTGGAAGATTTGTATAGTTTTA | 60 | AUGAUCACUUGGAAGAUUUG | 112 |
| 710 | TGATTTATGATCACTTGGAAGATTTGTATAGTTTTATAAAACTCA | 61 | UGGAAGAUUUGUAUAGUUUU | 113 |

TABLE 4-continued

SOD1_target sequences

| ID | Gene Region | SEQ ID NO: | Target Sequence | SEQ ID NO: |
|---|---|---|---|---|
| 724 | TTGGAAGATTTGTATAG TTTTATAAAACTCAGTT AAAATGTCTGT | 62 | AGUUUUAUAAAAC UCAGUUA | 114 |
| 744 | TATAAAACTCAGTTAAA ATGTCTGTTTCAATGAC CTGTATTTTGC | 63 | AAAUGUCUGUUUC AAUGACC | 115 |
| 750 | ACTCAGTTAAAATGTCT GTTTCAATGACCTGTAT TTTGCCAGACT | 64 | CUGUUUCAAUGAC CUGUAUU | 116 |
| 752 | TCAGTTAAAATGTCTGT TTCAATGACCTGTATTT TGCCAGACTTA | 65 | GUUUCAAUGACCU GUAUUUU | 117 |
| 754 | AGTTAAAATGTCTGTTT CAATGACCTGTATTTTG CCAGACTTAAA | 66 | UUCAAUGACCUGU AUUUUGC | 118 |
| 768 | TTTCAATGACCTGTATT TTGCCAGACTTAAATCA CAGATGGGTAT | 67 | UUUUGCCAGACUU AAAUCAC | 119 |
| 769 | TTCAATGACCTGTATTT TGCCAGACTTAAATCAC AGATGGGTATT | 68 | UUUGCCAGACUUA AAUCACA | 120 |
| 786 | TGCCAGACTTAAATCAC AGATGGGTATTAAACTT GTCAGAATTTC | 69 | ACAGAUGGGUAUU AAACUUG | 121 |
| 790 | AGACTTAAATCACAGAT GGGTATTAAACTTGTCA GAATTTCTTTG | 70 | AUGGGUAUUAAAC UUGUCAG | 122 |
| 796 | AAATCACAGATGGGTAT TAAACTTGTCAGAATTT CTTTGTCATTC | 71 | AUUAAACUUGUCA GAAUUUC | 123 |
| 797 | AATCACAGATGGGTATT AAACTTGTCAGAATTTC TTTGTCATTCA | 72 | UUAAACUUGUCAG AAUUUCU | 124 |
| 798 | ATCACAGATGGGTATTA AACTTGTCAGAATTTCT TTGTCATTCAA | 73 | UAAACUUGUCAGA AUUUCUU | 125 |
| 813 | TAAACTTGTCAGAATTT CTTTGTCATTCAAGCCT GTGAATAAAAA | 74 | UUCUUUGUCAUUC AAGCCUG | 126 |
| 821 | TCAGAATTTCTTTGTCA TTCAAGCCTGTGAATAA AAACCCTGTAT | 75 | CAUUCAAGCCUGU GAAUAAA | 127 |
| 848 | TGAATAAAAACCCTGTA TGGCACTTATTATGAGG CTATTAAAAGA | 76 | UAUGGCACUUAUU AUGAGGC | 128 |

Table 5 below recites the chemically modified siRNA antisense strands used to generate the data in FIG. 1 and FIG. 2. Table 6 below recites the chemically modified siRNA sense strands used to generate the data in FIG. 1 and FIG. 2. Table 7 below recites the chemically modified siRNA antisense strands used to generate the data in FIG. 3 and FIG. 4. Table 8 below recites the chemically modified siRNA sense strands used to generate the data in FIG. 3 and FIG. 4.

TABLE 5

SOD1_targeting chemically modified antisense strands.

| AS Strand ID | Modified AS sequence | SEQ ID NO: |
|---|---|---|
| SOD1_as_123 | P(mU)#(fC)#(mG)(mA)(mA)(fA)(mU)(mU)(mG)(mA)(mU)(mG)(mA)#(fU)#(mG)#(fC)#(mC)#(mC)#(mU)#(fG) | 129 |
| SOD1_as_249 | P(mU)#(fG)#(mA)(mG)(mG)(fA)(mC)(mC)(mU)(mG)(mC)(mA)(mC)#(fU)#(mG)#(fG)#(mU)#(mA)#(mC)#(fA) | 130 |
| SOD1_as_263 | P(mU)#(fU)#(mA)(mG)(mA)(fG)(mG)(mA)(mU)(mU)(mA)(mA)(mA)#(fG)#(mU)#(fG)#(mA)#(mG)#(mG)#(fA) | 131 |
| SOD1_as_345 | P(mU)#(fC)#(mC)(mA)(mC)(fA)(mC)(mC)(mA)(mU)(mC)(mU)(mU)#(fU)#(mG)#(fU)#(mC)#(mA)#(mG)#(fC) | 132 |
| SOD1_as_368 | P(mU)#(fA)#(mG)(mA)(mA)(fU)(mC)(mU)(mU)(mC)(mA)(mA)(mU)#(fA)#(mG)#(fA)#(mC)#(mA)#(mC)#(fA) | 133 |
| SOD1_as_384 | P(mU)#(fC)#(mU)(mG)(mA)(fG)(mA)(mG)(mU)(mG)(mA)(mG)(mA)#(fU)#(mC)#(fA)#(mC)#(mA)#(mG)#(fA) | 134 |
| SOD1_as_457 | P(mU)#(fU)#(mC)(mA)(mU)(fU)(mU)(mC)(mC)(mA)(mC)(mC)(mU)#(fU)#(mU)#(fG)#(mC)#(mC)#(mC)#(fA) | 135 |
| SOD1_as_516 | P(mU)#(fC)#(mG)(mA)(mU)(fC)(mC)(mC)(mA)(mA)(mU)(mU)(mA)#(fC)#(mA)#(fC)#(mC)#(mA)#(mC)#(fA) | 136 |
| SOD1_as_573 | P(mU)#(fC)#(mA)(mG)(mG)(fA)(mU)(mA)(mA)(mC)(mA)(mG)(mA)#(fU)#(mG)#(fA)#(mG)#(mU)#(mU)#(fA) | 137 |
| SOD1_as_594 | P(mU)#(fA)#(mG)(mG)(mA)(fU)(mA)(mC)(mA)(mU)(mU)(mU)(mC)#(fU)#(mA)#(fC)#(mA)#(mG)#(mC)#(fU) | 138 |

TABLE 5-continued

SOD1_targeting chemically modified antisense strands.

| AS Strand ID | Modified AS sequence | SEQ ID NO: |
|---|---|---|
| SOD1_as_614 | P(mU)#(fU)#(mA)(mC)(mA)(fG)(mU)(mG)(mU)(mU)(mU)(mA)(mA)#(fU)#(mG)#(fU)#(mU)#(mU)#(mA)#(fU) | 139 |
| SOD1_as_627 | P(mU)#(fA)#(mC)(mA)(mC)(fU)(mU)(mU)(mU)(mA)(mA)(mG)(mA)#(fU)#(mU)#(fA)#(mC)#(mA)#(mG)#(fU) | 140 |
| SOD1_as_636 | P(mU)#(fC)#(mA)(mC)(mA)(fC)(mA)(mA)(mU)(mU)(mA)(mC)(mA)#(fC)#(mU)#(fU)#(mU)#(mU)#(mA)#(fA) | 141 |
| SOD1_as_681 | P(mU)#(fA)#(mA)(mU)(mC)(fA)(mG)(mU)(mU)(mU)(mC)(mU)(mC)#(fA)#(mC)#(fU)#(mA)#(mC)#(mA)#(fG) | 142 |
| SOD1_as_682 | P(mU)#(fA)#(mA)(mA)(mU)(fC)(mA)(mG)(mU)(mU)(mU)(mC)(mU)#(fC)#(mA)#(fC)#(mU)#(mA)#(mC)#(fA) | 143 |
| SOD1_as_701 | P(mU)#(fA)#(mA)(mA)(mU)(fC)(mU)(mU)(mC)(mC)(mA)(mA)(mG)#(fU)#(mG)#(fA)#(mU)#(mC)#(mA)#(fU) | 144 |
| SOD1_as_710 | P(mU)#(fA)#(mA)(mA)(mC)(fU)(mA)(mU)(mA)(mC)(mA)(mA)(mA)#(fU)#(mC)#(fU)#(mU)#(mC)#(mC)#(fA) | 145 |
| SOD1_as_724 | P(mU)#(fA)#(mA)(mC)(mU)(fG)(mA)(mG)(mU)(mU)(mU)(mU)(mA)#(fU)#(mA)#(fA)#(mA)#(mA)#(mC)#(fU) | 146 |
| SOD1_as_752 | P(mU)#(fA)#(mA)(mA)(mU)(fA)(mC)(mA)(mG)(mG)(mU)(mC)(mA)#(fU)#(mU)#(fG)#(mA)#(mA)#(mA)#(fC) | 147 |
| SOD1_as_769 | P(mU)#(fG)#(mU)(mG)(mA)(fU)(mU)(mU)(mA)(mA)(mG)(mU)(mC)#(fU)#(mG)#(fG)#(mC)#(mA)#(mA)#(fA) | 148 |
| SOD1_as_790 | P(mU)#(fU)#(mG)(mA)(mC)(fA)(mA)(mG)(mU)(mU)(mU)(mA)(mA)#(fU)#(mA)#(fC)#(mC)#(mC)#(mA)#(fU) | 149 |
| SOD1_as_797 | P(mU)#(fG)#(mA)(mA)(mA)(fU)(mU)(mC)(mU)(mG)(mA)(mC)(mA)#(fA)#(mG)#(fU)#(mU)#(mU)#(mA)#(fA) | 150 |
| SOD1_as_813 | P(mU)#(fA)#(mG)(mG)(mC)(fU)(mU)(mG)(mA)(mA)(mU)(mG)(mA)#(fC)#(mA)#(fA)#(mA)#(mG)#(mA)#(fA) | 151 |
| SOD1_as_848 | P(mU)#(fC)#(mC)(mU)(mC)(fA)(mU)(mA)(mA)(mU)(mA)(mA)(mG)#(fU)#(mG)#(fC)#(mC)#(mA)#(mU)#(fA) | 152 |

TABLE 6

SOD1_targeting chemically modified sense strands.

| Sense Strand ID | Modified Sense Sequence | SEQ ID NO: |
|---|---|---|
| SOD1_s_123 | (mC)#(mA)#(mU)(mC)(fA)(fU)(fC)(mA)(fA)(mU)(mU)(mU)(mC)#(mG)#(mA)-TegChol | 153 |
| SOD1_s_249 | (mC)#(mA)#(mG)(mU)(fG)(fC)(fA)(mG)(fG)(mU)(mC)(mC)(mU)#(mC)#(mA)-TegChol | 154 |
| SOD1_s_263 | (mA)#(mC)#(mU)(mU)(fU)(fA)(fA)(mU)(fC)(mC)(mU)(mC)(mU)#(mA)#(mA)-TegChol | 155 |
| SOD1_s_345 | (mC)#(mA)#(mA)(mA)(fG)(fA)(fU)(mG)(fG)(mU)(mG)(mU)(mG)#(mG)#(mA)-TegChol | 156 |
| SOD1_s_368 | (mC)#(mU)#(mA)(mU)(fU)(fG)(fA)(mA)(fG)(mA)(mU)(mU)(mC)#(mU)#(mA)-TegChol | 157 |
| SOD1_s_384 | (mG)#(mA)#(mU)(mC)(fU)(fC)(fA)(mC)(fU)(mC)(mU)(mC)(mA)#(mG)#(mA)-TegChol | 158 |
| SOD1_s_457 | (mA)#(mA)#(mA)(mG)(fG)(fU)(fG)(mG)(fA)(mA)(mA)(mU)(mG)#(mA)#(mA)-TegChol | 159 |
| SOD1_s_516 | (mU)#(mG)#(mU)(mA)(fA)(fU)(fU)(mG)(fG)(mG)(mA)(mU)(mC)#(mG)#(mA)-TegChol | 160 |

TABLE 6-continued

SOD1_targeting chemically modified sense strands.

| Sense Strand ID | Modified Sense Sequence | SEQ ID NO: |
|---|---|---|
| SOD1_s_573 | (mC)#(mA)#(mU)(mC)(fU)(fG)(fU)(mU)(fA)(mU)(mC)(mC)(mU)#(mG)#(mA)-TegChol | 161 |
| SOD1_s_594 | (mU)#(mA)#(mG)(mA)(fA)(fA)(fU)(mG)(fU)(mA)(mU)(mC)(mC)#(mU)#(mA)-TegChol | 162 |
| SOD1_s_614 | (mC)#(mA)#(mU)(mU)(fA)(fA)(fA)(mC)(fA)(mC)(mU)(mG)(mU)#(mA)#(mA)-TegChol | 163 |
| SOD1_s_627 | (mA)#(mA)#(mU)(mC)(fU)(fU)(fA)(mA)(fA)(mA)(mG)(mU)(mG)#(mU)#(mA)-TegChol | 164 |
| SOD1_s_636 | (mA)#(mG)#(mU)(mG)(fU)(fA)(fA)(mU)(fU)(mG)(mU)(mG)(mU)#(mG)#(mA)-TegChol | 165 |
| SOD1_s_681 | (mG)#(mU)#(mG)(mA)(fG)(fA)(fA)(mA)(fC)(mU)(mG)(mA)(mU)#(mU)#(mA)-TegChol | 166 |
| SOD1_s_682 | (mU)#(mG)#(mA)(mG)(fA)(fA)(fA)(mC)(fU)(mG)(mA)(mU)(mU)#(mU)#(mA)-TegChol | 167 |
| SOD1_s_701 | (mC)#(mA)#(mC)(mU)(fU)(fG)(fG)(mA)(fA)(mG)(mA)(mU)(mU)#(mU)#(mA)-TegChol | 168 |
| SOD1_s_710 | (mG)#(mA)#(mU)(mU)(fU)(fG)(fU)(mA)(fU)(mA)(mG)(mU)(mU)#(mU)#(mA)-TegChol | 169 |
| SOD1_s_724 | (mU)#(mA)#(mU)(mA)(fA)(fA)(fA)(mC)(fU)(mC)(mA)(mG)(mU)#(mU)#(mA)-TegChol | 170 |
| SOD1_s_752 | (mA)#(mA)#(mU)(mG)(fA)(fC)(fC)(mU)(fG)(mU)(mA)(mU)(mU)#(mU)#(mA)-TegChol | 171 |
| SOD1_s_769 | (mC)#(mA)#(mG)(mA)(fC)(fU)(fU)(mA)(fA)(mA)(mU)(mC)(mA)#(mC)#(mA)-TegChol | 172 |
| SOD1_s_790 | (mU)#(mA)#(mU)(mU)(fA)(fA)(fA)(mC)(fU)(mU)(mG)(mU)(mC)#(mA)#(mA)-TegChol | 173 |
| SOD1_s_797 | (mC)#(mU)#(mU)(mG)(fU)(fC)(fA)(mG)(fA)(mA)(mU)(mU)(mU)#(mC)#(mA)-TegChol | 174 |
| SOD1_s_813 | (mU)#(mG)#(mU)(mC)(fA)(fU)(fU)(mC)(fA)(mA)(mG)(mC)(mC)#(mU)#(mA)-TegChol | 175 |
| SOD1_s_848 | (mC)#(mA)#(mC)(mU)(fU)(fA)(fU)(mU)(fA)(mU)(mG)(mA)(mG)#(mG)#(mA)-TegChol | 176 |

TABLE 7

SOD1_targeting chemically modified antisense strands.

| AS Strand ID | Modified AS sequence | SEQ ID NO: |
|---|---|---|
| SOD1_112_as | P(mU)#(fA)#(mU)(fG)(fC)(fC)(mC)(fU)(mG)(fC)(mA)(fC)(mU)(fG)#(mG)#(fG)#(mC)#(mC)#(mG)#(fU)#(mU) | 177 |
| SOD1_113_as | P(mU)#(fG)#(mA)(fU)(fG)(fC)(mC)(fC)(mU)(fG)(mC)(fA)(mC)(fU)#(mG)#(fG)#(mG)#(mC)#(mC)#(fG)#(mU) | 178 |
| SOD1_114_as | P(mU)#(fU)#(mG)(fA)(fU)(fG)(mC)(fC)(mC)(fU)(mG)(fC)(mA)(fC)#(mU)#(fG)#(mG)#(mG)#(mC)#(fC)#(mU) | 179 |
| SOD1_115_as | P(mU)#(fA)#(mU)(fG)(fA)(fU)(mG)(fC)(mC)(fC)(mU)(fG)(mC)(fA)#(mC)#(fU)#(mG)#(mG)#(mG)#(fC)#(mU) | 180 |
| SOD1_116_as | P(mU)#(fG)#(mA)(fU)(fG)(fA)(mU)(fG)(mC)(fC)(mC)(fU)(mG)(fC)#(mA)#(fC)#(mU)#(mG)#(mG)#(fG)#(mU) | 181 |
| SOD1_117_as | P(mU)#(fU)#(mG)(fA)(fU)(fG)(mA)(fU)(mG)(fC)(mC)(fC)(mU)(fG)#(mC)#(fA)#(mC)#(mU)#(mG)#(fG)#(mU) | 182 |

TABLE 7-continued

SOD1_targeting chemically modified antisense strands.

| AS Strand ID | Modified AS sequence | SEQ ID NO: |
|---|---|---|
| SOD1_118_as | P(mU)#(fU)#(mU)(fG)(fA)(fU)(mG)(fA)(mU)(fG)(mC)(fC)(mC)(fU)#(mG)#(fC)#(mA)#(mC)#(mU)#(fG)#(mU) | 183 |
| SOD1_119_as | P(mU)#(fA)#(mU)(fU)(fG)(fA)(mU)(fG)(mA)(fU)(mG)(fC)(mC)(fC)#(mU)#(fG)#(mC)#(mA)#(mC)#(fU)#(mU) | 184 |
| SOD1_120_as | P(mU)#(fA)#(mA)(fU)(fU)(fG)(mA)(fU)(mG)(fA)(mU)(fG)(mC)(fC)#(mC)#(fU)#(mG)#(mC)#(mA)#(fC)#(mU) | 185 |
| SOD1_121_as | P(mU)#(fA)#(mA)(fA)(fU)(fU)(mG)(fA)(mU)(fG)(mA)(fU)(mG)(fC)#(mC)#(fC)#(mU)#(mG)#(mC)#(fA)#(mU) | 186 |
| SOD1_122_as | P(mU)#(fG)#(mA)(fA)(fA)(fU)(mU)(fG)(mA)(fU)(mG)(fA)(mU)(fG)#(mC)#(fC)#(mC)#(mU)#(mG)#(fC)#(mU) | 187 |
| SOD1_123_as | P(mU)#(fC)#(mG)(fA)(fA)(fA)(mU)(fU)(mG)(fA)(mU)(fG)(mA)(fU)#(mG)#(fC)#(mC)#(mC)#(mU)#(fG)#(mU) | 188 |
| SOD1_124_as | P(mU)#(fU)#(mC)(fG)(fA)(fA)(mA)(fU)(mU)(fG)(mA)(fU)(mG)(fA)#(mU)#(fG)#(mC)#(mC)#(mC)#(fU)#(mU) | 189 |
| SOD1_125_as | P(mU)#(fC)#(mU)(fC)(fG)(fA)(mA)(fA)(mU)(fU)(mG)(fA)(mU)(fG)#(mA)#(fU)#(mG)#(mC)#(mC)#(fC)#(mU) | 190 |
| SOD1_126_as | P(mU)#(fG)#(mC)(fU)(fC)(fG)(mA)(fA)(mA)(fU)(mU)(fG)(mA)(fU)#(mG)#(fA)#(mU)#(mG)#(mC)#(fC)#(mU) | 191 |
| SOD1_127_as | P(mU)#(fU)#(mG)(fC)(fU)(fC)(mG)(fA)(mA)(fA)(mU)(fU)(mG)(fA)#(mU)#(fG)#(mA)#(mU)#(mG)#(fC)#(mU) | 192 |
| SOD1_128_as | P(mU)#(fC)#(mU)(fG)(fC)(fU)(mC)(fG)(mA)(fA)(mA)(fU)(mU)(fG)#(mA)#(fU)#(mG)#(mA)#(mU)#(fG)#(mU) | 193 |
| SOD1_129_as | P(mU)#(fU)#(mC)(fU)(fG)(fC)(mU)(fC)(mG)(fA)(mA)(fA)(mU)(fU)#(mG)#(fA)#(mU)#(mG)#(mA)#(fU)#(mU) | 194 |
| SOD1_130_as | P(mU)#(fU)#(mU)(fC)(fU)(fG)(mC)(fU)(mC)(fG)(mA)(fA)(mA)(fU)#(mU)#(fG)#(mA)#(mU)#(mG)#(fA)#(mU) | 195 |
| SOD1_131_as | P(mU)#(fC)#(mU)(fU)(fC)(fU)(mG)(fC)(mU)(fC)(mG)(fA)(mA)(fA)#(mU)#(fU)#(mG)#(mA)#(mU)#(fG)#(mU) | 196 |
| SOD1_132_as | P(mU)#(fC)#(mC)(fU)(fU)(fC)(mU)(fG)(mC)(fU)(mC)(fG)(mA)(fA)#(mA)#(fU)#(mU)#(mG)#(mA)#(fU)#(mU) | 197 |
| SOD1_133_as | P(mU)#(fU)#(mC)(fC)(fU)(fU)(mC)(fU)(mG)(fC)(mU)(fC)(mG)(fA)#(mA)#(fA)#(mU)#(mU)#(mG)#(fA)#(mU) | 198 |
| SOD1_134_as | P(mU)#(fU)#(mU)(fC)(fC)(fU)(mU)(fC)(mU)(fG)(mC)(fU)(mC)(fG)#(mA)#(fA)#(mA)#(mU)#(mU)#(fG)#(mU) | 199 |
| SOD1_135_as | P(mU)#(fU)#(mU)(fU)(fC)(fC)(mU)(fU)(mC)(fU)(mG)(fC)(mU)(fC)#(mG)#(fA)#(mA)#(mA)#(mU)#(fU)#(mU) | 200 |

TABLE 8

SOD1_targeting chemically modified sense strands.

| Sense Strand ID | Modified Sense Sequence | SEQ ID NO: |
|---|---|---|
| SOD1_112_s | (mC)#(mC)#(mC)(fA)(mG)(fU)(mG)(fC)(mA)(fG)(mG)(mG)(mC)(fA)#(mU)#(mA)-TegChol | 201 |
| SOD1_113_s | (mC)#(mC)#(mA)(fG)(mU)(fG)(mC)(fA)(mG)(fG)(mG)(mC)(mA)(fU)#(mC)#(mA)-TegChol | 202 |
| SOD1_114_s | (mC)#(mA)#(mG)(fU)(mG)(fC)(mA)(fG)(mG)(fG)(mC)(mA)(mU)(fC)#(mA)#(mA)-TegChol | 203 |
| SOD1_115_s | (mA)#(mG)#(mU)(fG)(mC)(fA)(mG)(fG)(mG)(fC)(mA)(mU)(mC)(fA)#(mU)#(mA)-TegChol | 204 |

TABLE 8-continued

| SOD1 targeting chemically modified sense strands. | | |
|---|---|---|
| Sense Strand ID | Modified Sense Sequence | SEQ ID NO: |
| SOD1_116_s | (mG)#(mU)#(mG)(fC)(mA)(fG)(mG)(fG)(mC)(fA)(mU)(mC)(mA)(fU)#(mC)#(mA)-TegChol | 205 |
| SOD1_117_s | (mU)#(mG)#(mC)(fA)(mG)(fG)(mG)(fC)(mA)(fU)(mC)(mA)(mU)(fC)#(mA)#(mA)-TegChol | 206 |
| SOD1_118_s | (mG)#(mC)#(mA)(fG)(mG)(fG)(mC)(fA)(mU)(fC)(mA)(mU)(mC)(fA)#(mA)#(mA)-TegChol | 207 |
| SOD1_119_s | (mC)#(mA)#(mG)(fG)(mG)(fC)(mA)(fU)(mC)(fA)(mU)(mC)(mA)(fA)#(mU)#(mA)-TegChol | 208 |
| SOD1_120_s | (mA)#(mG)#(mG)(fG)(mC)(fA)(mU)(fC)(mA)(fU)(mC)(mA)(mA)(fU)#(mU)#(mA)-TegChol | 209 |
| SOD1_121_s | (mG)#(mG)#(mG)(fC)(mA)(fU)(mC)(fA)(mU)(fC)(mA)(mA)(mU)(fU)#(mU)#(mA)-TegChol | 210 |
| SOD1_122_s | (mG)#(mG)#(mC)(fA)(mU)(fC)(mA)(fU)(mC)(fA)(mA)(mU)(mU)(fU)#(mC)#(mA)-TegChol | 211 |
| SOD1_123_s | (mG)#(mC)#(mA)(fU)(mC)(fA)(mU)(fC)(mA)(fA)(mU)(mU)(mU)(fC)#(mG)#(mA)-TegChol | 212 |
| SOD1_124_s | (mC)#(mA)#(mU)(fC)(mA)(fU)(mC)(fA)(mA)(fU)(mU)(mU)(mC)(fG)#(mA)#(mA)-TegChol | 213 |
| SOD1_125_s | (mA)#(mU)#(mC)(fA)(mU)(fC)(mA)(fA)(mU)(fU)(mU)(mC)(mG)(fA)#(mG)#(mA)-TegChol | 214 |
| SOD1_126_s | (mU)#(mC)#(mA)(fU)(mC)(fA)(mA)(fU)(mU)(fU)(mC)(mG)(mA)(fG)#(mC)#(mA)-TegChol | 215 |
| SOD1_127_s | (mC)#(mA)#(mU)(fC)(mA)(fA)(mU)(fU)(mU)(fC)(mG)(mA)(mG)(fC)#(mA)#(mA)-TegChol | 216 |
| SOD1_128_s | (mA)#(mU)#(mC)(fA)(mA)(fU)(mU)(fU)(mC)(fG)(mA)(mG)(mC)(fA)#(mG)#(mA)-TegChol | 217 |
| SOD1_129_s | (mU)#(mC)#(mA)(fA)(mU)(fU)(mU)(fC)(mG)(fA)(mG)(mC)(mA)(fG)#(mA)#(mA)-TegChol | 218 |
| SOD1_130_s | (mC)#(mA)#(mA)(fU)(mU)(fU)(mC)(fG)(mA)(fG)(mC)(mA)(mG)(fA)#(mA)#(mA)-TegChol | 219 |
| SOD1_131_s | (mA)#(mA)#(mU)(fU)(mU)(fC)(mG)(fA)(mG)(fC)(mA)(mG)(mA)(fA)#(mG)#(mA)-TegChol | 220 |
| SOD1_132_s | (mA)#(mU)#(mU)(fU)(mC)(fG)(mA)(fG)(mC)(fA)(mG)(mA)(mA)(fG)#(mG)#(mA)-TegChol | 221 |
| SOD1_133_s | (mU)#(mU)#(mU)(fC)(mG)(fA)(mG)(fC)(mA)(fG)(mA)(mA)(mG)(fG)#(mA)#(mA)-TegChol | 222 |
| SOD1_134_s | (mU)#(mU)#(mC)(fG)(mA)(fG)(mC)(fA)(mG)(fA)(mA)(mG)(mG)(fA)#(mA)#(mA)-TegChol | 223 |
| SOD1_135_s | (mU)#(mC)#(mG)(fA)(mG)(fC)(mA)(fG)(mA)(fA)(mG)(mG)(mA)(fA)#(mA)#(mA)-TegChol | 224 |

Example 2. In Vivo Silencing of SOD1 in a Mouse Model of ALS

Based on the results of the screens performed in Example 1, the SOD1 target site designated SOD1 123 was selected for further study in live mice. Sequences are recited below of SOD1 123 targeting siRNAs used for in vivo studies. The siRNA comprises a 21-nucleotide long antisense strand and a 16-nucleotide sense strand. The antisense strand comprises a 3' U nucleotide that is not complementary to the target SOD1 mRNA. The inclusion of the non-complementary 3' U nucleotide does not negatively effect silencing.

SOD1 123-Targeting Sense and Antisense Strands:

Sense strand:
(SEQ ID NO: 23)
GCAUCAUCAAUUUCGA

Antisense strand:
(SEQ ID NO: 24)
UCGAAAUUGAUGAUGCCCUGU

SOD1 123-Targeting Sense and Antisense Strands with Chemical Modification (P3 Chemistry Pattern):

Sense strand:
(SEQ ID NO: 225)
(mG)#(mC)#(mA)(fU)(mC)(fA)(mU)(fC)(mA)(fA)(mU)(mU)

(mU)(fC)#(mG)#(mA)-DIO

Antisense strand:
(SEQ ID NO: 226)
V(mU)#(fC)#(mG)(fA)(fA)(fA)(mU)(fU)(mG)(fA)(mU)

(fG)(mA)(fU)#(mG)#(fC)#(mC)#(mC)#(mU)#(fG)#(mU)

For the above recited chemical modification patterns, "m" corresponds to a 2'-O-methyl modification; "f" corresponds to a 2'-fluoro modification; "#" corresponds to a phosphorothioate internucleotide linkage; "V" corresponds to a 5' vinylphosphonate; and "DIO" corresponds to a 3' di-oligonucleotide linker (i.e., a linker that attaches the 3' end of a first sense strand to the 3' end of a second sense strand that is identical to the first sense strand).

Mice representing a model of ALS containing a G93A mutation in the SOD1 gene (G93A) were administered a single bilateral injection of SOD1 123-targeting di-siRNA with sequence and modification pattern shown above at 60 days, 5 nmol (125 μg) per ventricle (250 μg/10 nmol total dose).

Figure 5:
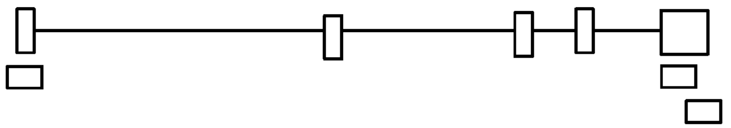
FIG. 5 depicts 10-point dose response curves obtained with antisense oligonucleotides Tofersen (ASO1), ASO2, and ASO333611 in SHSY5Y human neuroblastoma cells. SOD1 mRNA levels were evaluated at a 24-hour timepoint. The figure is taken from McCampbell et al. (J Clin Invest. 128(8): 3558-3567. 2018), incorporated herein by reference. Figure discloses SEQ ID NOS 231-233, respectively, in order of appearance.
Figure 5:
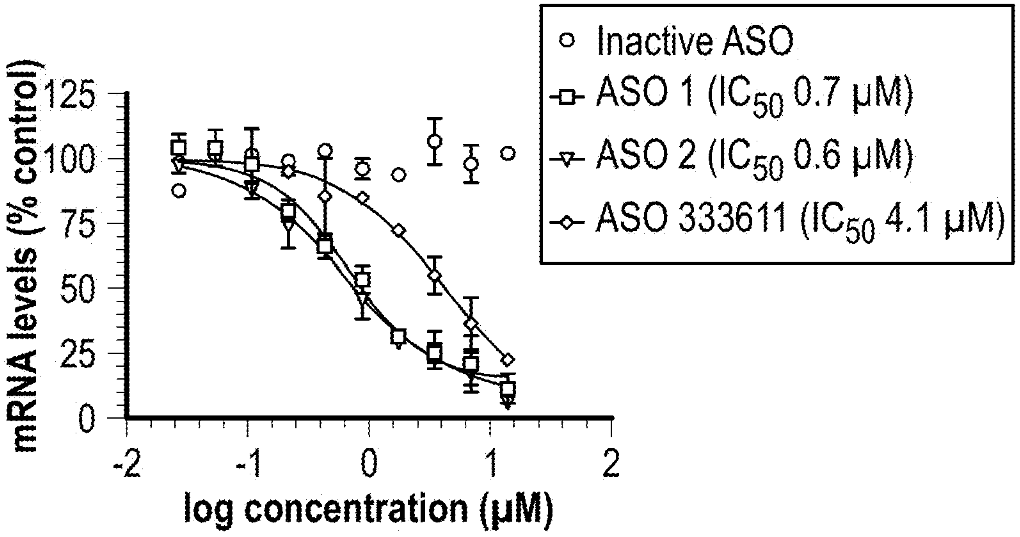
Figure 6:
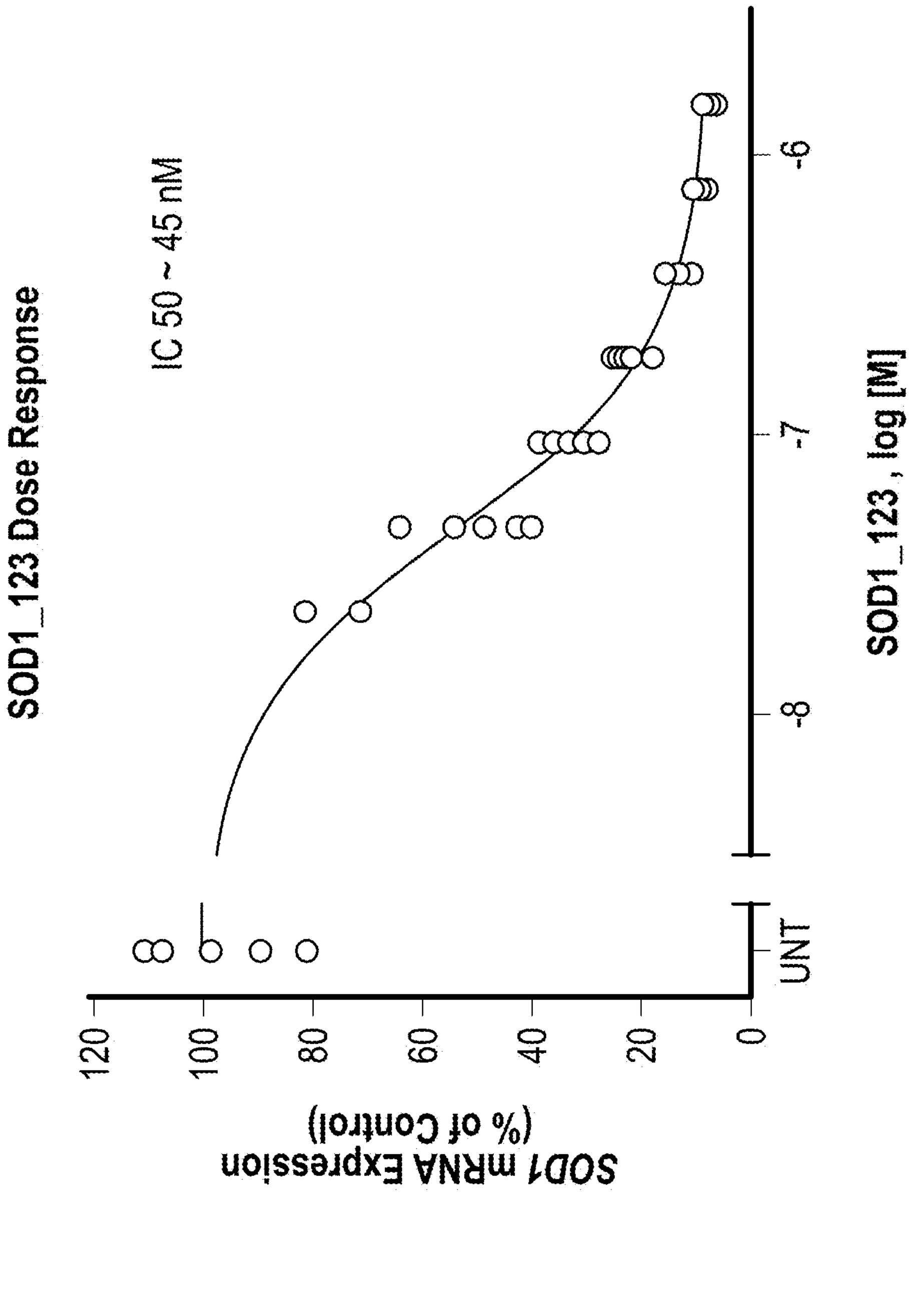
FIG. 6 depicts an 8-point dose response curve obtained with an siRNA targeting SOD1 123 used for in vivo studies.

Published 8-point dose response curves of Tofersen (ASO1)(McCampbell et al., supra) are shown in FIG. 5 for comparison with the SOD1 123-targeting di-siRNA used for in vivo studies in FIG. 6. The comparison shows that Tofersen has an IC50 of 700 nM while the SOD1 123-targeting di-siRNA has a superior IC50 of 45 nM, 15-fold lower than Tofersen. The sequence of Tofersen with the corresponding chemical modifications is provided below:

(SEQ ID NO: 227)
(moeC)#(moeA)(moeG)#(moeG)(moeA)#(dT)#(dA)#(dC)#

(dA)#(dT)#(dT)#(dT)#(dC)#(dT)#(dA)#(moeC)(moeA)#

(moeG)(moeC)#(moeU),

"#" corresponds to a phosphorothioate internucleotide linkage, "moe" corresponds to a 2'-O-methoxyethylribose, and "d" corresponds to a 2'-deoxyribose.

Figure 7:
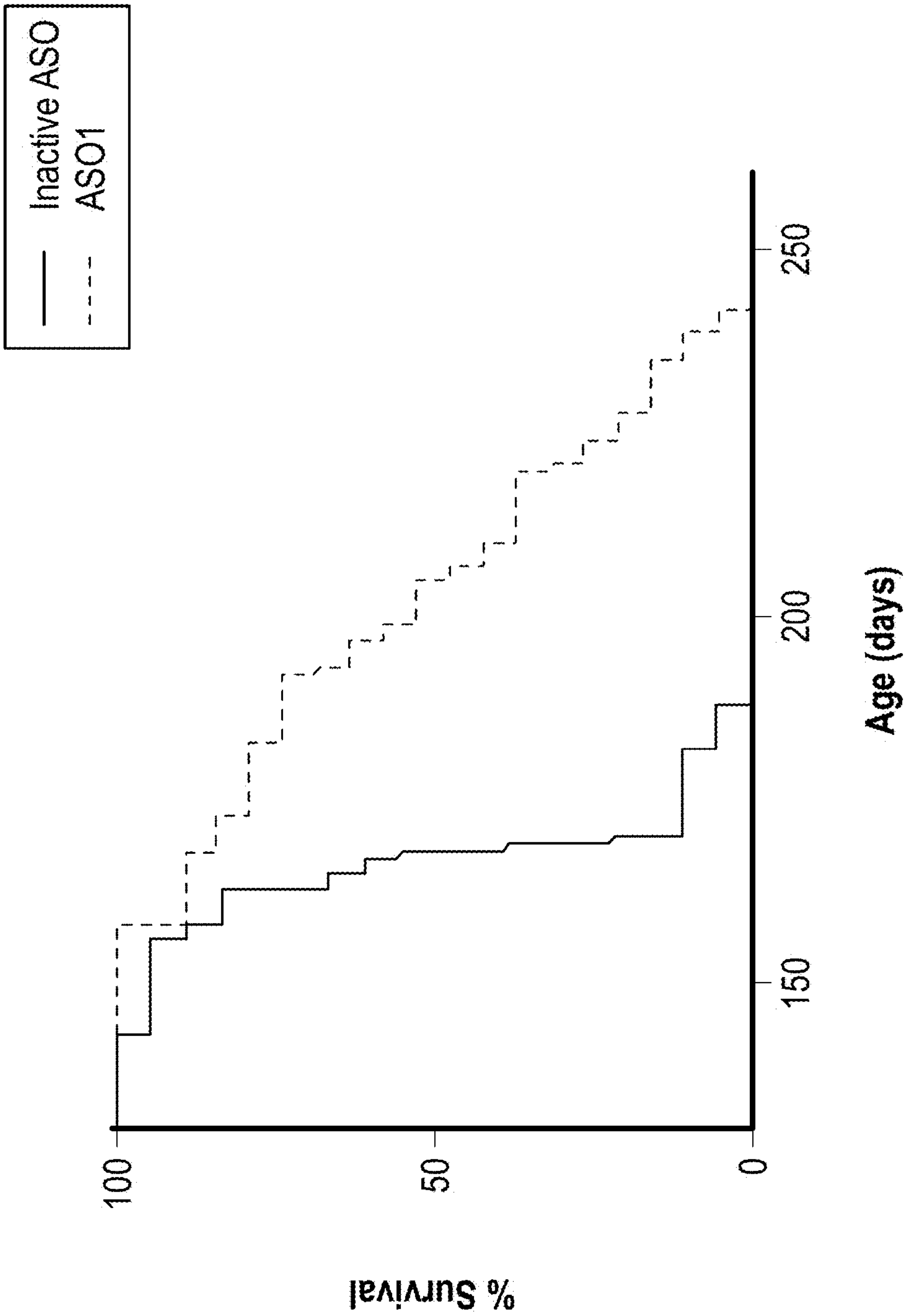
FIG. 7 depicts survival curves of G93A mice administered two injections of Tofersen (ASO1) at 300 μg at 50 and 94 days. The figure is taken from McCampbell et al, supra.
Figure 8:
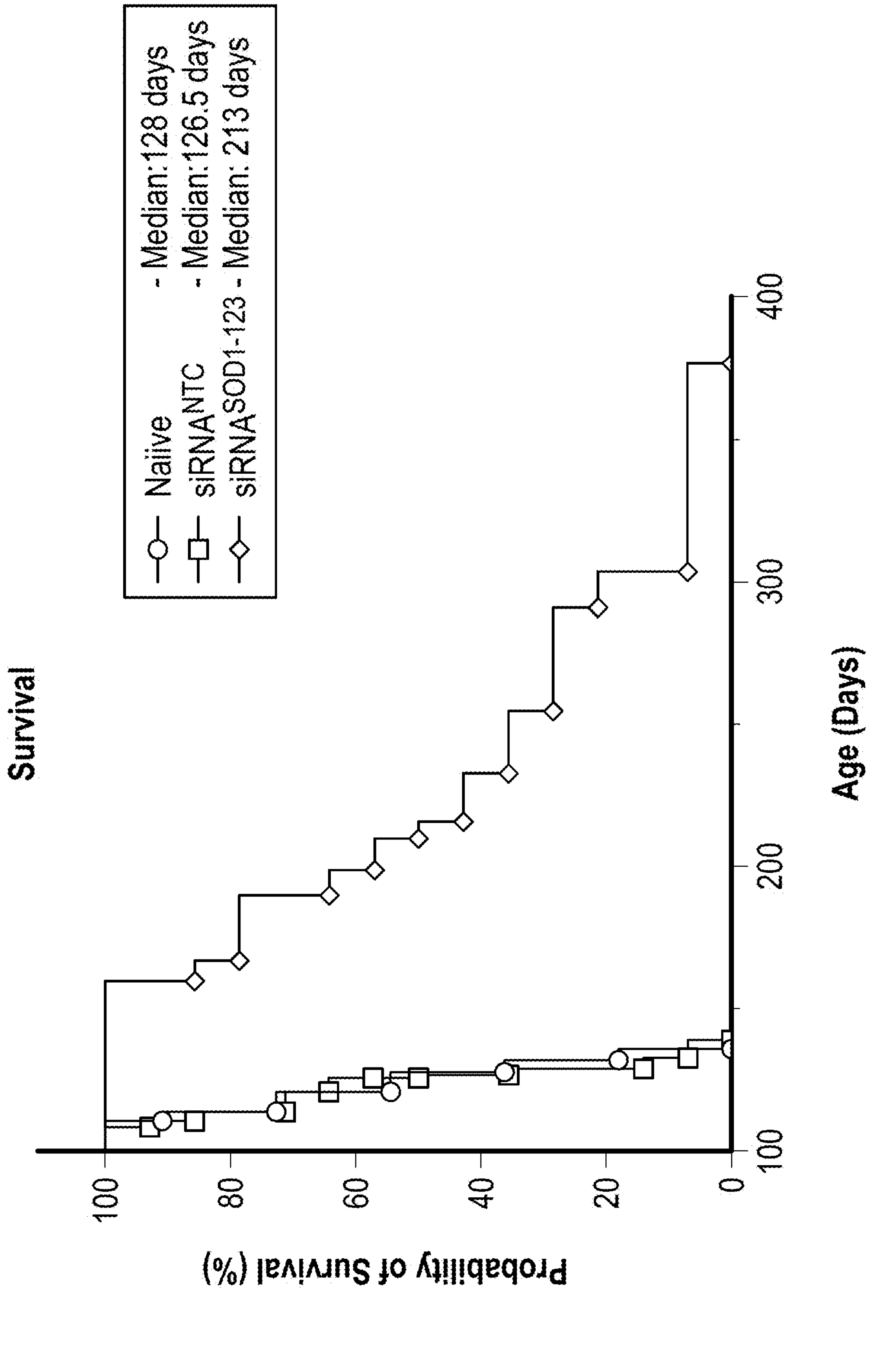
FIG. 8 depicts survival curves of G93A mice administered a single bilateral ICV injection of SOD1 123-targeting di-siRNA at 60 days, 5 nmol (125 μg) per ventricle. Mice injected with a non-targeting control siRNA and mice injected with PBS were used as controls.
Figure 9A:
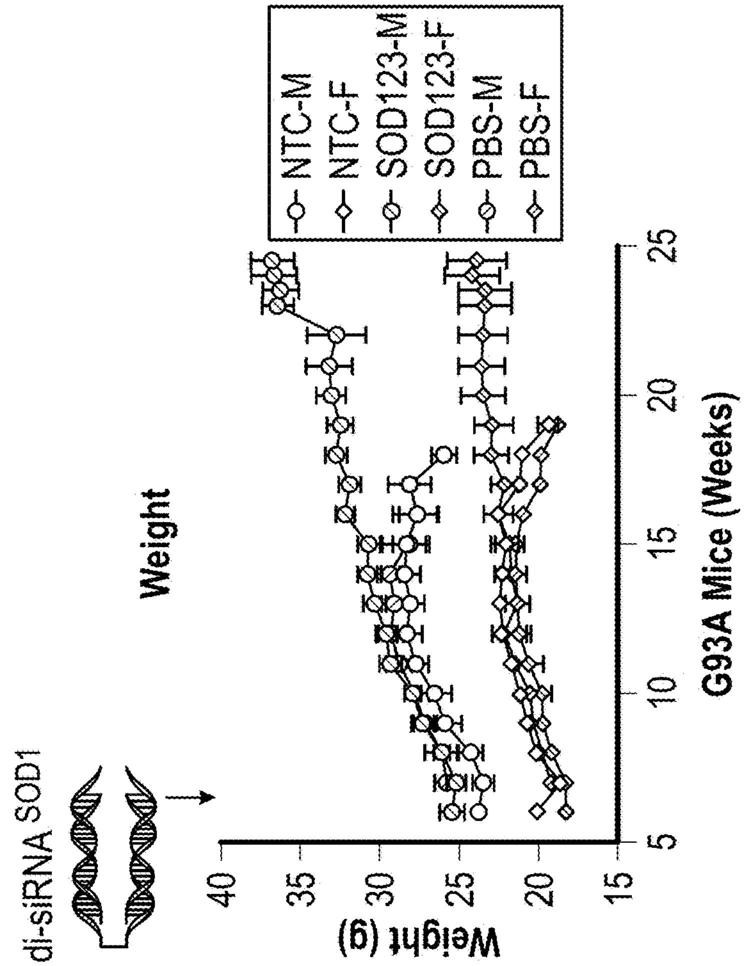
FIG. 9A-FIG. 9B depict body weight over 25 weeks (FIG. 9A) and 45 weeks (FIG. 9B) showing pathological loss of weight in control groups and maintenance of normal weight in SOD1 123-targeting di-siRNA treated G93A mice.
Figure 9B:
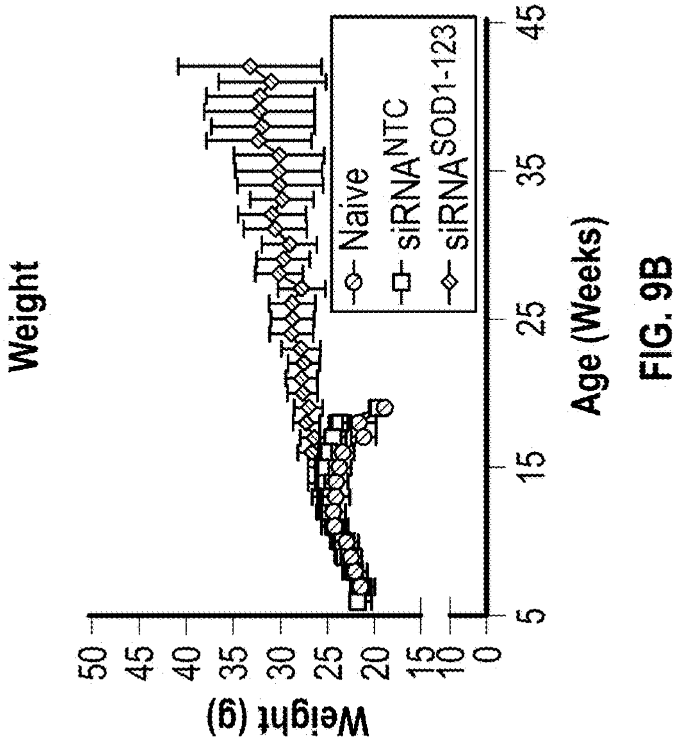
Figure 10:
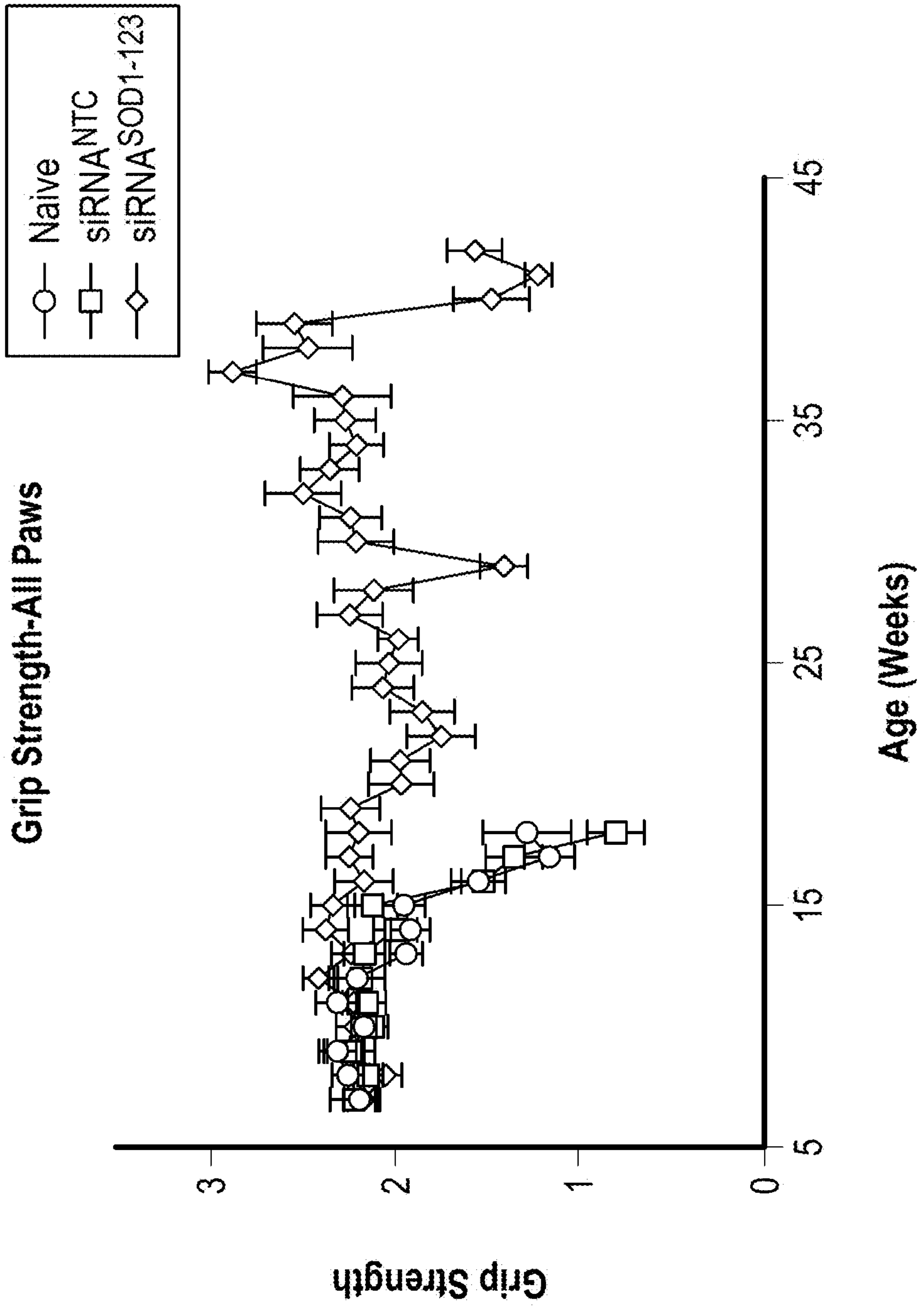
FIG. 10 depicts SOD1 123 di-siRNA treated G93A mice maintained normal grip strength compared to decline in control groups.
Figure 11:
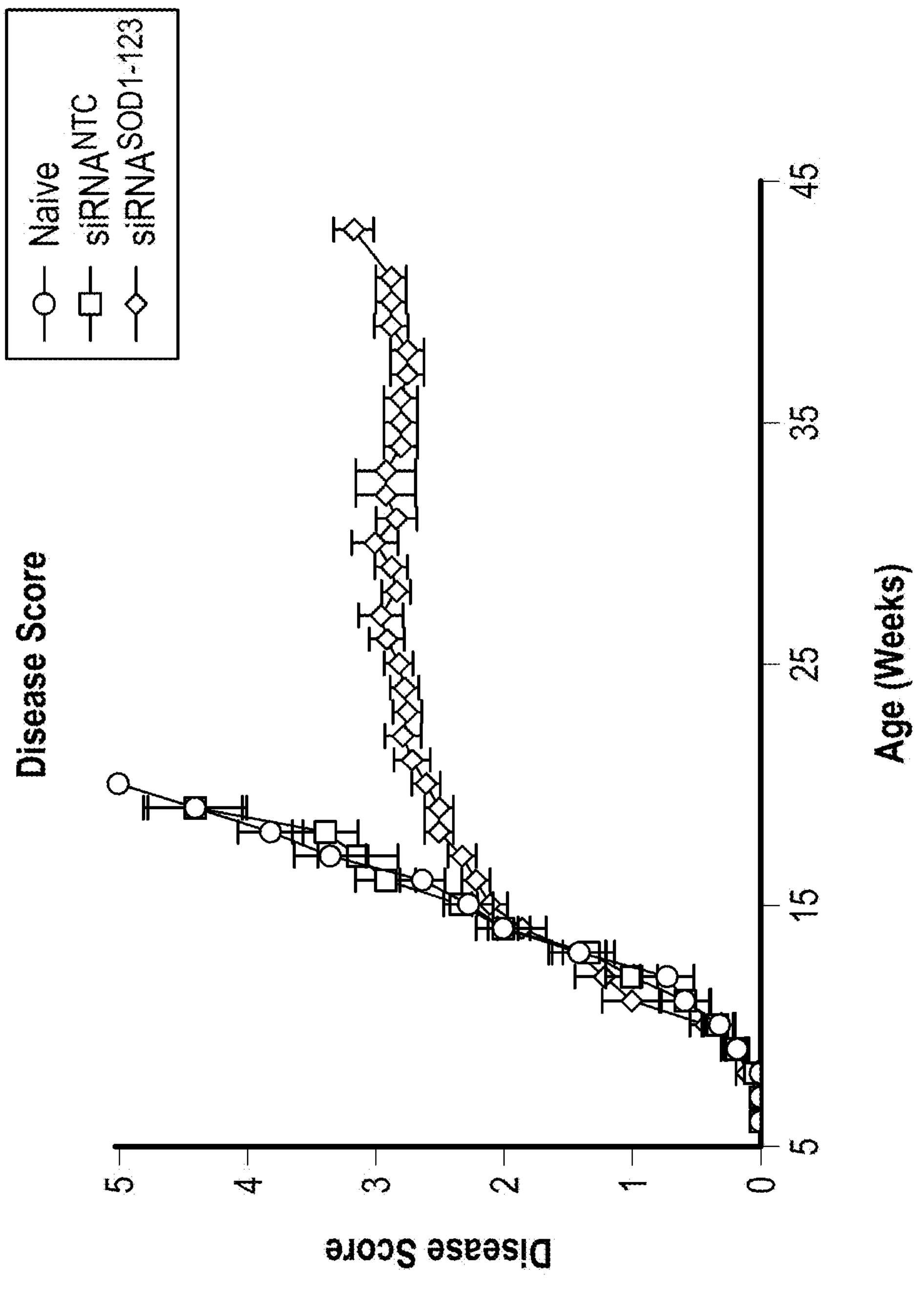
FIG. 11 depicts disease score comparisons between SOD1 123 di-siRNA treated and control groups.
Figure 14:
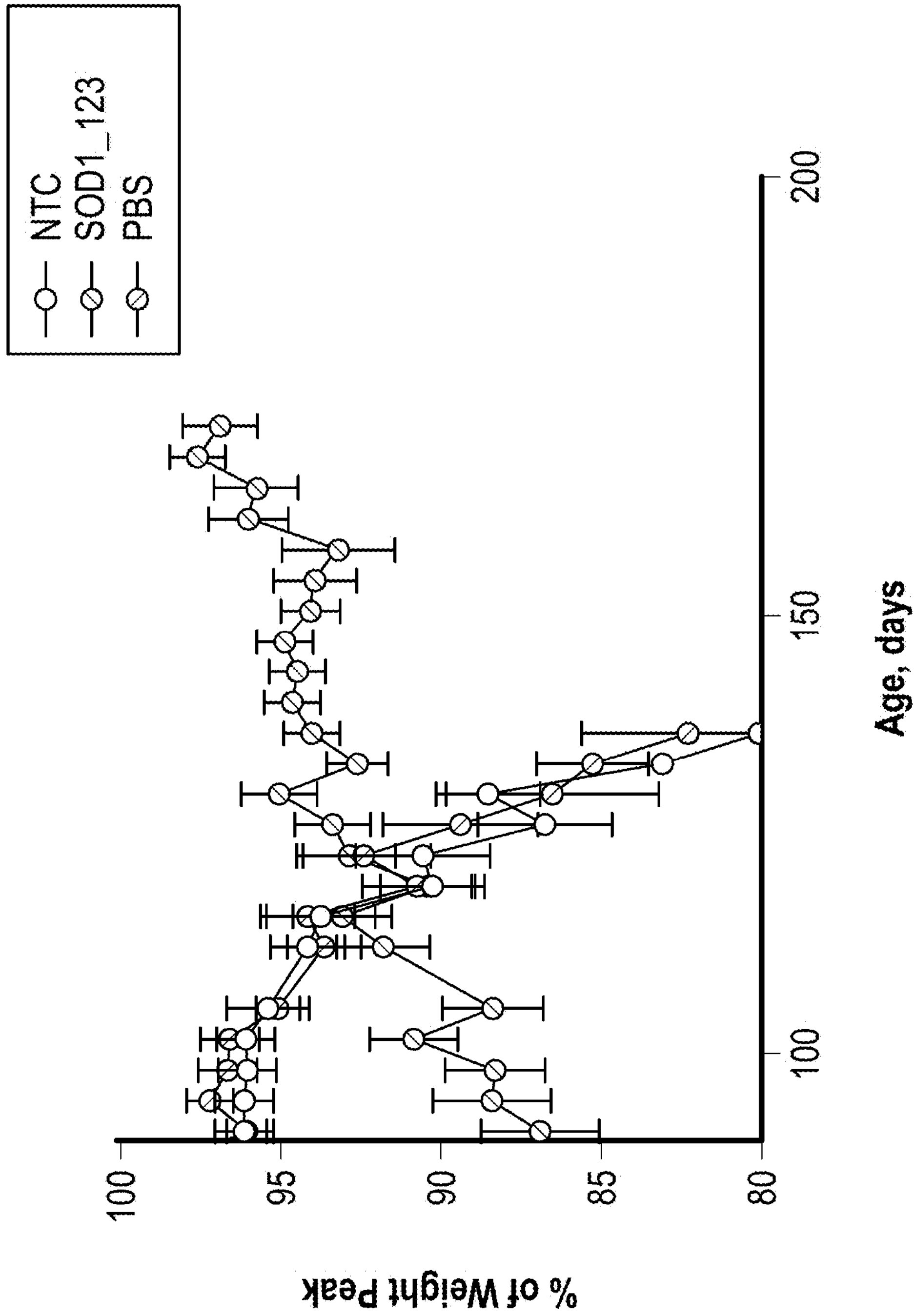
FIG. 14 depicts disease onset as scored by percentage of G93A mice showing a 10% loss of peak body weight in SOD1 123 di-siRNA treated and control animals.
Figure 15:
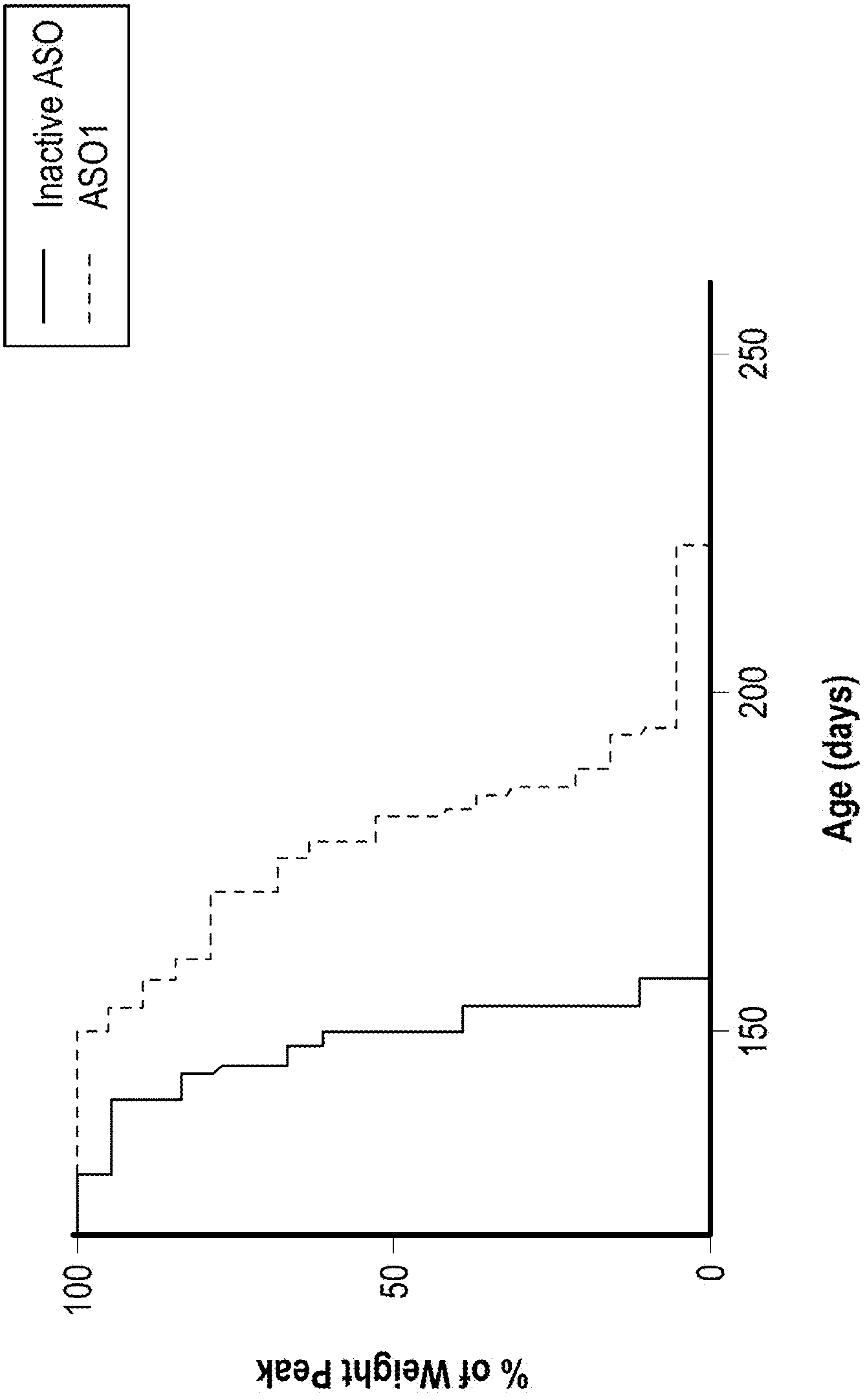
FIG. 15 depicts disease onset as scored by percentage of G93A mice showing a 10% loss of peak body weight in Tofersen (ASO1) treated and control animals. The figure is taken from McCampbell et al, supra.
Figure 16:
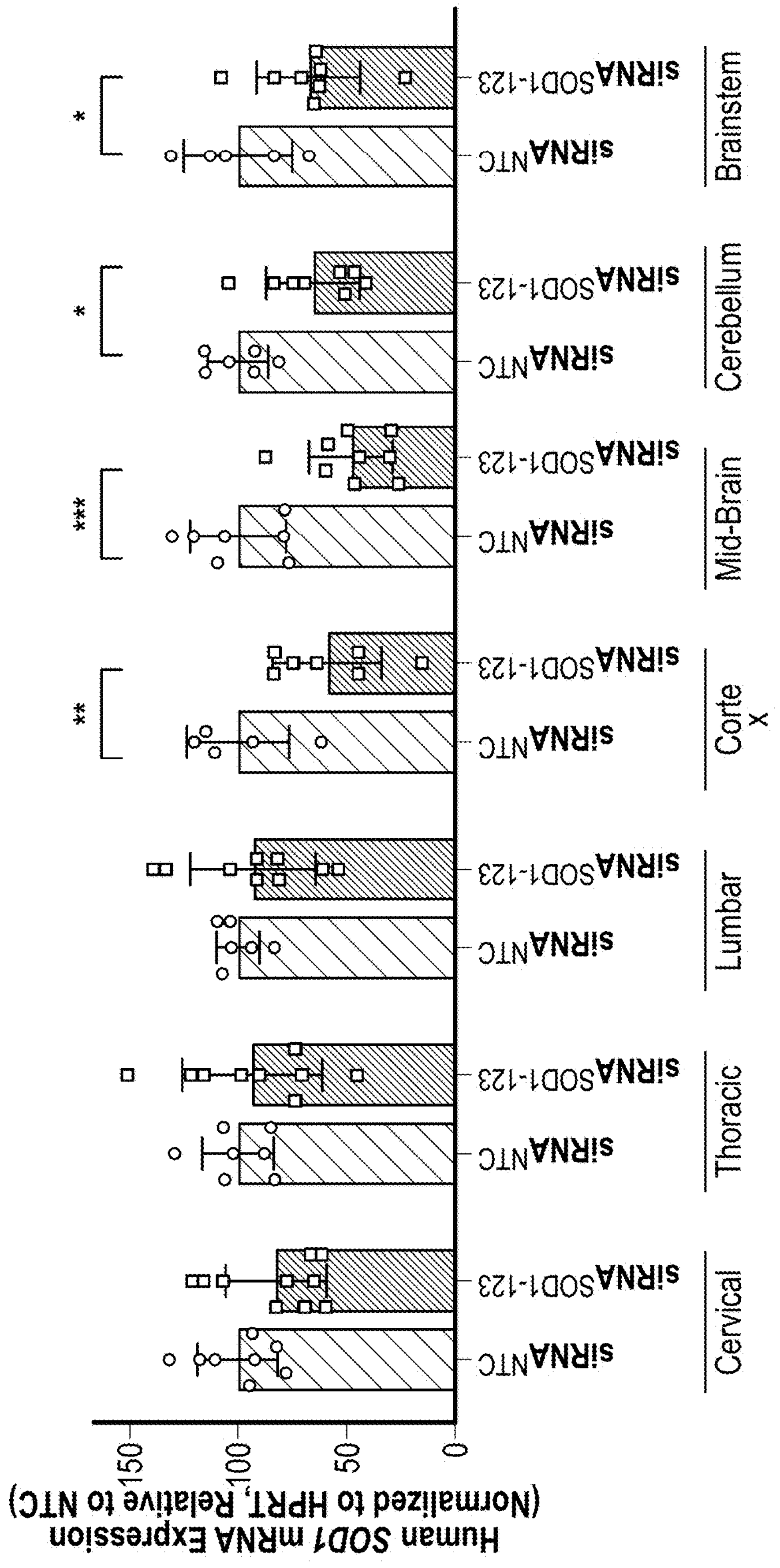
FIG. 16 depicts SOD1 mRNA silencing at time of take down at endpoint of G93A mice administered a single bilateral injection of SOD1 123 di-siRNA at 60 days, 5 nmol (125 μm) per ventricle. 2 mm punch of each tissue lysed for mRNA evaluation by QuantiGene gene expression assay (ThermoFisher, Waltham, MA) and normalized to HPRT. Unpaired t-test with Welch's correction *=>0.05, =>0.005 *=>0.0005.

Median survival was tested next. Median survival of at least 213 days was observed, and survival curves for SOD1 123-targeting di-siRNA shown in FIG. 8 were compared to published results with Tofersen (ASO1 in FIG. 7)(McCampbell et al., supra). Survival curves depicted in FIG. 7 represent G93A mice administered two injections of Tofersen (ASO1) 300 μg at 50 and 94 days (two injections for a total of a 600 μg dose/85 nmol). A survival shift of 70% was observed in mice treated with 240-250 μg of SOD1 123-targeting di-siRNA compared to a survival shift of 22% observed in mice treated with 600 μg of Tofersen. That is, a single dose less than half that of Tofersen was capable of achieving a substantial increase in survival. Pathological loss of weight at 25 weeks (FIG. 9A) and 45 weeks (FIG. 9B) was observed in control groups but maintained in the SOD1 123-targeting di-siRNA injected mice. Grip strength (FIG. 10) was also measured and was maintained compared to the control group. Further characterization of progression of disease was assessed according to criteria recited in Table 9 and significant reduction of morbidity was observed in mice treated with SOD1 123-targeting di-siRNA (FIG. 12, FIG. 13) compared to control groups (FIG. 11). Disease onset was scored by percentage of G93A mice showing a 10% loss of peak body weight. In SOD1 123-targeting di-siRNA (FIG. 14) there was no peak weight reduction while there was a 20% reduction in peak weight in Tofersen (ASO1) treated animals (FIG. 15)(McCampbell et al., supra). SOD1 mRNA silencing was maintained 5-11 months after injection, as shown in multiple tissues in FIG. 16. To test tissue mRNA levels, a 2 mm punch of each tissue was lysed for mRNA evaluation by Quantigene. mRNA values normalized to HPRT.

TABLE 9

Figure 12:
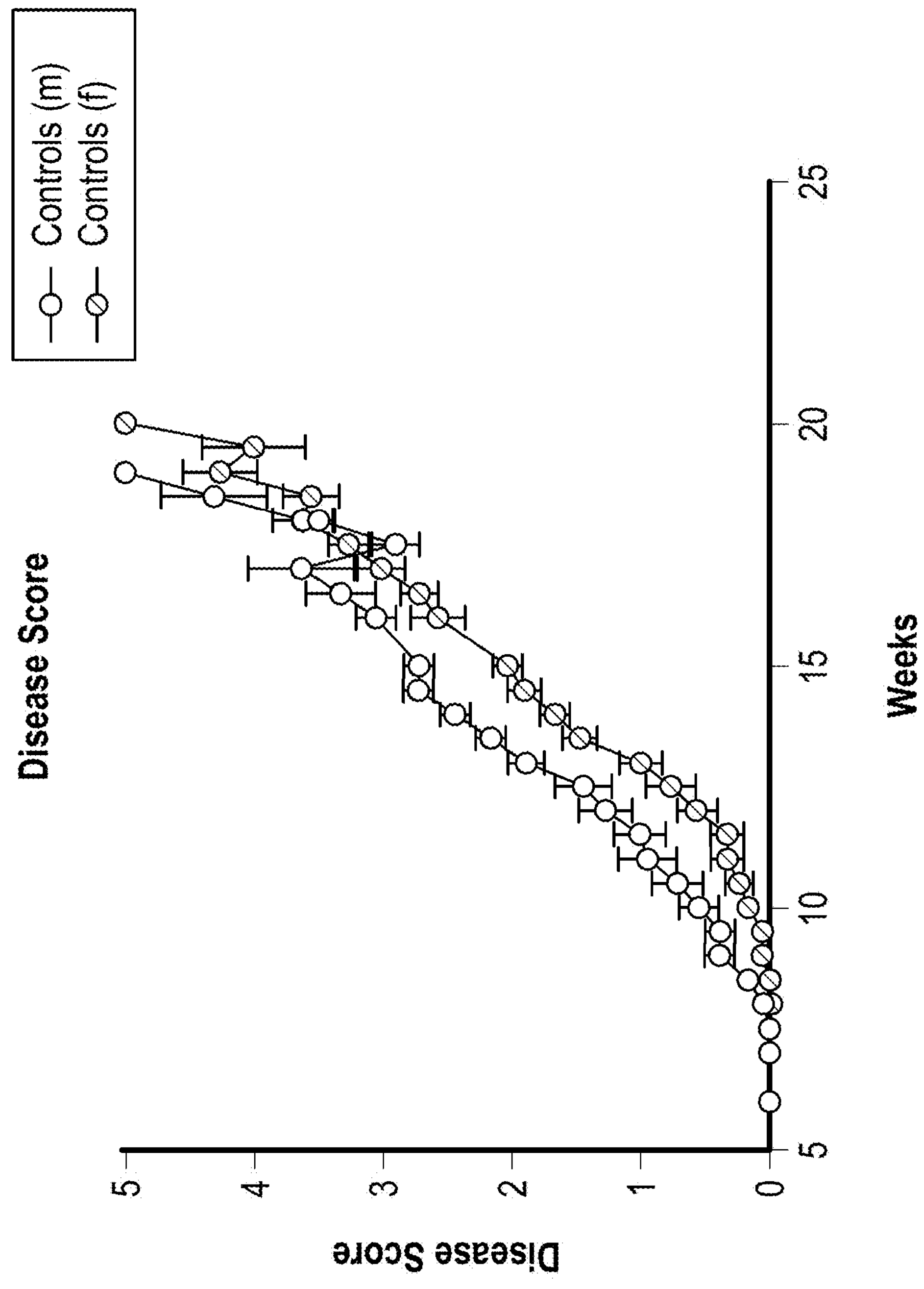
FIG. 12 depicts disease scores in controls with males and females plotted separately.
Figure 13:
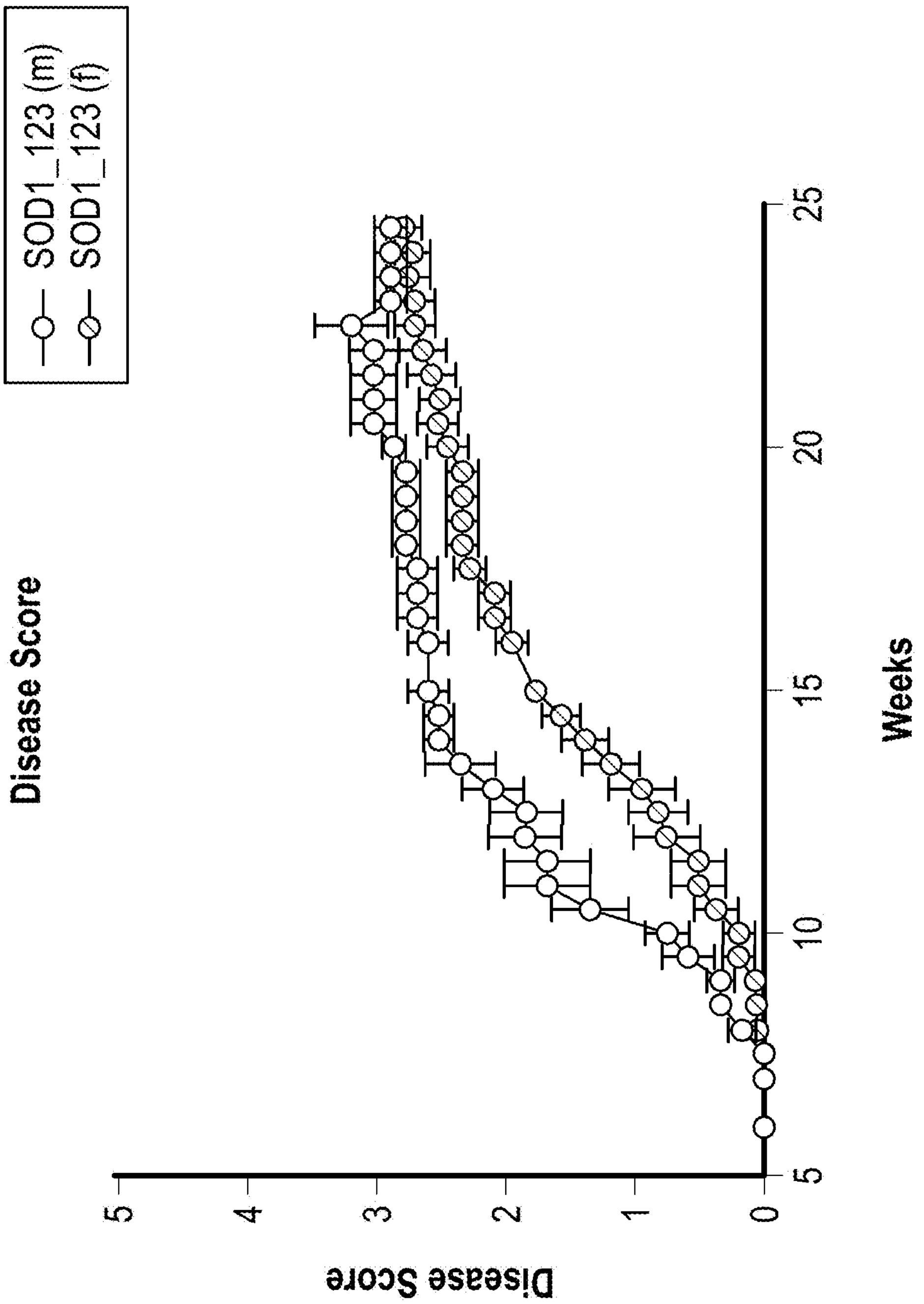
FIG. 13 depicts disease scores in SOD1 123 di-siRNA treated animals with males and females plodded separately.

Disease score criteria used in in vivo experiments in FIG. 11, FIG. 12, and FIG. 13.

| Score | Score Criteria |
|---|---|
| 0 | Healthy, clinically unremarkable. Full extension of hind legs away from lateral midline when mouse is suspended by its tail. |
| 1 | Collapse or partial collapse of leg extension towrds lateral midline (weakness) and/or weak hind limb tremor during tail suspension. |
| 2 | Definite tremor and lack of hind limb abduction. |
| 3 | Initial manifestation of paralysis displayed by decreased range of limb motion. Minimal joint movement, foot not being used for generating forward motion. Gait may resemble a waddle. |
| 4 | Paralysis in one or more hind limb. |
| 5 | Mouse endpoint: Mouse cannot right itself within 10 seconds after being placed on back. |

Figure 17B:
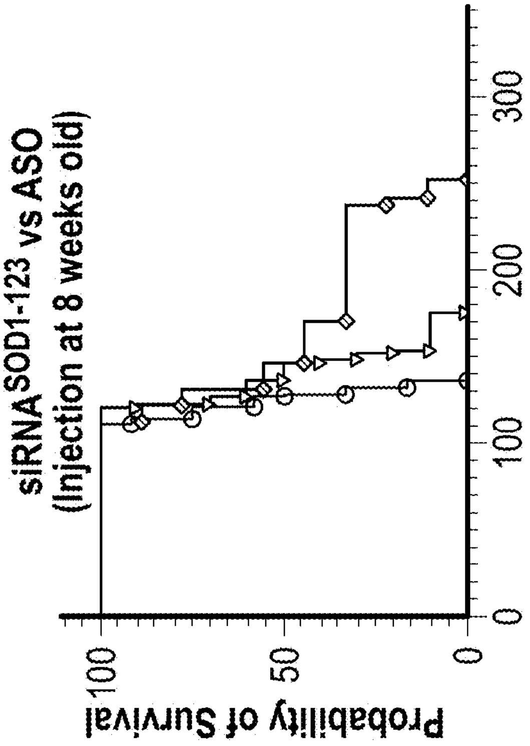
FIG. 17A-FIG. 17C depicts side-by-side comparison of survival between G93A mice treated at either 6 (FIG. 17A), 8 (FIG. 17B), or 12 (FIG. 17C) weeks old with Toferesen or SOD-123 siRNA (compared to untreated controls). Each animal received a single bilateral ICV injection of siRNA (20 nmol) or ASO (42 nmol). P3 chemistry, di-siRNA.
Figure 17A:
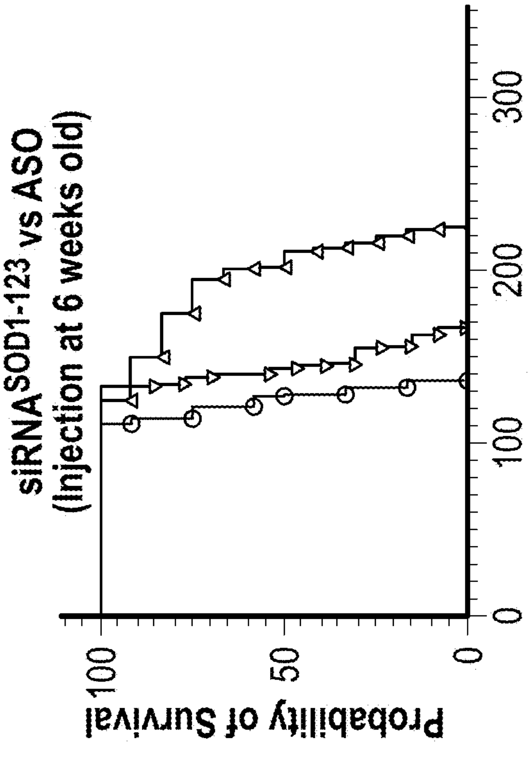
Figure 17C:
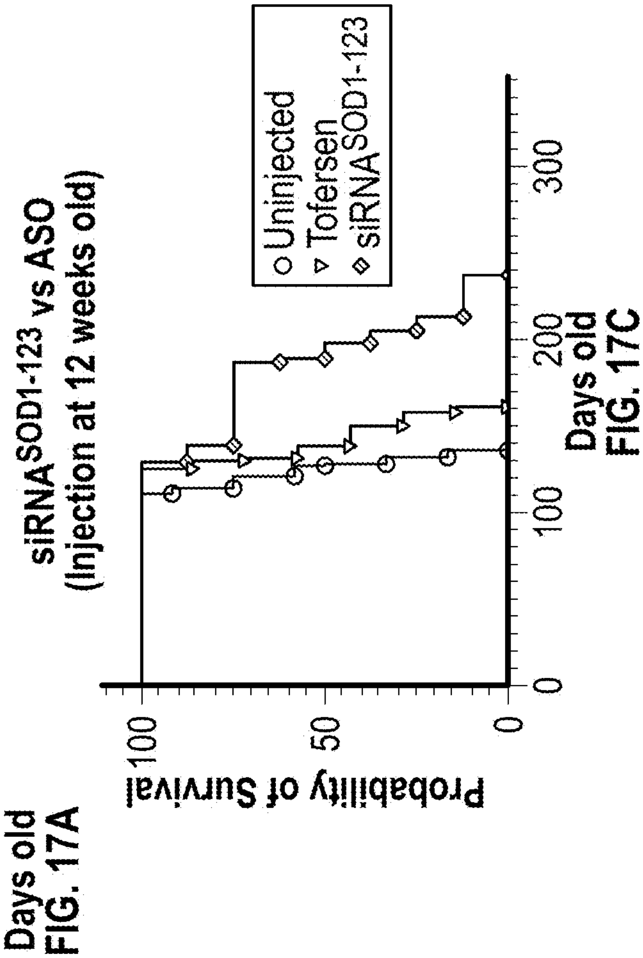

Head-to-head comparisons of the SOD-123 siRNA and the ASO Toferesen were tested next. As shown in FIG. 17A-FIG. 17C, survival between G93A mice treated at either 6, 8, or 12 weeks old with Toferesen or SOD-123 siRNA (compared to untreated controls) was measured. Each animal received a single bilateral ICV injection of siRNA (20 nmol) or ASO (42 nmol). P3 chemistry, di-siRNA. siRNA-SOD123 extended survival regardless of the treatment time point when compared to controls.

A variation of the P3 chemical modification pattern was employed next, designated P3B. This pattern uses fewer phosphorothioate internucleotide linkages along with two exNA internucleotide linkages. The pattern used is shown below:

SOD1 123-Targeting Sense and Antisense Strands with Chemical Modification (P3B Chemistry Pattern):

Sense strand:
(SEQ ID NO: 225)
(mG)#(mC)#(mA)(fU)(mC)(fA)(mU)(fC)(mA)(fA)(mU)

(mU)(mU)(fC)#(mG)#(mA)-DIO

Antisense strand:
(SEQ ID NO: 228)
V(mU)#(fC)#(mG)(fA)(fA)(fA)(mU)(fU)(mG)(fA)(mU)

(fG)(mA)(fU)(mG)(fC)(mC)(mC)(mU)exNA#(mG)exNA#

(fU)

For the above recited chemical modification patterns, "m" corresponds to a 2'-O-methyl modification; "f" corresponds to a 2'-fluoro modification; "#" corresponds to a phosphorothioate internucleotide linkage; "V" corresponds to a 5' vinylphosphonate; "DIO" corresponds to a 3' di-oligonucleotide linker (i.e., a linker that attaches the 3' end of a first sense strand to the 3' end of a second sense strand that is identical to the first sense strand); and "exNA" corresponds to an internucleotide linkage of Formula (I).

Figure 18A:
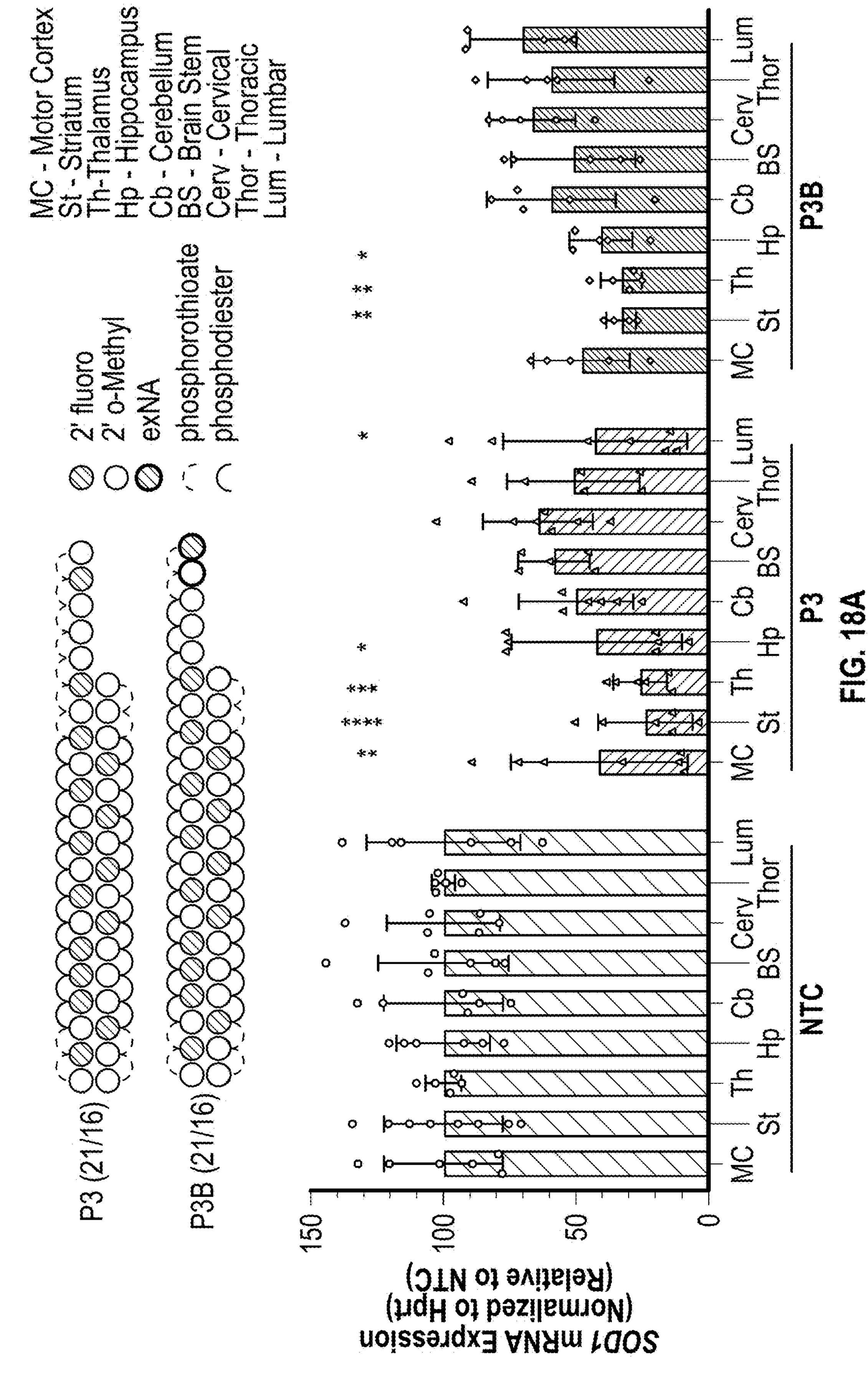
FIG. 18A-FIG. 18C depicts side-by-side comparison of (FIG. 18A) mRNA and (FIG. 18B) protein silencing efficacy in G93A mice between two siRNA chemical scaffolds (P3 and P3B).
Figure 18B:
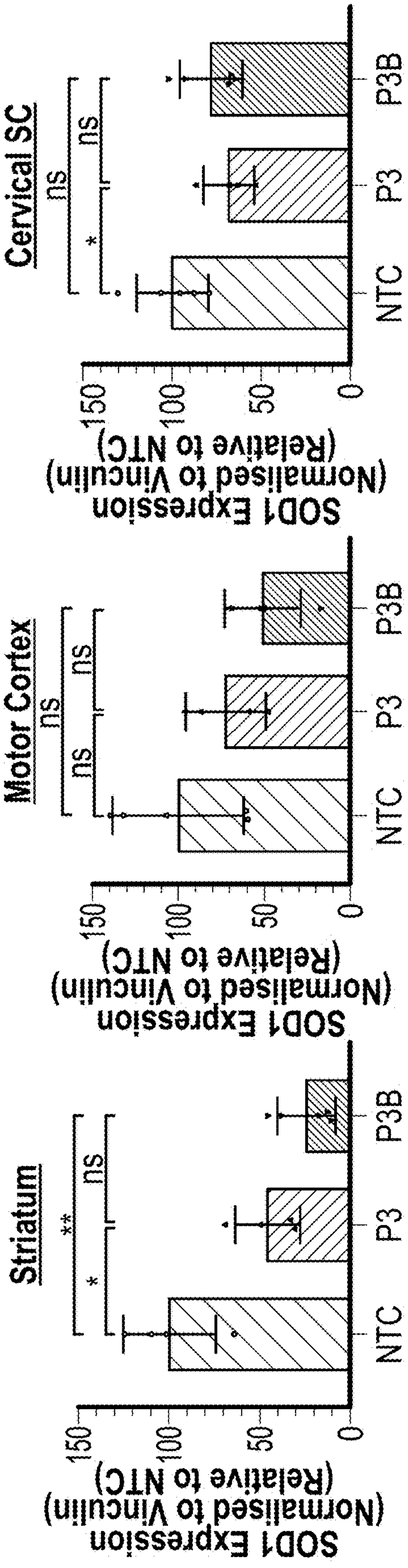
Figure 18C:
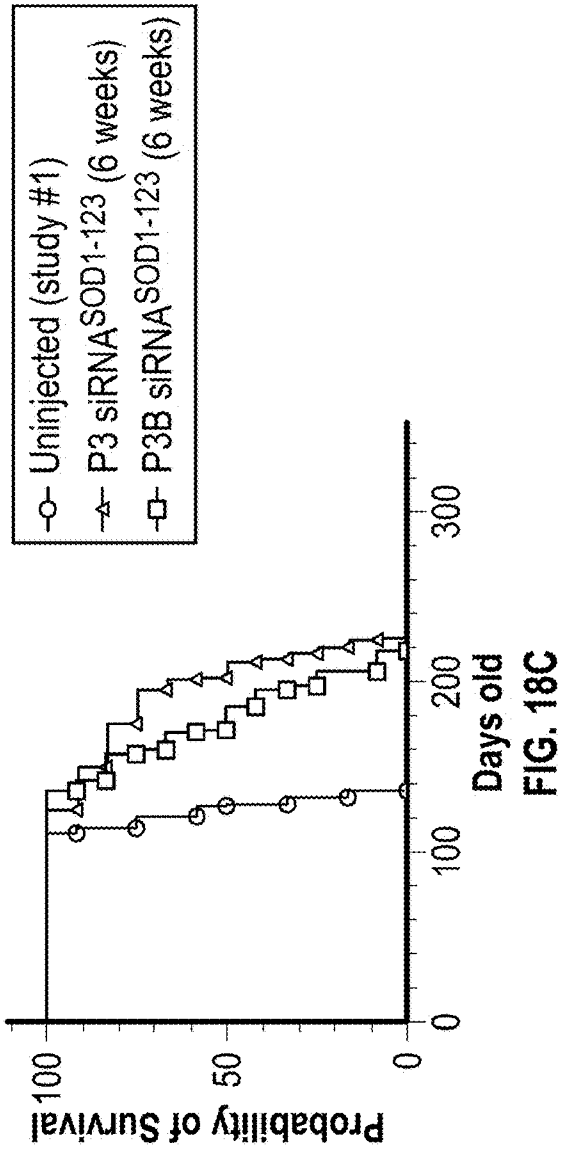

As shown in FIG. 18A and FIG. 18B, SOD1 mRNA and protein levels were reduced to a similar level with either chemical modification pattern. Moreover, the survival benefit in G93A mise was similar between the two chemical modification patterns (FIG. 18C).

Further comparisons were made with alternative chemical modification patterns. The P3 pattern described above was compared to a P5 pattern, as shown below:

SOD1 123-Targeting Sense and Antisense Strands with Chemical Modification (P5 Chemistry Pattern):

```
Sense strand:
                                        (SEQ ID NO: 229)
(mG)#(mC)#(mA)(mU)(mC)(fA)(fU)(fC)(mA)(fA)(mU)

(mU)(mU)(mC)#(mG)#(mA)-DIO

Antisense strand:
                                        (SEQ ID NO: 230)
V(mU)#(fC)#(mG)(mA)(mA)(fA)(mU)(mU)(mG)(mA)(mU)

(mG)(mA)(fU)#(mG)#(fC)#(mC)#(mC)#(mU)#(fG)#(mU)
```

Figure 19:
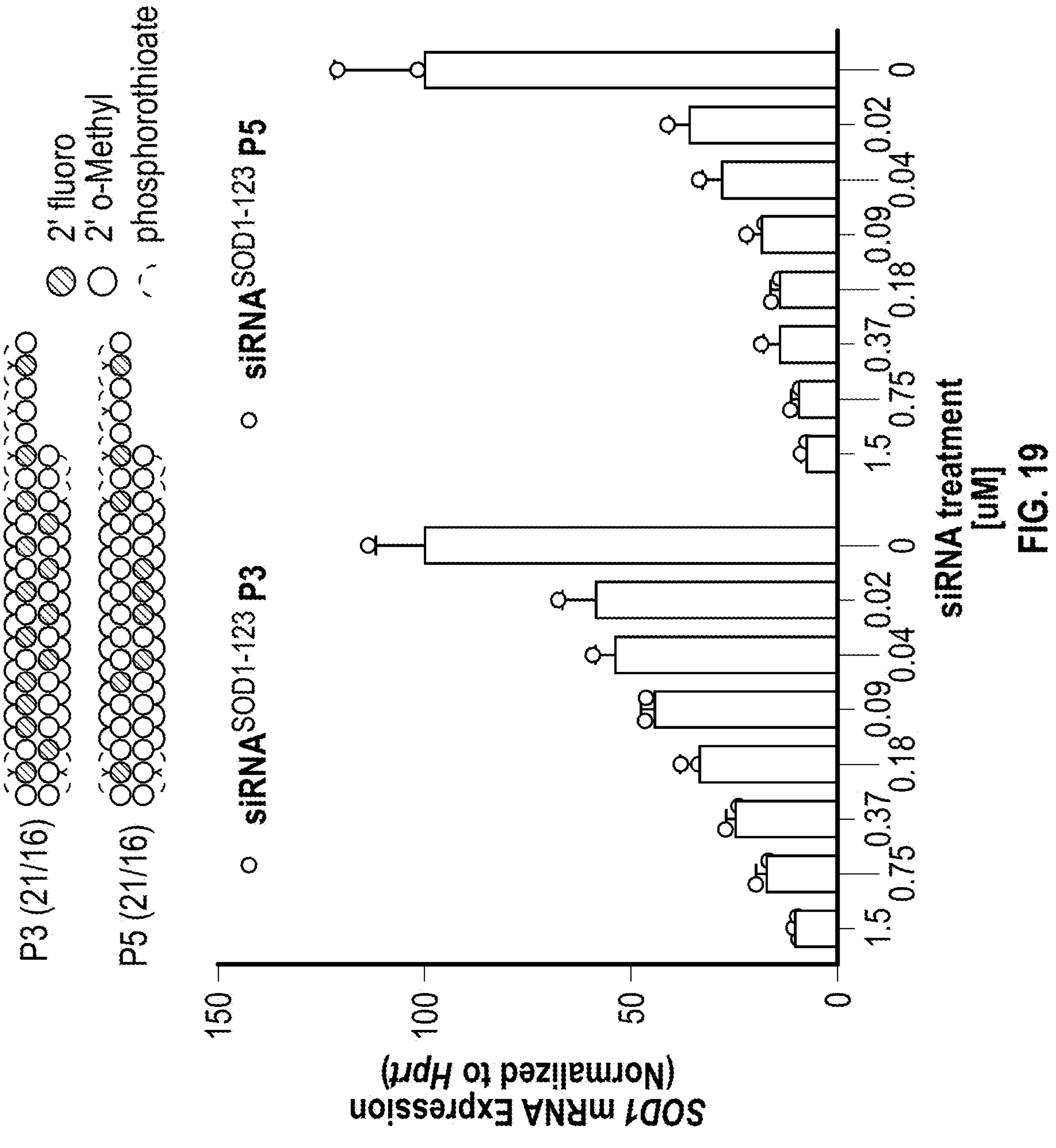
FIG. 19 depicts 8-point dose response curves obtained with SOD1 123 siRNA P3 and P5 chemical patterns in cells. The siRNAs were each tested at a concentration range and the mRNA levels were evaluated at a 72-hour timepoint.

As shown in FIG. 19, 8-point dose response curves were obtained with SOD1 123 siRNA P3 and P5 chemical patterns in cells. The siRNAs were each tested at a concentration range and the mRNA levels were evaluated at a 72-hour timepoint. Both patterns reduced SOD1 levels by 50% or more across all tested doses.

Figure 20A:
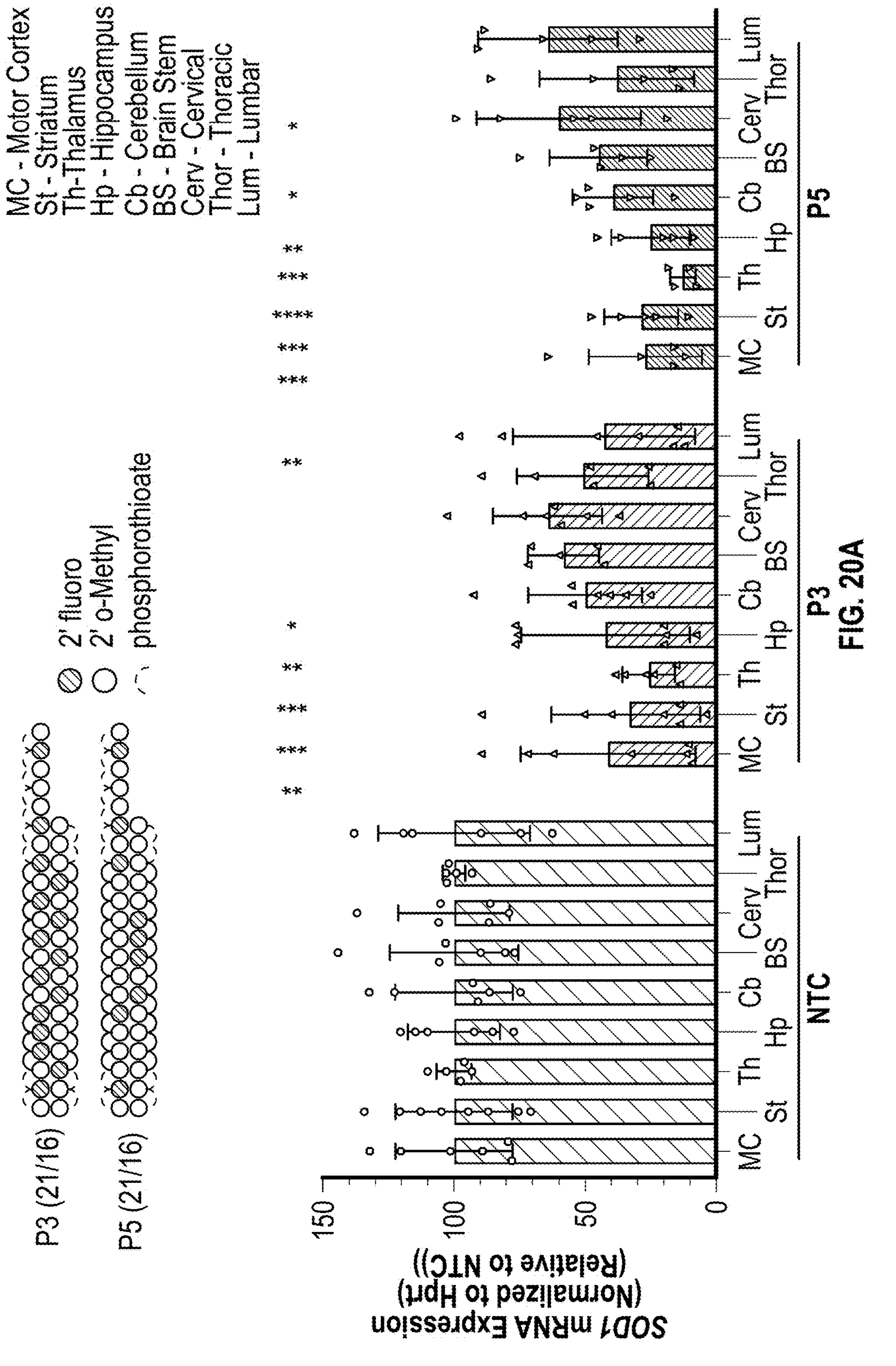
FIG. 20A-FIG. 20B depicts side-by-side comparison of (FIG. 20A) mRNA and (FIG. 20B) protein silencing efficacy in G93A mice between two siRNA chemical scaffolds (P3 and P5). Animals were treated at 8 weeks old with SOD-123 siRNA (compared to untreated controls). Each animal received a single bilateral ICV injection of siRNA (20 nmol).
Figure 20B:
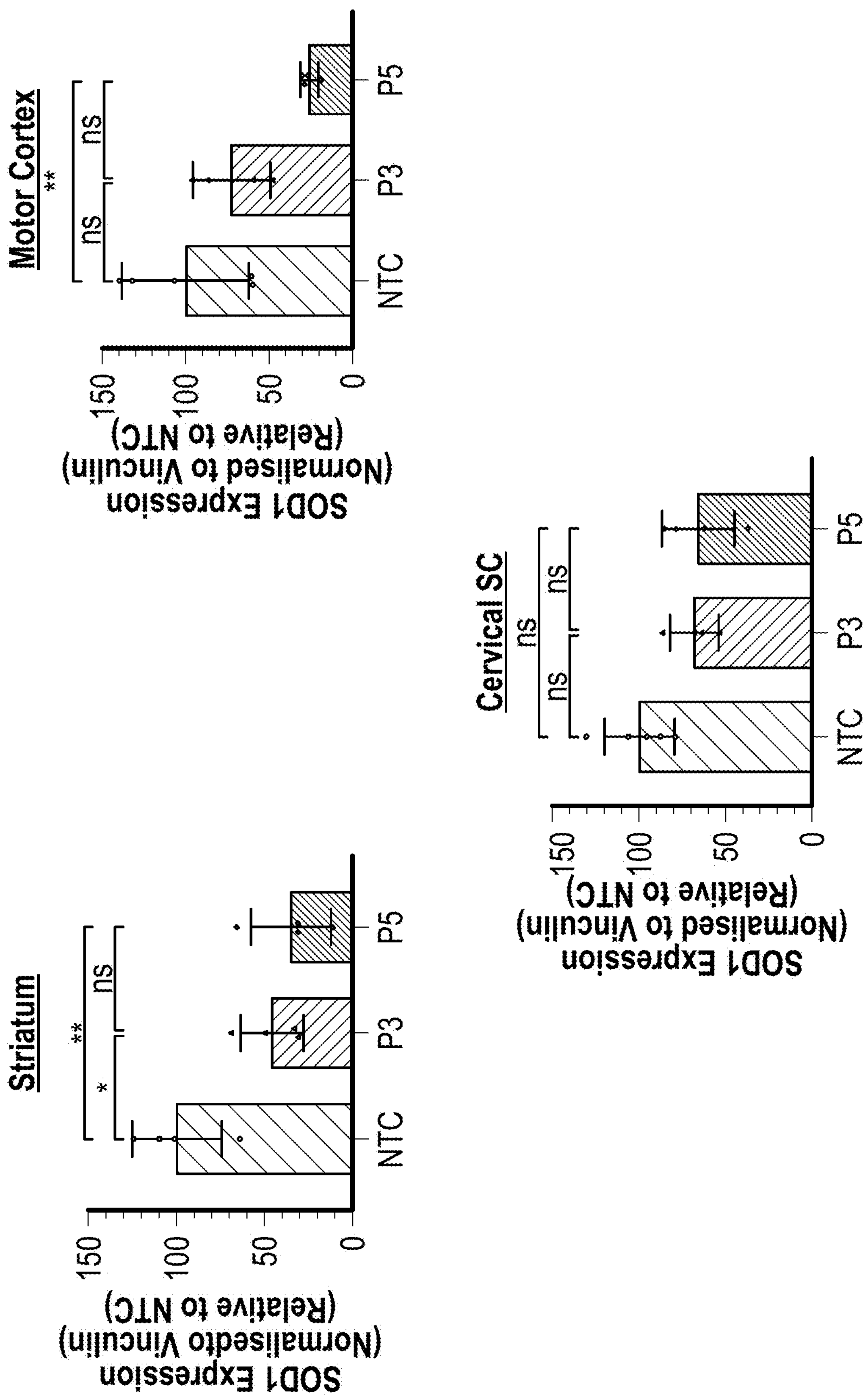

As shown in FIG. 20A-FIG. 20B, a side-by-side comparison of (FIG. 20A) mRNA and (FIG. 20B) protein silencing efficacy in G93A mice between two siRNA chemical scaffolds (P3 and P5) was made. Animals were treated at 8 weeks old with SOD-123 siRNA (compared to untreated controls). Each animal received a single bilateral ICV injection of siRNA (20 nmol). Once again, both patterns effectively silenced SOD1.

Figure 21A:
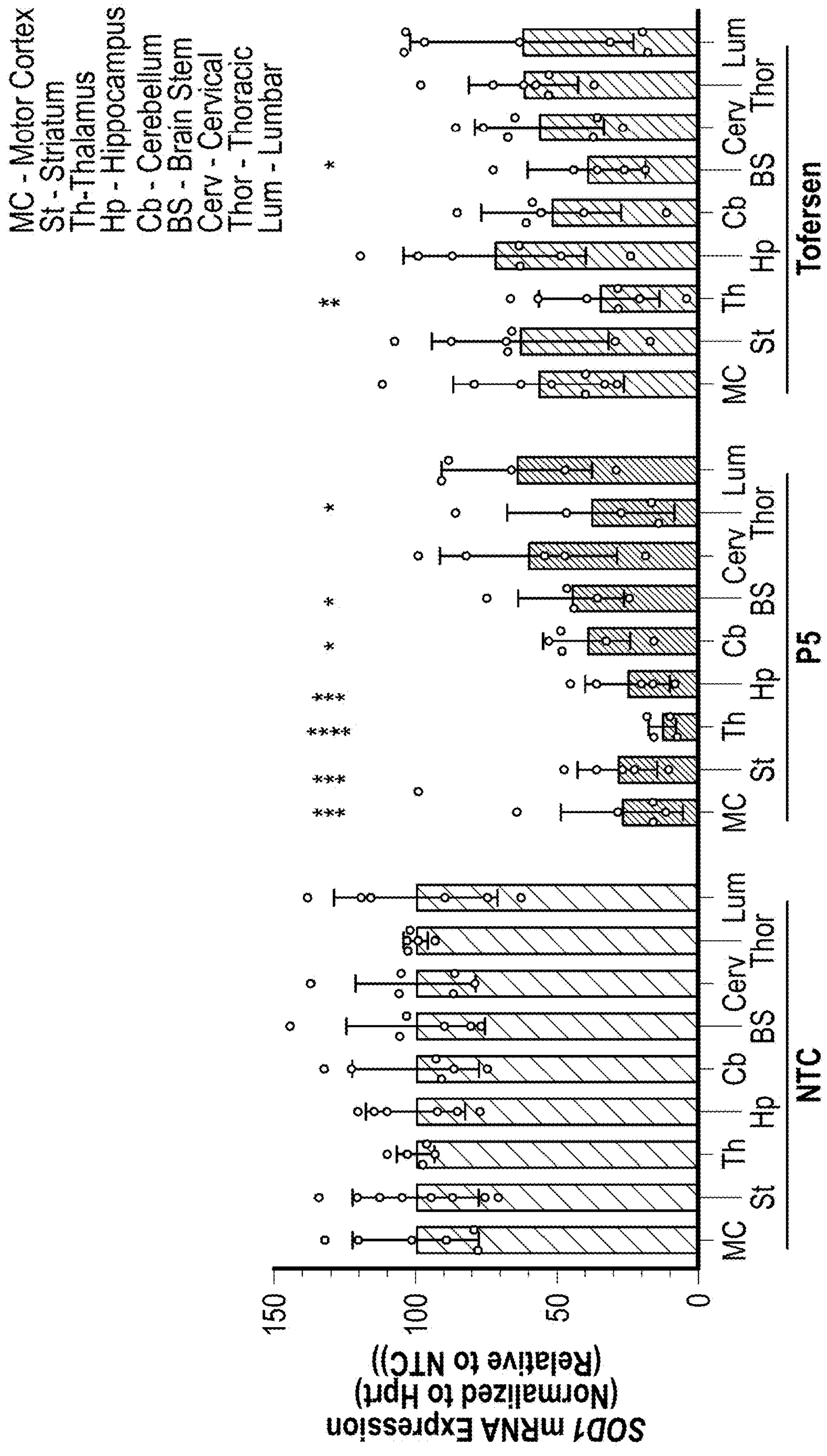
FIG. 21A-FIG. 21B depicts side-by-side comparison of (FIG. 21A) mRNA and (FIG. 21B) protein silencing efficacy in G93A mice between siRNA-123 (P5) and Tofersen (ASO). Animals were treated at 8 weeks old with SOD-123 siRNA (compared to untreated controls). Each animal received a single bilateral ICV injection of siRNA or ASO (20 nmol).
Figure 21B:
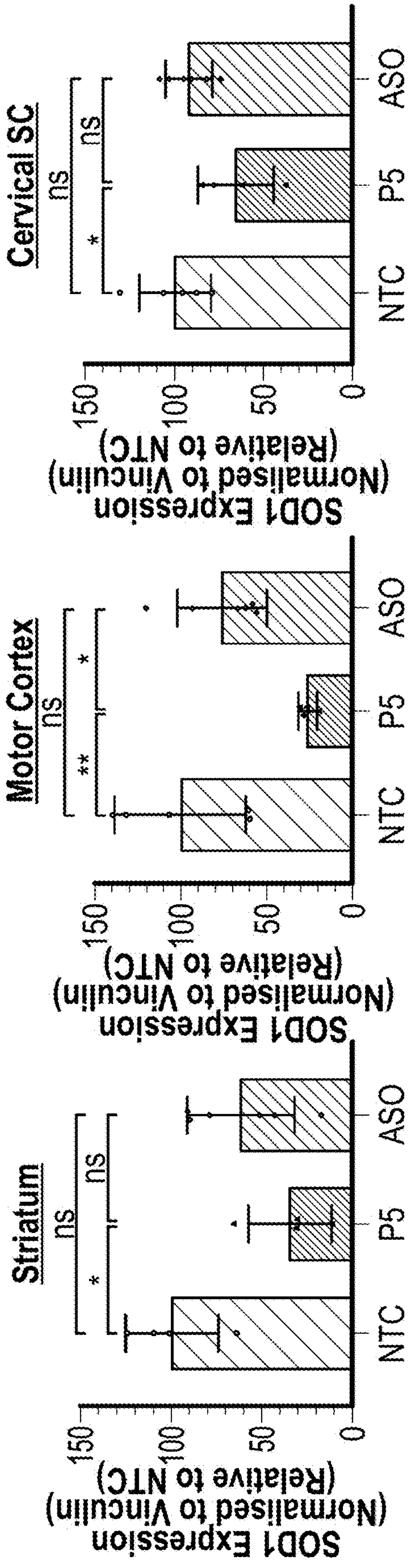

The P5 pattern was next tested against Tofersen. As shown in FIG. 21A-FIG. 21B mRNA and protein silencing efficacy in G93A mice between siRNA-123 (P5) and Tofersen (ASO) was determined. Animals were treated at 8 weeks old with SOD-123 siRNA (compared to untreated controls). Each animal received a single bilateral ICV injection of siRNA or ASO (20 nmol). The siRNA-123 (P5) silenced SOD1 better in several instances compared to Tofersen.

Figures 22A, 22B, 22C:
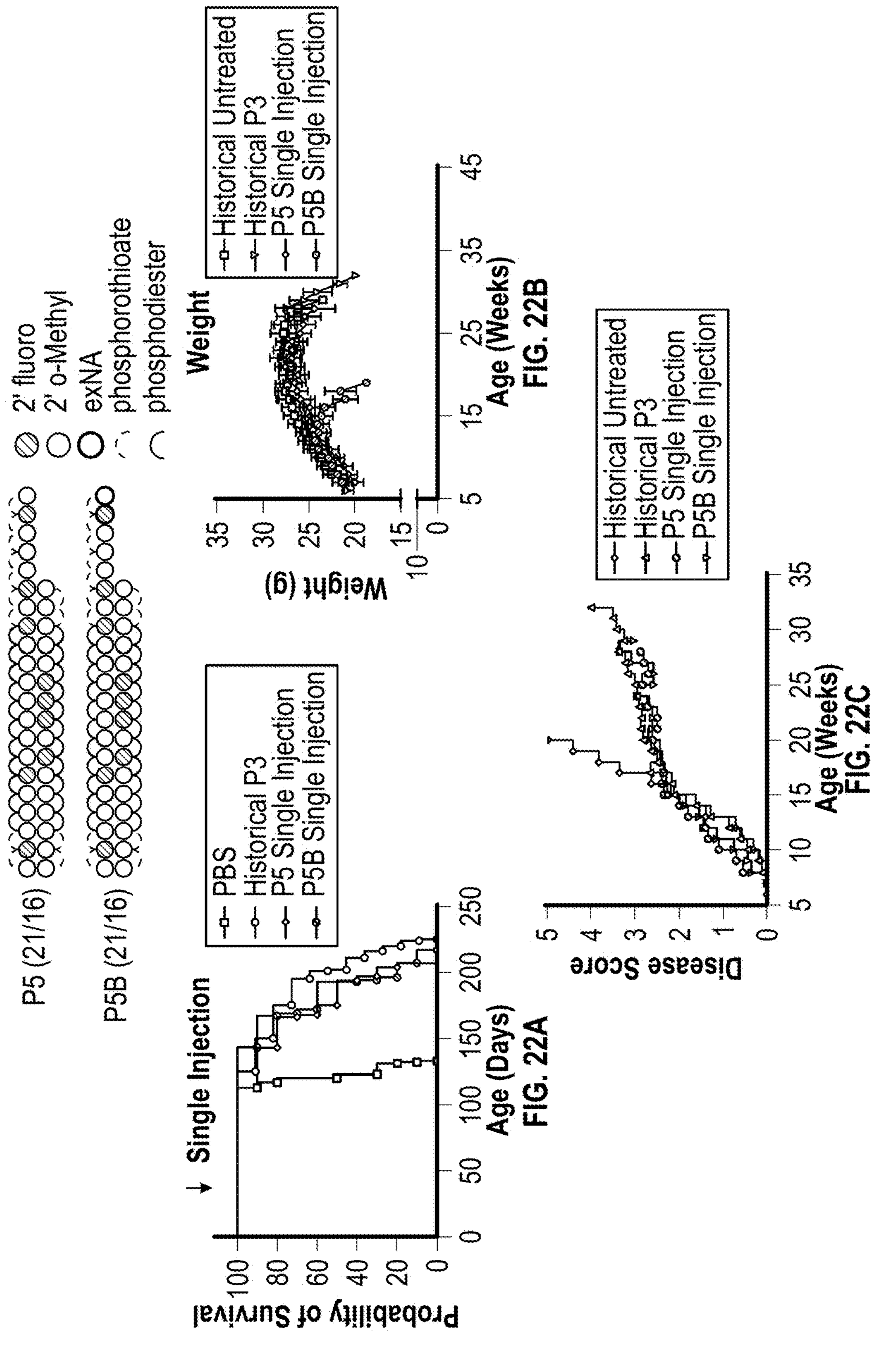
FIG. 22A-FIG. 22C depicts side-by-side comparison of (FIG. 22A) survival, (FIG. 22B) weight, and (FIG. 22C) disease score in G93A mice between siRNA-123 P5 versus P5B (advanced). Animals were treated at 8 weeks old with SOD-123 siRNA (compared to untreated controls). Each animal received a single bilateral ICV injection of siRNA or ASO (20 nmol).

As shown in FIG. 22A-FIG. 22C, a side-by-side comparison of (FIG. 22A) survival, (FIG. 22B) weight, and (FIG. 22C) disease score in G93A mice between siRNA-123 P5 versus P5B was performed. The P5B pattern employs fewer phosphorothioate internucleotide modifications and two exNA modifications in a manner similar to the P3B pattern. Animals were treated at 8 weeks old with SOD-123 siRNA (compared to untreated controls). Each animal received a single bilateral ICV injection of siRNA or ASO (20 nmol).

Figure 23:
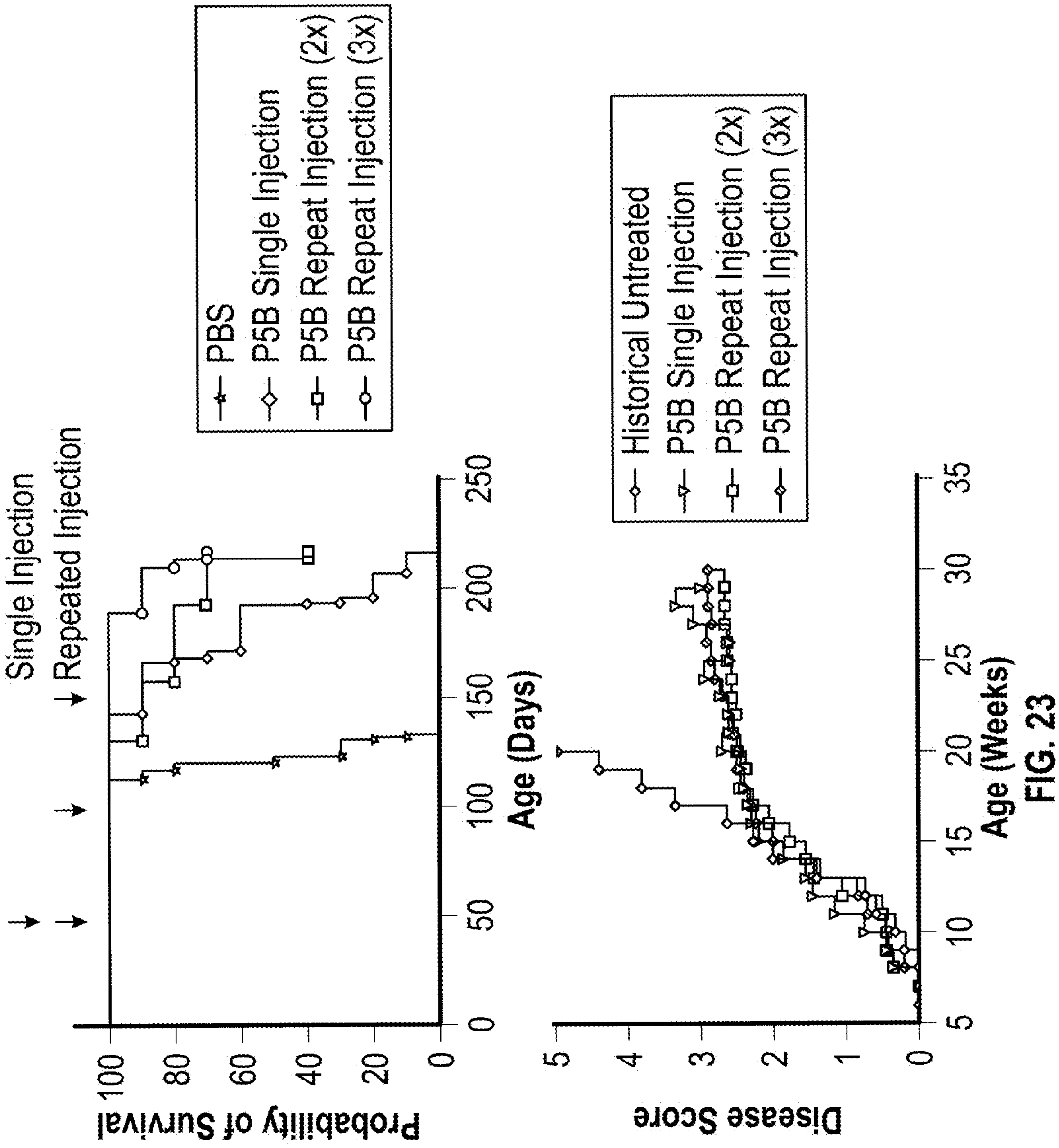
FIG. 23 depicts repeated administration of siRNA-SOD123 P5B. Repeated injection shows early survival benefit and no early impact on disease score.

FIG. 23 depicts repeated administration of siRNA-SOD123 P5B. Repeated injection shows early survival benefit and no early impact on disease score.

The data above for FIGS. 17-23 demonstrate that siRNA-SOD123 in various chemical modification patterns are capable of effectively silencing SOD1 and promoting survival of the ALS mouse model. Moreover, siRNA-SOD123 in various chemical modification patterns are capable of effectively silencing SOD1 and promoting survival of the ALS mouse model better than Tofersen.

INCORPORATION BY REFERENCE

The contents of all cited references (including literature references, patents, patent applications, and websites) that maybe cited throughout this application are hereby expressly incorporated by reference in their entirety for any purpose, as are the references cited therein. The disclosure will employ, unless otherwise indicated, conventional techniques of immunology, molecular biology and cell biology, which are well known in the art.

The present disclosure also incorporates by reference in their entirety techniques well known in the field of molecular biology and drug delivery. These techniques include, but are not limited to, techniques described in the following publications:

Atwell et al. J. Mol. Biol. 1997, 270: 26-35;

Ausubel et al. (eds.), Current Protocols in Molecular Biology, John Wiley &Sons, N Y (1993);

Ausubel, F. M. et al. eds., Short Protocols In Molecular Biology (4th Ed. 1999) John Wiley & Sons, NY. (ISBN 0-471-32938-X);

Controlled Drug Bioavailability, Drug Product Design and Performance, Smolen and Ball (eds.), Wiley, New York (1984);

Giege, R. and Ducruix, A. Barrett, Crystallization of Nucleic Acids and Proteins, a Practical Approach, 2nd ea., pp. 20 1-16, Oxford University Press, New York, N.Y., (1999);

Goodson, in Medical Applications of Controlled Release, vol. 2, pp. 115-138 (1984);

Hammerling, et al., in: Monoclonal Antibodies and T-Cell Hybridomas 563-681 (Elsevier, N.Y., 1981;

Harlow et al., Antibodies: a Laboratory Manual, (Cold Spring Harbor Laboratory Press, 2nd ed. 1988);

Kabat et al., Sequences of Proteins of Immunological Interest (National Institutes of Health, Bethesda, Md. (1987) and (1991);

Kabat, E. A., et al. (1991) Sequences of Proteins of Immunological Interest, Fifth Edition, U.S. Department of Health and Human Services, NIH Publication No. 91-3242;

Kontermann and Dubel eds., Antibody Engineering (2001) Springer-Verlag. New York. 790 pp. (ISBN 3-540-41354-5).

Kriegler, Gene Transfer and Expression, A Laboratory Manual, Stockton Press, N Y (1990);

Lu and Weiner eds., Cloning and Expression Vectors for Gene Function Analysis (2001) BioTechniques Press. Westborough, MA 298 pp. (ISBN 1-881299-21-X).

Medical Applications of Controlled Release, Langer and Wise (eds.), CRC Pres., Boca Raton, Fla. (1974);

Old, R. W. & S. B. Primrose, Principles of Gene Manipulation: An Introduction To Genetic Engineering (3d Ed. 1985) Blackwell Scientific Publications, Boston. Studies in Microbiology; V. 2:409 pp. (ISBN 0-632-01318-4).

Sambrook, J. et al. eds., Molecular Cloning: A Laboratory Manual (2d Ed. 1989) Cold Spring Harbor Laboratory Press, NY. Vols. 1-3. (ISBN 0-87969-309-6).

Sustained and Controlled Release Drug Delivery Systems, J. R. Robinson, ed., Marcel Dekker, Inc., New York, 1978

Winnacker, E. L. From Genes To Clones: Introduction To Gene Technology (1987) VCH Publishers, NY (translated by Horst Ibelgaufts). 634 pp. (ISBN 0-89573-614-4).

EQUIVALENTS

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

What is claimed is:

1. A double stranded RNA (dsRNA) molecule comprising an antisense strand and a sense strand, each strand with a 5' end and a 3' end, wherein:

(1) the antisense strand comprises a sequence complementary to a superoxide dismutase 1 (SOD1) nucleic acid sequence of any one of SEQ ID NOs: 1-11;

(2) the antisense strand comprises alternating 2'-methoxy-ribonucleotides and 2'-fluoro-ribonucleotides;

(3) the nucleotides at positions 2 and 14 from the 5' end of the antisense strand are not 2'-methoxy-ribonucleotides;

(4) the nucleotides at positions 1-2 to 1-7 from the 3' end of the antisense strand are connected to each other via phosphorothioate internucleotide linkages;

(5) a portion of the antisense strand is complementary to a portion of the sense strand;

(6) the sense strand comprises alternating 2'-methoxy-ribonucleotides and 2'-fluoro-ribonucleotides; and (7) the nucleotides at positions 1-2 from the 5' end of the sense strand are connected to each other via phosphorothioate internucleotide linkages;

(1) the antisense strand comprises a sequence complementary to a SOD1 nucleic acid sequence of any one of SEQ ID NOs: 1-11;

(2) the antisense strand comprises at least 70% 2'-O-methyl modifications;

(3) the nucleotide at position 14 from the 5' end of the antisense strand is not a 2'-methoxy-ribonucleotide;

(4) the nucleotides at positions 1-2 to 1-7 from the 3' end of the antisense strand are connected to each other via phosphorothioate internucleotide linkages;

(5) a portion of the antisense strand is complementary to a portion of the sense strand;

(6) the sense strand comprises at least 70% 2'-O-methyl modifications; and (7) the nucleotides at positions 1-2 from the 5' end of the sense strand are connected to each other via phosphorothioate internucleotide linkages;

(1) the antisense strand comprises a sequence complementary to a SOD1 nucleic acid sequence of any one of SEQ ID NOs: 1-11;

(2) the antisense strand comprises at least 75% 2'-O-methyl modifications;

(3) the nucleotides at positions 2, 6, 14, and 16 from the 5' end of the antisense strand are not 2'-methoxy-ribonucleotides;

(4) the nucleotides at positions 1-2 to 1-7 from the 3' end of the antisense strand are connected to each other via phosphorothioate internucleotide linkages;

(5) a portion of the antisense strand is complementary to a portion of the sense strand;

(6) the sense strand comprises at least 65% 2'-O-methyl modifications;

(7) the nucleotides at positions 7, 9, 10, and 11 from the 3' end of the sense strand are not 2'-methoxy-ribonucleotides; and (8) the nucleotides at positions 1-2 from the 5' end of the sense strand are connected to each other via phosphorothioate internucleotide linkages;

(1) the antisense strand comprises a sequence complementary to a SOD1 nucleic acid sequence of any one of SEQ ID NOs: 1-11;

(2) the antisense strand comprises at least 75% 2'-O-methyl modifications;

(3) the nucleotides at positions 2 and 14 from the 5' end of the antisense strand are not 2'-methoxy-ribonucleotides;

(4) the nucleotides at positions 1-2 to 1-7 from the 3' end of the antisense strand are connected to each other via phosphorothioate internucleotide linkages;

(5) a portion of the antisense strand is complementary to a portion of the sense strand;

(6) the sense strand comprises at least 75% 2'-O-methyl modifications;

(7) the nucleotides at positions 7, 10, and 11 from the 3' end of the sense strand are not 2'-methoxy-ribonucleotides; and (8) the nucleotides at positions 1-2 from the 5' end of the sense strand are connected to each other via phosphorothioate internucleotide linkages; or (1) the antisense strand comprises a sequence complementary to a SOD1 nucleic acid sequence of any one of SEQ ID NOs: 1-11;

(2) the antisense strand comprises at least 50% 2'-O-methyl modifications;

(3) the nucleotides at positions 2 and 14 from the 5' end of the antisense strand are not 2'-methoxy-ribonucleotides;

(4) the nucleotides at positions 1-2 to 1-7 from the 3' end of the antisense strand are connected to each other via phosphorothioate internucleotide linkages;

(5) a portion of the antisense strand is complementary to a portion of the sense strand;

(6) the sense strand comprises at least 65% 2'-O-methyl modifications;

(7) the nucleotides at positions 3, 7, 9, 11, and 13 from the 3' end of the sense strand are not 2'-methoxy-ribonucleotides; and (8) the nucleotides at positions 1-2 from the 5' end of the sense strand are connected to each other via phosphorothioate internucleotide linkages.

2. The dsRNA molecule of claim 1, wherein the antisense strand comprises 15 nucleotides to 25 nucleotides in length.

3. The dsRNA molecule of claim 1, wherein:

the dsRNA molecule further comprises at least one modified internucleotide linkage of Formula I:

(I)

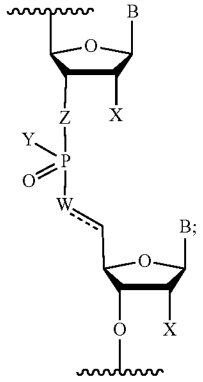

wherein:

B is a base pairing moiety;

W is selected from the group consisting of O, $OCH_2$, OCH, $CH_2$, and CH;

X is selected from the group consisting of halo, hydroxy, and $C_{1-6}$ alkoxy;

Y is selected from the group consisting of $O^-$, OH, OR, NH, $NH_2$, S, and SH;

Z is selected from the group consisting of O and $CH_2$;

R is a protecting group; and

⎓ is an optional double bond.

4. The dsRNA molecule of claim 1, further comprising a functional moiety linked to the 5' end and/or the 3' end of the antisense strand or the sense strand.

5. The dsRNA molecule of claim 1, wherein the antisense strand further comprises a 5' phosphate, a 5'-alkyl phosphonate, a 5' alkylene phosphonate, or a 5' alkenyl phosphonate.

6. The dsRNA molecule of claim 5, wherein the 5' alkenyl phosphonate is a 5' vinyl phosphonate.

7. A pharmaceutical composition for inhibiting the expression of the SOD1 gene in an organism, comprising the dsRNA molecule of claim 1 and a pharmaceutically acceptable carrier.

8. The pharmaceutical composition of claim 7, wherein the dsRNA molecule inhibits expression of the SOD1 gene by at least 50% or at least 80%.

9. A dsRNA comprising an antisense strand and a sense strand, each strand with a 5' end and a 3' end, wherein:

(1) the antisense strand comprises a sequence complementary to a superoxide dismutase 1 (SOD1) nucleic acid sequence of any one of SEQ ID NOs: 1-11;

(2) the antisense strand comprises the chemical modification pattern of:

(mX)#(fX)#(mX)(fX)(fX)(fX)(mX)(fX)(mX)(fX)(mX)(fX)(mX)(fX)#(mX)#(fX)#(mX)#(mX)#(mX)#(fX)#(mX);

(3) a portion of the antisense strand is complementary to a portion of the sense strand; and (4) the sense strand comprises the chemical modification pattern of:

(mX)#(mX)#(mX)(fX)(mX)(fX)(mX)(fX)(mX)(fX)(mX)(mX)(mX)(fX)#(mX)#(mX), wherein "m" corresponds to a 2'-O-methyl modification; "f" corresponds to a 2'-fluoro modification; "#" corresponds to a phosphorothioate internucleotide linkage; and "X" corresponds to any nucleotide of A, U, G, or C; or (1) the antisense strand comprises a sequence complementary to a SOD1 nucleic acid sequence of any one of SEQ ID NOs: 1-11;

(2) the antisense strand comprises the chemical modification pattern of: (mX)#(fX)#(mX)(mX)(mX)(fX)(mX)(mX)(mX)(mX)(mX)(mX)(mX)(fX)#(mX)#(fX)#(mX) #(mX)#(mX)#(fX)#(mX);

(3) a portion of the antisense strand is complementary to a portion of the sense strand; and (4) the sense strand comprises the chemical modification pattern of:

(mX)#(mX)#(mX)(mX)(mX)(fX)(fX)(fX)(mX)(fX)(mX)(mX)(mX)(mX)#(mX)#(mX), wherein "m" corresponds to a 2'-O-methyl modification; "f" corresponds to a 2'-fluoro modification; "#" corresponds to a phosphorothioate antinucleotide linkage; and "X" corresponds to any nucleotide of A, U, G, or C.

10. A branched RNA compound comprising:

two or more RNA molecules comprising 15 to 35 nucleotides in length, wherein at least one of the two or more RNA molecules comprises a double stranded RNA (dsRNA), wherein two of the two or more RNA molecules are connected to one another by one or more moieties independently selected from a linker, a spacer, and a branching point; and a sequence complementary to a superoxide dismutase 1 (SOD1) mRNA, wherein the dsRNA comprises an antisense strand and a sense strand, each strand with a 5' end and a 3' end, wherein:

A:

(1) the antisense strand comprises a sequence complementary to a SOD1 nucleic acid sequence of any one of SEQ ID NOs: 1-11;

(2) the antisense strand comprises alternating 2'-methoxy-ribonucleotides and 2'-fluoro-ribonucleotides;

(3) the nucleotides at positions 2 and 14 from the 5' end of the antisense strand are not 2'-methoxy-ribonucleotides;

(4) the nucleotides at positions 1-2 to 1-7 from the 3' end of the antisense strand are connected to each other via phosphorothioate internucleotide linkages;

(5) a portion of the antisense strand is complementary to a portion of the sense strand;

(6) the sense strand comprises alternating 2'-methoxy-ribonucleotides and 2'-fluoro-ribonucleotides; and (7) the nucleotides at positions 1-2 from the 5' end of the sense strand are connected to each other via phosphorothioate internucleotide linkages;

B:

(1) the antisense strand comprises a sequence complementary to a SOD1 nucleic acid sequence of any one of SEQ ID NOs: 1-11;

(2) the antisense strand comprises at least 70% 2'-O-methyl modifications;

(3) the nucleotide at position 14 from the 5' end of the antisense strand are not 2'-methoxy-ribonucleotides;

(4) the nucleotides at positions 1-2 to 1-7 from the 3' end of the antisense strand are connected to each other via phosphorothioate internucleotide linkages;

(5) a portion of the antisense strand is complementary to a portion of the sense strand;

(6) the sense strand comprises at least 70% 2'-O-methyl modifications; and (7) the nucleotides at positions 1-2 from the 5' end of the sense strand are connected to each other via phosphorothioate internucleotide linkages;

C:

(1) the antisense strand comprises a sequence complementary to a SOD1 nucleic acid sequence of any one of SEQ ID NOs: 1-11;

(2) the antisense strand comprises at least 75% 2'-O-methyl modifications;

(3) the nucleotides at positions 4, 5, 6, and 14 from the 5' end of the antisense strand are not 2'-methoxy-ribonucleotides;

(4) the nucleotides at positions 1-2 to 1-7 from the 3' end of the antisense strand are connected to each other via phosphorothioate internucleotide linkages;

(5) a portion of the antisense strand is complementary to a portion of the sense strand;

(6) the sense strand comprises 100% 2'-O-methyl modifications; and (7) the nucleotides at positions 1-2 from the 5' end of the sense strand are connected to each other via phosphorothioate internucleotide linkages;

D:

(1) the antisense strand comprises a sequence complementary to a SOD1 nucleic acid sequence of any one of SEQ ID NOs: 1-11;

(2) the antisense strand comprises at least 75% 2'-O-methyl modifications;

(3) the nucleotides at positions 2, 6, 14, and 16 from the 5' end of the antisense strand are not 2'-methoxy-ribonucleotides;

(4) the nucleotides at positions 1-2 to 1-7 from the 3' end of the antisense strand are connected to each other via phosphorothioate internucleotide linkages;

(5) a portion of the antisense strand is complementary to a portion of the sense strand;

(6) the sense strand comprises at least 65% 2'-O-methyl modifications;

(7) the nucleotides at positions 7, 9, 10, and 11 from the 3' end of the sense strand are not 2'-methoxy-ribonucleotides; and (8) the nucleotides at positions 1-2 from the 5' end of the sense strand are connected to each other via phosphorothioate internucleotide linkages;

E:

(1) the antisense strand comprises a sequence complementary to a SOD1 nucleic acid sequence of any one of SEQ ID NOs: 1-11;

(2) the antisense strand comprises at least 75% 2'-O-methyl modifications;

(3) the nucleotides at positions 2 and 14 from the 5' end of the antisense strand are not 2'-methoxy-ribonucleotides;

(4) the nucleotides at positions 1-2 to 1-7 from the 3' end of the antisense strand are connected to each other via phosphorothioate internucleotide linkages;

(5) a portion of the antisense strand is complementary to a portion of the sense strand;

(6) the sense strand comprises at least 75% 2'-O-methyl modifications;

(7) the nucleotides at positions 7, 10, and 11 from the 3' end of the sense strand are not 2'-methoxy-ribonucleotides; and (8) the nucleotides at positions 1-2 from the 5' end of the sense strand are connected to each other via phosphorothioate internucleotide linkages; or

F:

(1) the antisense strand comprises a sequence complementary to a SOD1 nucleic acid sequence of any one of SEQ ID NOs: 1-11;

(2) the antisense strand comprises at least 50% 2'-O-methyl modifications;

(3) the nucleotides at positions 2 and 14 from the 5' end of the antisense strand are not 2'-methoxy-ribonucleotides;

(4) the nucleotides at positions 1-2 to 1-7 from the 3' end of the antisense strand are connected to each other via phosphorothioate internucleotide linkages;

(5) a portion of the antisense strand is complementary to a portion of the sense strand;

(6) the sense strand comprises at least 65% 2'-O-methyl modifications;

(7) the nucleotides at positions 3, 7, 9, 11, and 13 from the 3' end of the sense strand are not 2'-methoxy-ribonucleotides; and (8) the nucleotides at positions 1-2 from the 5' end of the sense strand are connected to each other via phosphorothioate internucleotide linkages.

11. The branched RNA compound of claim 10, wherein at least one of the two or more dsRNA molecules further comprises at least one modified internucleotide linkage of Formula I:

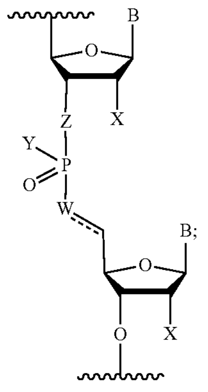

(I)

wherein:

B is a base pairing moiety;

W is selected from the group consisting of O, $OCH_2$, OCH, $CH_2$, and CH;

X is selected from the group consisting of halo, hydroxy, and $C_{1-6}$ alkoxy;

Y is selected from the group consisting of O, OH, OR, NH, $NH_2$, S, and SH;

Z is selected from the group consisting of O and $CH_2$;

R is a protecting group; and $\overset{---}{=}$ is an optional double bond.

12. The branched RNA compound of claim 10, wherein the antisense strand further comprises a 5' phosphate, a 5'-alkyl phosphonate, a 5' alkylene phosphonate, a 5' alkenyl phosphonate, or a mixture thereof.

13. The branched RNA compound of claim 12, wherein the 5' alkenyl phosphonate is a 5' vinyl phosphonate.

14. The branched RNA compound of claim 10, wherein the linker comprises an ethylene glycol chain, an alkyl chain, a peptide, an RNA, a DNA, a phosphate, a phosphonate, a phosphoramidate, an ester, an amide, a triazole, or combinations thereof.

15. A pharmaceutical composition for inhibiting the expression of the SOD1 gene in an organism, comprising the branched RNA compound of claim 10, and a pharmaceutically acceptable carrier.

16. A branched RNA compound comprising:

two or more double stranded RNA (dsRNA), each dsRNA comprising an antisense strand and a sense strand, each strand with a 5' end, a 3' end, and a length of 15 to 35 nucleotides; and a sequence complementary to a superoxide dismutase 1 (SOD1) mRNA, wherein:

(1) the antisense strand comprises a sequence complementary to a SOD1 nucleic acid sequence of any one of SEQ ID NOs: 1-11;

(2) the antisense strand comprises the chemical modification pattern of:

(mX)#(fX)#(mX)(fX)(fX)(fX)(mX)(fX)(mX)(fX)(mX)(fX)(mX)(fX)#(mX)#(fX)#(mX)#(mX) #(mX)#(fX)#(mX);

(3) a portion of the antisense strand is complementary to a portion of the sense strand; and (4) the sense strand comprises the chemical modification pattern of:

(mX)#(mX)#(mX)(fX)(mX)(fX)(mX)(fX)(mX)(fX)(mX)(mX)(mX)(fX)#(mX)#(mX), wherein "m" corresponds to a 2'-O-methyl modification; "f" corresponds to a 2'-fluoro modification; "#" corresponds to a phosphorothioate internucleotide linkage; and "X" corresponds to any nucleotide of A, U, G, or C, wherein the two or more dsRNA are connected to one another by one or more moieties independently selected from a linker, a spacer and a branching point.

17. The branched RNA compound of claim 16, wherein the antisense strand further comprises a 5' phosphate, a 5'-alkyl phosphonate, a 5' alkylene phosphonate, or a 5' alkenyl phosphonate.

18. The branched RNA compound of claim 17, wherein the 5' alkenyl phosphonate is a 5' vinyl phosphonate.

* * * * *

SEQUENCE LISTING

```
Sequence total quantity: 233
SEQ ID NO: 1            moltype = DNA  length = 45
FEATURE                 Location/Qualifiers
source                  1..45
                        mol_type = genomic DNA
                        organism = Homo sapiens
SEQUENCE: 1
ggcgacggcc cagtgcaggg catcatcaat ttcgagcaga aggaa                  45

SEQ ID NO: 2            moltype = DNA  length = 45
FEATURE                 Location/Qualifiers
source                  1..45
                        mol_type = genomic DNA
                        organism = Homo sapiens
SEQUENCE: 2
gcgacggccc agtgcagggc atcatcaatt tcgagcagaa ggaaa                  45

SEQ ID NO: 3            moltype = DNA  length = 45
FEATURE                 Location/Qualifiers
source                  1..45
                        mol_type = genomic DNA
                        organism = Homo sapiens
SEQUENCE: 3
gacggcccag tgcagggcat catcaatttc gagcagaagg aaagt                  45

SEQ ID NO: 4            moltype = DNA  length = 45
FEATURE                 Location/Qualifiers
source                  1..45
                        mol_type = genomic DNA
                        organism = Homo sapiens
SEQUENCE: 4
ggcccagtgc agggcatcat caatttcgag cagaaggaaa gtaat                  45

SEQ ID NO: 5            moltype = DNA  length = 45
FEATURE                 Location/Qualifiers
source                  1..45
                        mol_type = genomic DNA
                        organism = Homo sapiens
SEQUENCE: 5
ccagtgcagg gcatcatcaa tttcgagcag aaggaaagta atgga                  45

SEQ ID NO: 6            moltype = DNA  length = 45
FEATURE                 Location/Qualifiers
source                  1..45
                        mol_type = genomic DNA
                        organism = Homo sapiens
SEQUENCE: 6
cagtgcaggg catcatcaat ttcgagcaga aggaaagtaa tggac                  45

SEQ ID NO: 7            moltype = DNA  length = 45
FEATURE                 Location/Qualifiers
source                  1..45
                        mol_type = genomic DNA
                        organism = Homo sapiens
SEQUENCE: 7
gtgcagggca tcatcaattt cgagcagaag gaaagtaatg gacca                  45

SEQ ID NO: 8            moltype = DNA  length = 45
FEATURE                 Location/Qualifiers
source                  1..45
                        mol_type = genomic DNA
                        organism = Homo sapiens
SEQUENCE: 8
tagtctgagg ccccttaact catctgttat cctgctagct gtaga                  45

SEQ ID NO: 9            moltype = DNA  length = 45
FEATURE                 Location/Qualifiers
source                  1..45
                        mol_type = genomic DNA
                        organism = Homo sapiens
SEQUENCE: 9
atctgttatc ctgctagctg tagaaatgta tcctgataaa catta                  45
```

```
SEQ ID NO: 10          moltype = DNA  length = 45
FEATURE                Location/Qualifiers
source                 1..45
                       mol_type = genomic DNA
                       organism = Homo sapiens
SEQUENCE: 10
tagaaatgta tcctgataaa cattaaacac tgtaatctta aaagt                    45

SEQ ID NO: 11          moltype = DNA  length = 45
FEATURE                Location/Qualifiers
source                 1..45
                       mol_type = genomic DNA
                       organism = Homo sapiens
SEQUENCE: 11
gttgctttaa agtacctgta gtgagaaact gatttatgat cactt                    45

SEQ ID NO: 12          moltype = RNA  length = 20
FEATURE                Location/Qualifiers
source                 1..20
                       mol_type = genomic RNA
                       organism = Homo sapiens
SEQUENCE: 12
cagggcatca tcaatttcga                                                20

SEQ ID NO: 13          moltype = RNA  length = 20
FEATURE                Location/Qualifiers
source                 1..20
                       mol_type = genomic RNA
                       organism = Homo sapiens
SEQUENCE: 13
agggcatcat caatttcgag                                                20

SEQ ID NO: 14          moltype = RNA  length = 20
FEATURE                Location/Qualifiers
source                 1..20
                       mol_type = genomic RNA
                       organism = Homo sapiens
SEQUENCE: 14
ggcatcatca atttcgagca                                                20

SEQ ID NO: 15          moltype = RNA  length = 20
FEATURE                Location/Qualifiers
source                 1..20
                       mol_type = genomic RNA
                       organism = Homo sapiens
SEQUENCE: 15
atcatcaatt tcgagcagaa                                                20

SEQ ID NO: 16          moltype = RNA  length = 20
FEATURE                Location/Qualifiers
source                 1..20
                       mol_type = genomic RNA
                       organism = Homo sapiens
SEQUENCE: 16
atcaatttcg agcagaagga                                                20

SEQ ID NO: 17          moltype = RNA  length = 20
FEATURE                Location/Qualifiers
source                 1..20
                       mol_type = genomic RNA
                       organism = Homo sapiens
SEQUENCE: 17
tcaatttcga gcagaaggaa                                                20

SEQ ID NO: 18          moltype = RNA  length = 20
FEATURE                Location/Qualifiers
source                 1..20
                       mol_type = genomic RNA
                       organism = Homo sapiens
SEQUENCE: 18
aatttcgagc agaaggaaag                                                20

SEQ ID NO: 19          moltype = RNA  length = 20
FEATURE                Location/Qualifiers
source                 1..20
                       mol_type = genomic RNA
                       organism = Homo sapiens
SEQUENCE: 19
taactcatct gttatcctgc                                                20
```

```
SEQ ID NO: 20          moltype = RNA  length = 20
FEATURE                Location/Qualifiers
source                 1..20
                       mol_type = genomic RNA
                       organism = Homo sapiens
SEQUENCE: 20
agctgtagaa atgtatcctg                                       20

SEQ ID NO: 21          moltype = RNA  length = 20
FEATURE                Location/Qualifiers
source                 1..20
                       mol_type = genomic RNA
                       organism = Homo sapiens
SEQUENCE: 21
ataaacatta aacactgtaa                                       20

SEQ ID NO: 22          moltype = RNA  length = 20
FEATURE                Location/Qualifiers
source                 1..20
                       mol_type = genomic RNA
                       organism = Homo sapiens
SEQUENCE: 22
ctgtagtgag aaactgattt                                       20

SEQ ID NO: 23          moltype = RNA  length = 16
FEATURE                Location/Qualifiers
source                 1..16
                       mol_type = other RNA
                       organism = synthetic construct
SEQUENCE: 23
gcatcatcaa tttcga                                           16

SEQ ID NO: 24          moltype = RNA  length = 21
FEATURE                Location/Qualifiers
source                 1..21
                       mol_type = other RNA
                       organism = synthetic construct
SEQUENCE: 24
tcgaaattga tgatgccctg t                                     21

SEQ ID NO: 25          moltype = DNA  length = 45
FEATURE                Location/Qualifiers
source                 1..45
                       mol_type = genomic DNA
                       organism = Homo sapiens
SEQUENCE: 25
gcgtgctgaa gggcgacggc ccagtgcagg gcatcatcaa tttcg           45

SEQ ID NO: 26          moltype = DNA  length = 45
FEATURE                Location/Qualifiers
source                 1..45
                       mol_type = genomic DNA
                       organism = Homo sapiens
SEQUENCE: 26
cgtgctgaag ggcgacggcc cagtgcaggg catcatcaat ttcga           45

SEQ ID NO: 27          moltype = DNA  length = 45
FEATURE                Location/Qualifiers
source                 1..45
                       mol_type = genomic DNA
                       organism = Homo sapiens
SEQUENCE: 27
gtgctgaagg gcgacggccc agtgcagggc atcatcaatt tcgag           45

SEQ ID NO: 28          moltype = DNA  length = 45
FEATURE                Location/Qualifiers
source                 1..45
                       mol_type = genomic DNA
                       organism = Homo sapiens
SEQUENCE: 28
tgctgaaggg cgacggccca gtgcagggca tcatcaattt cgagc           45

SEQ ID NO: 29          moltype = DNA  length = 45
FEATURE                Location/Qualifiers
source                 1..45
                       mol_type = genomic DNA
                       organism = Homo sapiens
SEQUENCE: 29
```

-continued

```
gctgaagggc gacggcccag tgcagggcat catcaatttc gagca                    45

SEQ ID NO: 30           moltype = DNA  length = 45
FEATURE                 Location/Qualifiers
source                  1..45
                        mol_type = genomic DNA
                        organism = Homo sapiens
SEQUENCE: 30
ctgaagggcg acggcccagt gcagggcatc atcaatttcg agcag                    45

SEQ ID NO: 31           moltype = DNA  length = 45
FEATURE                 Location/Qualifiers
source                  1..45
                        mol_type = genomic DNA
                        organism = Homo sapiens
SEQUENCE: 31
tgaagggcga cggcccagtg cagggcatca tcaatttcga gcaga                    45

SEQ ID NO: 32           moltype = DNA  length = 45
FEATURE                 Location/Qualifiers
source                  1..45
                        mol_type = genomic DNA
                        organism = Homo sapiens
SEQUENCE: 32
gaagggcgac ggcccagtgc agggcatcat caatttcgag cagaa                    45

SEQ ID NO: 33           moltype = DNA  length = 45
FEATURE                 Location/Qualifiers
source                  1..45
                        mol_type = genomic DNA
                        organism = Homo sapiens
SEQUENCE: 33
aagggcgacg gcccagtgca gggcatcatc aatttcgagc agaag                    45

SEQ ID NO: 34           moltype = DNA  length = 45
FEATURE                 Location/Qualifiers
source                  1..45
                        mol_type = genomic DNA
                        organism = Homo sapiens
SEQUENCE: 34
agggcgacgg cccagtgcag ggcatcatca atttcgagca gaagg                    45

SEQ ID NO: 35           moltype = DNA  length = 45
FEATURE                 Location/Qualifiers
source                  1..45
                        mol_type = genomic DNA
                        organism = Homo sapiens
SEQUENCE: 35
gggcgacggc ccagtgcagg gcatcatcaa tttcgagcag aagga                    45

SEQ ID NO: 36           moltype = DNA  length = 45
FEATURE                 Location/Qualifiers
source                  1..45
                        mol_type = genomic DNA
                        organism = Homo sapiens
SEQUENCE: 36
cgacggccca gtgcagggca tcatcaattt cgagcagaag gaaag                    45

SEQ ID NO: 37           moltype = DNA  length = 45
FEATURE                 Location/Qualifiers
source                  1..45
                        mol_type = genomic DNA
                        organism = Homo sapiens
SEQUENCE: 37
acggcccagt gcagggcatc atcaatttcg agcagaagga aagta                    45

SEQ ID NO: 38           moltype = DNA  length = 45
FEATURE                 Location/Qualifiers
source                  1..45
                        mol_type = genomic DNA
                        organism = Homo sapiens
SEQUENCE: 38
cggcccagtg cagggcatca tcaatttcga gcagaaggaa agtaa                    45

SEQ ID NO: 39           moltype = DNA  length = 45
FEATURE                 Location/Qualifiers
source                  1..45
                        mol_type = genomic DNA
                        organism = Homo sapiens
```

-continued

```
SEQUENCE: 39
gcccagtgca gggcatcatc aatttcgagc agaaggaaag taatg                   45

SEQ ID NO: 40          moltype = DNA  length = 45
FEATURE                Location/Qualifiers
source                 1..45
                       mol_type = genomic DNA
                       organism = Homo sapiens
SEQUENCE: 40
cccagtgcag ggcatcatca atttcgagca gaaggaaagt aatgg                   45

SEQ ID NO: 41          moltype = DNA  length = 45
FEATURE                Location/Qualifiers
source                 1..45
                       mol_type = genomic DNA
                       organism = Homo sapiens
SEQUENCE: 41
agtgcagggc atcatcaatt tcgagcagaa ggaaagtaat ggacc                   45

SEQ ID NO: 42          moltype = DNA  length = 45
FEATURE                Location/Qualifiers
source                 1..45
                       mol_type = genomic DNA
                       organism = Homo sapiens
SEQUENCE: 42
gactgactga aggcctgcat ggattccatg ttcatgagtt tggag                   45

SEQ ID NO: 43          moltype = DNA  length = 45
FEATURE                Location/Qualifiers
source                 1..45
                       mol_type = genomic DNA
                       organism = Homo sapiens
SEQUENCE: 43
gcatggattc catgttcatg agtttggaga taatacagca ggctg                   45

SEQ ID NO: 44          moltype = DNA  length = 45
FEATURE                Location/Qualifiers
source                 1..45
                       mol_type = genomic DNA
                       organism = Homo sapiens
SEQUENCE: 44
gataatacag caggctgtac cagtgcaggt cctcacttta atcct                   45

SEQ ID NO: 45          moltype = DNA  length = 45
FEATURE                Location/Qualifiers
source                 1..45
                       mol_type = genomic DNA
                       organism = Homo sapiens
SEQUENCE: 45
aatacagcag gctgtaccag tgcaggtcct cactttaatc ctcta                   45

SEQ ID NO: 46          moltype = DNA  length = 45
FEATURE                Location/Qualifiers
source                 1..45
                       mol_type = genomic DNA
                       organism = Homo sapiens
SEQUENCE: 46
ctgtaccagt gcaggtcctc actttaatcc tctatccaga aaaca                   45

SEQ ID NO: 47          moltype = DNA  length = 45
FEATURE                Location/Qualifiers
source                 1..45
                       mol_type = genomic DNA
                       organism = Homo sapiens
SEQUENCE: 47
ttgggcaatg tgactgctga caaagatggt gtggccgatg tgtct                   45

SEQ ID NO: 48          moltype = DNA  length = 45
FEATURE                Location/Qualifiers
source                 1..45
                       mol_type = genomic DNA
                       organism = Homo sapiens
SEQUENCE: 48
agatggtgtg gccgatgtgt ctattgaaga ttctgtgatc tcact                   45

SEQ ID NO: 49          moltype = DNA  length = 45
FEATURE                Location/Qualifiers
source                 1..45
                       mol_type = genomic DNA
```

```
                      organism = Homo sapiens
SEQUENCE: 49
gtgtctattg aagattctgt gatctcactc tcaggagacc attgc                  45

SEQ ID NO: 50         moltype = DNA  length = 45
FEATURE               Location/Qualifiers
source                1..45
                      mol_type = genomic DNA
                      organism = Homo sapiens
SEQUENCE: 50
tctcactctc aggagaccat tgcatcattg gccgcacact ggtgg                  45

SEQ ID NO: 51         moltype = DNA  length = 45
FEATURE               Location/Qualifiers
source                1..45
                      mol_type = genomic DNA
                      organism = Homo sapiens
SEQUENCE: 51
atgacttggg caaaggtgga aatgaagaaa gtacaaagac aggaa                  45

SEQ ID NO: 52         moltype = DNA  length = 45
FEATURE               Location/Qualifiers
source                1..45
                      mol_type = genomic DNA
                      organism = Homo sapiens
SEQUENCE: 52
ggaagtcgtt tggcttgtgg tgtaattggg atcgcccaat aaaca                  45

SEQ ID NO: 53         moltype = DNA  length = 45
FEATURE               Location/Qualifiers
source                1..45
                      mol_type = genomic DNA
                      organism = Homo sapiens
SEQUENCE: 53
tttggcttgt ggtgtaattg ggatcgccca ataaacattc ccttg                  45

SEQ ID NO: 54         moltype = DNA  length = 45
FEATURE               Location/Qualifiers
source                1..45
                      mol_type = genomic DNA
                      organism = Homo sapiens
SEQUENCE: 54
tctgttatcc tgctagctgt agaaatgtat cctgataaac attaa                  45

SEQ ID NO: 55         moltype = DNA  length = 45
FEATURE               Location/Qualifiers
source                1..45
                      mol_type = genomic DNA
                      organism = Homo sapiens
SEQUENCE: 55
tgataaacat taaacactgt aatcttaaaa gtgtaattgt gtgac                  45

SEQ ID NO: 56         moltype = DNA  length = 45
FEATURE               Location/Qualifiers
source                1..45
                      mol_type = genomic DNA
                      organism = Homo sapiens
SEQUENCE: 56
ttaaacactg taatcttaaa agtgtaattg tgtgactttt tcaga                  45

SEQ ID NO: 57         moltype = DNA  length = 45
FEATURE               Location/Qualifiers
source                1..45
                      mol_type = genomic DNA
                      organism = Homo sapiens
SEQUENCE: 57
gtgtaattgt gtgacttttt cagagttgct ttaaagtacc tgtag                  45

SEQ ID NO: 58         moltype = DNA  length = 45
FEATURE               Location/Qualifiers
source                1..45
                      mol_type = genomic DNA
                      organism = Homo sapiens
SEQUENCE: 58
ttgctttaaa gtacctgtag tgagaaactg atttatgatc acttg                  45

SEQ ID NO: 59         moltype = DNA  length = 45
FEATURE               Location/Qualifiers
source                1..45
```

```
                         mol_type = genomic DNA
                         organism = Homo sapiens
SEQUENCE: 59
tacctgtagt gagaaactga tttatgatca cttggaagat ttgta                    45

SEQ ID NO: 60            moltype = DNA  length = 45
FEATURE                  Location/Qualifiers
source                   1..45
                         mol_type = genomic DNA
                         organism = Homo sapiens
SEQUENCE: 60
gtgagaaact gatttatgat cacttggaag atttgtatag tttta                    45

SEQ ID NO: 61            moltype = DNA  length = 45
FEATURE                  Location/Qualifiers
source                   1..45
                         mol_type = genomic DNA
                         organism = Homo sapiens
SEQUENCE: 61
tgatttatga tcacttggaa gatttgtata gttttataaa actca                    45

SEQ ID NO: 62            moltype = DNA  length = 45
FEATURE                  Location/Qualifiers
source                   1..45
                         mol_type = genomic DNA
                         organism = Homo sapiens
SEQUENCE: 62
ttggaagatt tgtatagttt tataaaactc agttaaaatg tctgt                    45

SEQ ID NO: 63            moltype = DNA  length = 45
FEATURE                  Location/Qualifiers
source                   1..45
                         mol_type = genomic DNA
                         organism = Homo sapiens
SEQUENCE: 63
tataaaactc agttaaaatg tctgtttcaa tgacctgtat tttgc                    45

SEQ ID NO: 64            moltype = DNA  length = 45
FEATURE                  Location/Qualifiers
source                   1..45
                         mol_type = genomic DNA
                         organism = Homo sapiens
SEQUENCE: 64
actcagttaa aatgtctgtt tcaatgacct gtattttgcc agact                    45

SEQ ID NO: 65            moltype = DNA  length = 45
FEATURE                  Location/Qualifiers
source                   1..45
                         mol_type = genomic DNA
                         organism = Homo sapiens
SEQUENCE: 65
tcagttaaaa tgtctgtttc aatgacctgt attttgccag actta                    45

SEQ ID NO: 66            moltype = DNA  length = 45
FEATURE                  Location/Qualifiers
source                   1..45
                         mol_type = genomic DNA
                         organism = Homo sapiens
SEQUENCE: 66
agttaaaatg tctgtttcaa tgacctgtat tttgccagac ttaaa                    45

SEQ ID NO: 67            moltype = DNA  length = 45
FEATURE                  Location/Qualifiers
source                   1..45
                         mol_type = genomic DNA
                         organism = Homo sapiens
SEQUENCE: 67
tttcaatgac ctgtattttg ccagacttaa atcacagatg ggtat                    45

SEQ ID NO: 68            moltype = DNA  length = 45
FEATURE                  Location/Qualifiers
source                   1..45
                         mol_type = genomic DNA
                         organism = Homo sapiens
SEQUENCE: 68
ttcaatgacc tgtattttgc cagacttaaa tcacagatgg gtatt                    45

SEQ ID NO: 69            moltype = DNA  length = 45
FEATURE                  Location/Qualifiers
```

-continued

```
source                  1..45
                        mol_type = genomic DNA
                        organism = Homo sapiens
SEQUENCE: 69
tgccagactt aaatcacaga tgggtattaa acttgtcaga atttc                   45

SEQ ID NO: 70           moltype = DNA  length = 45
FEATURE                 Location/Qualifiers
source                  1..45
                        mol_type = genomic DNA
                        organism = Homo sapiens
SEQUENCE: 70
agacttaaat cacagatggg tattaaactt gtcagaattt ctttg                   45

SEQ ID NO: 71           moltype = DNA  length = 45
FEATURE                 Location/Qualifiers
source                  1..45
                        mol_type = genomic DNA
                        organism = Homo sapiens
SEQUENCE: 71
aaatcacaga tgggtattaa acttgtcaga atttctttgt cattc                   45

SEQ ID NO: 72           moltype = DNA  length = 45
FEATURE                 Location/Qualifiers
source                  1..45
                        mol_type = genomic DNA
                        organism = Homo sapiens
SEQUENCE: 72
aatcacagat gggtattaaa cttgtcagaa tttctttgtc attca                   45

SEQ ID NO: 73           moltype = DNA  length = 45
FEATURE                 Location/Qualifiers
source                  1..45
                        mol_type = genomic DNA
                        organism = Homo sapiens
SEQUENCE: 73
atcacagatg ggtattaaac ttgtcagaat ttctttgtca ttcaa                   45

SEQ ID NO: 74           moltype = DNA  length = 45
FEATURE                 Location/Qualifiers
source                  1..45
                        mol_type = genomic DNA
                        organism = Homo sapiens
SEQUENCE: 74
taaacttgtc agaatttctt tgtcattcaa gcctgtgaat aaaaa                   45

SEQ ID NO: 75           moltype = DNA  length = 45
FEATURE                 Location/Qualifiers
source                  1..45
                        mol_type = genomic DNA
                        organism = Homo sapiens
SEQUENCE: 75
tcagaatttc tttgtcattc aagcctgtga ataaaaaccc tgtat                   45

SEQ ID NO: 76           moltype = DNA  length = 45
FEATURE                 Location/Qualifiers
source                  1..45
                        mol_type = genomic DNA
                        organism = Homo sapiens
SEQUENCE: 76
tgaataaaaa ccctgtatgg cacttattat gaggctatta aaaga                   45

SEQ ID NO: 77           moltype = RNA  length = 20
FEATURE                 Location/Qualifiers
source                  1..20
                        mol_type = genomic RNA
                        organism = Homo sapiens
SEQUENCE: 77
acggcccagt gcagggcatc                                               20

SEQ ID NO: 78           moltype = RNA  length = 20
FEATURE                 Location/Qualifiers
source                  1..20
                        mol_type = genomic RNA
                        organism = Homo sapiens
SEQUENCE: 78
cggcccagtg cagggcatca                                               20

SEQ ID NO: 79           moltype = RNA  length = 20
```

-continued

```
FEATURE                 Location/Qualifiers
source                  1..20
                        mol_type = genomic RNA
                        organism = Homo sapiens
SEQUENCE: 79
ggcccagtgc agggcatcat                                                20

SEQ ID NO: 80           moltype = RNA  length = 20
FEATURE                 Location/Qualifiers
source                  1..20
                        mol_type = genomic RNA
                        organism = Homo sapiens
SEQUENCE: 80
gcccagtgca gggcatcatc                                                20

SEQ ID NO: 81           moltype = RNA  length = 20
FEATURE                 Location/Qualifiers
source                  1..20
                        mol_type = genomic RNA
                        organism = Homo sapiens
SEQUENCE: 81
cccagtgcag ggcatcatca                                                20

SEQ ID NO: 82           moltype = RNA  length = 20
FEATURE                 Location/Qualifiers
source                  1..20
                        mol_type = genomic RNA
                        organism = Homo sapiens
SEQUENCE: 82
ccagtgcagg gcatcatcaa                                                20

SEQ ID NO: 83           moltype = RNA  length = 20
FEATURE                 Location/Qualifiers
source                  1..20
                        mol_type = genomic RNA
                        organism = Homo sapiens
SEQUENCE: 83
cagtgcaggg catcatcaat                                                20

SEQ ID NO: 84           moltype = RNA  length = 20
FEATURE                 Location/Qualifiers
source                  1..20
                        mol_type = genomic RNA
                        organism = Homo sapiens
SEQUENCE: 84
agtgcagggc atcatcaatt                                                20

SEQ ID NO: 85           moltype = RNA  length = 20
FEATURE                 Location/Qualifiers
source                  1..20
                        mol_type = genomic RNA
                        organism = Homo sapiens
SEQUENCE: 85
gtgcagggca tcatcaattt                                                20

SEQ ID NO: 86           moltype = RNA  length = 20
FEATURE                 Location/Qualifiers
source                  1..20
                        mol_type = genomic RNA
                        organism = Homo sapiens
SEQUENCE: 86
tgcagggcat catcaatttc                                                20

SEQ ID NO: 87           moltype = RNA  length = 20
FEATURE                 Location/Qualifiers
source                  1..20
                        mol_type = genomic RNA
                        organism = Homo sapiens
SEQUENCE: 87
gcagggcatc atcaatttcg                                                20

SEQ ID NO: 88           moltype = RNA  length = 20
FEATURE                 Location/Qualifiers
source                  1..20
                        mol_type = genomic RNA
                        organism = Homo sapiens
SEQUENCE: 88
gggcatcatc aatttcgagc                                                20
```

```
SEQ ID NO: 89          moltype = RNA  length = 20
FEATURE                Location/Qualifiers
source                 1..20
                       mol_type = genomic RNA
                       organism = Homo sapiens
SEQUENCE: 89
gcatcatcaa tttcgagcag                                              20

SEQ ID NO: 90          moltype = RNA  length = 20
FEATURE                Location/Qualifiers
source                 1..20
                       mol_type = genomic RNA
                       organism = Homo sapiens
SEQUENCE: 90
catcatcaat ttcgagcaga                                              20

SEQ ID NO: 91          moltype = RNA  length = 20
FEATURE                Location/Qualifiers
source                 1..20
                       mol_type = genomic RNA
                       organism = Homo sapiens
SEQUENCE: 91
tcatcaattt cgagcagaag                                              20

SEQ ID NO: 92          moltype = RNA  length = 20
FEATURE                Location/Qualifiers
source                 1..20
                       mol_type = genomic RNA
                       organism = Homo sapiens
SEQUENCE: 92
catcaatttc gagcagaagg                                              20

SEQ ID NO: 93          moltype = RNA  length = 20
FEATURE                Location/Qualifiers
source                 1..20
                       mol_type = genomic RNA
                       organism = Homo sapiens
SEQUENCE: 93
caatttcgag cagaaggaaa                                              20

SEQ ID NO: 94          moltype = RNA  length = 20
FEATURE                Location/Qualifiers
source                 1..20
                       mol_type = genomic RNA
                       organism = Homo sapiens
SEQUENCE: 94
tgcatggatt ccatgttcat                                              20

SEQ ID NO: 95          moltype = RNA  length = 20
FEATURE                Location/Qualifiers
source                 1..20
                       mol_type = genomic RNA
                       organism = Homo sapiens
SEQUENCE: 95
tcatgagttt ggagataata                                              20

SEQ ID NO: 96          moltype = RNA  length = 20
FEATURE                Location/Qualifiers
source                 1..20
                       mol_type = genomic RNA
                       organism = Homo sapiens
SEQUENCE: 96
tgtaccagtg caggtcctca                                              20

SEQ ID NO: 97          moltype = RNA  length = 20
FEATURE                Location/Qualifiers
source                 1..20
                       mol_type = genomic RNA
                       organism = Homo sapiens
SEQUENCE: 97
accagtgcag gtcctcactt                                              20

SEQ ID NO: 98          moltype = RNA  length = 20
FEATURE                Location/Qualifiers
source                 1..20
                       mol_type = genomic RNA
                       organism = Homo sapiens
SEQUENCE: 98
tcctcacttt aatcctctat                                              20
```

```
SEQ ID NO: 99           moltype = RNA  length = 20
FEATURE                 Location/Qualifiers
source                  1..20
                        mol_type = genomic RNA
                        organism = Homo sapiens
SEQUENCE: 99
gctgacaaag atggtgtggc                                                20

SEQ ID NO: 100          moltype = RNA  length = 20
FEATURE                 Location/Qualifiers
source                  1..20
                        mol_type = genomic RNA
                        organism = Homo sapiens
SEQUENCE: 100
tgtgtctatt gaagattctg                                                20

SEQ ID NO: 101          moltype = RNA  length = 20
FEATURE                 Location/Qualifiers
source                  1..20
                        mol_type = genomic RNA
                        organism = Homo sapiens
SEQUENCE: 101
tctgtgatct cactctcagg                                                20

SEQ ID NO: 102          moltype = RNA  length = 20
FEATURE                 Location/Qualifiers
source                  1..20
                        mol_type = genomic RNA
                        organism = Homo sapiens
SEQUENCE: 102
accattgcat cattggccgc                                                20

SEQ ID NO: 103          moltype = RNA  length = 20
FEATURE                 Location/Qualifiers
source                  1..20
                        mol_type = genomic RNA
                        organism = Homo sapiens
SEQUENCE: 103
gtggaaatga agaaagtaca                                                20

SEQ ID NO: 104          moltype = RNA  length = 20
FEATURE                 Location/Qualifiers
source                  1..20
                        mol_type = genomic RNA
                        organism = Homo sapiens
SEQUENCE: 104
tgtggtgtaa ttgggatcgc                                                20

SEQ ID NO: 105          moltype = RNA  length = 20
FEATURE                 Location/Qualifiers
source                  1..20
                        mol_type = genomic RNA
                        organism = Homo sapiens
SEQUENCE: 105
aattgggatc gcccaataaa                                                20

SEQ ID NO: 106          moltype = RNA  length = 20
FEATURE                 Location/Qualifiers
source                  1..20
                        mol_type = genomic RNA
                        organism = Homo sapiens
SEQUENCE: 106
gctgtagaaa tgtatcctga                                                20

SEQ ID NO: 107          moltype = RNA  length = 20
FEATURE                 Location/Qualifiers
source                  1..20
                        mol_type = genomic RNA
                        organism = Homo sapiens
SEQUENCE: 107
actgtaatct taaaagtgta                                                20

SEQ ID NO: 108          moltype = RNA  length = 20
FEATURE                 Location/Qualifiers
source                  1..20
                        mol_type = genomic RNA
                        organism = Homo sapiens
SEQUENCE: 108
```

-continued

```
ttaaaagtgt aattgtgtga                                              20

SEQ ID NO: 109         moltype = RNA  length = 20
FEATURE                Location/Qualifiers
source                 1..20
                       mol_type = genomic RNA
                       organism = Homo sapiens
SEQUENCE: 109
tttttcagag ttgctttaaa                                              20

SEQ ID NO: 110         moltype = RNA  length = 20
FEATURE                Location/Qualifiers
source                 1..20
                       mol_type = genomic RNA
                       organism = Homo sapiens
SEQUENCE: 110
tgtagtgaga aactgattta                                              20

SEQ ID NO: 111         moltype = RNA  length = 20
FEATURE                Location/Qualifiers
source                 1..20
                       mol_type = genomic RNA
                       organism = Homo sapiens
SEQUENCE: 111
actgatttat gatcacttgg                                              20

SEQ ID NO: 112         moltype = RNA  length = 20
FEATURE                Location/Qualifiers
source                 1..20
                       mol_type = genomic RNA
                       organism = Homo sapiens
SEQUENCE: 112
atgatcactt ggaagatttg                                              20

SEQ ID NO: 113         moltype = RNA  length = 20
FEATURE                Location/Qualifiers
source                 1..20
                       mol_type = genomic RNA
                       organism = Homo sapiens
SEQUENCE: 113
tggaagattt gtatagtttt                                              20

SEQ ID NO: 114         moltype = RNA  length = 20
FEATURE                Location/Qualifiers
source                 1..20
                       mol_type = genomic RNA
                       organism = Homo sapiens
SEQUENCE: 114
agttttataa aactcagtta                                              20

SEQ ID NO: 115         moltype = RNA  length = 20
FEATURE                Location/Qualifiers
source                 1..20
                       mol_type = genomic RNA
                       organism = Homo sapiens
SEQUENCE: 115
aaatgtctgt ttcaatgacc                                              20

SEQ ID NO: 116         moltype = RNA  length = 20
FEATURE                Location/Qualifiers
source                 1..20
                       mol_type = genomic RNA
                       organism = Homo sapiens
SEQUENCE: 116
ctgtttcaat gacctgtatt                                              20

SEQ ID NO: 117         moltype = RNA  length = 20
FEATURE                Location/Qualifiers
source                 1..20
                       mol_type = genomic RNA
                       organism = Homo sapiens
SEQUENCE: 117
gtttcaatga cctgtatttt                                              20

SEQ ID NO: 118         moltype = RNA  length = 20
FEATURE                Location/Qualifiers
source                 1..20
                       mol_type = genomic RNA
                       organism = Homo sapiens
```

```
SEQUENCE: 118
ttcaatgacc tgtattttgc                                              20

SEQ ID NO: 119          moltype = RNA  length = 20
FEATURE                 Location/Qualifiers
source                  1..20
                        mol_type = genomic RNA
                        organism = Homo sapiens
SEQUENCE: 119
ttttgccaga cttaaatcac                                              20

SEQ ID NO: 120          moltype = RNA  length = 20
FEATURE                 Location/Qualifiers
source                  1..20
                        mol_type = genomic RNA
                        organism = Homo sapiens
SEQUENCE: 120
tttgccagac ttaaatcaca                                              20

SEQ ID NO: 121          moltype = RNA  length = 20
FEATURE                 Location/Qualifiers
source                  1..20
                        mol_type = genomic RNA
                        organism = Homo sapiens
SEQUENCE: 121
acagatgggt attaaacttg                                              20

SEQ ID NO: 122          moltype = RNA  length = 20
FEATURE                 Location/Qualifiers
source                  1..20
                        mol_type = genomic RNA
                        organism = Homo sapiens
SEQUENCE: 122
atgggtatta aacttgtcag                                              20

SEQ ID NO: 123          moltype = RNA  length = 20
FEATURE                 Location/Qualifiers
source                  1..20
                        mol_type = genomic RNA
                        organism = Homo sapiens
SEQUENCE: 123
attaaacttg tcagaatttc                                              20

SEQ ID NO: 124          moltype = RNA  length = 20
FEATURE                 Location/Qualifiers
source                  1..20
                        mol_type = genomic RNA
                        organism = Homo sapiens
SEQUENCE: 124
ttaaacttgt cagaatttct                                              20

SEQ ID NO: 125          moltype = RNA  length = 20
FEATURE                 Location/Qualifiers
source                  1..20
                        mol_type = genomic RNA
                        organism = Homo sapiens
SEQUENCE: 125
taaacttgtc agaatttctt                                              20

SEQ ID NO: 126          moltype = RNA  length = 20
FEATURE                 Location/Qualifiers
source                  1..20
                        mol_type = genomic RNA
                        organism = Homo sapiens
SEQUENCE: 126
ttctttgtca ttcaagcctg                                              20

SEQ ID NO: 127          moltype = RNA  length = 20
FEATURE                 Location/Qualifiers
source                  1..20
                        mol_type = genomic RNA
                        organism = Homo sapiens
SEQUENCE: 127
cattcaagcc tgtgaataaa                                              20

SEQ ID NO: 128          moltype = RNA  length = 20
FEATURE                 Location/Qualifiers
source                  1..20
                        mol_type = genomic RNA
```

-continued

```
                        organism = Homo sapiens
SEQUENCE: 128
tatggcactt attatgaggc                                             20

SEQ ID NO: 129          moltype = RNA  length = 20
FEATURE                 Location/Qualifiers
source                  1..20
                        mol_type = other RNA
                        organism = synthetic construct
modified_base           1
                        mod_base = OTHER
                        note = 5'-phosphate-2'-O-methyl uridine phosphorothioate
modified_base           2
                        mod_base = OTHER
                        note = 2'-fluoro cytidine phosphorothioate
modified_base           3
                        mod_base = OTHER
                        note = 2'-O-methyl guanosine
modified_base           4
                        mod_base = OTHER
                        note = 2'-O-methyl adenosine
modified_base           5
                        mod_base = OTHER
                        note = 2'-O-methyl adenosine
modified_base           6
                        mod_base = OTHER
                        note = 2'-fluoro adenosine
modified_base           7
                        mod_base = OTHER
                        note = 2'-O-methyl uridine
modified_base           8
                        mod_base = OTHER
                        note = 2'-O-methyl uridine
modified_base           9
                        mod_base = OTHER
                        note = 2'-O-methyl guanosine
modified_base           10
                        mod_base = OTHER
                        note = 2'-O-methyl adenosine
modified_base           11
                        mod_base = OTHER
                        note = 2'-O-methyl uridine
modified_base           12
                        mod_base = OTHER
                        note = 2'-O-methyl guanosine
modified_base           13
                        mod_base = OTHER
                        note = 2'-O-methyl adenosine phosphorothioate
modified_base           14
                        mod_base = OTHER
                        note = 2'-fluoro uridine phosphorothioate
modified_base           15
                        mod_base = OTHER
                        note = 2'-O-methyl guanosine phosphorothioate
modified_base           16
                        mod_base = OTHER
                        note = 2'-fluoro cytidine phosphorothioate
modified_base           17
                        mod_base = OTHER
                        note = 2'-O-methyl cytidine phosphorothioate
modified_base           18
                        mod_base = OTHER
                        note = 2'-O-methyl cytidine phosphorothioate
modified_base           19
                        mod_base = OTHER
                        note = 2'-O-methyl uridine phosphorothioate
modified_base           20
                        mod_base = OTHER
                        note = 2'-fluoro guanosine
SEQUENCE: 129
tcgaaattga tgatgccctg                                             20

SEQ ID NO: 130          moltype = RNA  length = 20
FEATURE                 Location/Qualifiers
source                  1..20
                        mol_type = other RNA
                        organism = synthetic construct
modified_base           1
                        mod_base = OTHER
```

```
                          note = 5'-phosphate-2'-O-methyl uridine phosphorothioate
modified_base             2
                          mod_base = OTHER
                          note = 2'-fluoro guanosine phosphorothioate
modified_base             3
                          mod_base = OTHER
                          note = 2'-O-methyl adenosine
modified_base             4
                          mod_base = OTHER
                          note = 2'-O-methyl guanosine
modified_base             5
                          mod_base = OTHER
                          note = 2'-O-methyl guanosine
modified_base             6
                          mod_base = OTHER
                          note = 2'-fluoro adenosine
modified_base             7
                          mod_base = OTHER
                          note = 2'-O-methyl cytidine
modified_base             8
                          mod_base = OTHER
                          note = 2'-O-methyl cytidine
modified_base             9
                          mod_base = OTHER
                          note = 2'-O-methyl uridine
modified_base             10
                          mod_base = OTHER
                          note = 2'-O-methyl guanosine
modified_base             11
                          mod_base = OTHER
                          note = 2'-O-methyl cytidine
modified_base             12
                          mod_base = OTHER
                          note = 2'-O-methyl adenosine
modified_base             13
                          mod_base = OTHER
                          note = 2'-O-methyl cytidine phosphorothioate
modified_base             14
                          mod_base = OTHER
                          note = 2'-fluoro uridine phosphorothioate
modified_base             15
                          mod_base = OTHER
                          note = 2'-O-methyl guanosine phosphorothioate
modified_base             16
                          mod_base = OTHER
                          note = 2'-fluoro guanosine phosphorothioate
modified_base             17
                          mod_base = OTHER
                          note = 2'-O-methyl uridine phosphorothioate
modified_base             18
                          mod_base = OTHER
                          note = 2'-O-methyl adenosine phosphorothioate
modified_base             19
                          mod_base = OTHER
                          note = 2'-O-methyl cytidine phosphorothioate
modified_base             20
                          mod_base = OTHER
                          note = 2'-fluoro adenosine
SEQUENCE: 130
tgaggacctg cactggtaca                                                      20

SEQ ID NO: 131            moltype = RNA  length = 20
FEATURE                   Location/Qualifiers
source                    1..20
                          mol_type = other RNA
                          organism = synthetic construct
modified_base             1
                          mod_base = OTHER
                          note = 5'-phosphate-2'-O-methyl uridine phosphorothioate
modified_base             2
                          mod_base = OTHER
                          note = 2'-fluoro uridine phosphorothioate
modified_base             3
                          mod_base = OTHER
                          note = 2'-O-methyl adenosine
modified_base             4
                          mod_base = OTHER
                          note = 2'-O-methyl guanosine
modified_base             5
```

-continued

```
                        mod_base = OTHER
                        note = 2'-O-methyl adenosine
modified_base           6
                        mod_base = OTHER
                        note = 2'-fluoro guanosine
modified_base           7
                        mod_base = OTHER
                        note = 2'-O-methyl guanosine
modified_base           8
                        mod_base = OTHER
                        note = 2'-O-methyl adenosine
modified_base           9
                        mod_base = OTHER
                        note = 2'-O-methyl uridine
modified_base           10
                        mod_base = OTHER
                        note = 2'-O-methyl uridine
modified_base           11
                        mod_base = OTHER
                        note = 2'-O-methyl adenosine
modified_base           12
                        mod_base = OTHER
                        note = 2'-O-methyl adenosine
modified_base           13
                        mod_base = OTHER
                        note = 2'-O-methyl adenosine phosphorothioate
modified_base           14
                        mod_base = OTHER
                        note = 2'-fluoro guanosine phosphorothioate
modified_base           15
                        mod_base = OTHER
                        note = 2'-O-methyl uridine phosphorothioate
modified_base           16
                        mod_base = OTHER
                        note = 2'-fluoro guanosine phosphorothioate
modified_base           17
                        mod_base = OTHER
                        note = 2'-O-methyl adenosine phosphorothioate
modified_base           18
                        mod_base = OTHER
                        note = 2'-O-methyl guanosine phosphorothioate
modified_base           19
                        mod_base = OTHER
                        note = 2'-O-methyl guanosine phosphorothioate
modified_base           20
                        mod_base = OTHER
                        note = 2'-fluoro adenosine
SEQUENCE: 131
ttagaggatt aaagtgagga                                                20

SEQ ID NO: 132          moltype = RNA  length = 20
FEATURE                 Location/Qualifiers
source                  1..20
                        mol_type = other RNA
                        organism = synthetic construct
modified_base           1
                        mod_base = OTHER
                        note = 5'-phosphate-2'-O-methyl uridine phosphorothioate
modified_base           2
                        mod_base = OTHER
                        note = 2'-fluoro cytidine phosphorothioate
modified_base           3
                        mod_base = OTHER
                        note = 2'-O-methyl cytidine
modified_base           4
                        mod_base = OTHER
                        note = 2'-O-methyl adenosine
modified_base           5
                        mod_base = OTHER
                        note = 2'-O-methyl cytidine
modified_base           6
                        mod_base = OTHER
                        note = 2'-fluoro adenosine
modified_base           7
                        mod_base = OTHER
                        note = 2'-O-methyl cytidine
modified_base           8
                        mod_base = OTHER
                        note = 2'-O-methyl cytidine
```

-continued

```
modified_base          9
                       mod_base = OTHER
                       note = 2'-O-methyl adenosine
modified_base          10
                       mod_base = OTHER
                       note = 2'-O-methyl uridine
modified_base          11
                       mod_base = OTHER
                       note = 2'-O-methyl cytidine
modified_base          12
                       mod_base = OTHER
                       note = 2'-O-methyl uridine
modified_base          13
                       mod_base = OTHER
                       note = 2'-O-methyl uridine phosphorothioate
modified_base          14
                       mod_base = OTHER
                       note = 2'-fluoro uridine phosphorothioate
modified_base          15
                       mod_base = OTHER
                       note = 2'-O-methyl guanosine phosphorothioate
modified_base          16
                       mod_base = OTHER
                       note = 2'-fluoro uridine phosphorothioate
modified_base          17
                       mod_base = OTHER
                       note = 2'-O-methyl cytidine phosphorothioate
modified_base          18
                       mod_base = OTHER
                       note = 2'-O-methyl adenosine phosphorothioate
modified_base          19
                       mod_base = OTHER
                       note = 2'-O-methyl guanosine phosphorothioate
modified_base          20
                       mod_base = OTHER
                       note = 2'-fluoro cytidine
SEQUENCE: 132
tccacaccat ctttgtcagc                                              20

SEQ ID NO: 133         moltype = RNA  length = 20
FEATURE                Location/Qualifiers
source                 1..20
                       mol_type = other RNA
                       organism = synthetic construct
modified_base          1
                       mod_base = OTHER
                       note = 5'-phosphate-2'-O-methyl uridine phosphorothioate
modified_base          2
                       mod_base = OTHER
                       note = 2'-fluoro adenosine phosphorothioate
modified_base          3
                       mod_base = OTHER
                       note = 2'-O-methyl guanosine
modified_base          4
                       mod_base = OTHER
                       note = 2'-O-methyl adenosine
modified_base          5
                       mod_base = OTHER
                       note = 2'-O-methyl adenosine
modified_base          6
                       mod_base = OTHER
                       note = 2'-fluoro uridine
modified_base          7
                       mod_base = OTHER
                       note = 2'-O-methyl cytidine
modified_base          8
                       mod_base = OTHER
                       note = 2'-O-methyl uridine
modified_base          9
                       mod_base = OTHER
                       note = 2'-O-methyl uridine
modified_base          10
                       mod_base = OTHER
                       note = 2'-O-methyl cytidine
modified_base          11
                       mod_base = OTHER
                       note = 2'-O-methyl adenosine
modified_base          12
                       mod_base = OTHER
```

```
                         note = 2'-O-methyl adenosine
modified_base            13
                         mod_base = OTHER
                         note = 2'-O-methyl uridine phosphorothioate
modified_base            14
                         mod_base = OTHER
                         note = 2'-fluoro adenosine phosphorothioate
modified_base            15
                         mod_base = OTHER
                         note = 2'-O-methyl guanosine phosphorothioate
modified_base            16
                         mod_base = OTHER
                         note = 2'-fluoro adenosine phosphorothioate
modified_base            17
                         mod_base = OTHER
                         note = 2'-O-methyl cytidine phosphorothioate
modified_base            18
                         mod_base = OTHER
                         note = 2'-O-methyl adenosine phosphorothioate
modified_base            19
                         mod_base = OTHER
                         note = 2'-O-methyl cytidine phosphorothioate
modified_base            20
                         mod_base = OTHER
                         note = 2'-fluoro adenosine
SEQUENCE: 133
tagaatcttc aatagacaca                                              20

SEQ ID NO: 134           moltype = RNA  length = 20
FEATURE                  Location/Qualifiers
source                   1..20
                         mol_type = other RNA
                         organism = synthetic construct
modified_base            1
                         mod_base = OTHER
                         note = 5'-phosphate-2'-O-methyl uridine phosphorothioate
modified_base            2
                         mod_base = OTHER
                         note = 2'-fluoro cytidine phosphorothioate
modified_base            3
                         mod_base = OTHER
                         note = 2'-O-methyl uridine
modified_base            4
                         mod_base = OTHER
                         note = 2'-O-methyl guanosine
modified_base            5
                         mod_base = OTHER
                         note = 2'-O-methyl adenosine
modified_base            6
                         mod_base = OTHER
                         note = 2'-fluoro guanosine
modified_base            7
                         mod_base = OTHER
                         note = 2'-O-methyl adenosine
modified_base            8
                         mod_base = OTHER
                         note = 2'-O-methyl guanosine
modified_base            9
                         mod_base = OTHER
                         note = 2'-O-methyl uridine
modified_base            10
                         mod_base = OTHER
                         note = 2'-O-methyl guanosine
modified_base            11
                         mod_base = OTHER
                         note = 2'-O-methyl adenosine
modified_base            12
                         mod_base = OTHER
                         note = 2'-O-methyl guanosine
modified_base            13
                         mod_base = OTHER
                         note = 2'-O-methyl adenosine phosphorothioate
modified_base            14
                         mod_base = OTHER
                         note = 2'-fluoro uridine phosphorothioate
modified_base            15
                         mod_base = OTHER
                         note = 2'-O-methyl cytidine phosphorothioate
modified_base            16
```

```
                         mod_base = OTHER
                         note = 2'-fluoro adenosine phosphorothioate
modified_base            17
                         mod_base = OTHER
                         note = 2'-O-methyl cytidine phosphorothioate
modified_base            18
                         mod_base = OTHER
                         note = 2'-O-methyl adenosine phosphorothioate
modified_base            19
                         mod_base = OTHER
                         note = 2'-O-methyl guanosine phosphorothioate
modified_base            20
                         mod_base = OTHER
                         note = 2'-fluoro adenosine
SEQUENCE: 134
tctgagagtg agatcacaga                                               20

SEQ ID NO: 135           moltype = RNA  length = 20
FEATURE                  Location/Qualifiers
source                   1..20
                         mol_type = other RNA
                         organism = synthetic construct
modified_base            1
                         mod_base = OTHER
                         note = 5'-phosphate-2'-O-methyl uridine phosphorothioate
modified_base            2
                         mod_base = OTHER
                         note = 2'-fluoro uridine phosphorothioate
modified_base            3
                         mod_base = OTHER
                         note = 2'-O-methyl cytidine
modified_base            4
                         mod_base = OTHER
                         note = 2'-O-methyl adenosine
modified_base            5
                         mod_base = OTHER
                         note = 2'-O-methyl uridine
modified_base            6
                         mod_base = OTHER
                         note = 2'-fluoro uridine
modified_base            7
                         mod_base = OTHER
                         note = 2'-O-methyl uridine
modified_base            8
                         mod_base = OTHER
                         note = 2'-O-methyl cytidine
modified_base            9
                         mod_base = OTHER
                         note = 2'-O-methyl cytidine
modified_base            10
                         mod_base = OTHER
                         note = 2'-O-methyl adenosine
modified_base            11
                         mod_base = OTHER
                         note = 2'-O-methyl cytidine
modified_base            12
                         mod_base = OTHER
                         note = 2'-O-methyl cytidine
modified_base            13
                         mod_base = OTHER
                         note = 2'-O-methyl uridine phosphorothioate
modified_base            14
                         mod_base = OTHER
                         note = 2'-fluoro uridine phosphorothioate
modified_base            15
                         mod_base = OTHER
                         note = 2'-O-methyl uridine phosphorothioate
modified_base            16
                         mod_base = OTHER
                         note = 2'-fluoro guanosine phosphorothioate
modified_base            17
                         mod_base = OTHER
                         note = 2'-O-methyl cytidine phosphorothioate
modified_base            18
                         mod_base = OTHER
                         note = 2'-O-methyl cytidine phosphorothioate
modified_base            19
                         mod_base = OTHER
                         note = 2'-O-methyl cytidine phosphorothioate
```

-continued

```
modified_base          20
                       mod_base = OTHER
                       note = 2'-fluoro adenosine
SEQUENCE: 135
ttcatttcca cctttgccca                                            20

SEQ ID NO: 136         moltype = RNA  length = 20
FEATURE                Location/Qualifiers
source                 1..20
                       mol_type = other RNA
                       organism = synthetic construct
modified_base          1
                       mod_base = OTHER
                       note = 5'-phosphate-2'-O-methyl uridine phosphorothioate
modified_base          2
                       mod_base = OTHER
                       note = 2'-fluoro cytidine phosphorothioate
modified_base          3
                       mod_base = OTHER
                       note = 2'-O-methyl guanosine
modified_base          4
                       mod_base = OTHER
                       note = 2'-O-methyl adenosine
modified_base          5
                       mod_base = OTHER
                       note = 2'-O-methyl uridine
modified_base          6
                       mod_base = OTHER
                       note = 2'-fluoro cytidine
modified_base          7
                       mod_base = OTHER
                       note = 2'-O-methyl cytidine
modified_base          8
                       mod_base = OTHER
                       note = 2'-O-methyl cytidine
modified_base          9
                       mod_base = OTHER
                       note = 2'-O-methyl adenosine
modified_base          10
                       mod_base = OTHER
                       note = 2'-O-methyl adenosine
modified_base          11
                       mod_base = OTHER
                       note = 2'-O-methyl uridine
modified_base          12
                       mod_base = OTHER
                       note = 2'-O-methyl uridine
modified_base          13
                       mod_base = OTHER
                       note = 2'-O-methyl adenosine phosphorothioate
modified_base          14
                       mod_base = OTHER
                       note = 2'-fluoro cytidine phosphorothioate
modified_base          15
                       mod_base = OTHER
                       note = 2'-O-methyl adenosine phosphorothioate
modified_base          16
                       mod_base = OTHER
                       note = 2'-fluoro cytidine phosphorothioate
modified_base          17
                       mod_base = OTHER
                       note = 2'-O-methyl cytidine phosphorothioate
modified_base          18
                       mod_base = OTHER
                       note = 2'-O-methyl adenosine phosphorothioate
modified_base          19
                       mod_base = OTHER
                       note = 2'-O-methyl cytidine phosphorothioate
modified_base          20
                       mod_base = OTHER
                       note = 2'-fluoro adenosine
SEQUENCE: 136
tcgatcccaa ttacaccaca                                            20

SEQ ID NO: 137         moltype = RNA  length = 20
FEATURE                Location/Qualifiers
source                 1..20
                       mol_type = other RNA
                       organism = synthetic construct
```

-continued

```
modified_base          1
                       mod_base = OTHER
                       note = 5'-phosphate-2'-O-methyl uridine phosphorothioate
modified_base          2
                       mod_base = OTHER
                       note = 2'-fluoro cytidine phosphorothioate
modified_base          3
                       mod_base = OTHER
                       note = 2'-O-methyl adenosine
modified_base          4
                       mod_base = OTHER
                       note = 2'-O-methyl guanosine
modified_base          5
                       mod_base = OTHER
                       note = 2'-O-methyl guanosine
modified_base          6
                       mod_base = OTHER
                       note = 2'-fluoro adenosine
modified_base          7
                       mod_base = OTHER
                       note = 2'-O-methyl uridine
modified_base          8
                       mod_base = OTHER
                       note = 2'-O-methyl adenosine
modified_base          9
                       mod_base = OTHER
                       note = 2'-O-methyl adenosine
modified_base          10
                       mod_base = OTHER
                       note = 2'-O-methyl cytidine
modified_base          11
                       mod_base = OTHER
                       note = 2'-O-methyl adenosine
modified_base          12
                       mod_base = OTHER
                       note = 2'-O-methyl guanosine
modified_base          13
                       mod_base = OTHER
                       note = 2'-O-methyl adenosine phosphorothioate
modified_base          14
                       mod_base = OTHER
                       note = 2'-fluoro uridine phosphorothioate
modified_base          15
                       mod_base = OTHER
                       note = 2'-O-methyl guanosine phosphorothioate
modified_base          16
                       mod_base = OTHER
                       note = 2'-fluoro adenosine phosphorothioate
modified_base          17
                       mod_base = OTHER
                       note = 2'-O-methyl guanosine phosphorothioate
modified_base          18
                       mod_base = OTHER
                       note = 2'-O-methyl uridine phosphorothioate
modified_base          19
                       mod_base = OTHER
                       note = 2'-O-methyl uridine phosphorothioate
modified_base          20
                       mod_base = OTHER
                       note = 2'-fluoro adenosine
SEQUENCE: 137
tcaggataac agatgagtta                                              20

SEQ ID NO: 138         moltype = RNA  length = 20
FEATURE                Location/Qualifiers
source                 1..20
                       mol_type = other RNA
                       organism = synthetic construct
modified_base          1
                       mod_base = OTHER
                       note = 5'-phosphate-2'-O-methyl uridine phosphorothioate
modified_base          2
                       mod_base = OTHER
                       note = 2'-fluoro adenosine phosphorothioate
modified_base          3
                       mod_base = OTHER
                       note = 2'-O-methyl guanosine
modified_base          4
                       mod_base = OTHER
```

```
                        note = 2'-O-methyl guanosine
modified_base           5
                        mod_base = OTHER
                        note = 2'-O-methyl adenosine
modified_base           6
                        mod_base = OTHER
                        note = 2'-fluoro uridine
modified_base           7
                        mod_base = OTHER
                        note = 2'-O-methyl adenosine
modified_base           8
                        mod_base = OTHER
                        note = 2'-O-methyl cytidine
modified_base           9
                        mod_base = OTHER
                        note = 2'-O-methyl adenosine
modified_base           10
                        mod_base = OTHER
                        note = 2'-O-methyl uridine
modified_base           11
                        mod_base = OTHER
                        note = 2'-O-methyl uridine
modified_base           12
                        mod_base = OTHER
                        note = 2'-O-methyl uridine
modified_base           13
                        mod_base = OTHER
                        note = 2'-O-methyl cytidine phosphorothioate
modified_base           14
                        mod_base = OTHER
                        note = 2'-fluoro uridine phosphorothioate
modified_base           15
                        mod_base = OTHER
                        note = 2'-O-methyl adenosine phosphorothioate
modified_base           16
                        mod_base = OTHER
                        note = 2'-fluoro cytidine phosphorothioate
modified_base           17
                        mod_base = OTHER
                        note = 2'-O-methyl adenosine phosphorothioate
modified_base           18
                        mod_base = OTHER
                        note = 2'-O-methyl guanosine phosphorothioate
modified_base           19
                        mod_base = OTHER
                        note = 2'-O-methyl cytidine phosphorothioate
modified_base           20
                        mod_base = OTHER
                        note = 2'-fluoro uridine
SEQUENCE: 138
taggatacat ttctacagct                                              20

SEQ ID NO: 139          moltype = RNA  length = 20
FEATURE                 Location/Qualifiers
source                  1..20
                        mol_type = other RNA
                        organism = synthetic construct
modified_base           1
                        mod_base = OTHER
                        note = 5'-phosphate-2'-O-methyl uridine phosphorothioate
modified_base           2
                        mod_base = OTHER
                        note = 2'-fluoro uridine phosphorothioate
modified_base           3
                        mod_base = OTHER
                        note = 2'-O-methyl adenosine
modified_base           4
                        mod_base = OTHER
                        note = 2'-O-methyl cytidine
modified_base           5
                        mod_base = OTHER
                        note = 2'-O-methyl adenosine
modified_base           6
                        mod_base = OTHER
                        note = 2'-fluoro guanosine
modified_base           7
                        mod_base = OTHER
                        note = 2'-O-methyl uridine
modified_base           8
```

```
                         mod_base = OTHER
                         note = 2'-O-methyl guanosine
modified_base            9
                         mod_base = OTHER
                         note = 2'-O-methyl uridine
modified_base            10
                         mod_base = OTHER
                         note = 2'-O-methyl uridine
modified_base            11
                         mod_base = OTHER
                         note = 2'-O-methyl uridine
modified_base            12
                         mod_base = OTHER
                         note = 2'-O-methyl adenosine
modified_base            13
                         mod_base = OTHER
                         note = 2'-O-methyl adenosine phosphorothioate
modified_base            14
                         mod_base = OTHER
                         note = 2'-fluoro uridine phosphorothioate
modified_base            15
                         mod_base = OTHER
                         note = 2'-O-methyl guanosine phosphorothioate
modified_base            16
                         mod_base = OTHER
                         note = 2'-fluoro uridine phosphorothioate
modified_base            17
                         mod_base = OTHER
                         note = 2'-O-methyl uridine phosphorothioate
modified_base            18
                         mod_base = OTHER
                         note = 2'-O-methyl uridine phosphorothioate
modified_base            19
                         mod_base = OTHER
                         note = 2'-O-methyl adenosine phosphorothioate
modified_base            20
                         mod_base = OTHER
                         note = 2'-fluoro uridine
SEQUENCE: 139
ttacagtgtt taatgtttat                                            20

SEQ ID NO: 140           moltype = RNA  length = 20
FEATURE                  Location/Qualifiers
source                   1..20
                         mol_type = other RNA
                         organism = synthetic construct
modified_base            1
                         mod_base = OTHER
                         note = 5'-phosphate-2'-O-methyl uridine phosphorothioate
modified_base            2
                         mod_base = OTHER
                         note = 2'-fluoro adenosine phosphorothioate
modified_base            3
                         mod_base = OTHER
                         note = 2'-O-methyl cytidine
modified_base            4
                         mod_base = OTHER
                         note = 2'-O-methyl adenosine
modified_base            5
                         mod_base = OTHER
                         note = 2'-O-methyl cytidine
modified_base            6
                         mod_base = OTHER
                         note = 2'-fluoro uridine
modified_base            7
                         mod_base = OTHER
                         note = 2'-O-methyl uridine
modified_base            8
                         mod_base = OTHER
                         note = 2'-O-methyl uridine
modified_base            9
                         mod_base = OTHER
                         note = 2'-O-methyl uridine
modified_base            10
                         mod_base = OTHER
                         note = 2'-O-methyl adenosine
modified_base            11
                         mod_base = OTHER
                         note = 2'-O-methyl adenosine
```

```
modified_base          12
                       mod_base = OTHER
                       note = 2'-O-methyl guanosine
modified_base          13
                       mod_base = OTHER
                       note = 2'-O-methyl adenosine phosphorothioate
modified_base          14
                       mod_base = OTHER
                       note = 2'-fluoro uridine phosphorothioate
modified_base          15
                       mod_base = OTHER
                       note = 2'-O-methyl uridine phosphorothioate
modified_base          16
                       mod_base = OTHER
                       note = 2'-fluoro adenosine phosphorothioate
modified_base          17
                       mod_base = OTHER
                       note = 2'-O-methyl cytidine phosphorothioate
modified_base          18
                       mod_base = OTHER
                       note = 2'-O-methyl adenosine phosphorothioate
modified_base          19
                       mod_base = OTHER
                       note = 2'-O-methyl guanosine phosphorothioate
modified_base          20
                       mod_base = OTHER
                       note = 2'-fluoro uridine
SEQUENCE: 140
tacactttta agattacagt                                              20

SEQ ID NO: 141         moltype = RNA  length = 20
FEATURE                Location/Qualifiers
source                 1..20
                       mol_type = other RNA
                       organism = synthetic construct
modified_base          1
                       mod_base = OTHER
                       note = 5'-phosphate-2'-O-methyl uridine phosphorothioate
modified_base          2
                       mod_base = OTHER
                       note = 2'-fluoro cytidine phosphorothioate
modified_base          3
                       mod_base = OTHER
                       note = 2'-O-methyl adenosine
modified_base          4
                       mod_base = OTHER
                       note = 2'-O-methyl cytidine
modified_base          5
                       mod_base = OTHER
                       note = 2'-O-methyl adenosine
modified_base          6
                       mod_base = OTHER
                       note = 2'-fluoro cytidine
modified_base          7
                       mod_base = OTHER
                       note = 2'-O-methyl adenosine
modified_base          8
                       mod_base = OTHER
                       note = 2'-O-methyl adenosine
modified_base          9
                       mod_base = OTHER
                       note = 2'-O-methyl uridine
modified_base          10
                       mod_base = OTHER
                       note = 2'-O-methyl uridine
modified_base          11
                       mod_base = OTHER
                       note = 2'-O-methyl adenosine
modified_base          12
                       mod_base = OTHER
                       note = 2'-O-methyl cytidine
modified_base          13
                       mod_base = OTHER
                       note = 2'-O-methyl adenosine phosphorothioate
modified_base          14
                       mod_base = OTHER
                       note = 2'-fluoro cytidine phosphorothioate
modified_base          15
                       mod_base = OTHER
```

```
                        note = 2'-O-methyl uridine phosphorothioate
modified_base           16
                        mod_base = OTHER
                        note = 2'-fluoro uridine phosphorothioate
modified_base           17
                        mod_base = OTHER
                        note = 2'-O-methyl uridine phosphorothioate
modified_base           18
                        mod_base = OTHER
                        note = 2'-O-methyl uridine phosphorothioate
modified_base           19
                        mod_base = OTHER
                        note = 2'-O-methyl adenosine phosphorothioate
modified_base           20
                        mod_base = OTHER
                        note = 2'-fluoro adenosine
SEQUENCE: 141
tcacacaatt acacttttaa                                                20

SEQ ID NO: 142          moltype = RNA  length = 20
FEATURE                 Location/Qualifiers
source                  1..20
                        mol_type = other RNA
                        organism = synthetic construct
modified_base           1
                        mod_base = OTHER
                        note = 5'-phosphate-2'-O-methyl uridine phosphorothioate
modified_base           2
                        mod_base = OTHER
                        note = 2'-fluoro adenosine phosphorothioate
modified_base           3
                        mod_base = OTHER
                        note = 2'-O-methyl adenosine
modified_base           4
                        mod_base = OTHER
                        note = 2'-O-methyl uridine
modified_base           5
                        mod_base = OTHER
                        note = 2'-O-methyl cytidine
modified_base           6
                        mod_base = OTHER
                        note = 2'-fluoro adenosine
modified_base           7
                        mod_base = OTHER
                        note = 2'-O-methyl guanosine
modified_base           8
                        mod_base = OTHER
                        note = 2'-O-methyl uridine
modified_base           9
                        mod_base = OTHER
                        note = 2'-O-methyl uridine
modified_base           10
                        mod_base = OTHER
                        note = 2'-O-methyl uridine
modified_base           11
                        mod_base = OTHER
                        note = 2'-O-methyl cytidine
modified_base           12
                        mod_base = OTHER
                        note = 2'-O-methyl uridine
modified_base           13
                        mod_base = OTHER
                        note = 2'-O-methyl cytidine phosphorothioate
modified_base           14
                        mod_base = OTHER
                        note = 2'-fluoro adenosine phosphorothioate
modified_base           15
                        mod_base = OTHER
                        note = 2'-O-methyl cytidine phosphorothioate
modified_base           16
                        mod_base = OTHER
                        note = 2'-fluoro uridine phosphorothioate
modified_base           17
                        mod_base = OTHER
                        note = 2'-O-methyl adenosine phosphorothioate
modified_base           18
                        mod_base = OTHER
                        note = 2'-O-methyl cytidine phosphorothioate
modified_base           19
```

```
                        mod_base = OTHER
                        note = 2'-O-methyl adenosine phosphorothioate
modified_base           20
                        mod_base = OTHER
                        note = 2'-fluoro guanosine
SEQUENCE: 142
taatcagttt ctcactacag                                             20

SEQ ID NO: 143          moltype = RNA  length = 20
FEATURE                 Location/Qualifiers
source                  1..20
                        mol_type = other RNA
                        organism = synthetic construct
modified_base           1
                        mod_base = OTHER
                        note = 5'-phosphate-2'-O-methyl uridine phosphorothioate
modified_base           2
                        mod_base = OTHER
                        note = 2'-fluoro adenosine phosphorothioate
modified_base           3
                        mod_base = OTHER
                        note = 2'-O-methyl adenosine
modified_base           4
                        mod_base = OTHER
                        note = 2'-O-methyl adenosine
modified_base           5
                        mod_base = OTHER
                        note = 2'-O-methyl uridine
modified_base           6
                        mod_base = OTHER
                        note = 2'-fluoro cytidine
modified_base           7
                        mod_base = OTHER
                        note = 2'-O-methyl adenosine
modified_base           8
                        mod_base = OTHER
                        note = 2'-O-methyl guanosine
modified_base           9
                        mod_base = OTHER
                        note = 2'-O-methyl uridine
modified_base           10
                        mod_base = OTHER
                        note = 2'-O-methyl uridine
modified_base           11
                        mod_base = OTHER
                        note = 2'-O-methyl uridine
modified_base           12
                        mod_base = OTHER
                        note = 2'-O-methyl cytidine
modified_base           13
                        mod_base = OTHER
                        note = 2'-O-methyl uridine phosphorothioate
modified_base           14
                        mod_base = OTHER
                        note = 2'-fluoro cytidine phosphorothioate
modified_base           15
                        mod_base = OTHER
                        note = 2'-O-methyl adenosine phosphorothioate
modified_base           16
                        mod_base = OTHER
                        note = 2'-fluoro cytidine phosphorothioate
modified_base           17
                        mod_base = OTHER
                        note = 2'-O-methyl uridine phosphorothioate
modified_base           18
                        mod_base = OTHER
                        note = 2'-O-methyl adenosine phosphorothioate
modified_base           19
                        mod_base = OTHER
                        note = 2'-O-methyl cytidine phosphorothioate
modified_base           20
                        mod_base = OTHER
                        note = 2'-fluoro adenosine
SEQUENCE: 143
taaatcagtt tctcactaca                                             20

SEQ ID NO: 144          moltype = RNA  length = 20
FEATURE                 Location/Qualifiers
source                  1..20
```

-continued

| | |
|---|---|
| | mol_type = other RNA |
| | organism = synthetic construct |
| modified_base | 1 |
| | mod_base = OTHER |
| | note = 5'-phosphate-2'-O-methyl uridine phosphorothioate |
| modified_base | 2 |
| | mod_base = OTHER |
| | note = 2'-fluoro adenosine phosphorothioate |
| modified_base | 3 |
| | mod_base = OTHER |
| | note = 2'-O-methyl adenosine |
| modified_base | 4 |
| | mod_base = OTHER |
| | note = 2'-O-methyl adenosine |
| modified_base | 5 |
| | mod_base = OTHER |
| | note = 2'-O-methyl uridine |
| modified_base | 6 |
| | mod_base = OTHER |
| | note = 2'-fluoro cytidine |
| modified_base | 7 |
| | mod_base = OTHER |
| | note = 2'-O-methyl uridine |
| modified_base | 8 |
| | mod_base = OTHER |
| | note = 2'-O-methyl uridine |
| modified_base | 9 |
| | mod_base = OTHER |
| | note = 2'-O-methyl cytidine |
| modified_base | 10 |
| | mod_base = OTHER |
| | note = 2'-O-methyl cytidine |
| modified_base | 11 |
| | mod_base = OTHER |
| | note = 2'-O-methyl adenosine |
| modified_base | 12 |
| | mod_base = OTHER |
| | note = 2'-O-methyl adenosine |
| modified_base | 13 |
| | mod_base = OTHER |
| | note = 2'-O-methyl guanosine phosphorothioate |
| modified_base | 14 |
| | mod_base = OTHER |
| | note = 2'-fluoro uridine phosphorothioate |
| modified_base | 15 |
| | mod_base = OTHER |
| | note = 2'-O-methyl guanosine phosphorothioate |
| modified_base | 16 |
| | mod_base = OTHER |
| | note = 2'-fluoro adenosine phosphorothioate |
| modified_base | 17 |
| | mod_base = OTHER |
| | note = 2'-O-methyl uridine phosphorothioate |
| modified_base | 18 |
| | mod_base = OTHER |
| | note = 2'-O-methyl cytidine phosphorothioate |
| modified_base | 19 |
| | mod_base = OTHER |
| | note = 2'-O-methyl adenosine phosphorothioate |
| modified_base | 20 |
| | mod_base = OTHER |
| | note = 2'-fluoro uridine |

SEQUENCE: 144
taaatcttcc aagtgatcat 20

| | |
|---|---|
| SEQ ID NO: 145 | moltype = RNA length = 20 |
| FEATURE | Location/Qualifiers |
| source | 1..20 |
| | mol_type = other RNA |
| | organism = synthetic construct |
| modified_base | 1 |
| | mod_base = OTHER |
| | note = 5'-phosphate-2'-O-methyl uridine phosphorothioate |
| modified_base | 2 |
| | mod_base = OTHER |
| | note = 2'-fluoro adenosine phosphorothioate |
| modified_base | 3 |
| | mod_base = OTHER |
| | note = 2'-O-methyl adenosine |

-continued

```
modified_base          4
                       mod_base = OTHER
                       note = 2'-O-methyl adenosine
modified_base          5
                       mod_base = OTHER
                       note = 2'-O-methyl cytidine
modified_base          6
                       mod_base = OTHER
                       note = 2'-fluoro uridine
modified_base          7
                       mod_base = OTHER
                       note = 2'-O-methyl adenosine
modified_base          8
                       mod_base = OTHER
                       note = 2'-O-methyl uridine
modified_base          9
                       mod_base = OTHER
                       note = 2'-O-methyl adenosine
modified_base          10
                       mod_base = OTHER
                       note = 2'-O-methyl cytidine
modified_base          11
                       mod_base = OTHER
                       note = 2'-O-methyl adenosine
modified_base          12
                       mod_base = OTHER
                       note = 2'-O-methyl adenosine
modified_base          13
                       mod_base = OTHER
                       note = 2'-O-methyl adenosine phosphorothioate
modified_base          14
                       mod_base = OTHER
                       note = 2'-fluoro uridine phosphorothioate
modified_base          15
                       mod_base = OTHER
                       note = 2'-O-methyl cytidine phosphorothioate
modified_base          16
                       mod_base = OTHER
                       note = 2'-fluoro uridine phosphorothioate
modified_base          17
                       mod_base = OTHER
                       note = 2'-O-methyl uridine phosphorothioate
modified_base          18
                       mod_base = OTHER
                       note = 2'-O-methyl cytidine phosphorothioate
modified_base          19
                       mod_base = OTHER
                       note = 2'-O-methyl cytidine phosphorothioate
modified_base          20
                       mod_base = OTHER
                       note = 2'-fluoro adenosine
SEQUENCE: 145
taaactatac aaatcttcca                                                    20

SEQ ID NO: 146         moltype = RNA  length = 20
FEATURE                Location/Qualifiers
source                 1..20
                       mol_type = other RNA
                       organism = synthetic construct
modified_base          1
                       mod_base = OTHER
                       note = 5'-phosphate-2'-O-methyl uridine phosphorothioate
modified_base          2
                       mod_base = OTHER
                       note = 2'-fluoro adenosine phosphorothioate
modified_base          3
                       mod_base = OTHER
                       note = 2'-O-methyl adenosine
modified_base          4
                       mod_base = OTHER
                       note = 2'-O-methyl cytidine
modified_base          5
                       mod_base = OTHER
                       note = 2'-O-methyl uridine
modified_base          6
                       mod_base = OTHER
                       note = 2'-fluoro guanosine
modified_base          7
                       mod_base = OTHER
```

```
                        note = 2'-O-methyl adenosine
modified_base           8
                        mod_base = OTHER
                        note = 2'-O-methyl guanosine
modified_base           9
                        mod_base = OTHER
                        note = 2'-O-methyl uridine
modified_base           10
                        mod_base = OTHER
                        note = 2'-O-methyl uridine
modified_base           11
                        mod_base = OTHER
                        note = 2'-O-methyl uridine
modified_base           12
                        mod_base = OTHER
                        note = 2'-O-methyl uridine
modified_base           13
                        mod_base = OTHER
                        note = 2'-O-methyl adenosine phosphorothioate
modified_base           14
                        mod_base = OTHER
                        note = 2'-fluoro uridine phosphorothioate
modified_base           15
                        mod_base = OTHER
                        note = 2'-O-methyl adenosine phosphorothioate
modified_base           16
                        mod_base = OTHER
                        note = 2'-fluoro adenosine phosphorothioate
modified_base           17
                        mod_base = OTHER
                        note = 2'-O-methyl adenosine phosphorothioate
modified_base           18
                        mod_base = OTHER
                        note = 2'-O-methyl adenosine phosphorothioate
modified_base           19
                        mod_base = OTHER
                        note = 2'-O-methyl cytidine phosphorothioate
modified_base           20
                        mod_base = OTHER
                        note = 2'-fluoro uridine
SEQUENCE: 146
taactgagtt ttataaaact                                          20

SEQ ID NO: 147          moltype = RNA  length = 20
FEATURE                 Location/Qualifiers
source                  1..20
                        mol_type = other RNA
                        organism = synthetic construct
modified_base           1
                        mod_base = OTHER
                        note = 5'-phosphate-2'-O-methyl uridine phosphorothioate
modified_base           2
                        mod_base = OTHER
                        note = 2'-fluoro adenosine phosphorothioate
modified_base           3
                        mod_base = OTHER
                        note = 2'-O-methyl adenosine
modified_base           4
                        mod_base = OTHER
                        note = 2'-O-methyl adenosine
modified_base           5
                        mod_base = OTHER
                        note = 2'-O-methyl uridine
modified_base           6
                        mod_base = OTHER
                        note = 2'-fluoro adenosine
modified_base           7
                        mod_base = OTHER
                        note = 2'-O-methyl cytidine
modified_base           8
                        mod_base = OTHER
                        note = 2'-O-methyl adenosine
modified_base           9
                        mod_base = OTHER
                        note = 2'-O-methyl guanosine
modified_base           10
                        mod_base = OTHER
                        note = 2'-O-methyl guanosine
modified_base           11
```

```
                         mod_base = OTHER
                         note = 2'-O-methyl uridine
modified_base            12
                         mod_base = OTHER
                         note = 2'-O-methyl cytidine
modified_base            13
                         mod_base = OTHER
                         note = 2'-O-methyl adenosine phosphorothioate
modified_base            14
                         mod_base = OTHER
                         note = 2'-fluoro uridine phosphorothioate
modified_base            15
                         mod_base = OTHER
                         note = 2'-O-methyl uridine phosphorothioate
modified_base            16
                         mod_base = OTHER
                         note = 2'-fluoro guanosine phosphorothioate
modified_base            17
                         mod_base = OTHER
                         note = 2'-O-methyl adenosine phosphorothioate
modified_base            18
                         mod_base = OTHER
                         note = 2'-O-methyl adenosine phosphorothioate
modified_base            19
                         mod_base = OTHER
                         note = 2'-O-methyl adenosine phosphorothioate
modified_base            20
                         mod_base = OTHER
                         note = 2'-fluoro cytidine
SEQUENCE: 147
taaatacagg tcattgaaac                                        20

SEQ ID NO: 148           moltype = RNA  length = 20
FEATURE                  Location/Qualifiers
source                   1..20
                         mol_type = other RNA
                         organism = synthetic construct
modified_base            1
                         mod_base = OTHER
                         note = 5'-phosphate-2'-O-methyl uridine phosphorothioate
modified_base            2
                         mod_base = OTHER
                         note = 2'-fluoro guanosine phosphorothioate
modified_base            3
                         mod_base = OTHER
                         note = 2'-O-methyl uridine
modified_base            4
                         mod_base = OTHER
                         note = 2'-O-methyl guanosine
modified_base            5
                         mod_base = OTHER
                         note = 2'-O-methyl adenosine
modified_base            6
                         mod_base = OTHER
                         note = 2'-fluoro uridine
modified_base            7
                         mod_base = OTHER
                         note = 2'-O-methyl uridine
modified_base            8
                         mod_base = OTHER
                         note = 2'-O-methyl uridine
modified_base            9
                         mod_base = OTHER
                         note = 2'-O-methyl adenosine
modified_base            10
                         mod_base = OTHER
                         note = 2'-O-methyl adenosine
modified_base            11
                         mod_base = OTHER
                         note = 2'-O-methyl guanosine
modified_base            12
                         mod_base = OTHER
                         note = 2'-O-methyl uridine
modified_base            13
                         mod_base = OTHER
                         note = 2'-O-methyl cytidine phosphorothioate
modified_base            14
                         mod_base = OTHER
                         note = 2'-fluoro uridine phosphorothioate
```

```
modified_base          15
                       mod_base = OTHER
                       note = 2'-O-methyl guanosine phosphorothioate
modified_base          16
                       mod_base = OTHER
                       note = 2'-fluoro guanosine phosphorothioate
modified_base          17
                       mod_base = OTHER
                       note = 2'-O-methyl cytidine phosphorothioate
modified_base          18
                       mod_base = OTHER
                       note = 2'-O-methyl adenosine phosphorothioate
modified_base          19
                       mod_base = OTHER
                       note = 2'-O-methyl adenosine phosphorothioate
modified_base          20
                       mod_base = OTHER
                       note = 2'-fluoro adenosine
SEQUENCE: 148
tgtgatttaa gtctggcaaa                                          20

SEQ ID NO: 149         moltype = RNA  length = 20
FEATURE                Location/Qualifiers
source                 1..20
                       mol_type = other RNA
                       organism = synthetic construct
modified_base          1
                       mod_base = OTHER
                       note = 5'-phosphate-2'-O-methyl uridine phosphorothioate
modified_base          2
                       mod_base = OTHER
                       note = 2'-fluoro uridine phosphorothioate
modified_base          3
                       mod_base = OTHER
                       note = 2'-O-methyl guanosine
modified_base          4
                       mod_base = OTHER
                       note = 2'-O-methyl adenosine
modified_base          5
                       mod_base = OTHER
                       note = 2'-O-methyl cytidine
modified_base          6
                       mod_base = OTHER
                       note = 2'-fluoro adenosine
modified_base          7
                       mod_base = OTHER
                       note = 2'-O-methyl adenosine
modified_base          8
                       mod_base = OTHER
                       note = 2'-O-methyl guanosine
modified_base          9
                       mod_base = OTHER
                       note = 2'-O-methyl uridine
modified_base          10
                       mod_base = OTHER
                       note = 2'-O-methyl uridine
modified_base          11
                       mod_base = OTHER
                       note = 2'-O-methyl uridine
modified_base          12
                       mod_base = OTHER
                       note = 2'-O-methyl adenosine
modified_base          13
                       mod_base = OTHER
                       note = 2'-O-methyl adenosine phosphorothioate
modified_base          14
                       mod_base = OTHER
                       note = 2'-fluoro uridine phosphorothioate
modified_base          15
                       mod_base = OTHER
                       note = 2'-O-methyl adenosine phosphorothioate
modified_base          16
                       mod_base = OTHER
                       note = 2'-fluoro cytidine phosphorothioate
modified_base          17
                       mod_base = OTHER
                       note = 2'-O-methyl cytidine phosphorothioate
modified_base          18
                       mod_base = OTHER
```

```
                        note = 2'-O-methyl cytidine phosphorothioate
modified_base           19
                        mod_base = OTHER
                        note = 2'-O-methyl adenosine phosphorothioate
modified_base           20
                        mod_base = OTHER
                        note = 2'-fluoro uridine
SEQUENCE: 149
ttgacaagtt taatacccat                                              20

SEQ ID NO: 150          moltype = RNA  length = 20
FEATURE                 Location/Qualifiers
source                  1..20
                        mol_type = other RNA
                        organism = synthetic construct
modified_base           1
                        mod_base = OTHER
                        note = 5'-phosphate-2'-O-methyl uridine phosphorothioate
modified_base           2
                        mod_base = OTHER
                        note = 2'-fluoro guanosine phosphorothioate
modified_base           3
                        mod_base = OTHER
                        note = 2'-O-methyl adenosine
modified_base           4
                        mod_base = OTHER
                        note = 2'-O-methyl adenosine
modified_base           5
                        mod_base = OTHER
                        note = 2'-O-methyl adenosine
modified_base           6
                        mod_base = OTHER
                        note = 2'-fluoro uridine
modified_base           7
                        mod_base = OTHER
                        note = 2'-O-methyl uridine
modified_base           8
                        mod_base = OTHER
                        note = 2'-O-methyl cytidine
modified_base           9
                        mod_base = OTHER
                        note = 2'-O-methyl uridine
modified_base           10
                        mod_base = OTHER
                        note = 2'-O-methyl guanosine
modified_base           11
                        mod_base = OTHER
                        note = 2'-O-methyl adenosine
modified_base           12
                        mod_base = OTHER
                        note = 2'-O-methyl cytidine
modified_base           13
                        mod_base = OTHER
                        note = 2'-O-methyl adenosine phosphorothioate
modified_base           14
                        mod_base = OTHER
                        note = 2'-fluoro adenosine phosphorothioate
modified_base           15
                        mod_base = OTHER
                        note = 2'-O-methyl guanosine phosphorothioate
modified_base           16
                        mod_base = OTHER
                        note = 2'-fluoro uridine phosphorothioate
modified_base           17
                        mod_base = OTHER
                        note = 2'-O-methyl uridine phosphorothioate
modified_base           18
                        mod_base = OTHER
                        note = 2'-O-methyl uridine phosphorothioate
modified_base           19
                        mod_base = OTHER
                        note = 2'-O-methyl adenosine phosphorothioate
modified_base           20
                        mod_base = OTHER
                        note = 2'-fluoro adenosine
SEQUENCE: 150
tgaaattctg acaagtttaa                                              20

SEQ ID NO: 151          moltype = RNA  length = 20
```

-continued

```
FEATURE                   Location/Qualifiers
source                    1..20
                          mol_type = other RNA
                          organism = synthetic construct
modified_base             1
                          mod_base = OTHER
                          note = 5'-phosphate-2'-O-methyl uridine phosphorothioate
modified_base             2
                          mod_base = OTHER
                          note = 2'-fluoro adenosine phosphorothioate
modified_base             3
                          mod_base = OTHER
                          note = 2'-O-methyl guanosine
modified_base             4
                          mod_base = OTHER
                          note = 2'-O-methyl guanosine
modified_base             5
                          mod_base = OTHER
                          note = 2'-O-methyl cytidine
modified_base             6
                          mod_base = OTHER
                          note = 2'-fluoro uridine
modified_base             7
                          mod_base = OTHER
                          note = 2'-O-methyl uridine
modified_base             8
                          mod_base = OTHER
                          note = 2'-O-methyl guanosine
modified_base             9
                          mod_base = OTHER
                          note = 2'-O-methyl adenosine
modified_base             10
                          mod_base = OTHER
                          note = 2'-O-methyl adenosine
modified_base             11
                          mod_base = OTHER
                          note = 2'-O-methyl uridine
modified_base             12
                          mod_base = OTHER
                          note = 2'-O-methyl guanosine
modified_base             13
                          mod_base = OTHER
                          note = 2'-O-methyl adenosine phosphorothioate
modified_base             14
                          mod_base = OTHER
                          note = 2'-fluoro cytidine phosphorothioate
modified_base             15
                          mod_base = OTHER
                          note = 2'-O-methyl adenosine phosphorothioate
modified_base             16
                          mod_base = OTHER
                          note = 2'-fluoro adenosine phosphorothioate
modified_base             17
                          mod_base = OTHER
                          note = 2'-O-methyl adenosine phosphorothioate
modified_base             18
                          mod_base = OTHER
                          note = 2'-O-methyl guanosine phosphorothioate
modified_base             19
                          mod_base = OTHER
                          note = 2'-O-methyl adenosine phosphorothioate
modified_base             20
                          mod_base = OTHER
                          note = 2'-fluoro adenosine
SEQUENCE: 151
taggcttgaa tgacaaagaa                                              20

SEQ ID NO: 152            moltype = RNA  length = 20
FEATURE                   Location/Qualifiers
source                    1..20
                          mol_type = other RNA
                          organism = synthetic construct
modified_base             1
                          mod_base = OTHER
                          note = 5'-phosphate-2'-O-methyl uridine phosphorothioate
modified_base             2
                          mod_base = OTHER
                          note = 2'-fluoro cytidine phosphorothioate
modified_base             3
```

```
                        mod_base = OTHER
                        note = 2'-O-methyl cytidine
modified_base           4
                        mod_base = OTHER
                        note = 2'-O-methyl uridine
modified_base           5
                        mod_base = OTHER
                        note = 2'-O-methyl cytidine
modified_base           6
                        mod_base = OTHER
                        note = 2'-fluoro adenosine
modified_base           7
                        mod_base = OTHER
                        note = 2'-O-methyl uridine
modified_base           8
                        mod_base = OTHER
                        note = 2'-O-methyl adenosine
modified_base           9
                        mod_base = OTHER
                        note = 2'-O-methyl adenosine
modified_base           10
                        mod_base = OTHER
                        note = 2'-O-methyl uridine
modified_base           11
                        mod_base = OTHER
                        note = 2'-O-methyl adenosine
modified_base           12
                        mod_base = OTHER
                        note = 2'-O-methyl adenosine
modified_base           13
                        mod_base = OTHER
                        note = 2'-O-methyl guanosine phosphorothioate
modified_base           14
                        mod_base = OTHER
                        note = 2'-fluoro uridine phosphorothioate
modified_base           15
                        mod_base = OTHER
                        note = 2'-O-methyl guanosine phosphorothioate
modified_base           16
                        mod_base = OTHER
                        note = 2'-fluoro cytidine phosphorothioate
modified_base           17
                        mod_base = OTHER
                        note = 2'-O-methyl cytidine phosphorothioate
modified_base           18
                        mod_base = OTHER
                        note = 2'-O-methyl adenosine phosphorothioate
modified_base           19
                        mod_base = OTHER
                        note = 2'-O-methyl uridine phosphorothioate
modified_base           20
                        mod_base = OTHER
                        note = 2'-fluoro adenosine
SEQUENCE: 152
tcctcataat aagtgccata                                              20

SEQ ID NO: 153          moltype = RNA  length = 15
FEATURE                 Location/Qualifiers
source                  1..15
                        mol_type = other RNA
                        organism = synthetic construct
modified_base           1
                        mod_base = OTHER
                        note = 2'-O-methyl cytidine phosphorothioate
modified_base           2
                        mod_base = OTHER
                        note = 2'-O-methyl adenosine phosphorothioate
modified_base           3
                        mod_base = OTHER
                        note = 2'-O-methyl uridine
modified_base           4
                        mod_base = OTHER
                        note = 2'-O-methyl cytidine
modified_base           5
                        mod_base = OTHER
                        note = 2'-fluoro adenosine
modified_base           6
                        mod_base = OTHER
                        note = 2'-fluoro uridine
```

```
modified_base          7
                       mod_base = OTHER
                       note = 2'-fluoro cytidine
modified_base          8
                       mod_base = OTHER
                       note = 2'-O-methyl adenosine
modified_base          9
                       mod_base = OTHER
                       note = 2'-fluoro adenosine
modified_base          10
                       mod_base = OTHER
                       note = 2'-O-methyl uridine
modified_base          11
                       mod_base = OTHER
                       note = 2'-O-methyl uridine
modified_base          12
                       mod_base = OTHER
                       note = 2'-O-methyl uridine
modified_base          13
                       mod_base = OTHER
                       note = 2'-O-methyl cytidine phosphorothioate
modified_base          14
                       mod_base = OTHER
                       note = 2'-O-methyl guanosine phosphorothioate
modified_base          15
                       mod_base = OTHER
                       note = 2'-O-methyl adenosine 3'-cholesterol-triethylene
                        glycol
SEQUENCE: 153
catcatcaat ttcga                                                    15

SEQ ID NO: 154         moltype = RNA  length = 15
FEATURE                Location/Qualifiers
source                 1..15
                       mol_type = other RNA
                       organism = synthetic construct
modified_base          1
                       mod_base = OTHER
                       note = 2'-O-methyl cytidine phosphorothioate
modified_base          2
                       mod_base = OTHER
                       note = 2'-O-methyl adenosine phosphorothioate
modified_base          3
                       mod_base = OTHER
                       note = 2'-O-methyl guanosine
modified_base          4
                       mod_base = OTHER
                       note = 2'-O-methyl uridine
modified_base          5
                       mod_base = OTHER
                       note = 2'-fluoro guanosine
modified_base          6
                       mod_base = OTHER
                       note = 2'-fluoro cytidine
modified_base          7
                       mod_base = OTHER
                       note = 2'-fluoro adenosine
modified_base          8
                       mod_base = OTHER
                       note = 2'-O-methyl guanosine
modified_base          9
                       mod_base = OTHER
                       note = 2'-fluoro guanosine
modified_base          10
                       mod_base = OTHER
                       note = 2'-O-methyl uridine
modified_base          11
                       mod_base = OTHER
                       note = 2'-O-methyl cytidine
modified_base          12
                       mod_base = OTHER
                       note = 2'-O-methyl cytidine
modified_base          13
                       mod_base = OTHER
                       note = 2'-O-methyl uridine phosphorothioate
modified_base          14
                       mod_base = OTHER
                       note = 2'-O-methyl cytidine phosphorothioate
modified_base          15
```

```
                        mod_base = OTHER
                        note = 2'-O-methyl adenosine 3'-cholesterol-triethylene
                         glycol
SEQUENCE: 154
cagtgcaggt cctca                                                   15

SEQ ID NO: 155          moltype = RNA  length = 15
FEATURE                 Location/Qualifiers
source                  1..15
                        mol_type = other RNA
                        organism = synthetic construct
modified_base           1
                        mod_base = OTHER
                        note = 2'-O-methyl adenosine phosphorothioate
modified_base           2
                        mod_base = OTHER
                        note = 2'-O-methyl cytidine phosphorothioate
modified_base           3
                        mod_base = OTHER
                        note = 2'-O-methyl uridine
modified_base           4
                        mod_base = OTHER
                        note = 2'-O-methyl uridine
modified_base           5
                        mod_base = OTHER
                        note = 2'-fluoro uridine
modified_base           6
                        mod_base = OTHER
                        note = 2'-fluoro adenosine
modified_base           7
                        mod_base = OTHER
                        note = 2'-fluoro adenosine
modified_base           8
                        mod_base = OTHER
                        note = 2'-O-methyl uridine
modified_base           9
                        mod_base = OTHER
                        note = 2'-fluoro cytidine
modified_base           10
                        mod_base = OTHER
                        note = 2'-O-methyl cytidine
modified_base           11
                        mod_base = OTHER
                        note = 2'-O-methyl uridine
modified_base           12
                        mod_base = OTHER
                        note = 2'-O-methyl cytidine
modified_base           13
                        mod_base = OTHER
                        note = 2'-O-methyl uridine phosphorothioate
modified_base           14
                        mod_base = OTHER
                        note = 2'-O-methyl adenosine phosphorothioate
modified_base           15
                        mod_base = OTHER
                        note = 2'-O-methyl adenosine 3'-cholesterol-triethylene
                         glycol
SEQUENCE: 155
actttaatcc tctaa                                                   15

SEQ ID NO: 156          moltype = RNA  length = 15
FEATURE                 Location/Qualifiers
source                  1..15
                        mol_type = other RNA
                        organism = synthetic construct
modified_base           1
                        mod_base = OTHER
                        note = 2'-O-methyl cytidine phosphorothioate
modified_base           2
                        mod_base = OTHER
                        note = 2'-O-methyl adenosine phosphorothioate
modified_base           3
                        mod_base = OTHER
                        note = 2'-O-methyl adenosine
modified_base           4
                        mod_base = OTHER
                        note = 2'-O-methyl adenosine
modified_base           5
                        mod_base = OTHER
```

```
                        note = 2'-fluoro guanosine
modified_base           6
                        mod_base = OTHER
                        note = 2'-fluoro adenosine
modified_base           7
                        mod_base = OTHER
                        note = 2'-fluoro uridine
modified_base           8
                        mod_base = OTHER
                        note = 2'-O-methyl guanosine
modified_base           9
                        mod_base = OTHER
                        note = 2'-fluoro guanosine
modified_base           10
                        mod_base = OTHER
                        note = 2'-O-methyl uridine
modified_base           11
                        mod_base = OTHER
                        note = 2'-O-methyl guanosine
modified_base           12
                        mod_base = OTHER
                        note = 2'-O-methyl uridine
modified_base           13
                        mod_base = OTHER
                        note = 2'-O-methyl guanosine phosphorothioate
modified_base           14
                        mod_base = OTHER
                        note = 2'-O-methyl guanosine phosphorothioate
modified_base           15
                        mod_base = OTHER
                        note = 2'-O-methyl adenosine 3'-cholesterol-triethylene
                         glycol
SEQUENCE: 156
caaagatggt gtgga                                                   15

SEQ ID NO: 157          moltype = RNA  length = 15
FEATURE                 Location/Qualifiers
source                  1..15
                        mol_type = other RNA
                        organism = synthetic construct
modified_base           1
                        mod_base = OTHER
                        note = 2'-O-methyl cytidine phosphorothioate
modified_base           2
                        mod_base = OTHER
                        note = 2'-O-methyl uridine phosphorothioate
modified_base           3
                        mod_base = OTHER
                        note = 2'-O-methyl adenosine
modified_base           4
                        mod_base = OTHER
                        note = 2'-O-methyl uridine
modified_base           5
                        mod_base = OTHER
                        note = 2'-fluoro uridine
modified_base           6
                        mod_base = OTHER
                        note = 2'-fluoro guanosine
modified_base           7
                        mod_base = OTHER
                        note = 2'-fluoro adenosine
modified_base           8
                        mod_base = OTHER
                        note = 2'-O-methyl adenosine
modified_base           9
                        mod_base = OTHER
                        note = 2'-fluoro guanosine
modified_base           10
                        mod_base = OTHER
                        note = 2'-O-methyl adenosine
modified_base           11
                        mod_base = OTHER
                        note = 2'-O-methyl uridine
modified_base           12
                        mod_base = OTHER
                        note = 2'-O-methyl uridine
modified_base           13
                        mod_base = OTHER
                        note = 2'-O-methyl cytidine phosphorothioate
```

```
modified_base          14
                       mod_base = OTHER
                       note = 2'-O-methyl uridine phosphorothioate
modified_base          15
                       mod_base = OTHER
                       note = 2'-O-methyl adenosine 3'-cholesterol-triethylene
                        glycol
SEQUENCE: 157
ctattgaaga ttcta                                                         15

SEQ ID NO: 158         moltype = RNA  length = 15
FEATURE                Location/Qualifiers
source                 1..15
                       mol_type = other RNA
                       organism = synthetic construct
modified_base          1
                       mod_base = OTHER
                       note = 2'-O-methyl guanosine phosphorothioate
modified_base          2
                       mod_base = OTHER
                       note = 2'-O-methyl adenosine phosphorothioate
modified_base          3
                       mod_base = OTHER
                       note = 2'-O-methyl uridine
modified_base          4
                       mod_base = OTHER
                       note = 2'-O-methyl cytidine
modified_base          5
                       mod_base = OTHER
                       note = 2'-fluoro uridine
modified_base          6
                       mod_base = OTHER
                       note = 2'-fluoro cytidine
modified_base          7
                       mod_base = OTHER
                       note = 2'-fluoro adenosine
modified_base          8
                       mod_base = OTHER
                       note = 2'-O-methyl cytidine
modified_base          9
                       mod_base = OTHER
                       note = 2'-fluoro uridine
modified_base          10
                       mod_base = OTHER
                       note = 2'-O-methyl cytidine
modified_base          11
                       mod_base = OTHER
                       note = 2'-O-methyl uridine
modified_base          12
                       mod_base = OTHER
                       note = 2'-O-methyl cytidine
modified_base          13
                       mod_base = OTHER
                       note = 2'-O-methyl adenosine phosphorothioate
modified_base          14
                       mod_base = OTHER
                       note = 2'-O-methyl guanosine phosphorothioate
modified_base          15
                       mod_base = OTHER
                       note = 2'-O-methyl adenosine 3'-cholesterol-triethylene
                        glycol
SEQUENCE: 158
gatctcactc tcaga                                                         15

SEQ ID NO: 159         moltype = RNA  length = 15
FEATURE                Location/Qualifiers
source                 1..15
                       mol_type = other RNA
                       organism = synthetic construct
modified_base          1
                       mod_base = OTHER
                       note = 2'-O-methyl adenosine phosphorothioate
modified_base          2
                       mod_base = OTHER
                       note = 2'-O-methyl adenosine phosphorothioate
modified_base          3
                       mod_base = OTHER
                       note = 2'-O-methyl adenosine
modified_base          4
```

-continued

```
                        mod_base = OTHER
                        note = 2'-O-methyl guanosine
modified_base           5
                        mod_base = OTHER
                        note = 2'-fluoro guanosine
modified_base           6
                        mod_base = OTHER
                        note = 2'-fluoro uridine
modified_base           7
                        mod_base = OTHER
                        note = 2'-fluoro guanosine
modified_base           8
                        mod_base = OTHER
                        note = 2'-O-methyl guanosine
modified_base           9
                        mod_base = OTHER
                        note = 2'-fluoro adenosine
modified_base           10
                        mod_base = OTHER
                        note = 2'-O-methyl adenosine
modified_base           11
                        mod_base = OTHER
                        note = 2'-O-methyl adenosine
modified_base           12
                        mod_base = OTHER
                        note = 2'-O-methyl uridine
modified_base           13
                        mod_base = OTHER
                        note = 2'-O-methyl guanosine phosphorothioate
modified_base           14
                        mod_base = OTHER
                        note = 2'-O-methyl adenosine phosphorothioate
modified_base           15
                        mod_base = OTHER
                        note = 2'-O-methyl adenosine 3'-cholesterol-triethylene
                         glycol
SEQUENCE: 159
aaaggtggaa atgaa                                                   15

SEQ ID NO: 160          moltype = RNA  length = 15
FEATURE                 Location/Qualifiers
source                  1..15
                        mol_type = other RNA
                        organism = synthetic construct
modified_base           1
                        mod_base = OTHER
                        note = 2'-O-methyl uridine phosphorothioate
modified_base           2
                        mod_base = OTHER
                        note = 2'-O-methyl guanosine phosphorothioate
modified_base           3
                        mod_base = OTHER
                        note = 2'-O-methyl uridine
modified_base           4
                        mod_base = OTHER
                        note = 2'-O-methyl adenosine
modified_base           5
                        mod_base = OTHER
                        note = 2'-fluoro adenosine
modified_base           6
                        mod_base = OTHER
                        note = 2'-fluoro uridine
modified_base           7
                        mod_base = OTHER
                        note = 2'-fluoro uridine
modified_base           8
                        mod_base = OTHER
                        note = 2'-O-methyl guanosine
modified_base           9
                        mod_base = OTHER
                        note = 2'-fluoro guanosine
modified_base           10
                        mod_base = OTHER
                        note = 2'-O-methyl guanosine
modified_base           11
                        mod_base = OTHER
                        note = 2'-O-methyl adenosine
modified_base           12
                        mod_base = OTHER
```

```
                        note = 2'-O-methyl uridine
modified_base           13
                        mod_base = OTHER
                        note = 2'-O-methyl cytidine phosphorothioate
modified_base           14
                        mod_base = OTHER
                        note = 2'-O-methyl guanosine phosphorothioate
modified_base           15
                        mod_base = OTHER
                        note = 2'-O-methyl adenosine 3'-cholesterol-triethylene
                         glycol
SEQUENCE: 160
tgtaattggg atcga                                                     15

SEQ ID NO: 161          moltype = RNA  length = 15
FEATURE                 Location/Qualifiers
source                  1..15
                        mol_type = other RNA
                        organism = synthetic construct
modified_base           1
                        mod_base = OTHER
                        note = 2'-O-methyl cytidine phosphorothioate
modified_base           2
                        mod_base = OTHER
                        note = 2'-O-methyl adenosine phosphorothioate
modified_base           3
                        mod_base = OTHER
                        note = 2'-O-methyl uridine
modified_base           4
                        mod_base = OTHER
                        note = 2'-O-methyl cytidine
modified_base           5
                        mod_base = OTHER
                        note = 2'-fluoro uridine
modified_base           6
                        mod_base = OTHER
                        note = 2'-fluoro guanosine
modified_base           7
                        mod_base = OTHER
                        note = 2'-fluoro uridine
modified_base           8
                        mod_base = OTHER
                        note = 2'-O-methyl uridine
modified_base           9
                        mod_base = OTHER
                        note = 2'-fluoro adenosine
modified_base           10
                        mod_base = OTHER
                        note = 2'-O-methyl uridine
modified_base           11
                        mod_base = OTHER
                        note = 2'-O-methyl cytidine
modified_base           12
                        mod_base = OTHER
                        note = 2'-O-methyl cytidine
modified_base           13
                        mod_base = OTHER
                        note = 2'-O-methyl uridine phosphorothioate
modified_base           14
                        mod_base = OTHER
                        note = 2'-O-methyl guanosine phosphorothioate
modified_base           15
                        mod_base = OTHER
                        note = 2'-O-methyl adenosine 3'-cholesterol-triethylene
                         glycol
SEQUENCE: 161
catctgttat cctga                                                     15

SEQ ID NO: 162          moltype = RNA  length = 15
FEATURE                 Location/Qualifiers
source                  1..15
                        mol_type = other RNA
                        organism = synthetic construct
modified_base           1
                        mod_base = OTHER
                        note = 2'-O-methyl uridine phosphorothioate
modified_base           2
                        mod_base = OTHER
                        note = 2'-O-methyl adenosine phosphorothioate
```

```
modified_base          3
                       mod_base = OTHER
                       note = 2'-O-methyl guanosine
modified_base          4
                       mod_base = OTHER
                       note = 2'-O-methyl adenosine
modified_base          5
                       mod_base = OTHER
                       note = 2'-fluoro adenosine
modified_base          6
                       mod_base = OTHER
                       note = 2'-fluoro adenosine
modified_base          7
                       mod_base = OTHER
                       note = 2'-fluoro uridine
modified_base          8
                       mod_base = OTHER
                       note = 2'-O-methyl guanosine
modified_base          9
                       mod_base = OTHER
                       note = 2'-fluoro uridine
modified_base          10
                       mod_base = OTHER
                       note = 2'-O-methyl adenosine
modified_base          11
                       mod_base = OTHER
                       note = 2'-O-methyl uridine
modified_base          12
                       mod_base = OTHER
                       note = 2'-O-methyl cytidine
modified_base          13
                       mod_base = OTHER
                       note = 2'-O-methyl cytidine phosphorothioate
modified_base          14
                       mod_base = OTHER
                       note = 2'-O-methyl uridine phosphorothioate
modified_base          15
                       mod_base = OTHER
                       note = 2'-O-methyl adenosine 3'-cholesterol-triethylene
                        glycol
SEQUENCE: 162
tagaaatgta tccta                                                   15

SEQ ID NO: 163         moltype = RNA  length = 15
FEATURE                Location/Qualifiers
source                 1..15
                       mol_type = other RNA
                       organism = synthetic construct
modified_base          1
                       mod_base = OTHER
                       note = 2'-O-methyl cytidine phosphorothioate
modified_base          2
                       mod_base = OTHER
                       note = 2'-O-methyl adenosine phosphorothioate
modified_base          3
                       mod_base = OTHER
                       note = 2'-O-methyl uridine
modified_base          4
                       mod_base = OTHER
                       note = 2'-O-methyl uridine
modified_base          5
                       mod_base = OTHER
                       note = 2'-fluoro adenosine
modified_base          6
                       mod_base = OTHER
                       note = 2'-fluoro adenosine
modified_base          7
                       mod_base = OTHER
                       note = 2'-fluoro adenosine
modified_base          8
                       mod_base = OTHER
                       note = 2'-O-methyl cytidine
modified_base          9
                       mod_base = OTHER
                       note = 2'-fluoro adenosine
modified_base          10
                       mod_base = OTHER
                       note = 2'-O-methyl cytidine
modified_base          11
```

-continued

```
                        mod_base = OTHER
                        note = 2'-O-methyl uridine
modified_base           12
                        mod_base = OTHER
                        note = 2'-O-methyl guanosine
modified_base           13
                        mod_base = OTHER
                        note = 2'-O-methyl uridine phosphorothioate
modified_base           14
                        mod_base = OTHER
                        note = 2'-O-methyl adenosine phosphorothioate
modified_base           15
                        mod_base = OTHER
                        note = 2'-O-methyl adenosine 3'-cholesterol-triethylene
                         glycol
SEQUENCE: 163
cattaaacac tgtaa                                                   15

SEQ ID NO: 164          moltype = RNA  length = 15
FEATURE                 Location/Qualifiers
source                  1..15
                        mol_type = other RNA
                        organism = synthetic construct
modified_base           1
                        mod_base = OTHER
                        note = 2'-O-methyl adenosine phosphorothioate
modified_base           2
                        mod_base = OTHER
                        note = 2'-O-methyl adenosine phosphorothioate
modified_base           3
                        mod_base = OTHER
                        note = 2'-O-methyl uridine
modified_base           4
                        mod_base = OTHER
                        note = 2'-O-methyl cytidine
modified_base           5
                        mod_base = OTHER
                        note = 2'-fluoro uridine
modified_base           6
                        mod_base = OTHER
                        note = 2'-fluoro uridine
modified_base           7
                        mod_base = OTHER
                        note = 2'-fluoro adenosine
modified_base           8
                        mod_base = OTHER
                        note = 2'-O-methyl adenosine
modified_base           9
                        mod_base = OTHER
                        note = 2'-fluoro adenosine
modified_base           10
                        mod_base = OTHER
                        note = 2'-O-methyl adenosine
modified_base           11
                        mod_base = OTHER
                        note = 2'-O-methyl guanosine
modified_base           12
                        mod_base = OTHER
                        note = 2'-O-methyl uridine
modified_base           13
                        mod_base = OTHER
                        note = 2'-O-methyl guanosine phosphorothioate
modified_base           14
                        mod_base = OTHER
                        note = 2'-O-methyl uridine phosphorothioate
modified_base           15
                        mod_base = OTHER
                        note = 2'-O-methyl adenosine 3'-cholesterol-triethylene
                         glycol
SEQUENCE: 164
aatcttaaaa gtgta                                                   15

SEQ ID NO: 165          moltype = RNA  length = 15
FEATURE                 Location/Qualifiers
source                  1..15
                        mol_type = other RNA
                        organism = synthetic construct
modified_base           1
                        mod_base = OTHER
```

```
                        note = 2'-O-methyl adenosine phosphorothioate
modified_base           2
                        mod_base = OTHER
                        note = 2'-O-methyl guanosine phosphorothioate
modified_base           3
                        mod_base = OTHER
                        note = 2'-O-methyl uridine
modified_base           4
                        mod_base = OTHER
                        note = 2'-O-methyl guanosine
modified_base           5
                        mod_base = OTHER
                        note = 2'-fluoro uridine
modified_base           6
                        mod_base = OTHER
                        note = 2'-fluoro adenosine
modified_base           7
                        mod_base = OTHER
                        note = 2'-fluoro adenosine
modified_base           8
                        mod_base = OTHER
                        note = 2'-O-methyl uridine
modified_base           9
                        mod_base = OTHER
                        note = 2'-fluoro uridine
modified_base           10
                        mod_base = OTHER
                        note = 2'-O-methyl guanosine
modified_base           11
                        mod_base = OTHER
                        note = 2'-O-methyl uridine
modified_base           12
                        mod_base = OTHER
                        note = 2'-O-methyl guanosine
modified_base           13
                        mod_base = OTHER
                        note = 2'-O-methyl uridine phosphorothioate
modified_base           14
                        mod_base = OTHER
                        note = 2'-O-methyl guanosine phosphorothioate
modified_base           15
                        mod_base = OTHER
                        note = 2'-O-methyl adenosine 3'-cholesterol-triethylene
                         glycol
SEQUENCE: 165
agtgtaattg tgtga                                                15

SEQ ID NO: 166          moltype = RNA  length = 15
FEATURE                 Location/Qualifiers
source                  1..15
                        mol_type = other RNA
                        organism = synthetic construct
modified_base           1
                        mod_base = OTHER
                        note = 2'-O-methyl guanosine phosphorothioate
modified_base           2
                        mod_base = OTHER
                        note = 2'-O-methyl uridine phosphorothioate
modified_base           3
                        mod_base = OTHER
                        note = 2'-O-methyl guanosine
modified_base           4
                        mod_base = OTHER
                        note = 2'-O-methyl adenosine
modified_base           5
                        mod_base = OTHER
                        note = 2'-fluoro guanosine
modified_base           6
                        mod_base = OTHER
                        note = 2'-fluoro adenosine
modified_base           7
                        mod_base = OTHER
                        note = 2'-fluoro adenosine
modified_base           8
                        mod_base = OTHER
                        note = 2'-O-methyl adenosine
modified_base           9
                        mod_base = OTHER
                        note = 2'-fluoro cytidine
```

-continued

```
modified_base          10
                       mod_base = OTHER
                       note = 2'-O-methyl uridine
modified_base          11
                       mod_base = OTHER
                       note = 2'-O-methyl guanosine
modified_base          12
                       mod_base = OTHER
                       note = 2'-O-methyl adenosine
modified_base          13
                       mod_base = OTHER
                       note = 2'-O-methyl uridine phosphorothioate
modified_base          14
                       mod_base = OTHER
                       note = 2'-O-methyl uridine phosphorothioate
modified_base          15
                       mod_base = OTHER
                       note = 2'-O-methyl adenosine 3'-cholesterol-triethylene
                        glycol
SEQUENCE: 166
gtgagaaact gatta                                                    15

SEQ ID NO: 167         moltype = RNA  length = 15
FEATURE                Location/Qualifiers
source                 1..15
                       mol_type = other RNA
                       organism = synthetic construct
modified_base          1
                       mod_base = OTHER
                       note = 2'-O-methyl uridine phosphorothioate
modified_base          2
                       mod_base = OTHER
                       note = 2'-O-methyl guanosine phosphorothioate
modified_base          3
                       mod_base = OTHER
                       note = 2'-O-methyl adenosine
modified_base          4
                       mod_base = OTHER
                       note = 2'-O-methyl guanosine
modified_base          5
                       mod_base = OTHER
                       note = 2'-fluoro adenosine
modified_base          6
                       mod_base = OTHER
                       note = 2'-fluoro adenosine
modified_base          7
                       mod_base = OTHER
                       note = 2'-fluoro adenosine
modified_base          8
                       mod_base = OTHER
                       note = 2'-O-methyl cytidine
modified_base          9
                       mod_base = OTHER
                       note = 2'-fluoro uridine
modified_base          10
                       mod_base = OTHER
                       note = 2'-O-methyl guanosine
modified_base          11
                       mod_base = OTHER
                       note = 2'-O-methyl adenosine
modified_base          12
                       mod_base = OTHER
                       note = 2'-O-methyl uridine
modified_base          13
                       mod_base = OTHER
                       note = 2'-O-methyl uridine phosphorothioate
modified_base          14
                       mod_base = OTHER
                       note = 2'-O-methyl uridine phosphorothioate
modified_base          15
                       mod_base = OTHER
                       note = 2'-O-methyl adenosine 3'-cholesterol-triethylene
                        glycol
SEQUENCE: 167
tgagaaactg attta                                                    15

SEQ ID NO: 168         moltype = RNA  length = 15
FEATURE                Location/Qualifiers
source                 1..15
```

-continued

```
                        mol_type = other RNA
                        organism = synthetic construct
modified_base           1
                        mod_base = OTHER
                        note = 2'-O-methyl cytidine phosphorothioate
modified_base           2
                        mod_base = OTHER
                        note = 2'-O-methyl adenosine phosphorothioate
modified_base           3
                        mod_base = OTHER
                        note = 2'-O-methyl cytidine
modified_base           4
                        mod_base = OTHER
                        note = 2'-O-methyl uridine
modified_base           5
                        mod_base = OTHER
                        note = 2'-fluoro uridine
modified_base           6
                        mod_base = OTHER
                        note = 2'-fluoro guanosine
modified_base           7
                        mod_base = OTHER
                        note = 2'-fluoro guanosine
modified_base           8
                        mod_base = OTHER
                        note = 2'-O-methyl adenosine
modified_base           9
                        mod_base = OTHER
                        note = 2'-fluoro adenosine
modified_base           10
                        mod_base = OTHER
                        note = 2'-O-methyl guanosine
modified_base           11
                        mod_base = OTHER
                        note = 2'-O-methyl adenosine
modified_base           12
                        mod_base = OTHER
                        note = 2'-O-methyl uridine
modified_base           13
                        mod_base = OTHER
                        note = 2'-O-methyl uridine phosphorothioate
modified_base           14
                        mod_base = OTHER
                        note = 2'-O-methyl uridine phosphorothioate
modified_base           15
                        mod_base = OTHER
                        note = 2'-O-methyl adenosine 3'-cholesterol-triethylene
                         glycol
SEQUENCE: 168
cacttggaag attta                                                   15

SEQ ID NO: 169          moltype = RNA  length = 15
FEATURE                 Location/Qualifiers
source                  1..15
                        mol_type = other RNA
                        organism = synthetic construct
modified_base           1
                        mod_base = OTHER
                        note = 2'-O-methyl guanosine phosphorothioate
modified_base           2
                        mod_base = OTHER
                        note = 2'-O-methyl adenosine phosphorothioate
modified_base           3
                        mod_base = OTHER
                        note = 2'-O-methyl uridine
modified_base           4
                        mod_base = OTHER
                        note = 2'-O-methyl uridine
modified_base           5
                        mod_base = OTHER
                        note = 2'-fluoro uridine
modified_base           6
                        mod_base = OTHER
                        note = 2'-fluoro guanosine
modified_base           7
                        mod_base = OTHER
                        note = 2'-fluoro uridine
modified_base           8
                        mod_base = OTHER
```

```
                        note = 2'-O-methyl adenosine
modified_base           9
                        mod_base = OTHER
                        note = 2'-fluoro uridine
modified_base           10
                        mod_base = OTHER
                        note = 2'-O-methyl adenosine
modified_base           11
                        mod_base = OTHER
                        note = 2'-O-methyl guanosine
modified_base           12
                        mod_base = OTHER
                        note = 2'-O-methyl uridine
modified_base           13
                        mod_base = OTHER
                        note = 2'-O-methyl uridine phosphorothioate
modified_base           14
                        mod_base = OTHER
                        note = 2'-O-methyl uridine phosphorothioate
modified_base           15
                        mod_base = OTHER
                        note = 2'-O-methyl adenosine 3'-cholesterol-triethylene
                         glycol
SEQUENCE: 169
gatttgtata gttta                                                  15

SEQ ID NO: 170          moltype = RNA  length = 15
FEATURE                 Location/Qualifiers
source                  1..15
                        mol_type = other RNA
                        organism = synthetic construct
modified_base           1
                        mod_base = OTHER
                        note = 2'-O-methyl uridine phosphorothioate
modified_base           2
                        mod_base = OTHER
                        note = 2'-O-methyl adenosine phosphorothioate
modified_base           3
                        mod_base = OTHER
                        note = 2'-O-methyl uridine
modified_base           4
                        mod_base = OTHER
                        note = 2'-O-methyl adenosine
modified_base           5
                        mod_base = OTHER
                        note = 2'-fluoro adenosine
modified_base           6
                        mod_base = OTHER
                        note = 2'-fluoro adenosine
modified_base           7
                        mod_base = OTHER
                        note = 2'-fluoro adenosine
modified_base           8
                        mod_base = OTHER
                        note = 2'-O-methyl cytidine
modified_base           9
                        mod_base = OTHER
                        note = 2'-fluoro uridine
modified_base           10
                        mod_base = OTHER
                        note = 2'-O-methyl cytidine
modified_base           11
                        mod_base = OTHER
                        note = 2'-O-methyl adenosine
modified_base           12
                        mod_base = OTHER
                        note = 2'-O-methyl guanosine
modified_base           13
                        mod_base = OTHER
                        note = 2'-O-methyl uridine phosphorothioate
modified_base           14
                        mod_base = OTHER
                        note = 2'-O-methyl uridine phosphorothioate
modified_base           15
                        mod_base = OTHER
                        note = 2'-O-methyl adenosine 3'-cholesterol-triethylene
                         glycol
SEQUENCE: 170
tataaaactc agtta                                                  15
```

```
SEQ ID NO: 171          moltype = RNA  length = 15
FEATURE                 Location/Qualifiers
source                  1..15
                        mol_type = other RNA
                        organism = synthetic construct
modified_base           1
                        mod_base = OTHER
                        note = 2'-O-methyl adenosine phosphorothioate
modified_base           2
                        mod_base = OTHER
                        note = 2'-O-methyl adenosine phosphorothioate
modified_base           3
                        mod_base = OTHER
                        note = 2'-O-methyl uridine
modified_base           4
                        mod_base = OTHER
                        note = 2'-O-methyl guanosine
modified_base           5
                        mod_base = OTHER
                        note = 2'-fluoro adenosine
modified_base           6
                        mod_base = OTHER
                        note = 2'-fluoro cytidine
modified_base           7
                        mod_base = OTHER
                        note = 2'-fluoro cytidine
modified_base           8
                        mod_base = OTHER
                        note = 2'-O-methyl uridine
modified_base           9
                        mod_base = OTHER
                        note = 2'-fluoro guanosine
modified_base           10
                        mod_base = OTHER
                        note = 2'-O-methyl uridine
modified_base           11
                        mod_base = OTHER
                        note = 2'-O-methyl adenosine
modified_base           12
                        mod_base = OTHER
                        note = 2'-O-methyl uridine
modified_base           13
                        mod_base = OTHER
                        note = 2'-O-methyl uridine phosphorothioate
modified_base           14
                        mod_base = OTHER
                        note = 2'-O-methyl uridine phosphorothioate
modified_base           15
                        mod_base = OTHER
                        note = 2'-O-methyl adenosine 3'-cholesterol-triethylene
                         glycol
SEQUENCE: 171
aatgacctgt attta                                                   15

SEQ ID NO: 172          moltype = RNA  length = 15
FEATURE                 Location/Qualifiers
source                  1..15
                        mol_type = other RNA
                        organism = synthetic construct
modified_base           1
                        mod_base = OTHER
                        note = 2'-O-methyl cytidine phosphorothioate
modified_base           2
                        mod_base = OTHER
                        note = 2'-O-methyl adenosine phosphorothioate
modified_base           3
                        mod_base = OTHER
                        note = 2'-O-methyl guanosine
modified_base           4
                        mod_base = OTHER
                        note = 2'-O-methyl adenosine
modified_base           5
                        mod_base = OTHER
                        note = 2'-fluoro cytidine
modified_base           6
                        mod_base = OTHER
                        note = 2'-fluoro uridine
modified_base           7
```

-continued

```
                        mod_base = OTHER
                        note = 2'-fluoro uridine
modified_base           8
                        mod_base = OTHER
                        note = 2'-O-methyl adenosine
modified_base           9
                        mod_base = OTHER
                        note = 2'-fluoro adenosine
modified_base           10
                        mod_base = OTHER
                        note = 2'-O-methyl adenosine
modified_base           11
                        mod_base = OTHER
                        note = 2'-O-methyl uridine
modified_base           12
                        mod_base = OTHER
                        note = 2'-O-methyl cytidine
modified_base           13
                        mod_base = OTHER
                        note = 2'-O-methyl adenosine phosphorothioate
modified_base           14
                        mod_base = OTHER
                        note = 2'-O-methyl cytidine phosphorothioate
modified_base           15
                        mod_base = OTHER
                        note = 2'-O-methyl adenosine 3'-cholesterol-triethylene
                         glycol
SEQUENCE: 172
cagacttaaa tcaca                                                            15

SEQ ID NO: 173          moltype = RNA  length = 15
FEATURE                 Location/Qualifiers
source                  1..15
                        mol_type = other RNA
                        organism = synthetic construct
modified_base           1
                        mod_base = OTHER
                        note = 2'-O-methyl uridine phosphorothioate
modified_base           2
                        mod_base = OTHER
                        note = 2'-O-methyl adenosine phosphorothioate
modified_base           3
                        mod_base = OTHER
                        note = 2'-O-methyl uridine
modified_base           4
                        mod_base = OTHER
                        note = 2'-O-methyl uridine
modified_base           5
                        mod_base = OTHER
                        note = 2'-fluoro adenosine
modified_base           6
                        mod_base = OTHER
                        note = 2'-fluoro adenosine
modified_base           7
                        mod_base = OTHER
                        note = 2'-fluoro adenosine
modified_base           8
                        mod_base = OTHER
                        note = 2'-O-methyl cytidine
modified_base           9
                        mod_base = OTHER
                        note = 2'-fluoro uridine
modified_base           10
                        mod_base = OTHER
                        note = 2'-O-methyl uridine
modified_base           11
                        mod_base = OTHER
                        note = 2'-O-methyl guanosine
modified_base           12
                        mod_base = OTHER
                        note = 2'-O-methyl uridine
modified_base           13
                        mod_base = OTHER
                        note = 2'-O-methyl cytidine phosphorothioate
modified_base           14
                        mod_base = OTHER
                        note = 2'-O-methyl adenosine phosphorothioate
modified_base           15
                        mod_base = OTHER
```

-continued

```
                        note = 2'-O-methyl adenosine 3'-cholesterol-triethylene
                         glycol
SEQUENCE: 173
tattaaactt gtcaa                                                   15

SEQ ID NO: 174          moltype = RNA  length = 15
FEATURE                 Location/Qualifiers
source                  1..15
                        mol_type = other RNA
                        organism = synthetic construct
modified_base           1
                        mod_base = OTHER
                        note = 2'-O-methyl cytidine phosphorothioate
modified_base           2
                        mod_base = OTHER
                        note = 2'-O-methyl uridine phosphorothioate
modified_base           3
                        mod_base = OTHER
                        note = 2'-O-methyl uridine
modified_base           4
                        mod_base = OTHER
                        note = 2'-O-methyl guanosine
modified_base           5
                        mod_base = OTHER
                        note = 2'-fluoro uridine
modified_base           6
                        mod_base = OTHER
                        note = 2'-fluoro cytidine
modified_base           7
                        mod_base = OTHER
                        note = 2'-fluoro adenosine
modified_base           8
                        mod_base = OTHER
                        note = 2'-O-methyl guanosine
modified_base           9
                        mod_base = OTHER
                        note = 2'-fluoro adenosine
modified_base           10
                        mod_base = OTHER
                        note = 2'-O-methyl adenosine
modified_base           11
                        mod_base = OTHER
                        note = 2'-O-methyl uridine
modified_base           12
                        mod_base = OTHER
                        note = 2'-O-methyl uridine
modified_base           13
                        mod_base = OTHER
                        note = 2'-O-methyl uridine phosphorothioate
modified_base           14
                        mod_base = OTHER
                        note = 2'-O-methyl cytidine phosphorothioate
modified_base           15
                        mod_base = OTHER
                        note = 2'-O-methyl adenosine 3'-cholesterol-triethylene
                         glycol
SEQUENCE: 174
cttgtcagaa tttca                                                   15

SEQ ID NO: 175          moltype = RNA  length = 15
FEATURE                 Location/Qualifiers
source                  1..15
                        mol_type = other RNA
                        organism = synthetic construct
modified_base           1
                        mod_base = OTHER
                        note = 2'-O-methyl uridine phosphorothioate
modified_base           2
                        mod_base = OTHER
                        note = 2'-O-methyl guanosine phosphorothioate
modified_base           3
                        mod_base = OTHER
                        note = 2'-O-methyl uridine
modified_base           4
                        mod_base = OTHER
                        note = 2'-O-methyl cytidine
modified_base           5
                        mod_base = OTHER
                        note = 2'-fluoro adenosine
```

-continued

```
modified_base          6
                       mod_base = OTHER
                       note = 2'-fluoro uridine
modified_base          7
                       mod_base = OTHER
                       note = 2'-fluoro uridine
modified_base          8
                       mod_base = OTHER
                       note = 2'-O-methyl cytidine
modified_base          9
                       mod_base = OTHER
                       note = 2'-fluoro adenosine
modified_base          10
                       mod_base = OTHER
                       note = 2'-O-methyl adenosine
modified_base          11
                       mod_base = OTHER
                       note = 2'-O-methyl guanosine
modified_base          12
                       mod_base = OTHER
                       note = 2'-O-methyl cytidine
modified_base          13
                       mod_base = OTHER
                       note = 2'-O-methyl cytidine phosphorothioate
modified_base          14
                       mod_base = OTHER
                       note = 2'-O-methyl uridine phosphorothioate
modified_base          15
                       mod_base = OTHER
                       note = 2'-O-methyl adenosine 3'-cholesterol-triethylene
                        glycol
SEQUENCE: 175
tgtcattcaa gccta                                                        15

SEQ ID NO: 176         moltype = RNA  length = 15
FEATURE                Location/Qualifiers
source                 1..15
                       mol_type = other RNA
                       organism = synthetic construct
modified_base          1
                       mod_base = OTHER
                       note = 2'-O-methyl cytidine phosphorothioate
modified_base          2
                       mod_base = OTHER
                       note = 2'-O-methyl adenosine phosphorothioate
modified_base          3
                       mod_base = OTHER
                       note = 2'-O-methyl cytidine
modified_base          4
                       mod_base = OTHER
                       note = 2'-O-methyl uridine
modified_base          5
                       mod_base = OTHER
                       note = 2'-fluoro uridine
modified_base          6
                       mod_base = OTHER
                       note = 2'-fluoro adenosine
modified_base          7
                       mod_base = OTHER
                       note = 2'-fluoro uridine
modified_base          8
                       mod_base = OTHER
                       note = 2'-O-methyl uridine
modified_base          9
                       mod_base = OTHER
                       note = 2'-fluoro adenosine
modified_base          10
                       mod_base = OTHER
                       note = 2'-O-methyl uridine
modified_base          11
                       mod_base = OTHER
                       note = 2'-O-methyl guanosine
modified_base          12
                       mod_base = OTHER
                       note = 2'-O-methyl adenosine
modified_base          13
                       mod_base = OTHER
                       note = 2'-O-methyl guanosine phosphorothioate
modified_base          14
```

-continued

```
                        mod_base = OTHER
                        note = 2'-O-methyl guanosine phosphorothioate
modified_base           15
                        mod_base = OTHER
                        note = 2'-O-methyl adenosine 3'-cholesterol-triethylene
                         glycol
SEQUENCE: 176
cacttattat gagga                                                 15

SEQ ID NO: 177          moltype = RNA  length = 21
FEATURE                 Location/Qualifiers
source                  1..21
                        mol_type = other RNA
                        organism = synthetic construct
modified_base           1
                        mod_base = OTHER
                        note = 5'-phosphate-2'-O-methyl uridine phosphorothioate
modified_base           2
                        mod_base = OTHER
                        note = 2'-fluoro adenosine phosphorothioate
modified_base           3
                        mod_base = OTHER
                        note = 2'-O-methyl uridine
modified_base           4
                        mod_base = OTHER
                        note = 2'-fluoro guanosine
modified_base           5
                        mod_base = OTHER
                        note = 2'-fluoro cytidine
modified_base           6
                        mod_base = OTHER
                        note = 2'-fluoro cytidine
modified_base           7
                        mod_base = OTHER
                        note = 2'-O-methyl cytidine
modified_base           8
                        mod_base = OTHER
                        note = 2'-fluoro uridine
modified_base           9
                        mod_base = OTHER
                        note = 2'-O-methyl guanosine
modified_base           10
                        mod_base = OTHER
                        note = 2'-fluoro cytidine
modified_base           11
                        mod_base = OTHER
                        note = 2'-O-methyl adenosine
modified_base           12
                        mod_base = OTHER
                        note = 2'-fluoro cytidine
modified_base           13
                        mod_base = OTHER
                        note = 2'-O-methyl uridine
modified_base           14
                        mod_base = OTHER
                        note = 2'-fluoro guanosine phosphorothioate
modified_base           15
                        mod_base = OTHER
                        note = 2'-O-methyl guanosine phosphorothioate
modified_base           16
                        mod_base = OTHER
                        note = 2'-fluoro guanosine phosphorothioate
modified_base           17
                        mod_base = OTHER
                        note = 2'-O-methyl cytidine phosphorothioate
modified_base           18
                        mod_base = OTHER
                        note = 2'-O-methyl cytidine phosphorothioate
modified_base           19
                        mod_base = OTHER
                        note = 2'-O-methyl guanosine phosphorothioate
modified_base           20
                        mod_base = OTHER
                        note = 2'-fluoro uridine phosphorothioate
modified_base           21
                        mod_base = OTHER
                        note = 2'-O-methyl uridine
SEQUENCE: 177
tatgccctgc actgggccgt t                                          21
```

-continued

```
SEQ ID NO: 178          moltype = RNA  length = 21
FEATURE                 Location/Qualifiers
source                  1..21
                        mol_type = other RNA
                        organism = synthetic construct
modified_base           1
                        mod_base = OTHER
                        note = 5'-phosphate-2'-O-methyl uridine phosphorothioate
modified_base           2
                        mod_base = OTHER
                        note = 2'-fluoro guanosine phosphorothioate
modified_base           3
                        mod_base = OTHER
                        note = 2'-O-methyl adenosine
modified_base           4
                        mod_base = OTHER
                        note = 2'-fluoro uridine
modified_base           5
                        mod_base = OTHER
                        note = 2'-fluoro guanosine
modified_base           6
                        mod_base = OTHER
                        note = 2'-fluoro cytidine
modified_base           7
                        mod_base = OTHER
                        note = 2'-O-methyl cytidine
modified_base           8
                        mod_base = OTHER
                        note = 2'-fluoro cytidine
modified_base           9
                        mod_base = OTHER
                        note = 2'-O-methyl uridine
modified_base           10
                        mod_base = OTHER
                        note = 2'-fluoro guanosine
modified_base           11
                        mod_base = OTHER
                        note = 2'-O-methyl cytidine
modified_base           12
                        mod_base = OTHER
                        note = 2'-fluoro adenosine
modified_base           13
                        mod_base = OTHER
                        note = 2'-O-methyl cytidine
modified_base           14
                        mod_base = OTHER
                        note = 2'-fluoro uridine phosphorothioate
modified_base           15
                        mod_base = OTHER
                        note = 2'-O-methyl guanosine phosphorothioate
modified_base           16
                        mod_base = OTHER
                        note = 2'-fluoro guanosine phosphorothioate
modified_base           17
                        mod_base = OTHER
                        note = 2'-O-methyl guanosine phosphorothioate
modified_base           18
                        mod_base = OTHER
                        note = 2'-O-methyl cytidine phosphorothioate
modified_base           19
                        mod_base = OTHER
                        note = 2'-O-methyl cytidine phosphorothioate
modified_base           20
                        mod_base = OTHER
                        note = 2'-fluoro guanosine phosphorothioate
modified_base           21
                        mod_base = OTHER
                        note = 2'-O-methyl uridine
SEQUENCE: 178
tgatgccctg cactgggccg t                                            21

SEQ ID NO: 179          moltype = RNA  length = 21
FEATURE                 Location/Qualifiers
source                  1..21
                        mol_type = other RNA
                        organism = synthetic construct
modified_base           1
                        mod_base = OTHER
```

```
                        note = 5'-phosphate-2'-O-methyl uridine phosphorothioate
modified_base           2
                        mod_base = OTHER
                        note = 2'-fluoro uridine phosphorothioate
modified_base           3
                        mod_base = OTHER
                        note = 2'-O-methyl guanosine
modified_base           4
                        mod_base = OTHER
                        note = 2'-fluoro adenosine
modified_base           5
                        mod_base = OTHER
                        note = 2'-fluoro uridine
modified_base           6
                        mod_base = OTHER
                        note = 2'-fluoro guanosine
modified_base           7
                        mod_base = OTHER
                        note = 2'-O-methyl cytidine
modified_base           8
                        mod_base = OTHER
                        note = 2'-fluoro cytidine
modified_base           9
                        mod_base = OTHER
                        note = 2'-O-methyl cytidine
modified_base           10
                        mod_base = OTHER
                        note = 2'-fluoro uridine
modified_base           11
                        mod_base = OTHER
                        note = 2'-O-methyl guanosine
modified_base           12
                        mod_base = OTHER
                        note = 2'-fluoro cytidine
modified_base           13
                        mod_base = OTHER
                        note = 2'-O-methyl adenosine
modified_base           14
                        mod_base = OTHER
                        note = 2'-fluoro cytidine phosphorothioate
modified_base           15
                        mod_base = OTHER
                        note = 2'-O-methyl uridine phosphorothioate
modified_base           16
                        mod_base = OTHER
                        note = 2'-fluoro guanosine phosphorothioate
modified_base           17
                        mod_base = OTHER
                        note = 2'-O-methyl guanosine phosphorothioate
modified_base           18
                        mod_base = OTHER
                        note = 2'-O-methyl guanosine phosphorothioate
modified_base           19
                        mod_base = OTHER
                        note = 2'-O-methyl cytidine phosphorothioate
modified_base           20
                        mod_base = OTHER
                        note = 2'-fluoro cytidine phosphorothioate
modified_base           21
                        mod_base = OTHER
                        note = 2'-O-methyl uridine
SEQUENCE: 179
ttgatgccct gcactgggcc t                                              21

SEQ ID NO: 180          moltype = RNA  length = 21
FEATURE                 Location/Qualifiers
source                  1..21
                        mol_type = other RNA
                        organism = synthetic construct
modified_base           1
                        mod_base = OTHER
                        note = 5'-phosphate-2'-O-methyl uridine phosphorothioate
modified_base           2
                        mod_base = OTHER
                        note = 2'-fluoro adenosine phosphorothioate
modified_base           3
                        mod_base = OTHER
                        note = 2'-O-methyl uridine
modified_base           4
```

-continued

```
                        mod_base = OTHER
                        note = 2'-fluoro guanosine
modified_base           5
                        mod_base = OTHER
                        note = 2'-fluoro adenosine
modified_base           6
                        mod_base = OTHER
                        note = 2'-fluoro uridine
modified_base           7
                        mod_base = OTHER
                        note = 2'-O-methyl guanosine
modified_base           8
                        mod_base = OTHER
                        note = 2'-fluoro cytidine
modified_base           9
                        mod_base = OTHER
                        note = 2'-O-methyl cytidine
modified_base           10
                        mod_base = OTHER
                        note = 2'-fluoro cytidine
modified_base           11
                        mod_base = OTHER
                        note = 2'-O-methyl uridine
modified_base           12
                        mod_base = OTHER
                        note = 2'-fluoro guanosine
modified_base           13
                        mod_base = OTHER
                        note = 2'-O-methyl cytidine
modified_base           14
                        mod_base = OTHER
                        note = 2'-fluoro adenosine phosphorothioate
modified_base           15
                        mod_base = OTHER
                        note = 2'-O-methyl cytidine phosphorothioate
modified_base           16
                        mod_base = OTHER
                        note = 2'-fluoro uridine phosphorothioate
modified_base           17
                        mod_base = OTHER
                        note = 2'-O-methyl guanosine phosphorothioate
modified_base           18
                        mod_base = OTHER
                        note = 2'-O-methyl guanosine phosphorothioate
modified_base           19
                        mod_base = OTHER
                        note = 2'-O-methyl guanosine phosphorothioate
modified_base           20
                        mod_base = OTHER
                        note = 2'-fluoro cytidine phosphorothioate
modified_base           21
                        mod_base = OTHER
                        note = 2'-O-methyl uridine
SEQUENCE: 180
tatgatgccc tgcactgggc t                                             21

SEQ ID NO: 181          moltype = RNA  length = 21
FEATURE                 Location/Qualifiers
source                  1..21
                        mol_type = other RNA
                        organism = synthetic construct
modified_base           1
                        mod_base = OTHER
                        note = 5'-phosphate-2'-O-methyl uridine phosphorothioate
modified_base           2
                        mod_base = OTHER
                        note = 2'-fluoro guanosine phosphorothioate
modified_base           3
                        mod_base = OTHER
                        note = 2'-O-methyl adenosine
modified_base           4
                        mod_base = OTHER
                        note = 2'-fluoro uridine
modified_base           5
                        mod_base = OTHER
                        note = 2'-fluoro guanosine
modified_base           6
                        mod_base = OTHER
                        note = 2'-fluoro adenosine
```

```
modified_base          7
                       mod_base = OTHER
                       note = 2'-O-methyl uridine
modified_base          8
                       mod_base = OTHER
                       note = 2'-fluoro guanosine
modified_base          9
                       mod_base = OTHER
                       note = 2'-O-methyl cytidine
modified_base          10
                       mod_base = OTHER
                       note = 2'-fluoro cytidine
modified_base          11
                       mod_base = OTHER
                       note = 2'-O-methyl cytidine
modified_base          12
                       mod_base = OTHER
                       note = 2'-fluoro uridine
modified_base          13
                       mod_base = OTHER
                       note = 2'-O-methyl guanosine
modified_base          14
                       mod_base = OTHER
                       note = 2'-fluoro cytidine phosphorothioate
modified_base          15
                       mod_base = OTHER
                       note = 2'-O-methyl adenosine phosphorothioate
modified_base          16
                       mod_base = OTHER
                       note = 2'-fluoro cytidine phosphorothioate
modified_base          17
                       mod_base = OTHER
                       note = 2'-O-methyl uridine phosphorothioate
modified_base          18
                       mod_base = OTHER
                       note = 2'-O-methyl guanosine phosphorothioate
modified_base          19
                       mod_base = OTHER
                       note = 2'-O-methyl guanosine phosphorothioate
modified_base          20
                       mod_base = OTHER
                       note = 2'-fluoro guanosine phosphorothioate
modified_base          21
                       mod_base = OTHER
                       note = 2'-O-methyl uridine
SEQUENCE: 181
tgatgatgcc ctgcactggg t                                                   21

SEQ ID NO: 182         moltype = RNA  length = 21
FEATURE                Location/Qualifiers
source                 1..21
                       mol_type = other RNA
                       organism = synthetic construct
modified_base          1
                       mod_base = OTHER
                       note = 5'-phosphate-2'-O-methyl uridine phosphorothioate
modified_base          2
                       mod_base = OTHER
                       note = 2'-fluoro uridine phosphorothioate
modified_base          3
                       mod_base = OTHER
                       note = 2'-O-methyl guanosine
modified_base          4
                       mod_base = OTHER
                       note = 2'-fluoro adenosine
modified_base          5
                       mod_base = OTHER
                       note = 2'-fluoro uridine
modified_base          6
                       mod_base = OTHER
                       note = 2'-fluoro guanosine
modified_base          7
                       mod_base = OTHER
                       note = 2'-O-methyl adenosine
modified_base          8
                       mod_base = OTHER
                       note = 2'-fluoro uridine
modified_base          9
                       mod_base = OTHER
```

-continued

```
                         note = 2'-O-methyl guanosine
modified_base            10
                         mod_base = OTHER
                         note = 2'-fluoro cytidine
modified_base            11
                         mod_base = OTHER
                         note = 2'-O-methyl cytidine
modified_base            12
                         mod_base = OTHER
                         note = 2'-fluoro cytidine
modified_base            13
                         mod_base = OTHER
                         note = 2'-O-methyl uridine
modified_base            14
                         mod_base = OTHER
                         note = 2'-fluoro guanosine phosphorothioate
modified_base            15
                         mod_base = OTHER
                         note = 2'-O-methyl cytidine phosphorothioate
modified_base            16
                         mod_base = OTHER
                         note = 2'-fluoro adenosine phosphorothioate
modified_base            17
                         mod_base = OTHER
                         note = 2'-O-methyl cytidine phosphorothioate
modified_base            18
                         mod_base = OTHER
                         note = 2'-O-methyl uridine phosphorothioate
modified_base            19
                         mod_base = OTHER
                         note = 2'-O-methyl guanosine phosphorothioate
modified_base            20
                         mod_base = OTHER
                         note = 2'-fluoro guanosine phosphorothioate
modified_base            21
                         mod_base = OTHER
                         note = 2'-O-methyl uridine
SEQUENCE: 182
ttgatgatgc cctgcactgg t                                            21

SEQ ID NO: 183           moltype = RNA  length = 21
FEATURE                  Location/Qualifiers
source                   1..21
                         mol_type = other RNA
                         organism = synthetic construct
modified_base            1
                         mod_base = OTHER
                         note = 5'-phosphate-2'-O-methyl uridine phosphorothioate
modified_base            2
                         mod_base = OTHER
                         note = 2'-fluoro uridine phosphorothioate
modified_base            3
                         mod_base = OTHER
                         note = 2'-O-methyl uridine
modified_base            4
                         mod_base = OTHER
                         note = 2'-fluoro guanosine
modified_base            5
                         mod_base = OTHER
                         note = 2'-fluoro adenosine
modified_base            6
                         mod_base = OTHER
                         note = 2'-fluoro uridine
modified_base            7
                         mod_base = OTHER
                         note = 2'-O-methyl guanosine
modified_base            8
                         mod_base = OTHER
                         note = 2'-fluoro adenosine
modified_base            9
                         mod_base = OTHER
                         note = 2'-O-methyl uridine
modified_base            10
                         mod_base = OTHER
                         note = 2'-fluoro guanosine
modified_base            11
                         mod_base = OTHER
                         note = 2'-O-methyl cytidine
modified_base            12
```

-continued

```
                        mod_base = OTHER
                        note = 2'-fluoro cytidine
modified_base           13
                        mod_base = OTHER
                        note = 2'-O-methyl cytidine
modified_base           14
                        mod_base = OTHER
                        note = 2'-fluoro uridine phosphorothioate
modified_base           15
                        mod_base = OTHER
                        note = 2'-O-methyl guanosine phosphorothioate
modified_base           16
                        mod_base = OTHER
                        note = 2'-fluoro cytidine phosphorothioate
modified_base           17
                        mod_base = OTHER
                        note = 2'-O-methyl adenosine phosphorothioate
modified_base           18
                        mod_base = OTHER
                        note = 2'-O-methyl cytidine phosphorothioate
modified_base           19
                        mod_base = OTHER
                        note = 2'-O-methyl uridine phosphorothioate
modified_base           20
                        mod_base = OTHER
                        note = 2'-fluoro guanosine phosphorothioate
modified_base           21
                        mod_base = OTHER
                        note = 2'-O-methyl uridine
SEQUENCE: 183
tttgatgatg ccctgcactg t                                     21

SEQ ID NO: 184          moltype = RNA  length = 21
FEATURE                 Location/Qualifiers
source                  1..21
                        mol_type = other RNA
                        organism = synthetic construct
modified_base           1
                        mod_base = OTHER
                        note = 5'-phosphate-2'-O-methyl uridine phosphorothioate
modified_base           2
                        mod_base = OTHER
                        note = 2'-fluoro adenosine phosphorothioate
modified_base           3
                        mod_base = OTHER
                        note = 2'-O-methyl uridine
modified_base           4
                        mod_base = OTHER
                        note = 2'-fluoro uridine
modified_base           5
                        mod_base = OTHER
                        note = 2'-fluoro guanosine
modified_base           6
                        mod_base = OTHER
                        note = 2'-fluoro adenosine
modified_base           7
                        mod_base = OTHER
                        note = 2'-O-methyl uridine
modified_base           8
                        mod_base = OTHER
                        note = 2'-fluoro guanosine
modified_base           9
                        mod_base = OTHER
                        note = 2'-O-methyl adenosine
modified_base           10
                        mod_base = OTHER
                        note = 2'-fluoro uridine
modified_base           11
                        mod_base = OTHER
                        note = 2'-O-methyl guanosine
modified_base           12
                        mod_base = OTHER
                        note = 2'-fluoro cytidine
modified_base           13
                        mod_base = OTHER
                        note = 2'-O-methyl cytidine
modified_base           14
                        mod_base = OTHER
                        note = 2'-fluoro cytidine phosphorothioate
```

```
modified_base         15
                      mod_base = OTHER
                      note = 2'-O-methyl uridine phosphorothioate
modified_base         16
                      mod_base = OTHER
                      note = 2'-fluoro guanosine phosphorothioate
modified_base         17
                      mod_base = OTHER
                      note = 2'-O-methyl cytidine phosphorothioate
modified_base         18
                      mod_base = OTHER
                      note = 2'-O-methyl adenosine phosphorothioate
modified_base         19
                      mod_base = OTHER
                      note = 2'-O-methyl cytidine phosphorothioate
modified_base         20
                      mod_base = OTHER
                      note = 2'-fluoro uridine phosphorothioate
modified_base         21
                      mod_base = OTHER
                      note = 2'-O-methyl uridine
SEQUENCE: 184
tattgatgat gccctgcact t                                            21

SEQ ID NO: 185        moltype = RNA  length = 21
FEATURE               Location/Qualifiers
source                1..21
                      mol_type = other RNA
                      organism = synthetic construct
modified_base         1
                      mod_base = OTHER
                      note = 5'-phosphate-2'-O-methyl uridine phosphorothioate
modified_base         2
                      mod_base = OTHER
                      note = 2'-fluoro adenosine phosphorothioate
modified_base         3
                      mod_base = OTHER
                      note = 2'-O-methyl adenosine
modified_base         4
                      mod_base = OTHER
                      note = 2'-fluoro uridine
modified_base         5
                      mod_base = OTHER
                      note = 2'-fluoro uridine
modified_base         6
                      mod_base = OTHER
                      note = 2'-fluoro guanosine
modified_base         7
                      mod_base = OTHER
                      note = 2'-O-methyl adenosine
modified_base         8
                      mod_base = OTHER
                      note = 2'-fluoro uridine
modified_base         9
                      mod_base = OTHER
                      note = 2'-O-methyl guanosine
modified_base         10
                      mod_base = OTHER
                      note = 2'-fluoro adenosine
modified_base         11
                      mod_base = OTHER
                      note = 2'-O-methyl uridine
modified_base         12
                      mod_base = OTHER
                      note = 2'-fluoro guanosine
modified_base         13
                      mod_base = OTHER
                      note = 2'-O-methyl cytidine
modified_base         14
                      mod_base = OTHER
                      note = 2'-fluoro cytidine phosphorothioate
modified_base         15
                      mod_base = OTHER
                      note = 2'-O-methyl cytidine phosphorothioate
modified_base         16
                      mod_base = OTHER
                      note = 2'-fluoro uridine phosphorothioate
modified_base         17
                      mod_base = OTHER
```

```
                       note = 2'-O-methyl guanosine phosphorothioate
modified_base          18
                       mod_base = OTHER
                       note = 2'-O-methyl cytidine phosphorothioate
modified_base          19
                       mod_base = OTHER
                       note = 2'-O-methyl adenosine phosphorothioate
modified_base          20
                       mod_base = OTHER
                       note = 2'-fluoro cytidine phosphorothioate
modified_base          21
                       mod_base = OTHER
                       note = 2'-O-methyl uridine
SEQUENCE: 185
taattgatga tgccctgcac t                                            21

SEQ ID NO: 186         moltype = RNA  length = 21
FEATURE                Location/Qualifiers
source                 1..21
                       mol_type = other RNA
                       organism = synthetic construct
modified_base          1
                       mod_base = OTHER
                       note = 5'-phosphate-2'-O-methyl uridine phosphorothioate
modified_base          2
                       mod_base = OTHER
                       note = 2'-fluoro adenosine phosphorothioate
modified_base          3
                       mod_base = OTHER
                       note = 2'-O-methyl adenosine
modified_base          4
                       mod_base = OTHER
                       note = 2'-fluoro adenosine
modified_base          5
                       mod_base = OTHER
                       note = 2'-fluoro uridine
modified_base          6
                       mod_base = OTHER
                       note = 2'-fluoro uridine
modified_base          7
                       mod_base = OTHER
                       note = 2'-O-methyl guanosine
modified_base          8
                       mod_base = OTHER
                       note = 2'-fluoro adenosine
modified_base          9
                       mod_base = OTHER
                       note = 2'-O-methyl uridine
modified_base          10
                       mod_base = OTHER
                       note = 2'-fluoro guanosine
modified_base          11
                       mod_base = OTHER
                       note = 2'-O-methyl adenosine
modified_base          12
                       mod_base = OTHER
                       note = 2'-fluoro uridine
modified_base          13
                       mod_base = OTHER
                       note = 2'-O-methyl guanosine
modified_base          14
                       mod_base = OTHER
                       note = 2'-fluoro cytidine phosphorothioate
modified_base          15
                       mod_base = OTHER
                       note = 2'-O-methyl cytidine phosphorothioate
modified_base          16
                       mod_base = OTHER
                       note = 2'-fluoro cytidine phosphorothioate
modified_base          17
                       mod_base = OTHER
                       note = 2'-O-methyl uridine phosphorothioate
modified_base          18
                       mod_base = OTHER
                       note = 2'-O-methyl guanosine phosphorothioate
modified_base          19
                       mod_base = OTHER
                       note = 2'-O-methyl cytidine phosphorothioate
modified_base          20
```

```
                        mod_base = OTHER
                        note = 2'-fluoro adenosine phosphorothioate
modified_base           21
                        mod_base = OTHER
                        note = 2'-O-methyl uridine
SEQUENCE: 186
taaattgatg atgccctgca t                                            21

SEQ ID NO: 187          moltype = RNA  length = 21
FEATURE                 Location/Qualifiers
source                  1..21
                        mol_type = other RNA
                        organism = synthetic construct
modified_base           1
                        mod_base = OTHER
                        note = 5'-phosphate-2'-O-methyl uridine phosphorothioate
modified_base           2
                        mod_base = OTHER
                        note = 2'-fluoro guanosine phosphorothioate
modified_base           3
                        mod_base = OTHER
                        note = 2'-O-methyl adenosine
modified_base           4
                        mod_base = OTHER
                        note = 2'-fluoro adenosine
modified_base           5
                        mod_base = OTHER
                        note = 2'-fluoro adenosine
modified_base           6
                        mod_base = OTHER
                        note = 2'-fluoro uridine
modified_base           7
                        mod_base = OTHER
                        note = 2'-O-methyl uridine
modified_base           8
                        mod_base = OTHER
                        note = 2'-fluoro guanosine
modified_base           9
                        mod_base = OTHER
                        note = 2'-O-methyl adenosine
modified_base           10
                        mod_base = OTHER
                        note = 2'-fluoro uridine
modified_base           11
                        mod_base = OTHER
                        note = 2'-O-methyl guanosine
modified_base           12
                        mod_base = OTHER
                        note = 2'-fluoro adenosine
modified_base           13
                        mod_base = OTHER
                        note = 2'-O-methyl uridine
modified_base           14
                        mod_base = OTHER
                        note = 2'-fluoro guanosine phosphorothioate
modified_base           15
                        mod_base = OTHER
                        note = 2'-O-methyl cytidine phosphorothioate
modified_base           16
                        mod_base = OTHER
                        note = 2'-fluoro cytidine phosphorothioate
modified_base           17
                        mod_base = OTHER
                        note = 2'-O-methyl cytidine phosphorothioate
modified_base           18
                        mod_base = OTHER
                        note = 2'-O-methyl uridine phosphorothioate
modified_base           19
                        mod_base = OTHER
                        note = 2'-O-methyl guanosine phosphorothioate
modified_base           20
                        mod_base = OTHER
                        note = 2'-fluoro cytidine phosphorothioate
modified_base           21
                        mod_base = OTHER
                        note = 2'-O-methyl uridine
SEQUENCE: 187
tgaaattgat gatgccctgc t                                            21
```

-continued

```
SEQ ID NO: 188          moltype = RNA  length = 21
FEATURE                 Location/Qualifiers
source                  1..21
                        mol_type = other RNA
                        organism = synthetic construct
modified_base           1
                        mod_base = OTHER
                        note = 5'-phosphate-2'-O-methyl uridine phosphorothioate
modified_base           2
                        mod_base = OTHER
                        note = 2'-fluoro cytidine phosphorothioate
modified_base           3
                        mod_base = OTHER
                        note = 2'-O-methyl guanosine
modified_base           4
                        mod_base = OTHER
                        note = 2'-fluoro adenosine
modified_base           5
                        mod_base = OTHER
                        note = 2'-fluoro adenosine
modified_base           6
                        mod_base = OTHER
                        note = 2'-fluoro adenosine
modified_base           7
                        mod_base = OTHER
                        note = 2'-O-methyl uridine
modified_base           8
                        mod_base = OTHER
                        note = 2'-fluoro uridine
modified_base           9
                        mod_base = OTHER
                        note = 2'-O-methyl guanosine
modified_base           10
                        mod_base = OTHER
                        note = 2'-fluoro adenosine
modified_base           11
                        mod_base = OTHER
                        note = 2'-O-methyl uridine
modified_base           12
                        mod_base = OTHER
                        note = 2'-fluoro guanosine
modified_base           13
                        mod_base = OTHER
                        note = 2'-O-methyl adenosine
modified_base           14
                        mod_base = OTHER
                        note = 2'-fluoro uridine phosphorothioate
modified_base           15
                        mod_base = OTHER
                        note = 2'-O-methyl guanosine phosphorothioate
modified_base           16
                        mod_base = OTHER
                        note = 2'-fluoro cytidine phosphorothioate
modified_base           17
                        mod_base = OTHER
                        note = 2'-O-methyl cytidine phosphorothioate
modified_base           18
                        mod_base = OTHER
                        note = 2'-O-methyl cytidine phosphorothioate
modified_base           19
                        mod_base = OTHER
                        note = 2'-O-methyl uridine phosphorothioate
modified_base           20
                        mod_base = OTHER
                        note = 2'-fluoro guanosine phosphorothioate
modified_base           21
                        mod_base = OTHER
                        note = 2'-O-methyl uridine
SEQUENCE: 188
tcgaaattga tgatgccctg t                                              21

SEQ ID NO: 189          moltype = RNA  length = 21
FEATURE                 Location/Qualifiers
source                  1..21
                        mol_type = other RNA
                        organism = synthetic construct
modified_base           1
                        mod_base = OTHER
                        note = 5'-phosphate-2'-O-methyl uridine phosphorothioate
```

-continued

```
modified_base         2
                      mod_base = OTHER
                      note = 2'-fluoro uridine phosphorothioate
modified_base         3
                      mod_base = OTHER
                      note = 2'-O-methyl cytidine
modified_base         4
                      mod_base = OTHER
                      note = 2'-fluoro guanosine
modified_base         5
                      mod_base = OTHER
                      note = 2'-fluoro adenosine
modified_base         6
                      mod_base = OTHER
                      note = 2'-fluoro adenosine
modified_base         7
                      mod_base = OTHER
                      note = 2'-O-methyl adenosine
modified_base         8
                      mod_base = OTHER
                      note = 2'-fluoro uridine
modified_base         9
                      mod_base = OTHER
                      note = 2'-O-methyl uridine
modified_base         10
                      mod_base = OTHER
                      note = 2'-fluoro guanosine
modified_base         11
                      mod_base = OTHER
                      note = 2'-O-methyl adenosine
modified_base         12
                      mod_base = OTHER
                      note = 2'-fluoro uridine
modified_base         13
                      mod_base = OTHER
                      note = 2'-O-methyl guanosine
modified_base         14
                      mod_base = OTHER
                      note = 2'-fluoro adenosine phosphorothioate
modified_base         15
                      mod_base = OTHER
                      note = 2'-O-methyl uridine phosphorothioate
modified_base         16
                      mod_base = OTHER
                      note = 2'-fluoro guanosine phosphorothioate
modified_base         17
                      mod_base = OTHER
                      note = 2'-O-methyl cytidine phosphorothioate
modified_base         18
                      mod_base = OTHER
                      note = 2'-O-methyl cytidine phosphorothioate
modified_base         19
                      mod_base = OTHER
                      note = 2'-O-methyl cytidine phosphorothioate
modified_base         20
                      mod_base = OTHER
                      note = 2'-fluoro uridine phosphorothioate
modified_base         21
                      mod_base = OTHER
                      note = 2'-O-methyl uridine
SEQUENCE: 189
ttcgaaattg atgatgccct t                                            21

SEQ ID NO: 190        moltype = RNA  length = 21
FEATURE               Location/Qualifiers
source                1..21
                      mol_type = other RNA
                      organism = synthetic construct
modified_base         1
                      mod_base = OTHER
                      note = 5'-phosphate-2'-O-methyl uridine phosphorothioate
modified_base         2
                      mod_base = OTHER
                      note = 2'-fluoro cytidine phosphorothioate
modified_base         3
                      mod_base = OTHER
                      note = 2'-O-methyl uridine
modified_base         4
                      mod_base = OTHER
```

```
                        note = 2'-fluoro cytidine
modified_base           5
                        mod_base = OTHER
                        note = 2'-fluoro guanosine
modified_base           6
                        mod_base = OTHER
                        note = 2'-fluoro adenosine
modified_base           7
                        mod_base = OTHER
                        note = 2'-O-methyl adenosine
modified_base           8
                        mod_base = OTHER
                        note = 2'-fluoro adenosine
modified_base           9
                        mod_base = OTHER
                        note = 2'-O-methyl uridine
modified_base           10
                        mod_base = OTHER
                        note = 2'-fluoro uridine
modified_base           11
                        mod_base = OTHER
                        note = 2'-O-methyl guanosine
modified_base           12
                        mod_base = OTHER
                        note = 2'-fluoro adenosine
modified_base           13
                        mod_base = OTHER
                        note = 2'-O-methyl uridine
modified_base           14
                        mod_base = OTHER
                        note = 2'-fluoro guanosine phosphorothioate
modified_base           15
                        mod_base = OTHER
                        note = 2'-O-methyl adenosine phosphorothioate
modified_base           16
                        mod_base = OTHER
                        note = 2'-fluoro uridine phosphorothioate
modified_base           17
                        mod_base = OTHER
                        note = 2'-O-methyl guanosine phosphorothioate
modified_base           18
                        mod_base = OTHER
                        note = 2'-O-methyl cytidine phosphorothioate
modified_base           19
                        mod_base = OTHER
                        note = 2'-O-methyl cytidine phosphorothioate
modified_base           20
                        mod_base = OTHER
                        note = 2'-fluoro cytidine phosphorothioate
modified_base           21
                        mod_base = OTHER
                        note = 2'-O-methyl uridine
SEQUENCE: 190
tctcgaaatt gatgatgccc t                                              21

SEQ ID NO: 191          moltype = RNA  length = 21
FEATURE                 Location/Qualifiers
source                  1..21
                        mol_type = other RNA
                        organism = synthetic construct
modified_base           1
                        mod_base = OTHER
                        note = 5'-phosphate-2'-O-methyl uridine phosphorothioate
modified_base           2
                        mod_base = OTHER
                        note = 2'-fluoro guanosine phosphorothioate
modified_base           3
                        mod_base = OTHER
                        note = 2'-O-methyl cytidine
modified_base           4
                        mod_base = OTHER
                        note = 2'-fluoro uridine
modified_base           5
                        mod_base = OTHER
                        note = 2'-fluoro cytidine
modified_base           6
                        mod_base = OTHER
                        note = 2'-fluoro guanosine
modified_base           7
```

```
                        mod_base = OTHER
                        note = 2'-O-methyl adenosine
modified_base           8
                        mod_base = OTHER
                        note = 2'-fluoro adenosine
modified_base           9
                        mod_base = OTHER
                        note = 2'-O-methyl adenosine
modified_base           10
                        mod_base = OTHER
                        note = 2'-fluoro uridine
modified_base           11
                        mod_base = OTHER
                        note = 2'-O-methyl uridine
modified_base           12
                        mod_base = OTHER
                        note = 2'-fluoro guanosine
modified_base           13
                        mod_base = OTHER
                        note = 2'-O-methyl adenosine
modified_base           14
                        mod_base = OTHER
                        note = 2'-fluoro uridine phosphorothioate
modified_base           15
                        mod_base = OTHER
                        note = 2'-O-methyl guanosine phosphorothioate
modified_base           16
                        mod_base = OTHER
                        note = 2'-fluoro adenosine phosphorothioate
modified_base           17
                        mod_base = OTHER
                        note = 2'-O-methyl uridine phosphorothioate
modified_base           18
                        mod_base = OTHER
                        note = 2'-O-methyl guanosine phosphorothioate
modified_base           19
                        mod_base = OTHER
                        note = 2'-O-methyl cytidine phosphorothioate
modified_base           20
                        mod_base = OTHER
                        note = 2'-fluoro cytidine phosphorothioate
modified_base           21
                        mod_base = OTHER
                        note = 2'-O-methyl uridine
SEQUENCE: 191
tgctcgaaat tgatgatgcc t                                             21

SEQ ID NO: 192          moltype = RNA  length = 21
FEATURE                 Location/Qualifiers
source                  1..21
                        mol_type = other RNA
                        organism = synthetic construct
modified_base           1
                        mod_base = OTHER
                        note = 5'-phosphate-2'-O-methyl uridine phosphorothioate
modified_base           2
                        mod_base = OTHER
                        note = 2'-fluoro uridine phosphorothioate
modified_base           3
                        mod_base = OTHER
                        note = 2'-O-methyl guanosine
modified_base           4
                        mod_base = OTHER
                        note = 2'-fluoro cytidine
modified_base           5
                        mod_base = OTHER
                        note = 2'-fluoro uridine
modified_base           6
                        mod_base = OTHER
                        note = 2'-fluoro cytidine
modified_base           7
                        mod_base = OTHER
                        note = 2'-O-methyl guanosine
modified_base           8
                        mod_base = OTHER
                        note = 2'-fluoro adenosine
modified_base           9
                        mod_base = OTHER
                        note = 2'-O-methyl adenosine
```

-continued

```
modified_base         10
                      mod_base = OTHER
                      note = 2'-fluoro adenosine
modified_base         11
                      mod_base = OTHER
                      note = 2'-O-methyl uridine
modified_base         12
                      mod_base = OTHER
                      note = 2'-fluoro uridine
modified_base         13
                      mod_base = OTHER
                      note = 2'-O-methyl guanosine
modified_base         14
                      mod_base = OTHER
                      note = 2'-fluoro adenosine phosphorothioate
modified_base         15
                      mod_base = OTHER
                      note = 2'-O-methyl uridine phosphorothioate
modified_base         16
                      mod_base = OTHER
                      note = 2'-fluoro guanosine phosphorothioate
modified_base         17
                      mod_base = OTHER
                      note = 2'-O-methyl adenosine phosphorothioate
modified_base         18
                      mod_base = OTHER
                      note = 2'-O-methyl uridine phosphorothioate
modified_base         19
                      mod_base = OTHER
                      note = 2'-O-methyl guanosine phosphorothioate
modified_base         20
                      mod_base = OTHER
                      note = 2'-fluoro cytidine phosphorothioate
modified_base         21
                      mod_base = OTHER
                      note = 2'-O-methyl uridine
SEQUENCE: 192
ttgctcgaaa ttgatgatgc t                                              21

SEQ ID NO: 193        moltype = RNA  length = 21
FEATURE               Location/Qualifiers
source                1..21
                      mol_type = other RNA
                      organism = synthetic construct
modified_base         1
                      mod_base = OTHER
                      note = 5'-phosphate-2'-O-methyl uridine phosphorothioate
modified_base         2
                      mod_base = OTHER
                      note = 2'-fluoro cytidine phosphorothioate
modified_base         3
                      mod_base = OTHER
                      note = 2'-O-methyl uridine
modified_base         4
                      mod_base = OTHER
                      note = 2'-fluoro guanosine
modified_base         5
                      mod_base = OTHER
                      note = 2'-fluoro cytidine
modified_base         6
                      mod_base = OTHER
                      note = 2'-fluoro uridine
modified_base         7
                      mod_base = OTHER
                      note = 2'-O-methyl cytidine
modified_base         8
                      mod_base = OTHER
                      note = 2'-fluoro guanosine
modified_base         9
                      mod_base = OTHER
                      note = 2'-O-methyl adenosine
modified_base         10
                      mod_base = OTHER
                      note = 2'-fluoro adenosine
modified_base         11
                      mod_base = OTHER
                      note = 2'-O-methyl adenosine
modified_base         12
                      mod_base = OTHER
```

```
                        note = 2'-fluoro uridine
modified_base           13
                        mod_base = OTHER
                        note = 2'-O-methyl uridine
modified_base           14
                        mod_base = OTHER
                        note = 2'-fluoro guanosine phosphorothioate
modified_base           15
                        mod_base = OTHER
                        note = 2'-O-methyl adenosine phosphorothioate
modified_base           16
                        mod_base = OTHER
                        note = 2'-fluoro uridine phosphorothioate
modified_base           17
                        mod_base = OTHER
                        note = 2'-O-methyl guanosine phosphorothioate
modified_base           18
                        mod_base = OTHER
                        note = 2'-O-methyl adenosine phosphorothioate
modified_base           19
                        mod_base = OTHER
                        note = 2'-O-methyl uridine phosphorothioate
modified_base           20
                        mod_base = OTHER
                        note = 2'-fluoro guanosine phosphorothioate
modified_base           21
                        mod_base = OTHER
                        note = 2'-O-methyl uridine
SEQUENCE: 193
tctgctcgaa attgatgatg t                                            21

SEQ ID NO: 194          moltype = RNA  length = 21
FEATURE                 Location/Qualifiers
source                  1..21
                        mol_type = other RNA
                        organism = synthetic construct
modified_base           1
                        mod_base = OTHER
                        note = 5'-phosphate-2'-O-methyl uridine phosphorothioate
modified_base           2
                        mod_base = OTHER
                        note = 2'-fluoro uridine phosphorothioate
modified_base           3
                        mod_base = OTHER
                        note = 2'-O-methyl cytidine
modified_base           4
                        mod_base = OTHER
                        note = 2'-fluoro uridine
modified_base           5
                        mod_base = OTHER
                        note = 2'-fluoro guanosine
modified_base           6
                        mod_base = OTHER
                        note = 2'-fluoro cytidine
modified_base           7
                        mod_base = OTHER
                        note = 2'-O-methyl uridine
modified_base           8
                        mod_base = OTHER
                        note = 2'-fluoro cytidine
modified_base           9
                        mod_base = OTHER
                        note = 2'-O-methyl guanosine
modified_base           10
                        mod_base = OTHER
                        note = 2'-fluoro adenosine
modified_base           11
                        mod_base = OTHER
                        note = 2'-O-methyl adenosine
modified_base           12
                        mod_base = OTHER
                        note = 2'-fluoro adenosine
modified_base           13
                        mod_base = OTHER
                        note = 2'-O-methyl uridine
modified_base           14
                        mod_base = OTHER
                        note = 2'-fluoro uridine phosphorothioate
modified_base           15
```

```
                        mod_base = OTHER
                        note = 2'-O-methyl guanosine phosphorothioate
modified_base           16
                        mod_base = OTHER
                        note = 2'-fluoro adenosine phosphorothioate
modified_base           17
                        mod_base = OTHER
                        note = 2'-O-methyl uridine phosphorothioate
modified_base           18
                        mod_base = OTHER
                        note = 2'-O-methyl guanosine phosphorothioate
modified_base           19
                        mod_base = OTHER
                        note = 2'-O-methyl adenosine phosphorothioate
modified_base           20
                        mod_base = OTHER
                        note = 2'-fluoro uridine phosphorothioate
modified_base           21
                        mod_base = OTHER
                        note = 2'-O-methyl uridine
SEQUENCE: 194
ttctgctcga aattgatgat t                                            21

SEQ ID NO: 195          moltype = RNA  length = 21
FEATURE                 Location/Qualifiers
source                  1..21
                        mol_type = other RNA
                        organism = synthetic construct
modified_base           1
                        mod_base = OTHER
                        note = 5'-phosphate-2'-O-methyl uridine phosphorothioate
modified_base           2
                        mod_base = OTHER
                        note = 2'-fluoro uridine phosphorothioate
modified_base           3
                        mod_base = OTHER
                        note = 2'-O-methyl uridine
modified_base           4
                        mod_base = OTHER
                        note = 2'-fluoro cytidine
modified_base           5
                        mod_base = OTHER
                        note = 2'-fluoro uridine
modified_base           6
                        mod_base = OTHER
                        note = 2'-fluoro guanosine
modified_base           7
                        mod_base = OTHER
                        note = 2'-O-methyl cytidine
modified_base           8
                        mod_base = OTHER
                        note = 2'-fluoro uridine
modified_base           9
                        mod_base = OTHER
                        note = 2'-O-methyl cytidine
modified_base           10
                        mod_base = OTHER
                        note = 2'-fluoro guanosine
modified_base           11
                        mod_base = OTHER
                        note = 2'-O-methyl adenosine
modified_base           12
                        mod_base = OTHER
                        note = 2'-fluoro adenosine
modified_base           13
                        mod_base = OTHER
                        note = 2'-O-methyl adenosine
modified_base           14
                        mod_base = OTHER
                        note = 2'-fluoro uridine phosphorothioate
modified_base           15
                        mod_base = OTHER
                        note = 2'-O-methyl uridine phosphorothioate
modified_base           16
                        mod_base = OTHER
                        note = 2'-fluoro guanosine phosphorothioate
modified_base           17
                        mod_base = OTHER
                        note = 2'-O-methyl adenosine phosphorothioate
```

```
modified_base          18
                       mod_base = OTHER
                       note = 2'-O-methyl uridine phosphorothioate
modified_base          19
                       mod_base = OTHER
                       note = 2'-O-methyl guanosine phosphorothioate
modified_base          20
                       mod_base = OTHER
                       note = 2'-fluoro adenosine phosphorothioate
modified_base          21
                       mod_base = OTHER
                       note = 2'-O-methyl uridine
SEQUENCE: 195
tttctgctcg aaattgatga t                                              21

SEQ ID NO: 196         moltype = RNA  length = 21
FEATURE                Location/Qualifiers
source                 1..21
                       mol_type = other RNA
                       organism = synthetic construct
modified_base          1
                       mod_base = OTHER
                       note = 5'-phosphate-2'-O-methyl uridine phosphorothioate
modified_base          2
                       mod_base = OTHER
                       note = 2'-fluoro cytidine phosphorothioate
modified_base          3
                       mod_base = OTHER
                       note = 2'-O-methyl uridine
modified_base          4
                       mod_base = OTHER
                       note = 2'-fluoro uridine
modified_base          5
                       mod_base = OTHER
                       note = 2'-fluoro cytidine
modified_base          6
                       mod_base = OTHER
                       note = 2'-fluoro uridine
modified_base          7
                       mod_base = OTHER
                       note = 2'-O-methyl guanosine
modified_base          8
                       mod_base = OTHER
                       note = 2'-fluoro cytidine
modified_base          9
                       mod_base = OTHER
                       note = 2'-O-methyl uridine
modified_base          10
                       mod_base = OTHER
                       note = 2'-fluoro cytidine
modified_base          11
                       mod_base = OTHER
                       note = 2'-O-methyl guanosine
modified_base          12
                       mod_base = OTHER
                       note = 2'-fluoro adenosine
modified_base          13
                       mod_base = OTHER
                       note = 2'-O-methyl adenosine
modified_base          14
                       mod_base = OTHER
                       note = 2'-fluoro adenosine phosphorothioate
modified_base          15
                       mod_base = OTHER
                       note = 2'-O-methyl uridine phosphorothioate
modified_base          16
                       mod_base = OTHER
                       note = 2'-fluoro uridine phosphorothioate
modified_base          17
                       mod_base = OTHER
                       note = 2'-O-methyl guanosine phosphorothioate
modified_base          18
                       mod_base = OTHER
                       note = 2'-O-methyl adenosine phosphorothioate
modified_base          19
                       mod_base = OTHER
                       note = 2'-O-methyl uridine phosphorothioate
modified_base          20
                       mod_base = OTHER
```

```
                        note = 2'-fluoro guanosine phosphorothioate
modified_base           21
                        mod_base = OTHER
                        note = 2'-O-methyl uridine
SEQUENCE: 196
tcttctgctc gaaattgatg t                                                21

SEQ ID NO: 197          moltype = RNA  length = 21
FEATURE                 Location/Qualifiers
source                  1..21
                        mol_type = other RNA
                        organism = synthetic construct
modified_base           1
                        mod_base = OTHER
                        note = 5'-phosphate-2'-O-methyl uridine phosphorothioate
modified_base           2
                        mod_base = OTHER
                        note = 2'-fluoro cytidine phosphorothioate
modified_base           3
                        mod_base = OTHER
                        note = 2'-O-methyl cytidine
modified_base           4
                        mod_base = OTHER
                        note = 2'-fluoro uridine
modified_base           5
                        mod_base = OTHER
                        note = 2'-fluoro uridine
modified_base           6
                        mod_base = OTHER
                        note = 2'-fluoro cytidine
modified_base           7
                        mod_base = OTHER
                        note = 2'-O-methyl uridine
modified_base           8
                        mod_base = OTHER
                        note = 2'-fluoro guanosine
modified_base           9
                        mod_base = OTHER
                        note = 2'-O-methyl cytidine
modified_base           10
                        mod_base = OTHER
                        note = 2'-fluoro uridine
modified_base           11
                        mod_base = OTHER
                        note = 2'-O-methyl cytidine
modified_base           12
                        mod_base = OTHER
                        note = 2'-fluoro guanosine
modified_base           13
                        mod_base = OTHER
                        note = 2'-O-methyl adenosine
modified_base           14
                        mod_base = OTHER
                        note = 2'-fluoro adenosine phosphorothioate
modified_base           15
                        mod_base = OTHER
                        note = 2'-O-methyl adenosine phosphorothioate
modified_base           16
                        mod_base = OTHER
                        note = 2'-fluoro uridine phosphorothioate
modified_base           17
                        mod_base = OTHER
                        note = 2'-O-methyl uridine phosphorothioate
modified_base           18
                        mod_base = OTHER
                        note = 2'-O-methyl guanosine phosphorothioate
modified_base           19
                        mod_base = OTHER
                        note = 2'-O-methyl adenosine phosphorothioate
modified_base           20
                        mod_base = OTHER
                        note = 2'-fluoro uridine phosphorothioate
modified_base           21
                        mod_base = OTHER
                        note = 2'-O-methyl uridine
SEQUENCE: 197
tccttctgct cgaaattgat t                                                21

SEQ ID NO: 198          moltype = RNA  length = 21
```

-continued

```
FEATURE                 Location/Qualifiers
source                  1..21
                        mol_type = other RNA
                        organism = synthetic construct
modified_base           1
                        mod_base = OTHER
                        note = 5'-phosphate-2'-O-methyl uridine phosphorothioate
modified_base           2
                        mod_base = OTHER
                        note = 2'-fluoro uridine phosphorothioate
modified_base           3
                        mod_base = OTHER
                        note = 2'-O-methyl cytidine
modified_base           4
                        mod_base = OTHER
                        note = 2'-fluoro cytidine
modified_base           5
                        mod_base = OTHER
                        note = 2'-fluoro uridine
modified_base           6
                        mod_base = OTHER
                        note = 2'-fluoro uridine
modified_base           7
                        mod_base = OTHER
                        note = 2'-O-methyl cytidine
modified_base           8
                        mod_base = OTHER
                        note = 2'-fluoro uridine
modified_base           9
                        mod_base = OTHER
                        note = 2'-O-methyl guanosine
modified_base           10
                        mod_base = OTHER
                        note = 2'-fluoro cytidine
modified_base           11
                        mod_base = OTHER
                        note = 2'-O-methyl uridine
modified_base           12
                        mod_base = OTHER
                        note = 2'-fluoro cytidine
modified_base           13
                        mod_base = OTHER
                        note = 2'-O-methyl guanosine
modified_base           14
                        mod_base = OTHER
                        note = 2'-fluoro adenosine phosphorothioate
modified_base           15
                        mod_base = OTHER
                        note = 2'-O-methyl adenosine phosphorothioate
modified_base           16
                        mod_base = OTHER
                        note = 2'-fluoro adenosine phosphorothioate
modified_base           17
                        mod_base = OTHER
                        note = 2'-O-methyl uridine phosphorothioate
modified_base           18
                        mod_base = OTHER
                        note = 2'-O-methyl uridine phosphorothioate
modified_base           19
                        mod_base = OTHER
                        note = 2'-O-methyl guanosine phosphorothioate
modified_base           20
                        mod_base = OTHER
                        note = 2'-fluoro adenosine phosphorothioate
modified_base           21
                        mod_base = OTHER
                        note = 2'-O-methyl uridine
SEQUENCE: 198
ttccttctgc tcgaaattga t                                               21

SEQ ID NO: 199          moltype = RNA  length = 21
FEATURE                 Location/Qualifiers
source                  1..21
                        mol_type = other RNA
                        organism = synthetic construct
modified_base           1
                        mod_base = OTHER
                        note = 5'-phosphate-2'-O-methyl uridine phosphorothioate
modified_base           2
```

```
                        mod_base = OTHER
                        note = 2'-fluoro uridine phosphorothioate
modified_base           3
                        mod_base = OTHER
                        note = 2'-O-methyl uridine
modified_base           4
                        mod_base = OTHER
                        note = 2'-fluoro cytidine
modified_base           5
                        mod_base = OTHER
                        note = 2'-fluoro cytidine
modified_base           6
                        mod_base = OTHER
                        note = 2'-fluoro uridine
modified_base           7
                        mod_base = OTHER
                        note = 2'-O-methyl uridine
modified_base           8
                        mod_base = OTHER
                        note = 2'-fluoro cytidine
modified_base           9
                        mod_base = OTHER
                        note = 2'-O-methyl uridine
modified_base           10
                        mod_base = OTHER
                        note = 2'-fluoro guanosine
modified_base           11
                        mod_base = OTHER
                        note = 2'-O-methyl cytidine
modified_base           12
                        mod_base = OTHER
                        note = 2'-fluoro uridine
modified_base           13
                        mod_base = OTHER
                        note = 2'-O-methyl cytidine
modified_base           14
                        mod_base = OTHER
                        note = 2'-fluoro guanosine phosphorothioate
modified_base           15
                        mod_base = OTHER
                        note = 2'-O-methyl adenosine phosphorothioate
modified_base           16
                        mod_base = OTHER
                        note = 2'-fluoro adenosine phosphorothioate
modified_base           17
                        mod_base = OTHER
                        note = 2'-O-methyl adenosine phosphorothioate
modified_base           18
                        mod_base = OTHER
                        note = 2'-O-methyl uridine phosphorothioate
modified_base           19
                        mod_base = OTHER
                        note = 2'-O-methyl uridine phosphorothioate
modified_base           20
                        mod_base = OTHER
                        note = 2'-fluoro guanosine phosphorothioate
modified_base           21
                        mod_base = OTHER
                        note = 2'-O-methyl uridine
SEQUENCE: 199
tttccttctg ctcgaaattg t                                     21

SEQ ID NO: 200          moltype = RNA  length = 21
FEATURE                 Location/Qualifiers
source                  1..21
                        mol_type = other RNA
                        organism = synthetic construct
modified_base           1
                        mod_base = OTHER
                        note = 5'-phosphate-2'-O-methyl uridine phosphorothioate
modified_base           2
                        mod_base = OTHER
                        note = 2'-fluoro uridine phosphorothioate
modified_base           3
                        mod_base = OTHER
                        note = 2'-O-methyl uridine
modified_base           4
                        mod_base = OTHER
                        note = 2'-fluoro uridine
```

-continued

```
modified_base          5
                       mod_base = OTHER
                       note = 2'-fluoro cytidine
modified_base          6
                       mod_base = OTHER
                       note = 2'-fluoro cytidine
modified_base          7
                       mod_base = OTHER
                       note = 2'-O-methyl uridine
modified_base          8
                       mod_base = OTHER
                       note = 2'-fluoro uridine
modified_base          9
                       mod_base = OTHER
                       note = 2'-O-methyl cytidine
modified_base          10
                       mod_base = OTHER
                       note = 2'-fluoro uridine
modified_base          11
                       mod_base = OTHER
                       note = 2'-O-methyl guanosine
modified_base          12
                       mod_base = OTHER
                       note = 2'-fluoro cytidine
modified_base          13
                       mod_base = OTHER
                       note = 2'-O-methyl uridine
modified_base          14
                       mod_base = OTHER
                       note = 2'-fluoro cytidine phosphorothioate
modified_base          15
                       mod_base = OTHER
                       note = 2'-O-methyl guanosine phosphorothioate
modified_base          16
                       mod_base = OTHER
                       note = 2'-fluoro adenosine phosphorothioate
modified_base          17
                       mod_base = OTHER
                       note = 2'-O-methyl adenosine phosphorothioate
modified_base          18
                       mod_base = OTHER
                       note = 2'-O-methyl adenosine phosphorothioate
modified_base          19
                       mod_base = OTHER
                       note = 2'-O-methyl uridine phosphorothioate
modified_base          20
                       mod_base = OTHER
                       note = 2'-fluoro uridine phosphorothioate
modified_base          21
                       mod_base = OTHER
                       note = 2'-O-methyl uridine
SEQUENCE: 200
ttttccttct gctcgaaatt t                                            21

SEQ ID NO: 201         moltype = RNA  length = 16
FEATURE                Location/Qualifiers
source                 1..16
                       mol_type = other RNA
                       organism = synthetic construct
modified_base          1
                       mod_base = OTHER
                       note = 2'-O-methyl cytidine phosphorothioate
modified_base          2
                       mod_base = OTHER
                       note = 2'-O-methyl cytidine phosphorothioate
modified_base          3
                       mod_base = OTHER
                       note = 2'-O-methyl cytidine
modified_base          4
                       mod_base = OTHER
                       note = 2'-fluoro adenosine
modified_base          5
                       mod_base = OTHER
                       note = 2'-O-methyl guanosine
modified_base          6
                       mod_base = OTHER
                       note = 2'-fluoro uridine
modified_base          7
                       mod_base = OTHER
```

```
                        note = 2'-O-methyl guanosine
modified_base           8
                        mod_base = OTHER
                        note = 2'-fluoro cytidine
modified_base           9
                        mod_base = OTHER
                        note = 2'-O-methyl adenosine
modified_base           10
                        mod_base = OTHER
                        note = 2'-fluoro guanosine
modified_base           11
                        mod_base = OTHER
                        note = 2'-O-methyl guanosine
modified_base           12
                        mod_base = OTHER
                        note = 2'-O-methyl guanosine
modified_base           13
                        mod_base = OTHER
                        note = 2'-O-methyl cytidine
modified_base           14
                        mod_base = OTHER
                        note = 2'-fluoro adenosine phosphorothioate
modified_base           15
                        mod_base = OTHER
                        note = 2'-O-methyl uridine phosphorothioate
modified_base           16
                        mod_base = OTHER
                        note = 2'-O-methyl adenosine 3'-cholesterol-triethylene
                         glycol
SEQUENCE: 201
cccagtgcag ggcata                                                   16

SEQ ID NO: 202          moltype = RNA  length = 16
FEATURE                 Location/Qualifiers
source                  1..16
                        mol_type = other RNA
                        organism = synthetic construct
modified_base           1
                        mod_base = OTHER
                        note = 2'-O-methyl cytidine phosphorothioate
modified_base           2
                        mod_base = OTHER
                        note = 2'-O-methyl cytidine phosphorothioate
modified_base           3
                        mod_base = OTHER
                        note = 2'-O-methyl adenosine
modified_base           4
                        mod_base = OTHER
                        note = 2'-fluoro guanosine
modified_base           5
                        mod_base = OTHER
                        note = 2'-O-methyl uridine
modified_base           6
                        mod_base = OTHER
                        note = 2'-fluoro guanosine
modified_base           7
                        mod_base = OTHER
                        note = 2'-O-methyl cytidine
modified_base           8
                        mod_base = OTHER
                        note = 2'-fluoro adenosine
modified_base           9
                        mod_base = OTHER
                        note = 2'-O-methyl guanosine
modified_base           10
                        mod_base = OTHER
                        note = 2'-fluoro guanosine
modified_base           11
                        mod_base = OTHER
                        note = 2'-O-methyl guanosine
modified_base           12
                        mod_base = OTHER
                        note = 2'-O-methyl cytidine
modified_base           13
                        mod_base = OTHER
                        note = 2'-O-methyl adenosine
modified_base           14
                        mod_base = OTHER
                        note = 2'-fluoro uridine phosphorothioate
```

```
modified_base          15
                       mod_base = OTHER
                       note = 2'-O-methyl cytidine phosphorothioate
modified_base          16
                       mod_base = OTHER
                       note = 2'-O-methyl adenosine 3'-cholesterol-triethylene
                        glycol
SEQUENCE: 202
ccagtgcagg gcatca                                                  16

SEQ ID NO: 203         moltype = RNA  length = 16
FEATURE                Location/Qualifiers
source                 1..16
                       mol_type = other RNA
                       organism = synthetic construct
modified_base          1
                       mod_base = OTHER
                       note = 2'-O-methyl cytidine phosphorothioate
modified_base          2
                       mod_base = OTHER
                       note = 2'-O-methyl adenosine phosphorothioate
modified_base          3
                       mod_base = OTHER
                       note = 2'-O-methyl guanosine
modified_base          4
                       mod_base = OTHER
                       note = 2'-fluoro uridine
modified_base          5
                       mod_base = OTHER
                       note = 2'-O-methyl guanosine
modified_base          6
                       mod_base = OTHER
                       note = 2'-fluoro cytidine
modified_base          7
                       mod_base = OTHER
                       note = 2'-O-methyl adenosine
modified_base          8
                       mod_base = OTHER
                       note = 2'-fluoro guanosine
modified_base          9
                       mod_base = OTHER
                       note = 2'-O-methyl guanosine
modified_base          10
                       mod_base = OTHER
                       note = 2'-fluoro guanosine
modified_base          11
                       mod_base = OTHER
                       note = 2'-O-methyl cytidine
modified_base          12
                       mod_base = OTHER
                       note = 2'-O-methyl adenosine
modified_base          13
                       mod_base = OTHER
                       note = 2'-O-methyl uridine
modified_base          14
                       mod_base = OTHER
                       note = 2'-fluoro cytidine phosphorothioate
modified_base          15
                       mod_base = OTHER
                       note = 2'-O-methyl adenosine phosphorothioate
modified_base          16
                       mod_base = OTHER
                       note = 2'-O-methyl adenosine 3'-cholesterol-triethylene
                        glycol
SEQUENCE: 203
cagtgcaggg catcaa                                                  16

SEQ ID NO: 204         moltype = RNA  length = 16
FEATURE                Location/Qualifiers
source                 1..16
                       mol_type = other RNA
                       organism = synthetic construct
modified_base          1
                       mod_base = OTHER
                       note = 2'-O-methyl adenosine phosphorothioate
modified_base          2
                       mod_base = OTHER
                       note = 2'-O-methyl guanosine phosphorothioate
modified_base          3
```

-continued

```
                        mod_base = OTHER
                        note = 2'-O-methyl uridine
modified_base           4
                        mod_base = OTHER
                        note = 2'-fluoro guanosine
modified_base           5
                        mod_base = OTHER
                        note = 2'-O-methyl cytidine
modified_base           6
                        mod_base = OTHER
                        note = 2'-fluoro adenosine
modified_base           7
                        mod_base = OTHER
                        note = 2'-O-methyl guanosine
modified_base           8
                        mod_base = OTHER
                        note = 2'-fluoro guanosine
modified_base           9
                        mod_base = OTHER
                        note = 2'-O-methyl guanosine
modified_base           10
                        mod_base = OTHER
                        note = 2'-fluoro cytidine
modified_base           11
                        mod_base = OTHER
                        note = 2'-O-methyl adenosine
modified_base           12
                        mod_base = OTHER
                        note = 2'-O-methyl uridine
modified_base           13
                        mod_base = OTHER
                        note = 2'-O-methyl cytidine
modified_base           14
                        mod_base = OTHER
                        note = 2'-fluoro adenosine phosphorothioate
modified_base           15
                        mod_base = OTHER
                        note = 2'-O-methyl uridine phosphorothioate
modified_base           16
                        mod_base = OTHER
                        note = 2'-O-methyl adenosine 3'-cholesterol-triethylene
                         glycol
SEQUENCE: 204
agtgcagggc atcata                                                  16

SEQ ID NO: 205          moltype = RNA  length = 16
FEATURE                 Location/Qualifiers
source                  1..16
                        mol_type = other RNA
                        organism = synthetic construct
modified_base           1
                        mod_base = OTHER
                        note = 2'-O-methyl guanosine phosphorothioate
modified_base           2
                        mod_base = OTHER
                        note = 2'-O-methyl uridine phosphorothioate
modified_base           3
                        mod_base = OTHER
                        note = 2'-O-methyl guanosine
modified_base           4
                        mod_base = OTHER
                        note = 2'-fluoro cytidine
modified_base           5
                        mod_base = OTHER
                        note = 2'-O-methyl adenosine
modified_base           6
                        mod_base = OTHER
                        note = 2'-fluoro guanosine
modified_base           7
                        mod_base = OTHER
                        note = 2'-O-methyl guanosine
modified_base           8
                        mod_base = OTHER
                        note = 2'-fluoro guanosine
modified_base           9
                        mod_base = OTHER
                        note = 2'-O-methyl cytidine
modified_base           10
                        mod_base = OTHER
```

-continued

```
                        note = 2'-fluoro adenosine
modified_base           11
                        mod_base = OTHER
                        note = 2'-O-methyl uridine
modified_base           12
                        mod_base = OTHER
                        note = 2'-O-methyl cytidine
modified_base           13
                        mod_base = OTHER
                        note = 2'-O-methyl adenosine
modified_base           14
                        mod_base = OTHER
                        note = 2'-fluoro uridine phosphorothioate
modified_base           15
                        mod_base = OTHER
                        note = 2'-O-methyl cytidine phosphorothioate
modified_base           16
                        mod_base = OTHER
                        note = 2'-O-methyl adenosine 3'-cholesterol-triethylene
                         glycol
SEQUENCE: 205
gtgcagggca tcatca                                                  16

SEQ ID NO: 206          moltype = RNA  length = 16
FEATURE                 Location/Qualifiers
source                  1..16
                        mol_type = other RNA
                        organism = synthetic construct
modified_base           1
                        mod_base = OTHER
                        note = 2'-O-methyl uridine phosphorothioate
modified_base           2
                        mod_base = OTHER
                        note = 2'-O-methyl guanosine phosphorothioate
modified_base           3
                        mod_base = OTHER
                        note = 2'-O-methyl cytidine
modified_base           4
                        mod_base = OTHER
                        note = 2'-fluoro adenosine
modified_base           5
                        mod_base = OTHER
                        note = 2'-O-methyl guanosine
modified_base           6
                        mod_base = OTHER
                        note = 2'-fluoro guanosine
modified_base           7
                        mod_base = OTHER
                        note = 2'-O-methyl guanosine
modified_base           8
                        mod_base = OTHER
                        note = 2'-fluoro cytidine
modified_base           9
                        mod_base = OTHER
                        note = 2'-O-methyl adenosine
modified_base           10
                        mod_base = OTHER
                        note = 2'-fluoro uridine
modified_base           11
                        mod_base = OTHER
                        note = 2'-O-methyl cytidine
modified_base           12
                        mod_base = OTHER
                        note = 2'-O-methyl adenosine
modified_base           13
                        mod_base = OTHER
                        note = 2'-O-methyl uridine
modified_base           14
                        mod_base = OTHER
                        note = 2'-fluoro cytidine phosphorothioate
modified_base           15
                        mod_base = OTHER
                        note = 2'-O-methyl adenosine phosphorothioate
modified_base           16
                        mod_base = OTHER
                        note = 2'-O-methyl adenosine 3'-cholesterol-triethylene
                         glycol
SEQUENCE: 206
tgcagggcat catcaa                                                  16
```

```
SEQ ID NO: 207          moltype = RNA  length = 16
FEATURE                 Location/Qualifiers
source                  1..16
                        mol_type = other RNA
                        organism = synthetic construct
modified_base           1
                        mod_base = OTHER
                        note = 2'-O-methyl guanosine phosphorothioate
modified_base           2
                        mod_base = OTHER
                        note = 2'-O-methyl cytidine phosphorothioate
modified_base           3
                        mod_base = OTHER
                        note = 2'-O-methyl adenosine
modified_base           4
                        mod_base = OTHER
                        note = 2'-fluoro guanosine
modified_base           5
                        mod_base = OTHER
                        note = 2'-O-methyl guanosine
modified_base           6
                        mod_base = OTHER
                        note = 2'-fluoro guanosine
modified_base           7
                        mod_base = OTHER
                        note = 2'-O-methyl cytidine
modified_base           8
                        mod_base = OTHER
                        note = 2'-fluoro adenosine
modified_base           9
                        mod_base = OTHER
                        note = 2'-O-methyl uridine
modified_base           10
                        mod_base = OTHER
                        note = 2'-fluoro cytidine
modified_base           11
                        mod_base = OTHER
                        note = 2'-O-methyl adenosine
modified_base           12
                        mod_base = OTHER
                        note = 2'-O-methyl uridine
modified_base           13
                        mod_base = OTHER
                        note = 2'-O-methyl cytidine
modified_base           14
                        mod_base = OTHER
                        note = 2'-fluoro adenosine phosphorothioate
modified_base           15
                        mod_base = OTHER
                        note = 2'-O-methyl adenosine phosphorothioate
modified_base           16
                        mod_base = OTHER
                        note = 2'-O-methyl adenosine 3'-cholesterol-triethylene
                         glycol
SEQUENCE: 207
gcagggcatc atcaaa                                                  16

SEQ ID NO: 208          moltype = RNA  length = 16
FEATURE                 Location/Qualifiers
source                  1..16
                        mol_type = other RNA
                        organism = synthetic construct
modified_base           1
                        mod_base = OTHER
                        note = 2'-O-methyl cytidine phosphorothioate
modified_base           2
                        mod_base = OTHER
                        note = 2'-O-methyl adenosine phosphorothioate
modified_base           3
                        mod_base = OTHER
                        note = 2'-O-methyl guanosine
modified_base           4
                        mod_base = OTHER
                        note = 2'-fluoro guanosine
modified_base           5
                        mod_base = OTHER
                        note = 2'-O-methyl guanosine
modified_base           6
```

```
                        mod_base = OTHER
                        note = 2'-fluoro cytidine
modified_base           7
                        mod_base = OTHER
                        note = 2'-O-methyl adenosine
modified_base           8
                        mod_base = OTHER
                        note = 2'-fluoro uridine
modified_base           9
                        mod_base = OTHER
                        note = 2'-O-methyl cytidine
modified_base           10
                        mod_base = OTHER
                        note = 2'-fluoro adenosine
modified_base           11
                        mod_base = OTHER
                        note = 2'-O-methyl uridine
modified_base           12
                        mod_base = OTHER
                        note = 2'-O-methyl cytidine
modified_base           13
                        mod_base = OTHER
                        note = 2'-O-methyl adenosine
modified_base           14
                        mod_base = OTHER
                        note = 2'-fluoro adenosine phosphorothioate
modified_base           15
                        mod_base = OTHER
                        note = 2'-O-methyl uridine phosphorothioate
modified_base           16
                        mod_base = OTHER
                        note = 2'-O-methyl adenosine 3'-cholesterol-triethylene
                         glycol
SEQUENCE: 208
cagggcatca tcaata                                                   16

SEQ ID NO: 209          moltype = RNA  length = 16
FEATURE                 Location/Qualifiers
source                  1..16
                        mol_type = other RNA
                        organism = synthetic construct
modified_base           1
                        mod_base = OTHER
                        note = 2'-O-methyl adenosine phosphorothioate
modified_base           2
                        mod_base = OTHER
                        note = 2'-O-methyl guanosine phosphorothioate
modified_base           3
                        mod_base = OTHER
                        note = 2'-O-methyl guanosine
modified_base           4
                        mod_base = OTHER
                        note = 2'-fluoro guanosine
modified_base           5
                        mod_base = OTHER
                        note = 2'-O-methyl cytidine
modified_base           6
                        mod_base = OTHER
                        note = 2'-fluoro adenosine
modified_base           7
                        mod_base = OTHER
                        note = 2'-O-methyl uridine
modified_base           8
                        mod_base = OTHER
                        note = 2'-fluoro cytidine
modified_base           9
                        mod_base = OTHER
                        note = 2'-O-methyl adenosine
modified_base           10
                        mod_base = OTHER
                        note = 2'-fluoro uridine
modified_base           11
                        mod_base = OTHER
                        note = 2'-O-methyl cytidine
modified_base           12
                        mod_base = OTHER
                        note = 2'-O-methyl adenosine
modified_base           13
                        mod_base = OTHER
```

```
                        note = 2'-O-methyl adenosine
modified_base           14
                        mod_base = OTHER
                        note = 2'-fluoro uridine phosphorothioate
modified_base           15
                        mod_base = OTHER
                        note = 2'-O-methyl uridine phosphorothioate
modified_base           16
                        mod_base = OTHER
                        note = 2'-O-methyl adenosine 3'-cholesterol-triethylene
                         glycol
SEQUENCE: 209
agggcatcat caatta                                                    16

SEQ ID NO: 210          moltype = RNA  length = 16
FEATURE                 Location/Qualifiers
source                  1..16
                        mol_type = other RNA
                        organism = synthetic construct
modified_base           1
                        mod_base = OTHER
                        note = 2'-O-methyl guanosine phosphorothioate
modified_base           2
                        mod_base = OTHER
                        note = 2'-O-methyl guanosine phosphorothioate
modified_base           3
                        mod_base = OTHER
                        note = 2'-O-methyl guanosine
modified_base           4
                        mod_base = OTHER
                        note = 2'-fluoro cytidine
modified_base           5
                        mod_base = OTHER
                        note = 2'-O-methyl adenosine
modified_base           6
                        mod_base = OTHER
                        note = 2'-fluoro uridine
modified_base           7
                        mod_base = OTHER
                        note = 2'-O-methyl cytidine
modified_base           8
                        mod_base = OTHER
                        note = 2'-fluoro adenosine
modified_base           9
                        mod_base = OTHER
                        note = 2'-O-methyl uridine
modified_base           10
                        mod_base = OTHER
                        note = 2'-fluoro cytidine
modified_base           11
                        mod_base = OTHER
                        note = 2'-O-methyl adenosine
modified_base           12
                        mod_base = OTHER
                        note = 2'-O-methyl adenosine
modified_base           13
                        mod_base = OTHER
                        note = 2'-O-methyl uridine
modified_base           14
                        mod_base = OTHER
                        note = 2'-fluoro uridine phosphorothioate
modified_base           15
                        mod_base = OTHER
                        note = 2'-O-methyl uridine phosphorothioate
modified_base           16
                        mod_base = OTHER
                        note = 2'-O-methyl adenosine 3'-cholesterol-triethylene
                         glycol
SEQUENCE: 210
gggcatcatc aattta                                                    16

SEQ ID NO: 211          moltype = RNA  length = 16
FEATURE                 Location/Qualifiers
source                  1..16
                        mol_type = other RNA
                        organism = synthetic construct
modified_base           1
                        mod_base = OTHER
                        note = 2'-O-methyl guanosine phosphorothioate
```

```
modified_base           2
                        mod_base = OTHER
                        note = 2'-O-methyl guanosine phosphorothioate
modified_base           3
                        mod_base = OTHER
                        note = 2'-O-methyl cytidine
modified_base           4
                        mod_base = OTHER
                        note = 2'-fluoro adenosine
modified_base           5
                        mod_base = OTHER
                        note = 2'-O-methyl uridine
modified_base           6
                        mod_base = OTHER
                        note = 2'-fluoro cytidine
modified_base           7
                        mod_base = OTHER
                        note = 2'-O-methyl adenosine
modified_base           8
                        mod_base = OTHER
                        note = 2'-fluoro uridine
modified_base           9
                        mod_base = OTHER
                        note = 2'-O-methyl cytidine
modified_base           10
                        mod_base = OTHER
                        note = 2'-fluoro adenosine
modified_base           11
                        mod_base = OTHER
                        note = 2'-O-methyl adenosine
modified_base           12
                        mod_base = OTHER
                        note = 2'-O-methyl uridine
modified_base           13
                        mod_base = OTHER
                        note = 2'-O-methyl uridine
modified_base           14
                        mod_base = OTHER
                        note = 2'-fluoro uridine phosphorothioate
modified_base           15
                        mod_base = OTHER
                        note = 2'-O-methyl cytidine phosphorothioate
modified_base           16
                        mod_base = OTHER
                        note = 2'-O-methyl adenosine 3'-cholesterol-triethylene
                         glycol
SEQUENCE: 211
ggcatcatca atttca                                               16

SEQ ID NO: 212          moltype = RNA  length = 16
FEATURE                 Location/Qualifiers
source                  1..16
                        mol_type = other RNA
                        organism = synthetic construct
modified_base           1
                        mod_base = OTHER
                        note = 2'-O-methyl guanosine phosphorothioate
modified_base           2
                        mod_base = OTHER
                        note = 2'-O-methyl cytidine phosphorothioate
modified_base           3
                        mod_base = OTHER
                        note = 2'-O-methyl adenosine
modified_base           4
                        mod_base = OTHER
                        note = 2'-fluoro uridine
modified_base           5
                        mod_base = OTHER
                        note = 2'-O-methyl cytidine
modified_base           6
                        mod_base = OTHER
                        note = 2'-fluoro adenosine
modified_base           7
                        mod_base = OTHER
                        note = 2'-O-methyl uridine
modified_base           8
                        mod_base = OTHER
                        note = 2'-fluoro cytidine
modified_base           9
```

```
                        mod_base = OTHER
                        note = 2'-O-methyl adenosine
modified_base           10
                        mod_base = OTHER
                        note = 2'-fluoro adenosine
modified_base           11
                        mod_base = OTHER
                        note = 2'-O-methyl uridine
modified_base           12
                        mod_base = OTHER
                        note = 2'-O-methyl uridine
modified_base           13
                        mod_base = OTHER
                        note = 2'-O-methyl uridine
modified_base           14
                        mod_base = OTHER
                        note = 2'-fluoro cytidine phosphorothioate
modified_base           15
                        mod_base = OTHER
                        note = 2'-O-methyl guanosine phosphorothioate
modified_base           16
                        mod_base = OTHER
                        note = 2'-O-methyl adenosine 3'-cholesterol-triethylene
                         glycol
SEQUENCE: 212
gcatcatcaa tttcga                                                    16

SEQ ID NO: 213          moltype = RNA  length = 16
FEATURE                 Location/Qualifiers
source                  1..16
                        mol_type = other RNA
                        organism = synthetic construct
modified_base           1
                        mod_base = OTHER
                        note = 2'-O-methyl cytidine phosphorothioate
modified_base           2
                        mod_base = OTHER
                        note = 2'-O-methyl adenosine phosphorothioate
modified_base           3
                        mod_base = OTHER
                        note = 2'-O-methyl uridine
modified_base           4
                        mod_base = OTHER
                        note = 2'-fluoro cytidine
modified_base           5
                        mod_base = OTHER
                        note = 2'-O-methyl adenosine
modified_base           6
                        mod_base = OTHER
                        note = 2'-fluoro uridine
modified_base           7
                        mod_base = OTHER
                        note = 2'-O-methyl cytidine
modified_base           8
                        mod_base = OTHER
                        note = 2'-fluoro adenosine
modified_base           9
                        mod_base = OTHER
                        note = 2'-O-methyl adenosine
modified_base           10
                        mod_base = OTHER
                        note = 2'-fluoro uridine
modified_base           11
                        mod_base = OTHER
                        note = 2'-O-methyl uridine
modified_base           12
                        mod_base = OTHER
                        note = 2'-O-methyl uridine
modified_base           13
                        mod_base = OTHER
                        note = 2'-O-methyl cytidine
modified_base           14
                        mod_base = OTHER
                        note = 2'-fluoro guanosine phosphorothioate
modified_base           15
                        mod_base = OTHER
                        note = 2'-O-methyl adenosine phosphorothioate
modified_base           16
                        mod_base = OTHER
```

```
                          note = 2'-O-methyl adenosine 3'-cholesterol-triethylene
                           glycol
SEQUENCE: 213
catcatcaat ttcgaa                                                                 16

SEQ ID NO: 214            moltype = RNA  length = 16
FEATURE                   Location/Qualifiers
source                    1..16
                          mol_type = other RNA
                          organism = synthetic construct
modified_base             1
                          mod_base = OTHER
                          note = 2'-O-methyl adenosine phosphorothioate
modified_base             2
                          mod_base = OTHER
                          note = 2'-O-methyl uridine phosphorothioate
modified_base             3
                          mod_base = OTHER
                          note = 2'-O-methyl cytidine
modified_base             4
                          mod_base = OTHER
                          note = 2'-fluoro adenosine
modified_base             5
                          mod_base = OTHER
                          note = 2'-O-methyl uridine
modified_base             6
                          mod_base = OTHER
                          note = 2'-fluoro cytidine
modified_base             7
                          mod_base = OTHER
                          note = 2'-O-methyl adenosine
modified_base             8
                          mod_base = OTHER
                          note = 2'-fluoro adenosine
modified_base             9
                          mod_base = OTHER
                          note = 2'-O-methyl uridine
modified_base             10
                          mod_base = OTHER
                          note = 2'-fluoro uridine
modified_base             11
                          mod_base = OTHER
                          note = 2'-O-methyl uridine
modified_base             12
                          mod_base = OTHER
                          note = 2'-O-methyl cytidine
modified_base             13
                          mod_base = OTHER
                          note = 2'-O-methyl guanosine
modified_base             14
                          mod_base = OTHER
                          note = 2'-fluoro adenosine phosphorothioate
modified_base             15
                          mod_base = OTHER
                          note = 2'-O-methyl guanosine phosphorothioate
modified_base             16
                          mod_base = OTHER
                          note = 2'-O-methyl adenosine 3'-cholesterol-triethylene
                           glycol
SEQUENCE: 214
atcatcaatt tcgaga                                                                 16

SEQ ID NO: 215            moltype = RNA  length = 16
FEATURE                   Location/Qualifiers
source                    1..16
                          mol_type = other RNA
                          organism = synthetic construct
modified_base             1
                          mod_base = OTHER
                          note = 2'-O-methyl uridine phosphorothioate
modified_base             2
                          mod_base = OTHER
                          note = 2'-O-methyl cytidine phosphorothioate
modified_base             3
                          mod_base = OTHER
                          note = 2'-O-methyl adenosine
modified_base             4
                          mod_base = OTHER
                          note = 2'-fluoro uridine
```

```
modified_base          5
                       mod_base = OTHER
                       note = 2'-O-methyl cytidine
modified_base          6
                       mod_base = OTHER
                       note = 2'-fluoro adenosine
modified_base          7
                       mod_base = OTHER
                       note = 2'-O-methyl adenosine
modified_base          8
                       mod_base = OTHER
                       note = 2'-fluoro uridine
modified_base          9
                       mod_base = OTHER
                       note = 2'-O-methyl uridine
modified_base          10
                       mod_base = OTHER
                       note = 2'-fluoro uridine
modified_base          11
                       mod_base = OTHER
                       note = 2'-O-methyl cytidine
modified_base          12
                       mod_base = OTHER
                       note = 2'-O-methyl guanosine
modified_base          13
                       mod_base = OTHER
                       note = 2'-O-methyl adenosine
modified_base          14
                       mod_base = OTHER
                       note = 2'-fluoro guanosine phosphorothioate
modified_base          15
                       mod_base = OTHER
                       note = 2'-O-methyl cytidine phosphorothioate
modified_base          16
                       mod_base = OTHER
                       note = 2'-O-methyl adenosine 3'-cholesterol-triethylene
                        glycol
SEQUENCE: 215
tcatcaattt cgagca                                             16

SEQ ID NO: 216         moltype = RNA  length = 16
FEATURE                Location/Qualifiers
source                 1..16
                       mol_type = other RNA
                       organism = synthetic construct
modified_base          1
                       mod_base = OTHER
                       note = 2'-O-methyl cytidine phosphorothioate
modified_base          2
                       mod_base = OTHER
                       note = 2'-O-methyl adenosine phosphorothioate
modified_base          3
                       mod_base = OTHER
                       note = 2'-O-methyl uridine
modified_base          4
                       mod_base = OTHER
                       note = 2'-fluoro cytidine
modified_base          5
                       mod_base = OTHER
                       note = 2'-O-methyl adenosine
modified_base          6
                       mod_base = OTHER
                       note = 2'-fluoro adenosine
modified_base          7
                       mod_base = OTHER
                       note = 2'-O-methyl uridine
modified_base          8
                       mod_base = OTHER
                       note = 2'-fluoro uridine
modified_base          9
                       mod_base = OTHER
                       note = 2'-O-methyl uridine
modified_base          10
                       mod_base = OTHER
                       note = 2'-fluoro cytidine
modified_base          11
                       mod_base = OTHER
                       note = 2'-O-methyl guanosine
modified_base          12
```

```
                         mod_base = OTHER
                         note = 2'-O-methyl adenosine
modified_base            13
                         mod_base = OTHER
                         note = 2'-O-methyl guanosine
modified_base            14
                         mod_base = OTHER
                         note = 2'-fluoro cytidine phosphorothioate
modified_base            15
                         mod_base = OTHER
                         note = 2'-O-methyl adenosine phosphorothioate
modified_base            16
                         mod_base = OTHER
                         note = 2'-O-methyl adenosine 3'-cholesterol-triethylene
                          glycol
SEQUENCE: 216
catcaatttc gagcaa                                                          16

SEQ ID NO: 217           moltype = RNA  length = 16
FEATURE                  Location/Qualifiers
source                   1..16
                         mol_type = other RNA
                         organism = synthetic construct
modified_base            1
                         mod_base = OTHER
                         note = 2'-O-methyl adenosine phosphorothioate
modified_base            2
                         mod_base = OTHER
                         note = 2'-O-methyl uridine phosphorothioate
modified_base            3
                         mod_base = OTHER
                         note = 2'-O-methyl cytidine
modified_base            4
                         mod_base = OTHER
                         note = 2'-fluoro adenosine
modified_base            5
                         mod_base = OTHER
                         note = 2'-O-methyl adenosine
modified_base            6
                         mod_base = OTHER
                         note = 2'-fluoro uridine
modified_base            7
                         mod_base = OTHER
                         note = 2'-O-methyl uridine
modified_base            8
                         mod_base = OTHER
                         note = 2'-fluoro uridine
modified_base            9
                         mod_base = OTHER
                         note = 2'-O-methyl cytidine
modified_base            10
                         mod_base = OTHER
                         note = 2'-fluoro guanosine
modified_base            11
                         mod_base = OTHER
                         note = 2'-O-methyl adenosine
modified_base            12
                         mod_base = OTHER
                         note = 2'-O-methyl guanosine
modified_base            13
                         mod_base = OTHER
                         note = 2'-O-methyl cytidine
modified_base            14
                         mod_base = OTHER
                         note = 2'-fluoro adenosine phosphorothioate
modified_base            15
                         mod_base = OTHER
                         note = 2'-O-methyl guanosine phosphorothioate
modified_base            16
                         mod_base = OTHER
                         note = 2'-O-methyl adenosine 3'-cholesterol-triethylene
                          glycol
SEQUENCE: 217
atcaatttcg agcaga                                                          16

SEQ ID NO: 218           moltype = RNA  length = 16
FEATURE                  Location/Qualifiers
source                   1..16
                         mol_type = other RNA
```

-continued

```
                        organism = synthetic construct
modified_base           1
                        mod_base = OTHER
                        note = 2'-O-methyl uridine phosphorothioate
modified_base           2
                        mod_base = OTHER
                        note = 2'-O-methyl cytidine phosphorothioate
modified_base           3
                        mod_base = OTHER
                        note = 2'-O-methyl adenosine
modified_base           4
                        mod_base = OTHER
                        note = 2'-fluoro adenosine
modified_base           5
                        mod_base = OTHER
                        note = 2'-O-methyl uridine
modified_base           6
                        mod_base = OTHER
                        note = 2'-fluoro uridine
modified_base           7
                        mod_base = OTHER
                        note = 2'-O-methyl uridine
modified_base           8
                        mod_base = OTHER
                        note = 2'-fluoro cytidine
modified_base           9
                        mod_base = OTHER
                        note = 2'-O-methyl guanosine
modified_base           10
                        mod_base = OTHER
                        note = 2'-fluoro adenosine
modified_base           11
                        mod_base = OTHER
                        note = 2'-O-methyl guanosine
modified_base           12
                        mod_base = OTHER
                        note = 2'-O-methyl cytidine
modified_base           13
                        mod_base = OTHER
                        note = 2'-O-methyl adenosine
modified_base           14
                        mod_base = OTHER
                        note = 2'-fluoro guanosine phosphorothioate
modified_base           15
                        mod_base = OTHER
                        note = 2'-O-methyl adenosine phosphorothioate
modified_base           16
                        mod_base = OTHER
                        note = 2'-O-methyl adenosine 3'-cholesterol-triethylene
                         glycol
SEQUENCE: 218
tcaatttcga gcagaa                                                    16

SEQ ID NO: 219          moltype = RNA  length = 16
FEATURE                 Location/Qualifiers
source                  1..16
                        mol_type = other RNA
                        organism = synthetic construct
modified_base           1
                        mod_base = OTHER
                        note = 2'-O-methyl cytidine phosphorothioate
modified_base           2
                        mod_base = OTHER
                        note = 2'-O-methyl adenosine phosphorothioate
modified_base           3
                        mod_base = OTHER
                        note = 2'-O-methyl adenosine
modified_base           4
                        mod_base = OTHER
                        note = 2'-fluoro uridine
modified_base           5
                        mod_base = OTHER
                        note = 2'-O-methyl uridine
modified_base           6
                        mod_base = OTHER
                        note = 2'-fluoro uridine
modified_base           7
                        mod_base = OTHER
                        note = 2'-O-methyl cytidine
```

```
modified_base          8
                       mod_base = OTHER
                       note = 2'-fluoro guanosine
modified_base          9
                       mod_base = OTHER
                       note = 2'-O-methyl adenosine
modified_base          10
                       mod_base = OTHER
                       note = 2'-fluoro guanosine
modified_base          11
                       mod_base = OTHER
                       note = 2'-O-methyl cytidine
modified_base          12
                       mod_base = OTHER
                       note = 2'-O-methyl adenosine
modified_base          13
                       mod_base = OTHER
                       note = 2'-O-methyl guanosine
modified_base          14
                       mod_base = OTHER
                       note = 2'-fluoro adenosine phosphorothioate
modified_base          15
                       mod_base = OTHER
                       note = 2'-O-methyl adenosine phosphorothioate
modified_base          16
                       mod_base = OTHER
                       note = 2'-O-methyl adenosine 3'-cholesterol-triethylene
                        glycol
SEQUENCE: 219
caatttcgag cagaaa                                                 16

SEQ ID NO: 220         moltype = RNA  length = 16
FEATURE                Location/Qualifiers
source                 1..16
                       mol_type = other RNA
                       organism = synthetic construct
modified_base          1
                       mod_base = OTHER
                       note = 2'-O-methyl adenosine phosphorothioate
modified_base          2
                       mod_base = OTHER
                       note = 2'-O-methyl adenosine phosphorothioate
modified_base          3
                       mod_base = OTHER
                       note = 2'-O-methyl uridine
modified_base          4
                       mod_base = OTHER
                       note = 2'-fluoro uridine
modified_base          5
                       mod_base = OTHER
                       note = 2'-O-methyl uridine
modified_base          6
                       mod_base = OTHER
                       note = 2'-fluoro cytidine
modified_base          7
                       mod_base = OTHER
                       note = 2'-O-methyl guanosine
modified_base          8
                       mod_base = OTHER
                       note = 2'-fluoro adenosine
modified_base          9
                       mod_base = OTHER
                       note = 2'-O-methyl guanosine
modified_base          10
                       mod_base = OTHER
                       note = 2'-fluoro cytidine
modified_base          11
                       mod_base = OTHER
                       note = 2'-O-methyl adenosine
modified_base          12
                       mod_base = OTHER
                       note = 2'-O-methyl guanosine
modified_base          13
                       mod_base = OTHER
                       note = 2'-O-methyl adenosine
modified_base          14
                       mod_base = OTHER
                       note = 2'-fluoro adenosine phosphorothioate
modified_base          15
```

```
                        mod_base = OTHER
                        note = 2'-O-methyl guanosine phosphorothioate
modified_base           16
                        mod_base = OTHER
                        note = 2'-O-methyl adenosine 3'-cholesterol-triethylene
                         glycol
SEQUENCE: 220
aatttcgagc agaaga                                                     16

SEQ ID NO: 221          moltype = RNA  length = 16
FEATURE                 Location/Qualifiers
source                  1..16
                        mol_type = other RNA
                        organism = synthetic construct
modified_base           1
                        mod_base = OTHER
                        note = 2'-O-methyl adenosine phosphorothioate
modified_base           2
                        mod_base = OTHER
                        note = 2'-O-methyl uridine phosphorothioate
modified_base           3
                        mod_base = OTHER
                        note = 2'-O-methyl uridine
modified_base           4
                        mod_base = OTHER
                        note = 2'-fluoro uridine
modified_base           5
                        mod_base = OTHER
                        note = 2'-O-methyl cytidine
modified_base           6
                        mod_base = OTHER
                        note = 2'-fluoro guanosine
modified_base           7
                        mod_base = OTHER
                        note = 2'-O-methyl adenosine
modified_base           8
                        mod_base = OTHER
                        note = 2'-fluoro guanosine
modified_base           9
                        mod_base = OTHER
                        note = 2'-O-methyl cytidine
modified_base           10
                        mod_base = OTHER
                        note = 2'-fluoro adenosine
modified_base           11
                        mod_base = OTHER
                        note = 2'-O-methyl guanosine
modified_base           12
                        mod_base = OTHER
                        note = 2'-O-methyl adenosine
modified_base           13
                        mod_base = OTHER
                        note = 2'-O-methyl adenosine
modified_base           14
                        mod_base = OTHER
                        note = 2'-fluoro guanosine phosphorothioate
modified_base           15
                        mod_base = OTHER
                        note = 2'-O-methyl guanosine phosphorothioate
modified_base           16
                        mod_base = OTHER
                        note = 2'-O-methyl adenosine 3'-cholesterol-triethylene
                         glycol
SEQUENCE: 221
atttcgagca gaagga                                                     16

SEQ ID NO: 222          moltype = RNA  length = 16
FEATURE                 Location/Qualifiers
source                  1..16
                        mol_type = other RNA
                        organism = synthetic construct
modified_base           1
                        mod_base = OTHER
                        note = 2'-O-methyl uridine phosphorothioate
modified_base           2
                        mod_base = OTHER
                        note = 2'-O-methyl uridine phosphorothioate
modified_base           3
                        mod_base = OTHER
```

```
                        note = 2'-O-methyl uridine
modified_base           4
                        mod_base = OTHER
                        note = 2'-fluoro cytidine
modified_base           5
                        mod_base = OTHER
                        note = 2'-O-methyl guanosine
modified_base           6
                        mod_base = OTHER
                        note = 2'-fluoro adenosine
modified_base           7
                        mod_base = OTHER
                        note = 2'-O-methyl guanosine
modified_base           8
                        mod_base = OTHER
                        note = 2'-fluoro cytidine
modified_base           9
                        mod_base = OTHER
                        note = 2'-O-methyl adenosine
modified_base           10
                        mod_base = OTHER
                        note = 2'-fluoro guanosine
modified_base           11
                        mod_base = OTHER
                        note = 2'-O-methyl adenosine
modified_base           12
                        mod_base = OTHER
                        note = 2'-O-methyl adenosine
modified_base           13
                        mod_base = OTHER
                        note = 2'-O-methyl guanosine
modified_base           14
                        mod_base = OTHER
                        note = 2'-fluoro guanosine phosphorothioate
modified_base           15
                        mod_base = OTHER
                        note = 2'-O-methyl adenosine phosphorothioate
modified_base           16
                        mod_base = OTHER
                        note = 2'-O-methyl adenosine 3'-cholesterol-triethylene
                         glycol
SEQUENCE: 222
tttcgagcag aaggaa                                                   16

SEQ ID NO: 223          moltype = RNA  length = 16
FEATURE                 Location/Qualifiers
source                  1..16
                        mol_type = other RNA
                        organism = synthetic construct
modified_base           1
                        mod_base = OTHER
                        note = 2'-O-methyl uridine phosphorothioate
modified_base           2
                        mod_base = OTHER
                        note = 2'-O-methyl uridine phosphorothioate
modified_base           3
                        mod_base = OTHER
                        note = 2'-O-methyl cytidine
modified_base           4
                        mod_base = OTHER
                        note = 2'-fluoro guanosine
modified_base           5
                        mod_base = OTHER
                        note = 2'-O-methyl adenosine
modified_base           6
                        mod_base = OTHER
                        note = 2'-fluoro guanosine
modified_base           7
                        mod_base = OTHER
                        note = 2'-O-methyl cytidine
modified_base           8
                        mod_base = OTHER
                        note = 2'-fluoro adenosine
modified_base           9
                        mod_base = OTHER
                        note = 2'-O-methyl guanosine
modified_base           10
                        mod_base = OTHER
                        note = 2'-fluoro adenosine
```

-continued

```
modified_base          11
                       mod_base = OTHER
                       note = 2'-O-methyl adenosine
modified_base          12
                       mod_base = OTHER
                       note = 2'-O-methyl guanosine
modified_base          13
                       mod_base = OTHER
                       note = 2'-O-methyl guanosine
modified_base          14
                       mod_base = OTHER
                       note = 2'-fluoro adenosine phosphorothioate
modified_base          15
                       mod_base = OTHER
                       note = 2'-O-methyl adenosine phosphorothioate
modified_base          16
                       mod_base = OTHER
                       note = 2'-O-methyl adenosine 3'-cholesterol-triethylene
                        glycol
SEQUENCE: 223
ttcgagcaga aggaaa                                                  16

SEQ ID NO: 224         moltype = RNA  length = 16
FEATURE                Location/Qualifiers
source                 1..16
                       mol_type = other RNA
                       organism = synthetic construct
modified_base          1
                       mod_base = OTHER
                       note = 2'-O-methyl uridine phosphorothioate
modified_base          2
                       mod_base = OTHER
                       note = 2'-O-methyl cytidine phosphorothioate
modified_base          3
                       mod_base = OTHER
                       note = 2'-O-methyl guanosine
modified_base          4
                       mod_base = OTHER
                       note = 2'-fluoro adenosine
modified_base          5
                       mod_base = OTHER
                       note = 2'-O-methyl guanosine
modified_base          6
                       mod_base = OTHER
                       note = 2'-fluoro cytidine
modified_base          7
                       mod_base = OTHER
                       note = 2'-O-methyl adenosine
modified_base          8
                       mod_base = OTHER
                       note = 2'-fluoro guanosine
modified_base          9
                       mod_base = OTHER
                       note = 2'-O-methyl adenosine
modified_base          10
                       mod_base = OTHER
                       note = 2'-fluoro adenosine
modified_base          11
                       mod_base = OTHER
                       note = 2'-O-methyl guanosine
modified_base          12
                       mod_base = OTHER
                       note = 2'-O-methyl guanosine
modified_base          13
                       mod_base = OTHER
                       note = 2'-O-methyl adenosine
modified_base          14
                       mod_base = OTHER
                       note = 2'-fluoro adenosine phosphorothioate
modified_base          15
                       mod_base = OTHER
                       note = 2'-O-methyl adenosine phosphorothioate
modified_base          16
                       mod_base = OTHER
                       note = 2'-O-methyl adenosine 3'-cholesterol-triethylene
                        glycol
SEQUENCE: 224
tcgagcagaa ggaaaa                                                  16
```

-continued

```
SEQ ID NO: 225          moltype = RNA  length = 16
FEATURE                 Location/Qualifiers
source                  1..16
                        mol_type = other RNA
                        organism = synthetic construct
modified_base           1
                        mod_base = OTHER
                        note = 2'-O-methyl guanosine phosphorothioate
modified_base           2
                        mod_base = OTHER
                        note = 2'-O-methyl cytidine phosphorothioate
modified_base           3
                        mod_base = OTHER
                        note = 2'-O-methyl adenosine
modified_base           4
                        mod_base = OTHER
                        note = 2'-fluoro uridine
modified_base           5
                        mod_base = OTHER
                        note = 2'-O-methyl cytidine
modified_base           6
                        mod_base = OTHER
                        note = 2'-fluoro adenosine
modified_base           7
                        mod_base = OTHER
                        note = 2'-O-methyl uridine
modified_base           8
                        mod_base = OTHER
                        note = 2'-fluoro cytidine
modified_base           9
                        mod_base = OTHER
                        note = 2'-O-methyl adenosine
modified_base           10
                        mod_base = OTHER
                        note = 2'-fluoro adenosine
modified_base           11
                        mod_base = OTHER
                        note = 2'-O-methyl uridine
modified_base           12
                        mod_base = OTHER
                        note = 2'-O-methyl uridine
modified_base           13
                        mod_base = OTHER
                        note = 2'-O-methyl uridine
modified_base           14
                        mod_base = OTHER
                        note = 2'-fluoro cytidine phosphorothioate
modified_base           15
                        mod_base = OTHER
                        note = 2'-O-methyl guanosine phosphorothioate
modified_base           16
                        mod_base = OTHER
                        note = 2'-O-methyladenosine attached to a 3'
                         di-oligonucleotide linker that connects to the 3' end of a
                         second sense strand that is identical to SEQ ID NO: 225
SEQUENCE: 225
gcatcatcaa tttcga                                                    16

SEQ ID NO: 226          moltype = RNA  length = 21
FEATURE                 Location/Qualifiers
source                  1..21
                        mol_type = other RNA
                        organism = synthetic construct
modified_base           1
                        mod_base = OTHER
                        note = 5'-vinylphosphonate-2'-O-methyl uridine
                         phosphorothioate
modified_base           2
                        mod_base = OTHER
                        note = 2'-fluoro cytidine phosphorothioate
modified_base           3
                        mod_base = OTHER
                        note = 2'-O-methyl guanosine
modified_base           4
                        mod_base = OTHER
                        note = 2'-fluoro adenosine
modified_base           5
                        mod_base = OTHER
                        note = 2'-fluoro adenosine
```

```
modified_base         6
                      mod_base = OTHER
                      note = 2'-fluoro adenosine
modified_base         7
                      mod_base = OTHER
                      note = 2'-O-methyl uridine
modified_base         8
                      mod_base = OTHER
                      note = 2'-fluoro uridine
modified_base         9
                      mod_base = OTHER
                      note = 2'-O-methyl guanosine
modified_base         10
                      mod_base = OTHER
                      note = 2'-fluoro adenosine
modified_base         11
                      mod_base = OTHER
                      note = 2'-O-methyl uridine
modified_base         12
                      mod_base = OTHER
                      note = 2'-fluoro guanosine
modified_base         13
                      mod_base = OTHER
                      note = 2'-O-methyl adenosine
modified_base         14
                      mod_base = OTHER
                      note = 2'-fluoro uridine phosphorothioate
modified_base         15
                      mod_base = OTHER
                      note = 2'-O-methyl guanosine phosphorothioate
modified_base         16
                      mod_base = OTHER
                      note = 2'-fluoro cytidine phosphorothioate
modified_base         17
                      mod_base = OTHER
                      note = 2'-O-methyl cytidine phosphorothioate
modified_base         18
                      mod_base = OTHER
                      note = 2'-O-methyl cytidine phosphorothioate
modified_base         19
                      mod_base = OTHER
                      note = 2'-O-methyl uridine phosphorothioate
modified_base         20
                      mod_base = OTHER
                      note = 2'-fluoro guanosine phosphorothioate
modified_base         21
                      mod_base = OTHER
                      note = 2'-O-methyl uridine
SEQUENCE: 226
tcgaaattga tgatgccctg t                                                21

SEQ ID NO: 227        moltype = DNA  length = 20
FEATURE               Location/Qualifiers
source                1..20
                      mol_type = other DNA
                      organism = synthetic construct
modified_base         1
                      mod_base = OTHER
                      note = 2'-O-methoxyethylribose cytidine phosphorothioate
modified_base         2
                      mod_base = OTHER
                      note = 2'-O-methoxyethylribose adenosine
modified_base         3
                      mod_base = OTHER
                      note = 2'-O-methoxyethylribose guanosine phosphorothioate
modified_base         4
                      mod_base = OTHER
                      note = 2'-O-methoxyethylribose guanosine
modified_base         5
                      mod_base = OTHER
                      note = 2'-O-methoxyethylribose adenosine phosphorothioate
modified_base         6
                      mod_base = OTHER
                      note = Thymidine phosphorothioate
modified_base         7
                      mod_base = OTHER
                      note = Adenosine phosphorothioate
modified_base         8
                      mod_base = OTHER
```

-continued

```
                        note = Cytidine phosphorothioate
modified_base           9
                        mod_base = OTHER
                        note = Adenosine phosphorothioate
modified_base           10
                        mod_base = OTHER
                        note = Thymidine phosphorothioate
modified_base           11
                        mod_base = OTHER
                        note = Thymidine phosphorothioate
modified_base           12
                        mod_base = OTHER
                        note = Thymidine phosphorothioate
modified_base           13
                        mod_base = OTHER
                        note = Cytidine phosphorothioate
modified_base           14
                        mod_base = OTHER
                        note = Thymidine phosphorothioate
modified_base           15
                        mod_base = OTHER
                        note = Adenosine phosphorothioate
modified_base           16
                        mod_base = OTHER
                        note = 2'-O-methoxyethylribose cytidine
modified_base           17
                        mod_base = OTHER
                        note = 2'-O-methoxyethylribose adenosine phosphorothioate
modified_base           18
                        mod_base = OTHER
                        note = 2'-O-methoxyethylribose guanosine
modified_base           19
                        mod_base = OTHER
                        note = 2'-O-methoxyethylribose cytidine phosphorothioate
modified_base           20
                        mod_base = OTHER
                        note = 2'-O-methoxyethylribose uridine
misc_feature            1..5
                        note = RNA
misc_feature            6..15
                        note = DNA
misc_feature            16..20
                        note = RNA
SEQUENCE: 227
caggatacat ttctacagct                                              20

SEQ ID NO: 228          moltype = RNA  length = 19
FEATURE                 Location/Qualifiers
source                  1..19
                        mol_type = other RNA
                        organism = synthetic construct
modified_base           1
                        mod_base = OTHER
                        note = 5'-vinylphosphonate-2'-O-methyl uridine
                         phosphorothioate
modified_base           2
                        mod_base = OTHER
                        note = 2'-fluoro cytidine phosphorothioate
modified_base           3
                        mod_base = OTHER
                        note = 2'-O-methyl guanosine
modified_base           4
                        mod_base = OTHER
                        note = 2'-fluoro adenosine
modified_base           5
                        mod_base = OTHER
                        note = 2'-fluoro adenosine
modified_base           6
                        mod_base = OTHER
                        note = 2'-fluoro adenosine
modified_base           7
                        mod_base = OTHER
                        note = 2'-O-methyl uridine
modified_base           8
                        mod_base = OTHER
                        note = 2'-fluoro uridine
modified_base           9
                        mod_base = OTHER
                        note = 2'-O-methyl guanosine
```

```
modified_base          10
                       mod_base = OTHER
                       note = 2'-fluoro adenosine
modified_base          11
                       mod_base = OTHER
                       note = 2'-O-methyl uridine
modified_base          12
                       mod_base = OTHER
                       note = 2'-fluoro guanosine
modified_base          13
                       mod_base = OTHER
                       note = 2'-O-methyl adenosine
modified_base          14
                       mod_base = OTHER
                       note = 2'-fluoro uridine
modified_base          15
                       mod_base = OTHER
                       note = 2'-O-methyl guanosine
modified_base          16
                       mod_base = OTHER
                       note = 2'-fluoro cytidine
modified_base          17
                       mod_base = OTHER
                       note = 2'-O-methyl cytidine
modified_base          18
                       mod_base = OTHER
                       note = 2'-O-methyl cytidine
modified_base          19
                       mod_base = OTHER
                       note = 2'-O-methyl uridine
SEQUENCE: 228
tcgaaattga tgatgccct                                                19

SEQ ID NO: 229         moltype = RNA  length = 16
FEATURE                Location/Qualifiers
source                 1..16
                       mol_type = other RNA
                       organism = synthetic construct
modified_base          1
                       mod_base = OTHER
                       note = 2'-O-methyl guanosine phosphorothioate
modified_base          2
                       mod_base = OTHER
                       note = 2'-O-methyl cytidine phosphorothioate
modified_base          3
                       mod_base = OTHER
                       note = 2'-O-methyl adenosine
modified_base          4
                       mod_base = OTHER
                       note = 2'-O-methyl uridine
modified_base          5
                       mod_base = OTHER
                       note = 2'-O-methyl cytidine
modified_base          6
                       mod_base = OTHER
                       note = 2'-fluoro adenosine
modified_base          7
                       mod_base = OTHER
                       note = 2'-fluoro uridine
modified_base          8
                       mod_base = OTHER
                       note = 2'-fluoro cytidine
modified_base          9
                       mod_base = OTHER
                       note = 2'-O-methyl adenosine
modified_base          10
                       mod_base = OTHER
                       note = 2'-fluoro adenosine
modified_base          11
                       mod_base = OTHER
                       note = 2'-O-methyl uridine
modified_base          12
                       mod_base = OTHER
                       note = 2'-O-methyl uridine
modified_base          13
                       mod_base = OTHER
                       note = 2'-O-methyl uridine
modified_base          14
                       mod_base = OTHER
```

```
                        note = 2'-O-methyl cytidine phosphorothioate
modified_base           15
                        mod_base = OTHER
                        note = 2'-O-methyl guanosine phosphorothioate
modified_base           16
                        mod_base = OTHER
                        note = 2'-O-methyladenosine attached to a 3'
                         di-oligonucleotide linker that connects to the 3' end of a
                         second sense strand that is identical to SEQ ID NO: 229
SEQUENCE: 229
gcatcatcaa tttcga                                                  16

SEQ ID NO: 230          moltype = RNA  length = 21
FEATURE                 Location/Qualifiers
source                  1..21
                        mol_type = other RNA
                        organism = synthetic construct
modified_base           1
                        mod_base = OTHER
                        note = 5'-vinylphosphonate-2'-O-methyl uridine
                         phosphorothioate
modified_base           2
                        mod_base = OTHER
                        note = 2'-fluoro cytidine phosphorothioate
modified_base           3
                        mod_base = OTHER
                        note = 2'-O-methyl guanosine
modified_base           4
                        mod_base = OTHER
                        note = 2'-O-methyl adenosine
modified_base           5
                        mod_base = OTHER
                        note = 2'-O-methyl adenosine
modified_base           6
                        mod_base = OTHER
                        note = 2'-fluoro adenosine
modified_base           7
                        mod_base = OTHER
                        note = 2'-O-methyl uridine
modified_base           8
                        mod_base = OTHER
                        note = 2'-O-methyl uridine
modified_base           9
                        mod_base = OTHER
                        note = 2'-O-methyl guanosine
modified_base           10
                        mod_base = OTHER
                        note = 2'-O-methyl adenosine
modified_base           11
                        mod_base = OTHER
                        note = 2'-O-methyl uridine
modified_base           12
                        mod_base = OTHER
                        note = 2'-O-methyl guanosine
modified_base           13
                        mod_base = OTHER
                        note = 2'-O-methyl adenosine
modified_base           14
                        mod_base = OTHER
                        note = 2'-fluoro uridine phosphorothioate
modified_base           15
                        mod_base = OTHER
                        note = 2'-O-methyl guanosine phosphorothioate
modified_base           16
                        mod_base = OTHER
                        note = 2'-fluoro cytidine phosphorothioate
modified_base           17
                        mod_base = OTHER
                        note = 2'-O-methyl cytidine phosphorothioate
modified_base           18
                        mod_base = OTHER
                        note = 2'-O-methyl cytidine phosphorothioate
modified_base           19
                        mod_base = OTHER
                        note = 2'-O-methyl uridine phosphorothioate
modified_base           20
                        mod_base = OTHER
                        note = 2'-fluoro guanosine phosphorothioate
modified_base           21
```

-continued

```
                        mod_base = OTHER
                        note = 2'-O-methyl uridine
SEQUENCE: 230
tcgaaattga tgatgccctg t                                            21

SEQ ID NO: 231          moltype = DNA  length = 20
FEATURE                 Location/Qualifiers
source                  1..20
                        mol_type = other DNA
                        organism = synthetic construct
modified_base           1
                        mod_base = OTHER
                        note = 2'-O-methoxyethylribose cytidine phosphorothioate
modified_base           2
                        mod_base = OTHER
                        note = 2'-O-methoxyethylribose adenosine
modified_base           3
                        mod_base = OTHER
                        note = 2'-O-methoxyethylribose guanosine phosphorothioate
modified_base           4
                        mod_base = OTHER
                        note = 2'-O-methoxyethylribose guanosine
modified_base           5
                        mod_base = OTHER
                        note = 2'-O-methoxyethylribose adenosine phosphorothioate
modified_base           6
                        mod_base = OTHER
                        note = Thymidine phosphorothioate
modified_base           7
                        mod_base = OTHER
                        note = Adenosine phosphorothioate
modified_base           8
                        mod_base = OTHER
                        note = Cytidine phosphorothioate
modified_base           9
                        mod_base = OTHER
                        note = Adenosine phosphorothioate
modified_base           10
                        mod_base = OTHER
                        note = Thymidine phosphorothioate
modified_base           11
                        mod_base = OTHER
                        note = Thymidine phosphorothioate
modified_base           12
                        mod_base = OTHER
                        note = Thymidine phosphorothioate
modified_base           13
                        mod_base = OTHER
                        note = Cytidine phosphorothioate
modified_base           14
                        mod_base = OTHER
                        note = Thymidine phosphorothioate
modified_base           15
                        mod_base = OTHER
                        note = Adenosine phosphorothioate
modified_base           16
                        mod_base = OTHER
                        note = 2'-O-methoxyethylribose cytidine
modified_base           17
                        mod_base = OTHER
                        note = 2'-O-methoxyethylribose adenosine phosphorothioate
modified_base           18
                        mod_base = OTHER
                        note = 2'-O-methoxyethylribose guanosine
modified_base           19
                        mod_base = OTHER
                        note = 2'-O-methoxyethylribose cytidine phosphorothioate
modified_base           20
                        mod_base = OTHER
                        note = 2'-O-methoxyethylribose thymidine
misc_feature            1..5
                        note = RNA
misc_feature            6..15
                        note = DNA
misc_feature            16..20
                        note = RNA
SEQUENCE: 231
caggatacat ttctacagct                                              20
```

```
SEQ ID NO: 232          moltype = DNA  length = 17
FEATURE                 Location/Qualifiers
source                  1..17
                        mol_type = other DNA
                        organism = synthetic construct
modified_base           1
                        mod_base = OTHER
                        note = 2'-O-methoxyethylribose thymidine phosphorothioate
modified_base           2
                        mod_base = OTHER
                        note = 2'-O-methoxyethylribose thymidine
modified_base           3
                        mod_base = OTHER
                        note = 2'-O-methoxyethylribose adenosine
modified_base           4
                        mod_base = OTHER
                        note = 2'-O-methoxyethylribose adenosine phosphorothioate
modified_base           5
                        mod_base = OTHER
                        note = Thymidine phosphorothioate
modified_base           6
                        mod_base = OTHER
                        note = Guanosine phosphorothioate
modified_base           7
                        mod_base = OTHER
                        note = Thymidine phosphorothioate
modified_base           8
                        mod_base = OTHER
                        note = Thymidine phosphorothioate
modified_base           9
                        mod_base = OTHER
                        note = Thymidine phosphorothioate
modified_base           10
                        mod_base = OTHER
                        note = Adenosine phosphorothioate
modified_base           11
                        mod_base = OTHER
                        note = Thymidine phosphorothioate
modified_base           12
                        mod_base = OTHER
                        note = Cytidine phosphorothioate
modified_base           13
                        mod_base = OTHER
                        note = (S)-2',4'-constrained 2'-O-ethyl adenosine
modified_base           14
                        mod_base = OTHER
                        note = (S)-2',4'-constrained 2'-O-ethyl guanosine
modified_base           15
                        mod_base = OTHER
                        note = 2'-O-methoxyethylribose guanosine phosphorothioate
modified_base           16
                        mod_base = OTHER
                        note = 2'-O-methoxyethylribose adenosine phosphorothioate
modified_base           17
                        mod_base = OTHER
                        note = 2'-O-methoxyethylribose thymidine
misc_feature            1..4
                        note = RNA
misc_feature            5..12
                        note = DNA
misc_feature            13..17
                        note = RNA
SEQUENCE: 232
ttaatgttta tcaggat                                                17

SEQ ID NO: 233          moltype = DNA  length = 20
FEATURE                 Location/Qualifiers
source                  1..20
                        mol_type = other DNA
                        organism = synthetic construct
modified_base           1
                        mod_base = OTHER
                        note = 2'-O-methoxyethylribose cytidine phosphorothioate
modified_base           2
                        mod_base = OTHER
                        note = 2'-O-methoxyethylribose cytidine phosphorothioate
modified_base           3
                        mod_base = OTHER
                        note = 2'-O-methoxyethylribose guanosine phosphorothioate
```

-continued

```
modified_base          4
                       mod_base = OTHER
                       note = 2'-O-methoxyethylribose thymidine phosphorothioate
modified_base          5
                       mod_base = OTHER
                       note = 2'-O-methoxyethylribose cytidine phosphorothioate
modified_base          6
                       mod_base = OTHER
                       note = Guanosine phosphorothioate
modified_base          7
                       mod_base = OTHER
                       note = Cytidine phosphorothioate
modified_base          8
                       mod_base = OTHER
                       note = Cytidine phosphorothioate
modified_base          9
                       mod_base = OTHER
                       note = Cytidine phosphorothioate
modified_base          10
                       mod_base = OTHER
                       note = Thymidine phosphorothioate
modified_base          11
                       mod_base = OTHER
                       note = Thymidine phosphorothioate
modified_base          12
                       mod_base = OTHER
                       note = Cytidine phosphorothioate
modified_base          13
                       mod_base = OTHER
                       note = Adenosine phosphorothioate
modified_base          14
                       mod_base = OTHER
                       note = Guanosine phosphorothioate
modified_base          15
                       mod_base = OTHER
                       note = Cytidine phosphorothioate
modified_base          16
                       mod_base = OTHER
                       note = 2'-O-methoxyethylribose adenosine phosphorothioate
modified_base          17
                       mod_base = OTHER
                       note = 2'-O-methoxyethylribose cytidine phosphorothioate
modified_base          18
                       mod_base = OTHER
                       note = 2'-O-methoxyethylribose guanosine phosphorothioate
modified_base          19
                       mod_base = OTHER
                       note = 2'-O-methoxyethylribose cytidine phosphorothioate
modified_base          20
                       mod_base = OTHER
                       note = 2'-O-methoxyethylribose adenosine
misc_feature           1..5
                       note = RNA
misc_feature           6..15
                       note = DNA
misc_feature           16..20
                       note = RNA
SEQUENCE: 233
ccgtcgccct tcagcacgca                                20
```